United States Patent [19]
Kawakita et al.

[11] Patent Number: 5,864,039
[45] Date of Patent: Jan. 26, 1999

[54] BENZOIC ACID COMPOUNDS AND USE THEREOF AS MEDICAMENTS

[75] Inventors: Takeshi Kawakita; Takanobu Kuroita; Takahiro Murozono, all of Chikujo-gun; Hidetoshi Hakira, Osaka; Keiichiro Haga, Chikujo-gun; Katsuhiko Ito, Chikujo-gun; Shuji Sonda, Chikujo-gun; Toshio Kawahara, Chikujo-gun; Kiyoshi Asano, Chikujo-gun, all of Japan

[73] Assignee: Yoshitomi Pharmaceutical Industries, Ltd., Japan

[21] Appl. No.: 982,389

[22] Filed: Dec. 2, 1997

Related U.S. Application Data

[63] Continuation-in-part of Ser. No. 716,372, filed as PCT/JP95/00616 Mar. 30, 1995, Pat. No. 5,802,887.

[30] Foreign Application Priority Data

| Mar. 30, 1994 | [JP] | Japan | 6-60941 |
| Jul. 5, 1994 | [JP] | Japan | 6-153686 |
| Jan. 20, 1995 | [JP] | Japan | 7-7492 |
| Sep. 22, 1995 | [JP] | Japan | 7-244040 |
| Mar. 29, 1996 | [JP] | Japan | 8-77232 |
| Mar. 21, 1997 | [JP] | Japan | 9-068739 |

[51] Int. Cl.$^6$ .................. C07D 221/02; C07D 265/14
[52] U.S. Cl. .................. 546/229; 546/232; 546/233; 546/234; 546/207; 546/214; 544/129; 544/130; 544/111
[58] Field of Search .................. 546/183, 229, 546/232, 233, 234; 544/106, 111

[56] References Cited

U.S. PATENT DOCUMENTS

| 3,972,994 | 8/1976 | Beregi et al. . |
| 4,870,074 | 9/1989 | Kon et al. . |
| 4,937,236 | 6/1990 | Vega-Noverola et al. . |
| 4,983,633 | 1/1991 | Itoh et al. . |
| 5,185,335 | 2/1993 | Van Daele et al. . |

FOREIGN PATENT DOCUMENTS

| 623621 | 11/1994 | European Pat. Off. . |
| 670319 | 9/1995 | European Pat. Off. . |

OTHER PUBLICATIONS

*The Merck Index*, eleventh edition, 6063. (1989).
*The Merck Index*, eleventh edition, 2318. (1989).
*The Journal of Pharmacology and Experimental Therapeutics*, vol. 252, pp. 1378–1386 (1990).
*European Journal of Pharmacology*, vol. 196, pp. 149–155 (1991).
*The Journal of Pharmacology and Experimental Therapeutics*, vol. 264, pp. 240–248 (1993).
English Abstract of Japanese Patent Unexamined Publication No. 157518/1994.
*British Journal of Pharmacology*, vol. 109, pp. 618–624. (1993).
*Nayn–Schmiedeberg's Archives of Pharmacology*, vol. 344, pp. 150–159, (1991).
*Trends in Pharmacological Sciences*, vol. 13, pp. 141–145 (1992).
*Pharmacological Reviews*, vol. 46, pp. 157–203 (1994).
*Trends in Pharmacological Sciences*, vol. 16, pp. 391–398 (1995).
*Arzneimittel Forschung*, vol. 43, pp. 913–918 (1993).
*British Journal of Pharmacology*, vol. 110, pp. 119–126 (1993).
*Journal of Medicinal Chemistry*, vol. 36, pp. 4121–4123 (1993).
*Drugs*, vol. 41, pp. 574–595 (1991).
English Abstract of Japanese Patent Unexamined Publication No. 262724/1993.
English Abstract of Japanese Patent Unexamined Publication No. 87810/1994.
S. Iwanami et al., *Journal of Medicinal Chemistry*, vol. 24, No. 10, pp. 1224–1230 (1981).
*Patent Abstracts of Japan*, vol. 014, No. 310 (Dainippon Pharmaceutical Co., Ltd.).
D. Flynn et al., *J. Med. Chem.*, 35, 1486–1489 (1992).
S. Kato et al., *Chem. Pharm. Bull.*, 40(3), 652–660 (1992).

*Primary Examiner*—Johann Richter
*Assistant Examiner*—Ebenezer Sackey
*Attorney, Agent, or Firm*—Wenderoth, Lind & Ponack, L.L.P.

[57] ABSTRACT

Benzoic acid compounds of the formula

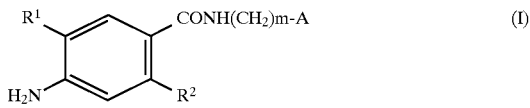

(I)

wherein each symbol is as defined in the specification, optical isomers thereof and pharmaceutically acceptable salts thereof; pharmaceutical composition comprising this compound and pharmaceutically acceptable additive; and serotonin 4 receptor agonists, gastrointestinal prokinetic agents and therapeutic agents for various gastrointestinal diseases, which comprise this compound as active ingredient. The compounds of the present invention have high and selective affinity for serotonin 4 receptor, and show agonistic effects thereon. Accordingly, they are useful medications for the prophylaxis and treatment of various gastrointestinal diseases, central nervous disorders, cardiac function disorders, urinary diseases, and the like, as well as useful anti-nociceptors for analgesic use which increase threshold of pain.

48 Claims, No Drawings

BENZOIC ACID COMPOUNDS AND USE THEREOF AS MEDICAMENTS

This is a continuation-in-part of application Ser. No. 08/716,372 filed Sep. 19, 1997 which is in turn a continuation-in-part of PCT/JP95/00616, filed Mar. 30, 1995.

FIELD OF THE INVENTION

The present invention relates to novel benzoic acid compounds. More particularly, the present invention relates to novel benzoic acid compounds having high and selective affinity for serotonin 4 (hereinafter referred to as 5-$HT_4$) receptors and capable of activating same, which are useful for the prophylaxis and therapy of various gastrointestinal diseases, central nervous disorders, cardiac function disorders, urinary diseases and the like, optical isomers thereof, pharmaceutically acceptable salts thereof, and use thereof as medicaments.

BACKGROUND OF THE INVENTION

When control mechanism of gastrointestinal motility fails and prokinetic function is declined, atonic constipation and digestive symptoms such as abdominal distention, anorexia and heartburn emerge. Declined gastrointestinal motility is found with aging, stress or diseases such as chronic gastritis, non-ulcer dyspepsia, reflux esophagitis, peptic ulcer, diabetes and the like, and gastrointestinal prokinetic agents have been used for treatment.

Ever since metoclopramide (The Merck Index, vol. 11, 6063) was developed as a gastrointestinal prokinetic agent, various substituted benzamide derivatives have been synthesized. At present, cisapride (The Merck Index, vol. 11, 2318) and others have been clinically used as gastrointestinal prokinetic agents besides metoclopramide. While benzamide derivatives such as metoclopramide and cisapride have been speculated to show effects via certain receptors in the digestive organs, the actual function of the receptors involved in the promotion of gastrointestinal motility has long been unclarified. Recently, however, 5-$HT_4$ receptor has been identified to be a new serotonin receptor subtype which stimulates adenylate cyclase activity, and benzamide derivatives have been found to promote gastrointestinal motility by activating 5-$HT_4$ receptor in the digestive organs [The Journal of Pharmacology and Experimental Therapeutics, vol. 252, pp. 1378–1386 (1990), European Journal of Pharmacology, vol. 196, pp. 149–155 (1991)]. Having found the action of metoclopramide and cisapride as 5-$HT_4$ receptor agonists, many attempts have been made to use 5-$HT_4$ receptor agonists as gastrointestinal prokinetic agents. The Journal of Pharmacology and Experimental Therapeutics, vol. 264, pp. 240–248 (1993) reports that substituted benzamide (SC53116) which is a 5-$HT_4$ receptor agonist stimulated gastrointestinal motility. As 5-$HT_4$ receptor agonists, Japanese Patent Unexamined Publication No. 157518/1994 discloses oxadiazole derivatives; Japanese Patent Unexamined Publication No. 10881/1995 discloses oxazabicyclo derivatives; and WO 94/12497 discloses endo-N-(8-methyl-8-azabicyclo[3.2.1]oct-3-yl)-1-isopropyl-2(1 H)-quinolone-3-carboxamide and acid addition salts thereof.

The 5-$HT_4$ receptor has been found to be also present in brain (e.g., prefrontal area, nigra, hippocampus and amygdaloid complex), heart, endocrine system and urinary system [British Journal of Pharmacology, vol. 109, pp. 618–624 and Naunyn-Schmiedeberg's Archives of Pharmacology, vol. 344, pp. 150–159, Trends in Pharmacological sciences, vol. 13, pp. 141–145 (1992), Pharmacological Reviews, vol. 46, pp. 182–185 (1994)].

In addition, since activation of 5-$HT_4$ receptor in the central nervous system promotes release of acetylcholine in prefrontal area, 5-$HT_4$ receptor is responsible for memory and learning mechanism through release of acetylcholine. Therefore, a 5-$HT_4$ agonist has a potential for a drug for the prophylaxis and treatment of disturbance of memory, dementia and the like. In view of a report documenting that 5-$HT_4$ receptor on GABA neuron is involved in anxiety, it also has a potential for a drug for the prophylaxis and treatment of anxiety. Furthermore, the action of 5-$HT_4$ receptor on heart and urinary system has been reported [Trends in Pharmacological Sciences, vol. 16, pp. 391–398 (1995)].

In view of such disclosures, a compound having affinity for 5-$HT_4$ receptor is considered to be clinically applicable to digestive organs, brain, heart and urinary system. In other words, a 5-$HT_4$ receptor agonist should be useful as a medication for the prophylaxis and treatment of various gastrointestinal diseases (e.g., reflux esophagitis; gastroesophageal reflux such as that accompanying cystic fibrosis; Barrett syndrome; intestinal pseudoileus; acute or chronic gastritis; gastric or duodenal ulcer; Crohn's disease; non-ulcer dyspepsia; ulcerative colitis; postgastrectomy syndrome; postoperative digestive function failure; delayed gastric emptying caused by gastric neurosis, gastroptosis, diabetes, and the like; gastrointestinal disorders such as indigestion, meteorism, abdominal indefinite complaint, and the like; constipation such as atonic constipation, chronic constipation, and that caused by spinal cord injury, pelvic diaphragm failure and the like; and irritable bowel syndrome), central nervous disorders (e.g., schizophrenia, depression, anxiety, disturbance of memory and dementia), cardiac function disorders (e.g., cardiac failure and myocardial ischemia), urinary diseases (e.g., dysuria caused by urinary obstruction, ureterolith, prostatomegaly, spinal cord injury, pelvic diaphragm failure, etc.) and the like.

In addition, a report has documented that 5-$HT_4$ receptor antagonist shows an antagonistic action on analgesic action of cisapride and metoclopramide [Arzneimittel Forschung, -vol. 43, pp. 913–918 (1993)]. Thus, a 5-$HT_4$ receptor agonist is expected to be useful as an anti-nociceptor for analgesic use which increases threshold of pain.

While there have been documented some compounds which selectively activate 5-$HT_4$ receptors [Journal of Medicinal Chemistry, vol. 35, pp. 1486–1489 (1992)], a compound has not been known at all, which has, at an alkyl moiety bound to nitrogen atom of cyclic amine, amide, urea, amino, (thio)ether, (thio)carbonyl, sulfinyl, sulfonyl or a heterocycle having amide or urea bonding in the ring.

The above-mentioned substituted benzamide derivatives, such as metoclopramide, have, besides 5-$HT_4$ receptor agonistic effect, dopamine 2 (hereinafter referred to as $D_2$) receptor antagonism or serotonin 3 (hereinafter referred to as 5-$HT_3$) receptor antagonism, and are not entirely satisfactory in terms of efficacy and safety, since they cause side effects such as extrapyramidal disorders due to $D_2$ receptor antagonism, and side effects such as constipation due to 5-$HT_3$ receptor antagonism [Drugs, vol. 41, pp. 574–595 (1991)], and are associated with such problems to be solved.

As gastrointestinal prokinetic agents, Japanese Patent Unexamined Publication Nos. 262724/1993, 50883/1989 and 211685/1992 disclose compounds having 5-$HT_3$ receptor antagonism. These compounds again cause side effects such as constipation, as mentioned above, and are not satisfactory. Since 5-HT$_4$ receptors are reportedly distributed widely in the entirety of digestive organs, a 5-HT$_4$ receptor agonist which shows low affinity for D$_2$ receptor and 5-HT$_3$ receptor, but shows high and selective affinity for 5-HT$_4$ receptors and activate same is expected to make a superior gastrointestinal prokinetic agent.

Accordingly, the present invention aims at providing a compound having high and selective affinity for 5-HT$_4$ receptors and capable of activating same in various tissues, which is useful as a medication for the prophylaxis and treatment of various gastrointestinal diseases (e.g., reflux esophagitis; gastroesophageal reflux such as that accompanying cystic fibrosis; Barrett syndrome; intestinal pseudoileus; acute or chronic gastritis; gastric or duodenal ulcer; Crohn's disease; non-ulcer dyspepsia; ulcerative colitis; postgastrectomy syndrome; postoperative digestive function failure; delayed gastric emptying caused by gastric neurosis, gastroptosis, diabetes, and the like; gastrointestinal disorders such as indigestion, meteorism, abdominal indefinite complaint, and the like; constipation such as atonic constipation, chronic constipation, and that caused by spinal cord injury, pelvic diaphragm failure and the like; and irritable bowel syndrome), central nervous disorders (e.g., schizophrenia, depression, anxiety, disturbance of memory and dementia), cardiac function disorders (e.g., cardiac failure and myocardial ischemia), urinary diseases (e.g., dysuria caused by urinary obstruction, ureterolith, prostatomegaly, spinal cord injury, pelvic diaphragm failure, etc.), and the like, and also useful as an anti-nociceptor for analgesic use which increases threshold of pain.

According to the present invention, there has now been found a new benzoic acid compound, namely, a benzoic acid compound having, at an alkyl moiety bound to nitrogen atom of cyclic amine of the following formulas (II-a)–(II-f) and (III), amide, urea, amino, (thio)ether, (thio)carbonyl, sulfinyl, sulfonyl or a heterocycle having amide or urea bonding in the ring, which shows superior selective activation of 5-HT$_4$ receptors.

SUMMARY OF THE INVENTION

Thus, the present invention provides the following.

(1) Benzoic acid compounds of the formula

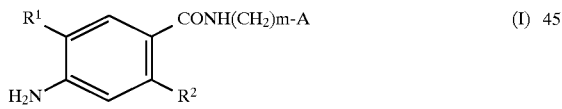 (I)

wherein
R$^1$ is a halogen;
R$^2$ is a lower alkoxy, a substituted lower alkoxy, a cycloalkyloxy or a cycloalkylalkoxy;
m is 1 or 2; and
A is

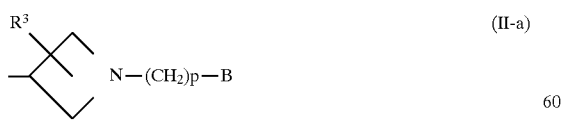 (II-a)

 (II-b)

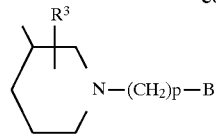 (II-c)

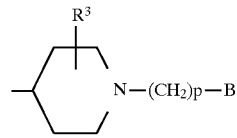 (II-d)

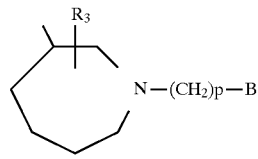 (II-e)

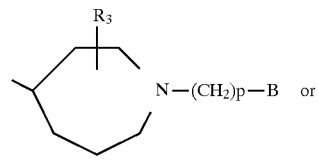 (II-f)

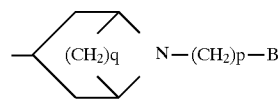 (III)

wherein
R$^3$ is hydrogen, hydroxy, lower alkyl or lower alkoxy, p is an integer of 1–10, q is 2 or 3, and B is a group of the formula

—N(R$^4$)—X$^1$—R$^5$,

—N(R$^4$)—X$^2$—N(R$^6$)(R$^7$)

—X$^1$—N(R$^8$)(R$^9$),

—Het,

—N(R$^{10}$)(R$^{11}$)

—X$^3$—R$^{12}$ or

—X$^4$—R$^{13}$ wherein
X$^1$ is CO, CS or SO$_2$, X$^2$ is CO or CS, R$^4$ is hydrogen, lower alkyl, phenyl, substituted phenyl, aralkyl or substituted aralkyl, R$^5$ is lower alkyl, cycloalkyl, crosslinked cycloalkyl, aryl, substituted aryl, aralkyl, substituted aralkyl, heteroaryl, substituted heteroaryl, heteroarylalkyl, substituted heteroarylalkyl or

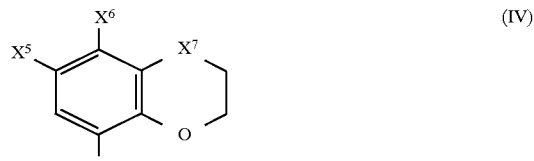 (IV)

wherein
X$^5$ is halogen, X$^6$ is hydrogen or amino, and X$^7$ is a direct bond, methylene, oxygen atom, NH or N—CH$_3$,
R$^6$ and R$^7$ are the same or different and each is hydrogen, lower alkyl, cycloalkyl, aryl, substituted aryl, aralkyl or substituted aralkyl, or $R^6$ and $R^7$ optionally form a ring together with the adjacent nitrogen atom, $R^8$ and $R^9$ are the same or different and each is hydrogen, lower alkyl, cycloalkyl, aryl, substituted aryl, aralkyl or substituted aralkyl or $R^8$ and $R^9$ optionally form a ring together with the adjacent nitrogen atom, Het is a 5- or 6-membered mono- or bicyclic heterocycle having amide or urea in the ring and having 1 to 5 hetero atom(s) selected from the group consisting of oxygen atom, sulfur atom and nitrogen atom, $R^{10}$ and $R^{11}$ are the same or different and each is hydrogen, lower alkyl, cycloalkyl, cycloalkylalkyl, aryl, substituted aryl, aralkyl, substituted aralkyl, heteroaryl, substituted heteroaryl, heteroarylalkyl or substituted heteroarylalkyl, $X^3$ is oxygen atom or sulfur atom, $R^{12}$ is lower alkyl, cycloalkyl, cycloalkylalkyl, aryl, substituted aryl, aralkyl, substituted aralkyl, heteroaryl, substituted heteroaryl, heteroarylalkyl or substituted heteroarylalkyl, $X^4$ is CO, CS, SO or $SO_2$, and $R^{13}$ is hydrogen, lower alkyl, cycloalkyl, cycloalkylalkyl, aryl, substituted aryl, aralkyl, substituted aralkyl, heteroaryl, substituted heteroaryl, heteroarylalkyl or substituted heteroarylalkyl, optical isomers thereof and pharmaceutically acceptable salts thereof.

(2) Benzoic acid compounds of the formula

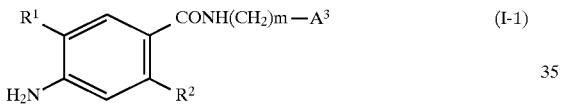  (I-1)

wherein $R^1$ is a halogen;

$R^2$ is a lower alkoxy, a substituted lower alkoxy, a cycloalkyloxy or a cycloalkylalkoxy;

m is 1 or 2; and $A^3$ is

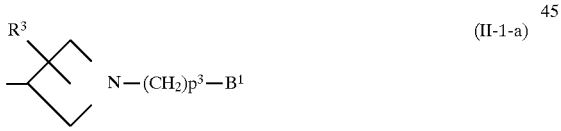  (II-1-a)

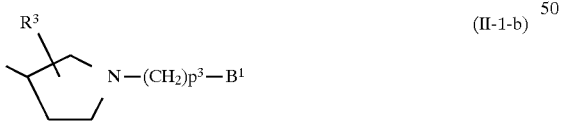  (II-1-b)

  (II-1-c)

  (II-1-d)

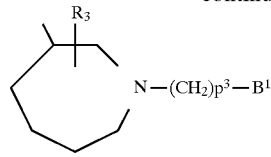  (II-1-e)

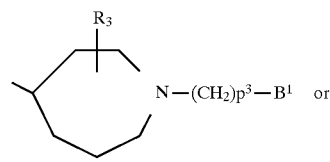  (II-1-f)  or

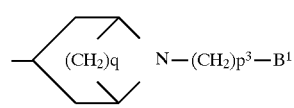  (III-1)

wherein $R^3$ is hydrogen, hydroxy, lower alkyl or lower alkoxy, $p^3$ is an integer of 1–6, q is 2 or 3, and $B^1$ is a group of the formula $-N(R^4)-X^1-R^5$, $-N(R^4)-X^2-N(R^6)(R^7)$ $-X^1-N(R^8)(R^9)$ or $-Het$ wherein $X^1$ is CO, CS or $SO_2$, $X^2$ is CO or CS, $R^4$ is hydrogen, lower alkyl, phenyl, substituted phenyl, aralkyl or substituted aralkyl, $R^5$ is lower alkyl, cycloalkyl, crosslinked cycloalkyl, aryl, substituted aryl, aralkyl, substituted aralkyl, heteroaryl, substituted heteroaryl, heteroarylalkyl, substituted heteroarylalkyl or

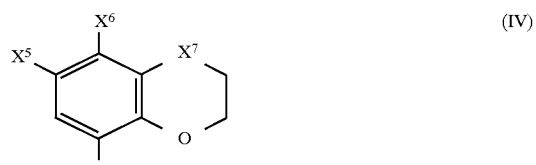  (IV)

wherein $X^5$ is halogen, $X^6$ is hydrogen or amino, and $X^7$ is a direct bond, methylene, oxygen atom, NH or $N-CH_3$, $R^6$ and $R^7$ are the same or different and each is hydrogen, lower alkyl, cycloalkyl, aryl, substituted aryl, aralkyl or substituted aralkyl, or $R^6$ and $R^7$ optionally form a ring together with the adjacent nitrogen atom, $R^8$ and $R^9$ are the same or different and each is hydrogen, lower alkyl, cycloalkyl, aryl, substituted aryl, aralkyl or substituted aralkyl or $R^8$ and $R^9$ optionally form a ring together with the adjacent nitrogen atom, and Het is a 5- or 6-membered mono- or bicyclic heterocycle having amide or urea in the ring and having 1 to 5 hetero atom(s) selected from the group consisting of oxygen atom, sulfur atom and nitrogen atom, optical isomers thereof and pharmaceutically acceptable salts thereof.

(3) Benzoic acid compounds of above (2), which are expressed by the formula

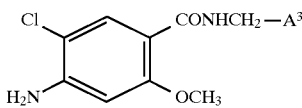
(I'-1)

wherein
$A^3$ is as defined above,
optical isomers thereof and pharmaceutically acceptable salts thereof.

(4) Benzoic acid compounds of above (2), which are expressed by the formula

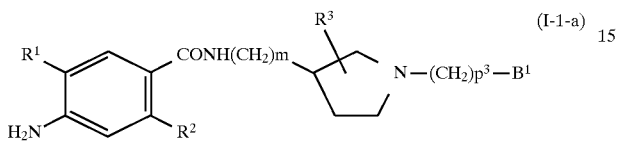
(I-1-a)

wherein
$R^1$, $R^2$, $R^3$, m, $p^3$ and $B^1$ are as defined above,
optical isomers thereof and pharmaceutically acceptable salts thereof.

(5) Benzoic acid compounds of above (2), which are expressed by the formula

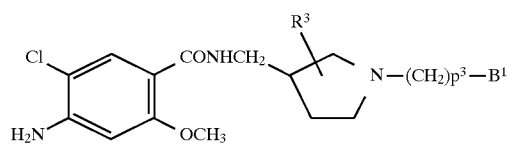
(I'-1-a)

wherein
$R^3$, $p^3$ and $B^1$ are as defined above,
optical isomers thereof and pharmaceutically acceptable salts thereof.

(6) Benzoic acid compounds of above (2), which are expressed by the formula

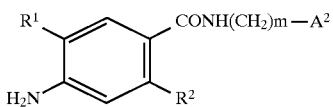
(I-b)

wherein
$R^1$, $R^2$ and m are as defined above, and $A^2$ is

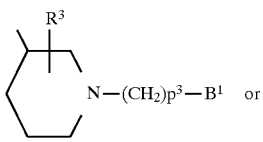
(II-1-c)

or

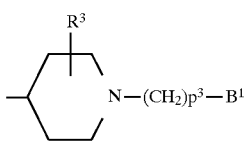
(II-1-d)

wherein
$R^3$, $p^3$ and $B^1$ are as defined above,
optical isomers thereof and pharmaceutically acceptable salts thereof.

(7) Benzoic acid compounds of above (6), which are expressed by the formula

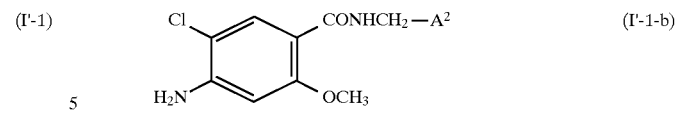
(I'-1-b)

wherein
$A^2$ is as defined above,
optical isomers thereof and pharmaceutically acceptable salts thereof.

(8) Benzoic acid compounds of above (2), wherein $B^1$ is a group of the formula

—N($R^4$)—CO—$R^5$,

—N($R^4$)—CO—N($R^6$)($R^7$),

—CO—N($R^8$)($R^9$) or

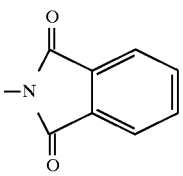

wherein
$R^4$, $R^5$, $R^6$, $R^7$, $R^8$ and $R^9$ are as defined above,
optical isomers thereof and pharmaceutically acceptable salts thereof.

(9) Benzoic acid compounds of above (4), wherein $B^1$ is a group of the formula

—N($R^4$)—CO—$R^5$,

—N($R^4$)—CO—N($R^6$)($R^7$),

—CO—N($R^8$)($R^9$) or

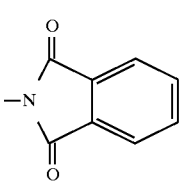

wherein
$R^4$, $R^5$, $R^6$, $R^7$, $R^8$ and $R^9$ are as defined above,
optical isomers thereof and pharmaceutically acceptable salts thereof.

(10) Benzoic acid compounds of above (6), wherein $B^1$ is a group of the formula

—N($R^4$)—CO—$R^5$,

—N($R^4$)—CO—N($R^6$)($R^7$),

—CO—N($R^8$)($R^9$) or

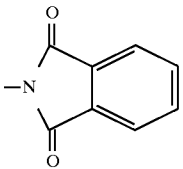

wherein
$R^4$, $R^5$, $R^6$, $R^7$, $R^8$ and $R^9$ are as defined above, optical isomers thereof and pharmaceutically acceptable salts thereof.

(11) Benzoic acid compounds of above (2), wherein $B^1$ is a group of the formula —N(R)—CO—$R^5$ or

—N($R^4$)—CO—N($R^6$)($R^7$)

wherein $R^4$, $R^5$, $R^6$ and $R^7$ are as defined above, optical isomers thereof and pharmaceutically acceptable salts thereof.

(12) Benzoic acid compounds of above (2), wherein $B^1$ is a group of the formula

—NHCOR$^5$ wherein $R^5$ is as defined above, optical isomers thereof and pharmaceutically acceptable salts thereof.

(13) Benzoic acid compounds of above (2), wherein $B^1$ is a group of the formula —NHCONHR$^{6\,a}$ wherein $R^{6\,a}$ is hydrogen, lower alkyl, cycloalkyl, aryl, substituted aryl, aralkyl or substituted aralkyl, optical isomers thereof and pharmaceutically acceptable salts thereof.

(14) Benzoic acid compounds of above (2), wherein $B^1$ is a group of the formula —CONHR$^{8\,a}$ wherein $R^{8\,a}$ is hydrogen, lower alkyl, cycloalkyl, aryl, substituted aryl, aralkyl or substituted aralkyl, optical isomers thereof and pharmaceutically acceptable salts thereof.

(15) Benzoic acid compounds of above (2), wherein $B^1$ is a group of the formula optical isomers thereof and pharmaceutically acceptable salts thereof.

(16) Benzoic acid compounds of above (2), wherein $R^5$ is aryl, substituted aryl, aralkyl, heteroaryl or substituted heteroaryl, optical isomers thereof and pharmaceutically acceptable salts thereof.

(17) Benzoic acid compounds of above (2), wherein $R^6$ is lower alkyl, aryl or substituted aryl, and $R^7$ is hydrogen, optical isomers thereof and pharmaceutically acceptable salts thereof. (18) Benzoic acid compounds of above (2), wherein $R^8$ is aryl or substituted aryl, and $R^9$ is hydrogen, optical isomers thereof and pharmaceutically acceptable salts thereof.

(19) Benzoic acid compounds of above (2), wherein $R^5$ is 1-methyl-3-indolyl, 1-isopropyl-3-indolyl, 1-benzyl-3-indolyl, 1-naphthyl, 2-naphthyl, phenyl, 2-chlorophenyl, 3-chlorophenyl, 4-chlorophenyl, 4-methylphenyl, 4-nitrophenyl, 4-amino-5-chloro-2-methoxyphenyl, 2-thienyl or 3-phenylpropyl, optical isomers thereof and pharmaceutically acceptable salts thereof.

(20) Benzoic acid compounds of above (2), wherein $R^6$ is ethyl, propyl, phenyl or 4-chlorophenyl, optical isomers thereof and pharmaceutically acceptable salts thereof.

(21) Benzoic acid compounds of above (2), wherein $R^8$ is phenyl, optical isomers thereof and pharmaceutically acceptable salts thereof.

(22) Benzoic acid compounds of above (2), wherein $p^3$ is an integer of 3 to 6, optical isomers thereof and pharmaceutically acceptable salts thereof. (23) Benzoic acid compounds of above (2), wherein $p^3$ is an integer of 4 or 5, optical isomers thereof and pharmaceutically acceptable salts thereof.

(24) Benzoic acid compounds of above (2), wherein $R^3$ is hydrogen, $p^3$ is an integer of 2–5, and $B^1$ is a group of the formula —NHCOR$^{5\,a}$, —NHCONHR$^{6\,b}$, —CONHR$^{8\,b}$ or wherein $R^{5\,a}$ is aryl, substituted aryl, aralkyl, heteroaryl or substituted heteroaryl, $R^{6b}$ is lower alkyl, aryl or substituted aryl, and $R^{8\,b}$ is aryl or substituted aryl, optical isomers thereof and pharmaceutically acceptable salts thereof.

(25) Benzoic acid compounds of above (2), which are selected from 4-amino-N-((3R)-1-(3-benzoylaminopropyl)pyrrolidin-3-ylmethyl)-5-chloro-2-methoxybenzamide, 4-amino-5-chloro-2-methoxy-N-((3R)-1-(4-(1-naphthoylamino)butyl)-pyrrolidin-3-ylmethyl)benzamide, 4-amino-N-((3R)-1-(5-benzoylaminopentyl)pyrrolidin-3-ylmethyl)-5-chloro-2-methoxybenzamide, 4-amino-N-((3R)-1-(5-(4-amino-5-chloro-2-methoxybenzoylamino)-pentyl)pyrrolidin-3-ylmethyl)-5-chloro-2-methoxybenzamide, N-(4-((3R)-3-(4-amino-5-chloro-2-methoxybenzoylaminomethyl)-pyrrolidin-1-yl)butyl)-1-methyl-1 H-indole-3-carboxamide, N-(5-((3R)-3-(4-amino-5-chloro-2-methoxybenzoylaminomethyl)-pyrrolidin-1-yl)pentyl)-1-methyl-1 H-indole-3-carboxamide, N-(4-((3R)-3-(4-amino-5-chloro-2-methoxybenzoylaminomethyl)-pyrrolidin-1-yl)butyl)-1-isopropyl-1 H-indole-3-carboxamide, N-(4-((3R)-3-(4-amino-5-chloro-2-methoxybenzoylaminomethyl)-pyrrolidin-1-yl)butyl)-1-benzyl-1 H-indole-3-carboxamide, 4-amino-5-chloro-2-methoxy-N-((3R)-1-(4-(2-naphthoylamino)butyl)-pyrrolidin-3-ylmethyl)benzamide, 4-amino-5-chloro-N-((3R)-1-(5-(4-chlorobenzoylamino)
  pentyl)-pyrrolidin-3-ylmethyl)-2-methoxybenzamide,
4-amino-5-chloro-N-(1-(3-(3-chlorobenzoylamino)propyl)
  pyrrolidin-3-ylmethyl)-2-methoxybenzamide,
4-amino-5-chloro-N-(1-(3-(2-chlorobenzoylamino)propyl)
  pyrrolidin-3-ylmethyl)-2-methoxybenzamide,
4-amino-5-chloro-2-methoxy-N-(1-(3-(4-nitrobenzoylamino)propyl)-pyrrolidin-3-ylmethyl)
  benzamide,
4-amino-5-chloro-2-methoxy-N-((3R)-1-(2-(4-phenylbutyrylamino)-ethyl)pyrrolidin-3-ylmethyl)
  benzamide,
4-amino-5-chloro-N-(1-(3-(4-chlorobenzoylamino)propyl)
  pyrrolidin-3-ylmethyl)-2-methoxybenzamide,
4-amino-5-chloro-2-methoxy-N-(1-(3-(4-methylbenzoylamino)propyl)-pyrrolidin-3-ylmethyl)
  benzamide and
4-amino-5-chloro-2-methoxy-N-(1-(3-(2-thiophenecarbonylamino)-propyl)pyrrolidin-3-ylmethyl)
  benzamide,
optical isomers thereof and pharmaceutically acceptable
salts thereof.

(26) Benzoic acid compounds of above (2), which are selected from
4-amino-5-chloro-2-methoxy-N-((3R)-1-(5-(3-n-propylureido)pentyl)-pyrrolidin-3-ylmethyl)benzamide,
4-amino-5-chloro-2-methoxy-N-((3R)-1-(5-(3-phenylureido)pentyl)-pyrrolidin-3-ylmethyl)benzamide
  and
4-amino-5-chloro-N-((3R)-1-(5-(3-ethylureido)pentyl)
  pyrrolidin-3-ylmethyl)-2-methoxybenzamide,
optical isomers thereof and pharmaceutically acceptable salts thereof.

(27) Benzoic acid compounds of above (2), which are 4-amino-5-chloro-2-methoxy-N-(1-(3-phenylcarbamoylpropyl)pyrrolidin-3-ylmethyl)benzamide,
optical isomers thereof and pharmaceutically acceptable salts thereof.

(28) Benzoic acid compounds of above (2), which are 4-amino-5-chloro-N-(1-(5-(2,3-dihydro-1,3-dioxo-1H-isoindol-2-yl)pentyl)pyrrolidin-3-yl-methyl)-2-methoxybenzamide,
optical isomers thereof and pharmaceutically acceptable salts thereof.

(29) Benzoic acid compounds of above (6), wherein $A^2$ is a group of the formula

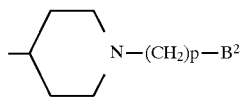

wherein
$p^2$ is 4 or 5, and $B^2$ is a group of the formula

—NHCOR$^{5a}$ or

—NHCONR$^{6b}$ wherein
$R^5a$ is aryl, substituted aryl, heteroaryl or substituted heteroaryl, and $R^6b$ is lower alkyl, aryl or substituted aryl, and pharmaceutically acceptable salts thereof.

(30) Benzoic acid compounds of above (2), which are selected from
N-(4-(4-(4-amino-5-chloro-2-methoxybenzoylaminomethyl)piperidin-1-yl)butyl)-1-methyl-1H-indole-3-carboxamide,
4-amino-5-chloro-2-methoxy-N-(1-(4-(1-naphthoylamino)butyl)-piperidin-4-ylmethyl)benzamide,
4-amino-5-chloro-2-methoxy-N-(1-(4-(2-naphthoylamino)butyl)-piperidin-4-ylmethyl)benzamide,
4-amino-N-(1-(5-benzoylaminopentyl)piperidin-4-ylmethyl)-5-chloro-2-methoxybenzamide,
4-amino-5-chloro-N-(1-(5-(3-chlorobenzoylamino)pentyl)piperidin-4-ylmethyl)-2-methoxybenzamide,
4-amino-5-chloro-N-(1-(5-(4-methylbenzoylamino)pentyl)piperidin-4-ylmethyl)-2-methoxybenzamide and
N-(5-(4-(4-amino-5-chloro-2-methoxybenzoylaminomethyl)piperidin-1-yl)pentyl)-1-methyl-1H-indole-3-carboxamide,
and pharmaceutically acceptable salts thereof.

(31) Benzoic acid compounds of above (2), which are selected from
4-amino-5-chloro-2-methoxy-N-(1-(4-(3-n-propylureido)butyl)-piperidin-4-ylmethyl)benzamide,
4-amino-5-chloro-2-methoxy-N-(1-(5-(3-n-propylureido)pentyl)-piperidin-4-ylmethyl)benzamide, and
4-amino-5-chloro-N-(1-(5-(3-(4-chlorophenyl)ureido)pentyl)piperidin-4-ylmethyl)-2-methoxybenzamide,
and pharmaceutically acceptable salts thereof.

(32) Benzoic acid compounds of the formula

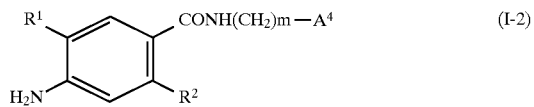

wherein $R^1$ is a halogen;

$R^2$ is a lower alkoxy, a substituted lower alkoxy, a cycloalkyloxy or a cycloalkylalkoxy;

m is 1 or 2; and $A^4$ is

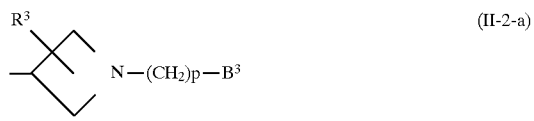 (II-2-a)

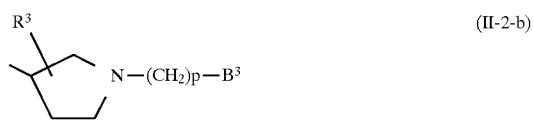 (II-2-b)

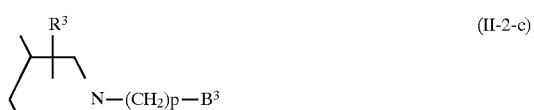 (II-2-c)

 (II-2-d)

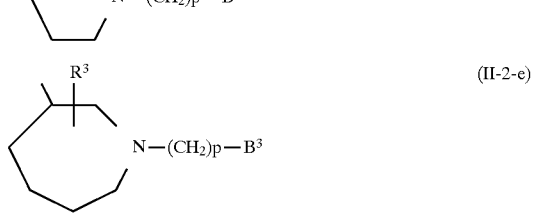 (II-2-e)

-continued

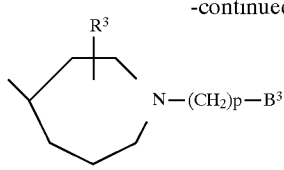
(II-2-f)

or

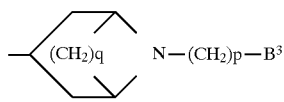
(III-2)

wherein
$R^3$ is hydrogen, hydroxy, lower alkyl or lower alkoxy, p is an integer of 1–10, q is 2 or 3, and $B^3$ is a group of the formula

—$N(R^{10})(R^{11})$,

—$X^3$—$R^{12}$ or

—$X^4$—$R^{13}$ wherein
$R^{10}$ and $R^{11}$ are the same or different and each is hydrogen, lower alkyl, cycloalkyl, cycloalkylalkyl, aryl, substituted aryl, aralkyl, substituted aralkyl, heteroaryl, substituted heteroaryl, heteroarylalkyl or substituted heteroarylalkyl, $X^3$ is oxygen atom or sulfur atom, $R^{12}$ is lower alkyl, cycloalkyl, cycloalkylalkyl, aryl, substituted aryl, aralkyl, substituted aralkyl, heteroaryl, substituted heteroaryl, heteroarylalkyl or substituted heteroarylalkyl, $X^4$ is CO, CS, SO or $SO_2$, and $R^{13}$ is hydrogen, lower alkyl, cycloalkyl, cycloalkylalkyl, aryl, substituted aryl, aralkyl, substituted aralkyl, heteroaryl, substituted heteroaryl, heteroarylalkyl or substituted heteroarylalkyl, optical isomers thereof and pharmaceutically acceptable salts thereof.

(33) Benzoic acid compounds of the formula

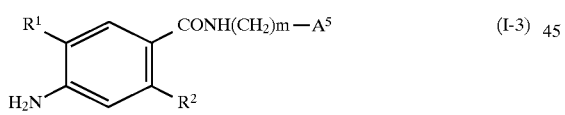
(I-3)

wherein
$R^1$ is a halogen;
$R^2$ is a lower alkoxy, a substituted lower alkoxy, a cycloalkyloxy or a cycloalkylalkoxy;
m is 1 or 2; and
$A^5$ is

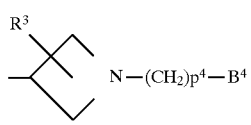
(II-3-a)

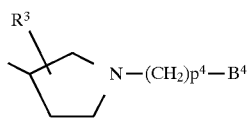
(II-3-b)

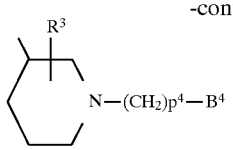
(II-3-c)

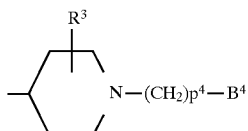
(II-3-d)

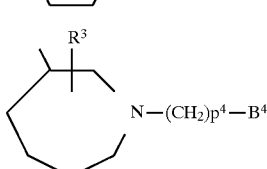
(II-3-e)

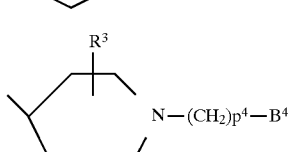
(II-3-f)

or

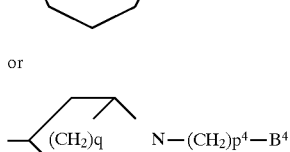
(III-3)

wherein
$R^3$ is hydrogen, hydroxy, lower alkyl or lower alkoxy, $p^4$ is an integer of 1–8, q is 2 or 3, and $B^4$ is a group of the formula —$N(R^{10})(R^{11})$ or

—$X^3$—$R^{12}$ wherein
$R^{10}$ and $R^{11}$ are the same or different and each is hydrogen, lower alkyl, cycloalkyl, cycloalkylalkyl, aryl, substituted aryl, aralkyl, substituted aralkyl, heteroaryl, substituted heteroaryl, heteroarylalkyl or substituted heteroarylalkyl, $X^3$ is oxygen atom or sulfur atom, and $R^{12}$ is lower alkyl, cycloalkyl, cycloalkylalkyl, aryl, substituted aryl, aralkyl, substituted aralkyl, heteroaryl, substituted heteroaryl, heteroarylalkyl or substituted heteroarylalkyl, optical isomers thereof and pharmaceutically acceptable salts thereof.

(34) Benzoic acid compounds of above (33), which are expressed by the formula

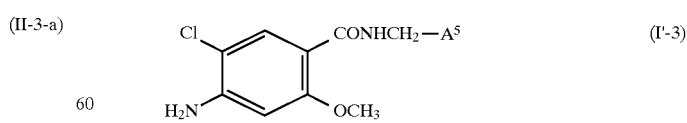
(I'-3)

wherein
$A^5$ is as defined above,
optical isomers thereof and pharmaceutically acceptable salts thereof.

(35) Benzoic acid compounds of above (33), which are expressed by the formula

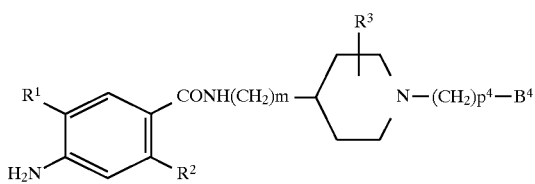

wherein
R¹, R², R³, m, p⁴ and B⁴ are as defined above,
and pharmaceutically acceptable salts thereof.

(36) Benzoic acid compounds of above (33), which are expressed by the formula

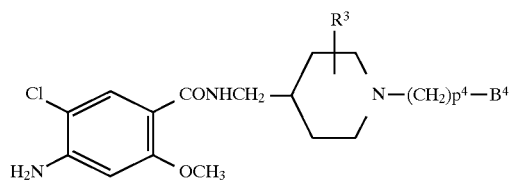

wherein
R³, p⁴ and B⁴ are as defined above,
and pharmaceutically acceptable salts thereof.

(37) Benzoic acid compounds of above (33), wherein $R^{10}$ and $R^{11}$ are the same or different and each is hydrogen, lower alkyl, cycloalkylalkyl, aralkyl, substituted aralkyl, heteroarylalkyl or substituted heteroarylalkyl,
optical isomers thereof and pharmaceutically acceptable salts thereof.

(38) Benzoic acid compounds of above (33), wherein $R^{12}$ is aryl, substituted aryl, aralkyl or substituted aralkyl,
optical isomers thereof and pharmaceutically acceptable salts thereof.

(39) Benzoic acid compounds of above (33), wherein $p^4$ is an integer of 3 to 8,
optical isomers thereof and pharmaceutically acceptable salts thereof.

(40) Benzoic acid compounds of above (33), wherein $p^4$ is an integer of 4 to 6,
optical isomers thereof and pharmaceutically acceptable salts thereof.

(41) Benzoic acid compounds of above (33), which are selected from
4-amino-5-chloro-N-((1-(6-(N-ethyl-N-benzylamino)hexyl) piperidin-4-yl)methyl)-2-methoxybenzamide,
4-amino-5-chloro-N-((1-(5-(N-benzylamino)pentyl) piperidin-4-yl)-methyl)-2-methoxybenzamide,
4-amino-5-chloro-2-methoxy-N-((1-(5-(1-naphthylmethylamino)pentyl)-piperidin-4-yl)methyl) benzamide,
4-amino-5-chloro-N-((1-(5-(N-ethyl-N-(4-fluorobenzyl) amino)pentyl)-piperidin-4-yl)methyl)-2-methoxybenzamide,
4-amino-5-chloro-2-methoxy-N-((1-(5-(N-n-propyl-N-benzylamino)-pentyl)piperidin-4-yl)methyl)benzamide,
4-amino-5-chloro-N-((1-(5-(cyclohexylmethylamino) pentyl)piperidin-4-yl)methyl)-2-methoxybenzamide,
4-amino-5-chloro-N-((1-(4-(N-(3,4-dichlorobenzyl)-N-ethylamino)-butyl)piperidin-4-yl)methyl)-2-methoxybenzamide,
4-amino-5-chloro-N-((1-(6-(3,4-dichlorobenzylamino) hexyl)piperidin-4-yl)methyl)-2-methoxybenzamide,
4-amino-5-chloro-N-((1-(6-(N-ethyl-N-(4-methylbenzyl) amino)hexyl)-piperidin-4-yl)methyl)-2-methoxybenzamide,
4-amino-5-chloro-N-((1-(6-(N-ethyl-N-(4-nitrobenzyl) amino)hexyl)-piperidin-4-yl)methyl)-2-methoxybenzamide,
4-amino-5-chloro-2-methoxy-N-((1-(5-(4-methylbenzylamino)pentyl)-piperidin-4-yl)methyl) benzamide,
4-amino-5-chloro-N-((1-(6-(N-ethyl-N-(2-thienylmethyl) amino)hexyl)-piperidin-4-yl)methyl)-2-methoxybenzamide,
4-amino-5-chloro-2-methoxy-N-((1-(5-(2-naphthylmethylamino)pentyl)-piperidin-4-yl)methyl) benzamide,
4-amino-5-chloro-2-methoxy-N-((1-(6-(4-methoxybenzylamino)hexyl)-piperidin-4-yl)methyl) benzamide and
4-amino-5-chloro-2-methoxy-N-((1-(6-(2-thienylmethylamino)hexyl)-piperidin-4-yl)methyl) benzamide, and pharmaceutically acceptable salts thereof.

(42) Benzoic acid compounds of above (33), which are selected from
4-amino-N-((1-(5-benzylthiopentyl)piperidin-4-yl)methyl)-5-chloro-2-methoxybenzamide,
4-amino-N-((1-(5-benzyloxypentyl)piperidin-4-yl)methyl)-5-chloro-2-methoxybenzamide,
4-amino-5-chloro-2-methoxy-N-((1-(5-phenoxypentyl) piperidin-4-yl)-methyl)benzamide,
4-amino-5-chloro-2-methoxy-N-((1-(5-phenylthiopentyl) piperidin-4-yl)-methyl)benzamide,
4-amino-5-chloro-N-((1-(5-(4-chlorobenzyloxy)pentyl) piperidin-4-yl)-methyl)-2-methoxybenzamide,
4-amino-5-chloro-2-methoxy-N-((1-(4-phenoxybutyl) piperidin-4-yl)-methyl)benzamide and
4-amino-N-((1-(6-benzyloxyhexyl)piperidin-4-yl)methyl)-5-chloro-2-methoxybenzamide, and pharmaceutically acceptable salts thereof.

(43) Benzoic acid compounds of the formula

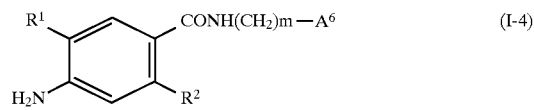

wherein
$R^1$ is a halogen;
$R^2$ is a lower alkoxy, a substituted lower alkoxy, a cycloalkyloxy or a cycloalkylalkoxy;
m is 1 or 2; and
$A^6$ is

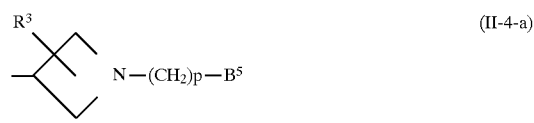

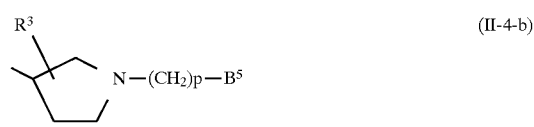

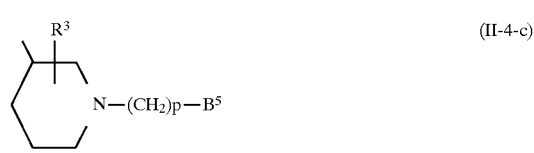

-continued

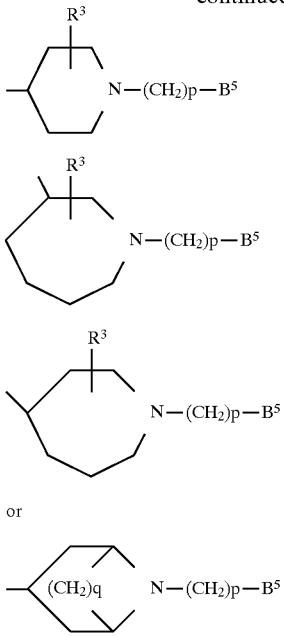

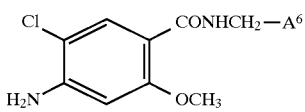

wherein
R³ is hydrogen, hydroxy, lower alkyl or lower alkoxy,
p is an integer of 1–10, q is 2 or 3, and B⁵ is a group of the formula $$-X^4-R^{13}$$

wherein
X⁴ is CO, CS, SO or SO₂, and R¹³ is hydrogen, lower alkyl, cycloalkyl, cycloalkylalkyl, aryl, substituted aryl, aralkyl, substituted aralkyl, heteroaryl, substituted heteroaryl, heteroarylalkyl or substituted heteroarylalkyl,
optical isomers thereof and pharmaceutically acceptable salts thereof.

(44) Benzoic acid compounds of above (43), which are expressed by the formula

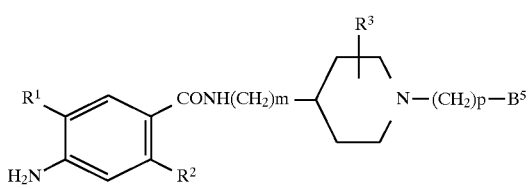

wherein
A⁶ is as defined above,
optical isomers thereof and pharmaceutically acceptable salts thereof.

(45) Benzoic acid compounds of above (43), which are expressed by the formula

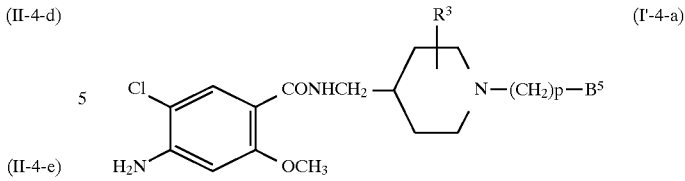

wherein
R¹, R², R³, m, p and B⁵ are as defined above,
and pharmaceutically acceptable salts thereof.

(46) Benzoic acid compounds of above (43), which are expressed by the formula

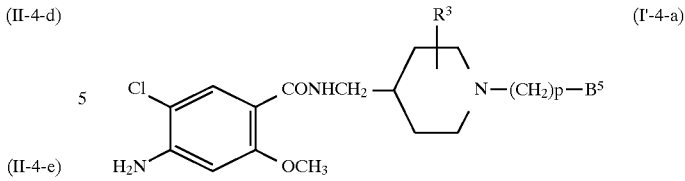

wherein
R³, p and B⁵ are as defined above,
and pharmaceutically acceptable salts thereof.

(47) Benzoic acid compounds of above (43), wherein X⁴ is CO and R¹³ is aryl, substituted aryl, heteroaryl or substituted heteroaryl,
optical isomers thereof and pharmaceutically acceptable salts thereof.

(48) Benzoic acid compounds of above (43), wherein X⁴ is SO₂ and R¹³ is aryl, substituted aryl, aralkyl or substituted aralkyl,
optical isomers thereof and pharmaceutically acceptable salts thereof.

(49) Benzoic acid compounds of above (43), wherein p is an integer of 3 to 8,
optical isomers thereof and pharmaceutically acceptable salts thereof.

(50) Benzoic acid compounds of above (43), wherein p is an integer of 4 to 6,
optical isomers thereof and pharmaceutically acceptable salts thereof.

(51) Benzoic acid compounds of above (43), which are selected from
4-amino-5-chloro-2-methoxy-N-((1-(6-oxo-6-phenylhexyl) piperidin-4-yl)methyl)benzamide,
4-amino-5-chloro-2-methoxy-N-((1-(7-oxo-7-phenylheptyl) piperidin-4-yl)methyl)benzamide,
4-amino-5-chloro-2-methoxy-N-((1-(6-(1-isopropyl-1 H-indol-3-yl)-6-oxohexyl)piperidin-4-yl)methyl) benzamide,
4-amino-5-chloro-2-methoxy-N-((1-(6-(1-ethyl-1 H-indol-3-yl)-6-oxohexyl)piperidin-4-yl)methyl)benzamide,
4-amino-5-chloro-2-methoxy-N-((1-(6-(1-naphthyl)-6-oxohexyl)-piperidin-4-yl)methyl)benzamide,
4-amino-5-chloro-N-((1-(6-(3-fluoro-4-methoxyphenyl)-6-oxohexyl)-piperidin-4-yl)methyl)-2-methoxybenzamide,
4-amino-5-chloro-N-((1-(6-(3-chloro-4-methoxyphenyl)-6-oxohexyl)- piperidin- 4-yl)methyl)-2-methoxybenzamide,
4-amino-5-chloro-N-((1-(6-(3,4-dimethoxyphenyl)-6-oxohexyl)piperidin-4-yl)methyl)-2-methoxybenzamide,
4-amino-5-chloro-N-((1-(6-(4-hydroxyphenyl)-6-oxohexyl) piperidin-4-yl)methyl)-2-methoxybenzamide,
4-amino-5-chloro-2-methoxy-N-((1-(6-(1-methyl-1 H-indol-3-yl)-6-oxohexyl)piperidin-4-yl)methyl) benzamide,
4-amino-5-chloro-2-methoxy-N-((1-(5-(1-methyl-1 H-indol-3-yl)-5-oxopentyl)piperidin-4-yl)methyl) benzamide,
4-amino-5-chloro-2-methoxy-N-((1-(7-(1-methyl-1 H-indol-3-yl)-7-oxoheptyl)piperidin-⁴-yl)methyl) benzamide,
4-amino-5-chloro-2-methoxy-N-((1-(5-oxo-5-phenylpentyl) piperidin-4-yl)methyl)benzamide and
4-amino-5-chloro-2-methoxy-N-((1-(6-(1 H-indol-3-yl)-6-oxohexyl)-piperidin-4-yl)methyl)benzamide,
and pharmaceutically acceptable salts thereof.

(52) Benzoic acid compounds of above (43), which are selected from 4-amino-5-chloro-2-methoxy-N-((1-(4-phenylsulfonylbutyl)piperidin-4-yl)methyl)benzamide and 4-amino-5-chloro-2-methoxy-N-((1-(5-phenylsulfonylpentyl)piperidin-4-yl)methyl)benzamide, and pharmaceutically acceptable salts thereof.

(53) Benzoic acid compounds of above (43), which is 4-amino-5-chloro-2-methoxy-N-((1-(3-benzylsulfonylpropyl)piperidin-4-yl)methyl)-benzamide and pharmaceutically acceptable salts thereof.

(54) Pharmaceutical compositions comprising benzoic acid compounds of any one of (1)-(53) or optical isomers thereof or pharmaceutically acceptable salts thereof, and a pharmaceutically acceptable additives.

(55) Serotonin 4 receptor agonistic method comprising administering benzoic acid compounds of any one of (1)-(53) or optical isomers thereof or pharmaceutically acceptable salts thereof as active ingredients to the patients in need of treatment.

(56) Gastrointestinal prokinetic method comprising administering benzoic acid compounds of any one of (1)-(53) or optical isomers thereof or pharmaceutically acceptable salts thereof as active ingredients to the patients in need of treatment.

(57) Method of treatment for various gastrointestinal diseases selected from the group consisting of reflux esophagitis; gastroesophageal reflux such as that accompanying cystic fibrosis; Barrett syndrome; intestinal pseudoileus; acute or chronic gastritis; gastric or duodenal ulcer; Crohn's disease; non-ulcer dyspepsia; ulcerative colitis; postgastrectomy syndrome; postoperative digestive function failure; delayed gastric emptying caused by gastric neurosis, gastroptosis, diabetes, and the like; gastrointestinal disorders such as indigestion, meteorism, abdominal indefinite complaint, and the like; constipation such as atonic constipation, chronic constipation, and that caused by spinal cord injury, pelvic diaphragm failure and the like; and irritable bowel syndrome, which comprises administering benzoic acid compounds of any one of (1)-(53) or optical isomers thereof or pharmaceutically acceptable salts thereof as active ingredients to the patients in need of treatment.

The compound of the present invention is characterized by substitution of amide, urea, amino, (thio)ether, (thio)carbonyl, sulfinyl, sulfonyl or heterocycle having amide or urea bonding in the ring, at the alkyl moiety bound to nitrogen atom of cyclic amine of the formulas (II-a)–(II-f) and (III), and, with regard to the cyclic amine of the formulas (II-a)–(II-f), bonding between the bonding site of the formula (I), namely, —CONH(CH$_2$)$_m$— and carbon atom other than that adjacent to the intercyclic nitrogen atom. Such characteristic chemical structure leads to 5-HT$_4$ receptor activation with much superior selectivity by the compound of the present invention. Naturally, the above-mentioned amide includes thioamide, sulfonamide, carbamoyl and sulfamoyl, and urea includes thiourea.

The compound of the present invention having (thio)carbonyl, sulfinyl or sulfonyl substituted at the alkyl moiety bound to nitrogen atom of cyclic amine of the formulas (II-a)–(II-f) and (III) shows the aforementioned 5-HT$_4$ receptor activation with superior selectivity and superior absorption by oral administration. In the present invention, "selectivity" means low affinity for D$_2$ receptors and 5-HT$_3$ receptors and high affinity for 5-HT$_4$ receptors.

Of the above-mentioned symbols, halogen at R$^1$ is exemplified by, for example, fluorine, chlorine, bromine and iodine, with particular preference given to chlorine.

Lower alkoxy at R$^2$ is a linear or branched alkoxy having 1 to 4 carbon atoms, and exemplified by, for example, methoxy, ethoxy, propoxy, isopropoxy, butoxy, isobutoxy and tert-butoxy, with particular preference given to methoxy.

Substituted lower alkoxy at R$^2$ is substituted by, for example, fluorine, alkoxy (e.g., methoxy, ethoxy and isopropoxy), acyl (e.g., acetyl and propionyl) and cyano. Specific examples of substituted lower alkoxy include, for example, fluoromethoxy, 2-fluoroethoxy, 3-fluoropropoxy, methoxymethoxy, ethoxymethoxy, 2-methoxyethoxy, 2-ethoxyethoxy, 3-methoxypropoxy, 3-ethoxypropoxy, 2-oxopropoxy, 2-oxobutoxy, 3-oxobutoxy, 3-oxopentyloxy, 4-oxopentyloxy, 4-oxohexyloxy, cyanomethoxy, 2-cyanoethoxy and 3-cyanopropoxy.

Cycloalkyloxy at R$^2$ is exemplified by cyclopropyloxy, cyclobutyloxy, cyclopentyloxy, cyclohexyloxy and the like.

Cycloalkylalkoxy at R$^2$ is exemplified by cyclopropylmethoxy, 1-cyclopropylethoxy, 2-cyclopropylethoxy, cyclobutylmethoxy, cyclopentylmethoxy, cyclohexylmethoxy and the like, with particular preference given to cyclopropylmethoxy.

Lower alkyl at R$^3$ is a linear or branched alkyl having 1 to 6 carbon atoms, and exemplified by, for example, methyl, ethyl, propyl, isopropyl, butyl, isobutyl, tert-butyl, pentyl and hexyl.

Lower alkoxy at R$^3$ is the same as that at R$^2$, with preference given to methoxy.

Lower alkyl at R$^4$ is the same as that at R$^3$, with preference given to methyl.

Examples of substituents for substituted phenyl at R$^4$ are, for example, halogen (e.g., fluorine, chlorine and bromine), lower alkyl having 1 to 4 carbon atoms such as methyl, ethyl, propyl, isopropyl, butyl, isobutyl and tert-butyl, lower alkoxy having 1 to 4 carbon atoms such as methoxy, ethoxy, propoxy, isopropoxy, butoxy, isobutoxy and tert-butoxy, aralkyl such as benzyl, hydroxy, nitro and amino.

Aralkyl at R$^4$ is linear or branched alkyl having 1 to 4 carbon atoms (e.g., methyl, ethyl, propyl, isopropyl, butyl, isobutyl and tert-butyl) which has been substituted by phenyl, and is exemplified by, for example, benzyl, 2-phenylethyl, 3-phenylpropyl and 4-phenylbutyl.

Substituents for substituted aralkyl at R$^4$ are the same as those for substituted phenyl at R$^4$.

Lower alkyl at R$^5$ is the same as lower alkyl at R$^3$, and particularly preferred is methyl.

Cycloalkyl at R$^5$ is that having 3 to 6 carbon atoms, such as cyclopropyl, cyclobutyl, cyclopentyl, cyclohexyl and the like, with particular preference given to cyclohexyl.

Crosslinked cycloalkyl at R$^5$ is exemplified by adamantyl, noradamantyl and the like, with preference given to adamantyl.

Aryl at R$^5$ and R$^{5\,a}$ includes, for example, phenyl, 1-naphthyl and 2-naphthyl.

Substituents for substituted aryl at R$^5$ and R$^{5\,a}$ are the same as those for substituted phenyl at R$^4$. Preferred are halogen, lower alkyl, lower alkoxy, amino and nitro, and particularly preferred are chlorine, methyl, methoxy, amino and nitro. Specific examples of substituted aryl include 4-chlorophenyl, 3-chlorophenyl, 2-chlorophenyl, 4-methylphenyl, 4-methoxyphenyl, 4-amino-5-chloro-2-methoxyphenyl, 4-nitrophenyl and the like, and preferred are 4-chlorophenyl, 3-chlorophenyl, 2-chlorophenyl, 4-amino-5-chloro-2-methoxyphenyl, 4-methylphenyl and 4-nitrophenyl.

Aralkyl at R$^5$ and R$^{5\,a}$ is the same as that at R$^4$, and preferred is 3-phenylpropyl.

Substituents for substituted aralkyl at R$^5$ are the same as those for substituted phenyl at R$^4$.

Heteroaryl at $R^5$ and $R^{5\,a}$ is exemplified by, for example, pyrrolyl, pyridyl, indolyl, indazolyl, thienyl, furyl, benzofuranyl, thionaphthenyl and the like, with preference given to 4-pyridyl, 2-thienyl, 2-indolyl and 3-indolyl.

Substituents for substituted heteroaryl at $R^5$ and $R^{5\,a}$ are the same as those for substituted phenyl at $R^4$. Preferred are lower alkyl and aralkyl. Specific examples of substituted heteroaryl include 1-methyl-3-indolyl, 1-ethyl-3-indolyl, 1-propyl-3-indolyl, 1-isopropyl-3-indolyl, 1-butyl-3-indolyl, 1-benzyl-3-indolyl, 1-(2-phenylethyl)-3-indolyl, 1-(3-phenylpropyl)-3-indolyl, 1-(4-phenylbutyl)-3-indolyl, 1-methyl-3-indazolyl and the like. Preferred are 1-methyl-3-indolyl, 1-isopropyl-3-indolyl, 1-benzyl-3-indolyl and 1-methyl-3-indazolyl.

Heteroarylalkyl at $R^5$ is linear or branched alkyl having 1 to 4 carbon atoms (e.g., methyl, ethyl, propyl, isopropyl, butyl, isobutyl, tert-butyl and the like) which has been substituted by heteroaryl at $R^5$ and $R^{5\,a}$, and examples of heteroarylalkyl include 2-thienylmethyl, 3-thienylmethyl, 2-(2-thienyl)ethyl, 3-(2-thienyl)-propyl, 2-(2-furyl)ethyl, 2-(3-furyl)ethyl, 2-pyridylmethyl, 3-pyridylmethyl, 4-pyridylmethyl, 3-indolylmethyl, 2-(3-indolyl)ethyl, 3-(3-indolyl)propyl and the like.

Substituted heteroarylalkyl at $R^5$ has, as substituent, lower alkyl (e.g., methyl, ethyl, propyl, isopropyl, butyl and the like), aralkyl (e.g., benzyl and the like), and the like, and is specifically (1-methyl-3-indolyl)methyl, (1-isopropyl-3-indolyl)methyl, (1-benzyl-3-indolyl)methyl, 2-(1-methyl-3-indolyl)ethyl, 3-(1-methyl-3-indolyl)propyl and the like.

Halogen at $X^3$ is the same as that at $R^1$, with particular preference given to chlorine. Examples of preferable group of the formula (IV) include 6-chloro-4-methyl-3,4-dihydro-2 H-1,4-benzoxazin-8-yl and the like.

Lower alkyl at $R^6$, $R^{6\,a}$, $R^{6\,b}$ and $R^7$ is the same as that at $R^3$, with preference given to methyl, ethyl, propyl, isopropyl and n-butyl, and particular preference given to ethyl and propyl.

Cycloalkyl at $R^6$, $R^{6\,a}$ and $R^7$ is the same as that at $R^5$.

Aryl at $R^6$, $R^{6\,a}$, $R^{6\,b}$ and $R^7$ is phenyl, 1-naphthyl or 2-naphthyl, with preference given to phenyl.

Substituents for substituted aryl at $R^6$, $R^{6\,a}$, $R^{6\,b}$ and $R^7$ are the same as those for substituted phenyl at $R^4$. Preferred is halogen, particularly chlorine. Specific examples of substituted aryl include, for example, 2-chlorophenyl, 3-chlorophenyl, 4-chlorophenyl, 2-bromophenyl, 3-bromophenyl, 4-bromophenyl, 2-fluorophenyl, 3-fluorophenyl and 4-fluorophenyl, with particular preference given to 4-chlorophenyl.

Aralkyl at $R^6$, $R^{6\,a}$ and $R^7$ is the same as that at $R^4$.

Substituents for substituted aralkyl at $R^6$, $R^{6\,a}$ and $R^7$ are the same as those for substituted phenyl at $R^4$.

The ring formed by $R^6$ and $R^7$ together with the adjacent nitrogen atom may have, in the ring, hetero atom such as sulfur atom, oxygen atom and nitrogen atom. Further, it may have, in the ring, lower alkyl such as methyl and ethyl or lower alkoxy such as methoxy and ethoxy. Specific examples of the ring include pyrrolidine, piperidine, morpholine, thiomorpholine, N-methylpiperazine and the like, with particular preference given to morpholine.

Lower alkyl at $R^8$, $R^{8\,a}$ and $R^9$ is the same as that at $R^3$.

Cycloalkyl at $R^8$, $R^{8\,a}$ and $R^9$ is the same as that at $R^5$.

Aryl at $R^8$, $R^{8\,a}$, $R^{8\,b}$ and $R^9$ is the same as that at $R^6$ and $R^7$, with preference given to phenyl.

Substituents for substituted aryl at $R^8$, $R^{8\,a}$, $R^{8\,b}$ and $R^9$ are the same as those for substituted phenyl at $R^4$. Examples of preferable substituents include, for example, halogen and lower alkyl, particularly chlorine and methyl. Specific examples of substituted aryl include 2-chlorophenyl, 3-chlorophenyl, 4-chlorophenyl, 2-bromophenyl, 3-bromophenyl, 4-bromophenyl, 2-fluorophenyl, 3-fluorophenyl, 4-fluorophenyl, 2-methylphenyl, 3-methylphenyl and 4-methylphenyl, with particular preference given to 3-chlorophenyl and 4-methylphenyl.

Aralkyl at $R^8$, $R^{8\,a}$ and $R^9$ is the same as that at $R^4$.

Substituents for substituted aralkyl at $R^8$, $R^{8\,a}$ and $R^9$ are the same as those for substituted phenyl at $R^4$.

The ring formed by $R^8$ and $R^9$ together with the adjacent nitrogen atom may have, in the ring, hetero atom such as sulfur atom, oxygen atom and nitrogen atom. Further, it may have, in the ring, lower alkyl such as methyl and ethyl or lower alkoxy such as methoxy and ethoxy. Specific examples of the ring include pyrrolidine, piperidine, morpholine, thiomorpholine and N-methylpiperazine.

Het at B in the case of monocyclic heterocycle can be expressed by the following formulas

(V-a)

(V-b)

(V-c)

(V-d)

(V-e)

wherein $Y^1$ is oxygen atom or sulfur atom, $Z^1$ is

—(CH$_2$)$_2$— or —CH=CH—

$Z^2$ is

—(CH$_2$)$_2$— or —(CH$_2$)$_3$— and $R^{14}$, $R^{15}$ and $R^{16}$ are each hydrogen, or linear or branched alkyl having 1 to 4 carbon atoms or aralkyl.

Het at B in the case of bicyclic heterocycle can be expressed by the following formulas

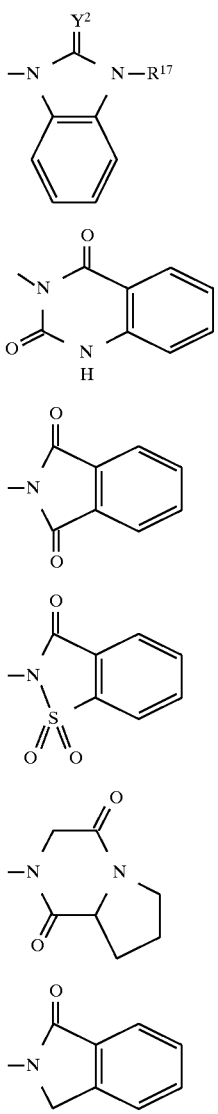

wherein $Y^2$ is oxygen atom or sulfur atom, and $R^{17}$ is hydrogen, or linear or branched alkyl having 1 to 4 carbon atoms or aralkyl.

Of the above-mentioned symbols, linear or branched alkyl having 1 to 4 carbon atoms at $R^{14}$, $R^{15}$, $R^{16}$ and $R^{17}$ is exemplified by, for example, methyl, ethyl, propyl, isopropyl, butyl, isobutyl, tert-butyl and the like, with preference given to methyl. Aralkyl at $R^{14}$, $R^{15}$, $R^{16}$ and $R^{17}$ is the same as that at $R^4$, wherein preferred is benzyl. Of the above-mentioned substituents, the group of the formula (VI-c) is preferable.

Lower alkyl at $R^{10}$ and $R^{11}$ is the same as that at $R^3$, with preference given to methyl, ethyl and propyl.

Cycloalkyl at $R^{10}$ and $R^{11}$ is the same as that at $R^5$, and preferred are cyclopropyl and cyclohexyl, and particularly preferred is cyclohexyl.

Cycloalkylalkyl at $R^{10}$ and $R^{11}$ is linear or branched alkyl having 1 to 4 carbon atoms (e.g., methyl, ethyl, propyl, isopropyl, butyl, isobutyl, tert-butyl and the like) which has been substituted by cycloalkyl, and examples of cycloalkylalkyl include cyclopropylmethyl, cyclohexylmethyl, 2-cyclohexylethyl, 3-cyclohexylpropyl and the like. Preferred is cyclohexylmethyl.

Aryl at $R^{10}$ and $R^{11}$ is the same as that at $R^6$, $R^{6\ a}$, $R^{6\ b}$ and $R^7$, and preferred is phenyl.

Substituent for substituted aryl at $R^{10}$ and $R^{11}$ includes, for example, halogen such as fluorine, chlorine and bromine; lower alkyl having 1 to 4 carbon atoms, such as methyl, ethyl, propyl, isopropyl, butyl, isobutyl and tert-butyl; lower alkoxy having 1 to 4 carbon atoms, such as methoxy, ethoxy, propoxy, isopropoxy, butoxy, isobutoxy and tert-butoxy; hydroxy; nitro; amino; cyano; and alkylenedioxy such as methylenedioxy and ethylenedioxy.

Aralkyl at $R^{10}$ and $R^{11}$ is linear or branched alkyl having 1 to 4 carbon atoms (e.g., methyl, ethyl, propyl, isopropyl, butyl, isobutyl, tert-butyl and the like) which has been substituted by aryl, and examples of aralkyl include benzyl, 2-phenylethyl, 3-phenylpropyl, 4-phenylbutyl, 1-naphthylmethyl, 2-naphthylmethyl and the like. Preferred are benzyl, 1-naphthylmethyl and 2-naphthylmethyl.

Substituent for substituted aralkyl at $R^{10}$ and $R^{11}$ is the same as that for substituted aryl at $R^{10}$ and $R^{11}$. Preferred are halogen, lower alkyl, lower alkoxy and nitro, with particular preference given to fluorine, chlorine, methyl, methoxy and nitro. Specific examples of substituted aralkyl include 4-fluorobenzyl, 4-methoxybenzyl, 4-chlorobenzyl, 4-methylbenzyl, 4-nitrobenzyl, 3,4-dichlorobenzyl and the like.

Heteroaryl at $R^{10}$ and $R^{11}$ is exemplified by pyrrolyl, pyridyl, pyrimidinyl, indolyl, indazolyl, imidazolinyl, thienyl, furyl and the like. Preferred are 4-pyridyl, 2-thienyl, 2-pyrimidinyl and 2-imidazolin-2-yl.

Substituent for substituted heteroaryl at $R^{10}$ and $R^{11}$ is the same as that for substituted aryl at $R^{10}$ and $R^{11}$.

Heteroarylalkyl at $R^{10}$ and $R^{11}$ is linear or branched alkyl having 1 to 4 carbon atoms (e.g., methyl, ethyl, propyl, isopropyl, butyl, isobutyl, tert-butyl and the like) which has been substituted by heteroaryl at $R^{10}$ and $R^{11}$, and examples of heteroarylalkyl include 4-pyridylmethyl, 2-(4-pyridyl) ethyl, 3-(4-pyridyl)propyl, 4-(4-pyridyl)-butyl, 2-thienylmethyl and the like. Preferred are 4-pyridylmethyl and 2-thienylmethyl.

Substituent for substituted heteroarylalkyl at $R^{10}$ and $R^{11}$ is the same as that for substituted aryl at $R^{10}$ and $R^{11}$. Preferred substituent is lower alkyl, particularly methyl. Specific examples of the substituted heteroarylalkyl include 1-methyl-(3-indolyl)methyl and the like.

Lower alkyl at $R^{12}$ is the same as that at $R^3$, and preferred are methyl, ethyl, isopropyl, isobutyl and hexyl. Particularly preferred are methyl and ethyl.

Cycloalkyl at $R^{12}$ is the same as that at $R^5$, and preferred are cyclopropyl and cyclohexyl.

Cycloalkylalkyl at $R^{12}$ is the same as that at $R^{10}$ and $R^{11}$, and preferred are cyclopropylmethyl and cyclohexylmethyl.

Aryl at $R^{12}$ is the same as that at $R^6$, $R^{6\ a}$, $R^{6\ b}$ and $R^7$, and preferred is phenyl.

Substituent for substituted aryl at $R^{12}$ is the same as that for substituted aryl at $R^{10}$ and $R^{11}$. Preferred substituents are halogen, lower alkyl, lower alkoxy and nitro, with particular preference given to fluorine, chlorine, methyl, methoxy and nitro. Specific examples of substituted aryl include 4-fluorophenyl, 3-methoxyphenyl, 4-chlorophenyl, 4-methylphenyl, 4-methoxyphenyl, 3,4-dimethoxyphenyl, 3,5-dimethoxyphenyl and the like.

Aralkyl at $R^{12}$ is the same as that at $R^{10}$ and $R^{11}$, and preferred are benzyl, 2-phenylethyl, 2-naphthylmethyl and 1-naphthylmethyl.

Substituent for substituted aralkyl at $R^{12}$ is the same as that for substituted aryl at $R^{10}$ and $R^{11}$. Specific examples of substituted aralkyl are 4-fluorobenzyl, 4-chlorobenzyl, 3-methoxybenzyl, 3,4-dimethoxybenzyl, 3,5-dimethoxybenzyl, 3,4-methylenedioxybenzyl, (1,4-benzodioxan-6-yl)methyl and the like.

Heteroaryl at $R^{12}$ is the same as that at $R^{10}$ and $R^{11}$.

Substituent for substituted heteroaryl at $R^{12}$ is the same as that for substituted aryl at $R^{10}$ and $R^{11}$.

Heteroarylalkyl at $R^{12}$ is the same as that at $R^{10}$ and $R^{11}$, and is exemplified by 4-pyridylmethyl, 2-(4-pyridyl)ethyl, 2-thienylmethyl and the like.

Substituent for substituted heteroarylalkyl at $R^{12}$ is the same as that for substituted aryl at $R^{10}$ and $R^{11}$.

Lower alkyl at $R^{13}$ is the same as that at $R^3$.

Cycloalkyl at $R^{13}$ is the same as that at $R^5$.

Cycloalkylalkyl at $R^{13}$ is the same as that at $R^{10}$ and $R^{11}$.

Aryl at $R^{13}$ is the same as that at $R^6$, $R^{6\ a}$, $R^{6\ b}$ and $R^7$.

Substituent for substituted aryl at $R^{13}$ includes, for example, halogen such as fluorine, chlorine and bromine; lower alkyl having 1 to 4 carbon atoms, such as methyl, ethyl, propyl, isopropyl, butyl, isobutyl and tert-butyl; lower alkoxy having 1 to 4 carbon atoms, such as methoxy, ethoxy, propoxy, isopropoxy, butoxy, isobutoxy and tert-butoxy; haloalkyl such as trifluoromethyl; hydroxy; nitro; amino; acylamino such as acetylamino; acyloxy such as acetoxy; cyano; alkylenedioxy such as methylenedioxy and ethylenedioxy; and the like. Preferred are lower alkyl having 1 to 4 carbon atoms, lower alkoxy having 1 to 4 carbon atoms, haloalkyl, halogen, hydroxy, amino, acylamino and alkylenedioxy. Particularly preferred are methyl, ethyl, methoxy, fluorine, chlorine, hydroxy, amino and methylenedioxy. Specific examples of substituted aryl include 4-methylphenyl, 2,4-dimethylphenyl, 3,4-dimethylphenyl, 4-ethylphenyl, 2-methoxyphenyl, 3-methoxyphenyl, 4-methoxyphenyl, 3,4-dimethoxyphenyl, 2-chlorophenyl, 3-chlorophenyl, 4-chlorophenyl, 2,3-dichlorophenyl, 2,4-dichlorophenyl, 3,4-dichlorophenyl, 2-fluorophenyl, 3-fluorophenyl, 4-fluorophenyl, 2,4-difluorophenyl, 3,4-difluorophenyl, 3-chloro-4-methoxyphenyl, 2-chloro-4-methylphenyl, 3-chloro-4-methylphenyl, 3-fluoro-4-methoxyphenyl, 4-hydroxyphenyl, 3,4-methylenedioxyphenyl, 4-nitrophenyl, 4-amino-5-chloro-2-methoxyphenyl and the like.

Aralkyl at $R^{13}$ is the same as that at $R^{10}$ and $R^{11}$, and preferred is 1-naphthylmethyl.

Substituent for substituted aralkyl at $R^{13}$ is the same as that for substituted aryl at $R^{13}$. Examples of substituted aralkyl include 4-fluorobenzyl, 4-chlorobenzyl, 3,4-dichlorobenzyl, 4-methoxybenzyl, 4-methylbenzyl, 4-nitrobenzyl and the like.

Heteroaryl at $R^{13}$ is, for example, pyrrolyl, pyridyl, indolyl, indazolyl, thienyl, furyl, thiazolyl, oxazolyl, benzothienyl, benzofuryl, benzimidazolyl, benzothiazolyl, benzisothiazolyl, benzoxazolyl or benzisoxazolyl. Preferred are 2-thienyl, 2-benzo[b]thienyl, 3-benzo[b]thienyl, 1 H-indol-3-yl, 3-benzisothiazolyl and 3-benzisoxazolyl.

Substituent for substituted heteroaryl at $R^{13}$ includes, for example, halogen such as fluorine, chlorine and bromine; lower alkyl having 1 to 4 carbon atoms, such as methyl, ethyl, propyl, isopropyl, butyl, isobutyl and tert-butyl; lower alkoxy having 1 to 4 carbon atoms, such as methoxy, ethoxy, propoxy, isopropoxy, butoxy, isobutoxy and tert-butoxy; cycloalkylalkyl such as cyclopropylmethyl and cyclohexylmethyl; aralkyl such as benzyl; hydroxy; nitro; amino; and cyano. Preferred are lower alkyl having 1 to 4 carbon atoms, lower alkoxy having 1 to 4 carbon atoms, halogen, cycloalkylalkyl and aralkyl, with particular preference given to methyl, ethyl, propyl, isopropyl, methoxy, chlorine, cyclohexylmethyl and benzyl. Specific examples of substituted heteroaryl include 1-methyl-1 H-3-indolyl, 1-ethyl-1 H-3-indolyl, 1-propyl-1 H-3-indolyl, 1-isopropyl-1 H-3-indolyl, 1-cyclohexylmethyl-1 H-3-indolyl, 1-benzyl-1 H-3-indolyl, 1,5-dimethyl-1 H-3-indolyl, 1-methyl-5-chloro-1 H-3-indolyl, 1-methyl-5-methoxy-1 H-3-indolyl, 2-methyl-3-benzofuryl, 1,2-dimethyl-1 H-3-indolyl, 1-butyl-1 H-3-indolyl and the like.

Heteroarylalkyl at $R^{13}$ is linear or branched alkyl having 1 to 4 carbon atoms (e.g., methyl, ethyl, propyl, isopropyl, butyl, isobutyl, tert-butyl and the like) which has been substituted by heteroaryl at $R^{13}$, and examples of heteroarylalkyl include 4-pyridylmethyl, 2-(4-pyridyl)ethyl, 3-(4-pyridyl)propyl, 4-(4-pyridyl)butyl, 2-thienylmethyl, (1 H-3-indolyl)methyl and the like.

Substituent for substituted heteroarylalkyl at $R^{13}$ is the same as that for substituted aryl at $R^{13}$. Preferred substituent includes, for example, lower alkyl, particularly methyl. Specific examples of substituted heteroarylalkyl include 1-methyl-(1 H-3-indolyl)methyl and the like.

Specific examples of cyclic amine of the formula (II-b) include, for example, 1-(2-acetylaminoethyl)pyrrolidin-3-yl, 1-(4-acetylamino-butyl)pyrrolidin-3-yl, 1-(5-acetylaminopentyl)pyrrolidin-3-yl, 1-(2-cyclohexanecarbonylaminoethyl)pyrrolidin-3-yl, 1-(3-cyclohexane-carbonylaminopropyl)pyrrolidin-3-yl, 1-(4-cyclohexanecarbonylamino-butyl)pyrrolidin-3-yl, 1-(2-benzoylaminoethyl)pyrrolidin-3-yl, 1-(3-benzoylaminopropyl)pyrrolidin-3-yl, 1-(3-(4-chlorobenzoylamino)propyl)-pyrrolidin-3-yl, 1-(3-(4-methylbenzoylamino)propyl)pyrrolidin-3yl, 1-(3-(4-methoxybenzoylamino)propyl)pyrrolidin-3-yl, 1-(3-(2-thiophenecarbonylamino)propyl)pyrrolidin-3-yl, 1-(4-benzoylaminobutyl)pyrrolidin-3-yl, 1-(2-(3-methylureido)ethyl)pyrrolidin-3-yl, 1-(3-(3-methylureido)-propyl)pyrrolidin-3-yl, 1-(4-(3-methylureido)butyl)pyrrolidin-3-yl, 1-(5-(3-methylureido)pentyl)pyrrolidin-3-yl, 1-(2-(3-n-propylureido)-ethyl)pyrrolidin-3-yl, 1-(3-(3-n-propylureido)propyl)pyrrolidin-3-yl, 1-(4-(3-n-propylureido)butyl)pyrrolidin-3-yl, 1-(2-(3-phenylureido)-ethyl)pyrrolidin-3-yl, 1-(3-(3-phenylureido)propyl)pyrrolidin-3-yl, 1-(4-(3-phenylureido)butyl)pyrrolidin-3-yl, 1-(5-(3-phenylureido)-pentyl)pyrrolidin-3-yl, 1-(2-(3-methylthioureido)ethyl)pyrrolidin-3-yl, 1-(3-(3-methylthioureido)propyl)pyrrolidin-3-yl, 1-(4-(3-methylthioureido)butyl)pyrrolidin-3-yl, 1-(2-(3-phenylthioureido)ethyl)pyrrolidin-3-yl, 1-(4-(3-phenylthioureido)butyl)pyrrolidin-3-yl, 1-(4-(2,3-dihydro-1,3-dioxo-1 H-isoindol-2-yl)butyl)pyrrolidin-3-yl, 1-(2-(2,3-dihydro-1,3-dioxo-1 H-isoindol-2-yl)ethyl)pyrrolidin-3-yl, 1-(3-(2,3-dihydro-1,3-dioxo-1 H-isoindol-2-yl)propyl)pyrrolidin-3-yl, 1-(5-(2,3-dihydro-1,3-dioxo-1 H-isoindol-2-yl)pentyl)pyrrolidin-3-yl, 1-(2-(4-amino-5-chloro-2-methoxybenzoylamino)ethyl)pyrrolidin-3-yl, 1-(3-(4-amino-5-chloro-2-methoxybenzoylamino)propyl)pyrrolidin-3-yl, 1-(3-(4-pyridinecarbonylamino)propyl)pyrrolidin-3-yl, 1-(3-((6-chloro-4-methyl-3,4-dihydro-2 H-1,4-benzoxazin-8-yl)carbonylamino)propyl)pyrrolidin-3-yl, 1-(4-((6-chloro-4-methyl-3,4-dihydro-2 H-1,4-benzoxazin-8-yl)-carbonylamino)butyl)pyrrolidin-3-yl, 1-(2-((1-methyl-1 H-indol-3-yl)-carbonylamino)ethyl)pyrrolidin-3-yl, 1-(3-((1-methyl-1 H-indol-3-yl)-carbonylamino)propyl)pyrrolidin- 3-yl, 1-(4-((1-methyl-1 H-indol-3-yl)-carbonylamino)butyl)pyrrolidin-3-yl, 1-(2-methylsulfonylaminoethyl)-pyrrolidin-3-yl, 1-(3-(1,1,3-trioxo-2,3-dihydro-1,2-benzisothiazol-2-yl)propyl)pyrrolidin-3-yl, 1-(3-(2,3-dihydro-2-oxobenzimidazol-1-yl)-propyl)pyrrolidin-3-yl, (R)-1-(3-benzoylaminopropyl)pyrrolidin-3-yl, (S)-1-(3-benzoylaminopropyl)pyrrolidin-3-yl, (R)-1-(4-(3-n-propyl-ureido)butyl)pyrrolidin-3-yl, (S)-i-(4-(3-n-propylureido)butyl)-pyrrolidin-3-yl, (R)-1-(5-(3-n- propylureido)pentyl)pyrrolidin-3-yl, (S)-1-(5-(3-n-propylureido)pentyl)pyrrolidin-3-yl, (R)-1-(6-(3-n-propylureido)hexyl)pyrrolidin-3-yl, (S)-1-(6-(3-n-propylureido)hexyl)-pyrrolidin-3-yl, (R)-1-(5-(3-phenylureido)pentyl)pyrrolidin-3-yl, (S)-1-(5-(3-phenylureido)pentyl)pyrrolidin-3-yl, (R)-1-(6-(3-phenylureido)-hexyl)pyrrolidin-3-yl, (S)-1-(6-(3-phenylureido)hexyl)pyrrolidin-3-yl, 1-(4-(4-amino-5-chloro-2-methoxybenzoylamino)butyl)pyrrolidin-3-yl, (R)-1-(4-(4-amino-5-chloro-2-methoxybenzoylamino)butyl)pyrrolidin-3-yl, (R)-1-(5-(4-amino-5-chloro-2-methoxybenzoylamino)pentyl)pyrrolidin-3-yl, (R)-1-(4-((1-methyl-1 H-indol-3-yl)carbonylamino)butyl)pyrrolidin-3-yl, (S)-1-(4-((1-methyl-1 H-indol-3-yl)carbonylamino)butyl)pyrrolidin-3-yl, 1-(5-((1-methyl-1 H-indol-3-yl)carbonylamino)pentyl)pyrrolidin-3-yl, (R)-1-(5-((1-methyl-1 H-indol-3-yl)carbonylamino)pentyl)pyrrolidin-3-yl, (S)-1-(5-((1-methyl-1 H-indol-3-yl)carbonylamino)pentyl)pyrrolidin-3-yl, (R)-1-(6-((1-methyl-1 H-indol-3-yl)carbonylamino) hexyl)pyrrolidin-3-yl, (S)-1-(6-((1-methyl-1 H-indol-3-yl)carbonylamino)hexyl)pyrrolidin-3-yl, (R)-1-(5-cyclohexanecarbonylaminopentyl) pyrrolidin-3-yl, (R)-1-(4-(1-adamantanecarbonylamino)butyl) pyrrolidin-3-yl, (R)-1-(4-(1-naphthoyl-amino)butyl) pyrrolidin-3-yl, (R)-1-(4-phenylacetylaminobutyl) pyrrolidin-3-yl, (R)-1-(5-benzoylaminopentyl)pyrrolidin-3-yl, (R)-1-(5-benzene-sulfonylaminopentyl)pyrrolidin-3-yl, (R)-1-(4-morpholinocarbonylaminobutyl)pyrrolidin-3-yl, (R)-1-(5-(3-n-butylureido)pentyl)pyrrolidin-3-yl, 1-(3-phenylcarbamoylpropyl)pyrrolidin-3-yl, 1-(3-(4-methylphenylcarbamoyl)propyl)pyrrolidin-3-yl, 1-(3-(3-chlorophenylcarbamoyl)-propyl)pyrrolidin-3-yl, (R)-1-(4-((1-methyl-1 H-indol-2-yl)carbonyl-amino)butyl)pyrrolidin-3-yl, (R)-1-(4-((1-isopropyl-1H-indol-3-yl)-carbonylamino)butyl)pyrrolidin- 3-yl, (R)-1-(4-((1-benzyl-1 H-indol-3-yl)carbonylamino)butyl)pyrrolidin-3-yl, 1-(4-(N-benzoyl-N-methylamino)-butyl)pyrrolidin-3-yl, (R)-1-(3-(3-phenylpropionylamino)propyl)-pyrrolidin-3-yl, (R)-1-(2-(4-phenylbutyrylamino)ethyl)pyrrolidin-3-yl, (R)-1-(4-(2-naphthoylamino)butyl)pyrrolidin-3-yl, (R)-1-(5-(4-chlorobenzoylamino)pentyl)pyrrolidin-3-yl, (R)-1-(5-(3-ethylureido)pentyl)-pyrrolidin-3-yl, (R)-1-(5-(3-isopropylureido)pentyl)pyrrolidin-3-yl, 1-(3-(3-chlorobenzoylamino)propyl)pyrrolidin-3-yl, 1-(3-(2-chlorobenzoylamino)propyl)pyrrolidin-3-yl, 1-(3-(4-nitrobenzoylamino)-propyl)pyrrolidin-3-yl, 1-(3-oxo-3-phenylpropyl)pyrrolidin-3-yl, 1-(4-oxo-4-phenylbutyl)pyrrolidin-3-yl, 1-(5-oxo-5-phenylpentyl)pyrrolidin-3-yl, 1-(6-oxo-6-phenylhexyl)pyrrolidin-3-yl, 1-(7-oxo-7-phenylheptyl)pyrrolidin-3-yl, 1-(8-oxo-8-phenyloctyl)pyrrolidin-3-yl, and the like.

Of these, preferred are (R)-1-(3-benzoylaminopropyl)pyrrolidin-3-yl, (R)-1-(4-(1-naphthoylamino)butyl)pyrrolidin-3-yl, (R)-1-(5-benzoylaminopentyl)pyrrolidin-3-yl, (R)-1-(5-(3-n-propylureido)pentyl)-pyrrolidin-3-yl, (R)-1-(5-(3-phenylureido)pentyl)pyrrolidin-3-yl, 1-(5-(2,3-dihydro-1,3-dioxo-1 H-isoindol-2-yl)pentyl)pyrrolidin-3-yl, 1-(3-phenylcarbamoylpropyl)pyrrolidin-3-yl, (R)-1-(5-(4-amino-5-chloro-2-methoxybenzoylamino)pentyl)pyrrolidin-3-yl, (R)-1-(4-((1-methyl-1 H-indol-3-yl)carbonylamino)butyl)pyrrolidin-3-yl, (R)-1-(5-((1-methyl-1 H-indol-3-yl)carbonylamino)pentyl)pyrrolidin-3-yl, (R)-1-(4-((1-isopropyl-1 H-indol-3-yl)carbonylamino)butyl)pyrrolidin-3-yl, (R)-1-(4-((1-benzyl-1 H-indol-3-yl)carbonylamino)butyl)pyrrolidin-3-yl, (R)-1-(2-(4-phenylbutyrylamino)ethyl)pyrrolidin-3-yl, (R)-1-(4-(2-naphthoylamino)butyl)-pyrrolidin-3-yl, (R)-1-(5-(4-chlorobenzoylamino)pentyl)pyrrolidin-3-yl, (R)-1-(5-(3-ethylureido)pentyl)pyrrolidin-3-yl, 1-(3-(3-chlorobenzoylamino)propyl)pyrrolidin-3-yl, 1-(3-(2-chlorobenzoylamino)propyl)-pyrrolidin-3-yl, 1-(3-(4-nitrobenzoylamino)propyl)pyrrolidin-3-yl, 1-(3-(4-chlorobenzoylamino)propyl)pyrrolidin-3-yl, 1-(3-(4-methylbenzoylamino)propyl)pyrrolidin-3-yl and 1-(3-(2-thiophenecarbonylamino)propyl)-pyrrolidin-3-yl. A group of the formula (II-b) wherein the absolute configuration at 3-position of pyrrolidine is R-configuration is more preferable.

Examples of the cyclic amine of the formula (II-d) include, for example, 1-(4-((1-methyl-1 H-indol-3-yl)carbonylamino)butyl)piperidin-4-yl, 1-(4-(1-naphthoylamino)butyl)piperidin-4-yl, 1-(4-(2-naphthoylamino)butyl)piperidin-4-yl, 1-(4-(3-n-propylureido)butyl)piperidin-4-yl, 1-(4-benzoylaminobutyl)piperidin-4-yl, 1-(4-(3-n-propylureido)-butyl)piperidin-4-yl, 1-(5-(3-n-propylureido)pentyl)piperidin-4-yl, 1-(5-benzoylaminopentyl)piperidin-4-yl, 1-(5-(3-chlorobenzoylamino)-pentyl)piperidin-4-yl, 1-(5-(4-methylbenzoylamino)pentyl)piperidin-4-yl, 1-(5-phenylureido)pentyl)piperidin-4-yl, 1-(5-(3-(4-chlorophenyl)ureido)pentyl)piperidin-4-yl, 1-(5-((1-methyl-1 H-indol-3-yl)-carbonylamino)pentyl)piperidin-4-yl, 1-(3-(2,3-dihydro-1,3-dioxo-1 H-isoindol-2-yl)propyl)piperidin-4-yl, 1-(5-(2,3-dihydro-1,3-dioxo-1 H-isoindol-2-yl)pentyl)piperidin-4-yl, 1-(6-(2,3-dihydro-1,3-dioxo-1 H-isoindol-2-yl)hexyl)piperidin-4-yl, 1-(3-benzoylaminopropyl)piperidin-4-yl, 1-(4-benzenesulfonylaminobutyl)piperidin-4-yl, 1-(5-((1-methyl-1 H-indazol-3-yl)carbonylamino)pentyl)piperidin-4-yl, 1-(5-(2-chlorobenzoyl)aminopentyl)piperidin-4-yl, 1-(5-(4-chlorobenzoyl)aminopentyl)-piperidin-4-yl, 1-(5-benzenesulfonylaminopentyl)piperidin-4-yl, 1-(6-((1-methyl-1 H-indol-3-yl)carbonylamino)hexyl)piperidin-4-yl, 1-(6-benzoylaminohexyl)piperidin-4-yl, 1-(6-phenylureido)hexyl)piperidin-4-yl, 1-(3-aminopropyl)piperidin-4-yl, 1-(4-aminobutyl)piperidin-4-yl, 1-(5-aminopentyl)piperidin-4-yl, 1-(6-aminohexyl)piperidin-4-yl, 1-(5-dimethylaminopentyl)piperidin-4-yl, 1-(5-diethylaminopentyl)piperidin-4-yl, 1-(6-diethylaminohexyl)piperidin-4-yl, 1-(5-cyclohexylaminopentyl)piperidin-4-yl, 1-(4-cyclohexylmethylaminobutyl)piperidin-4-yl, 1-(5-cyclohexylmethylaminopentyl)piperidin-4-yl, 1-(6-cyclohexylmethylaminohexyl)piperidin-4-yl, 1-(3-benzylaminopropyl)piperidin-4-yl, 1-(4-benzylaminobutyl)piperidin-4-yl, 1-(5-benzylaminopentyl)-piperidin-4-yl, 1-(6-benzylaminohexyl)piperidin-4-yl, 1-(4-(4-fluorobenzylamino)butyl)piperidin-4-yl, 1-(5-(4-fluorobenzylamino)-pentyl)piperidin-4-yl, 1-(4-(4-chlorobenzylamino)butyl)piperidin-4-yl, 1-(5-(4-chlorobenzylamino)pentyl)piperidin-4-yl, 1-(4-(4-methoxybenzylamino)butyl)piperidin-4-yl, 1-(5-(4-methoxybenzylamino)pentyl)-piperidin-4-yl, 1-(6-(4-methoxybenzylamino)hexyl)piperidin-4-yl, 1-(4-(4-methylbenzylamino)butyl)piperidin-4-yl, 1-(5-(4-methylbenzylamino)-pentyl)piperidin-4-yl, 1-(6-(4-methylbenzylamino)hexyl)piperidin-4-yl, 1-(5-(4-nitrobenzylamino)pentyl)piperidin-4-yl, 1-(6-(4-nitrobenzylamino)hexyl)piperidin-4-yl, 1-(3-(3,4-dichlorobenzylamino)propyl)-piperidin-4-yl, 1-(4-(3,4-dichlorobenzylamino)butyl)piperidin-4-yl, 1-(5-(3,4-dichlorobenzylamino)pentyl)piperidin-4-yl, 1-(6-(3,4-dichlorobenzylamino)hexyl)piperidin-4-yl, 1-(5-(2-thienylmethylamino)pentyl)-piperidin-4-yl, 1-(6-(2-thienylmethylamino)hexyl)piperidin-4-yl, 1-(4-(4-pyridylmethylamino)butyl)piperidin-4-yl, 1-(5-(4- pyridylmethylamino)pentyl)piperidin-4-yl, 1-(5-(1-naphthylmethylamino)pentyl)-piperidin-4-yl, 1-(6-(1-naphthylmethylamino)hexyl)piperidin-4-yl, 1-(5-(2-naphthylmethylamino)pentyl)piperidin-4-yl, 1-(6-(2-naphthylmethylamino)hexyl)piperidin-4-yl, 1-(4-(N-methyl-N-benzylamino)-butyl)piperidin-4-yl, 1-(5-(N-methyl-N-benzylamino)pentyl)piperidin-4-yl, 1-(3-(N-ethyl-N-benzylamino)propyl)piperidin-4-yl, 1-(4-(N-ethyl-N-benzylamino)butyl)piperidin-4-yl, 1-(5-(N-ethyl-N-benzylamino)-pentyl)piperidin-4-yl, 1-(6-(N-ethyl-N-benzylamino)hexyl)piperidin-4-yl, 1-(5-(N-n-propyl-N-benzylamino)pentyl)piperidin-4-yl, 1-(5-(N-ethyl-N-cyclohexylamino)pentyl)piperidin-4-yl, 1-(4-(N-ethyl-N-(cyclohexylmethyl)amino)butyl)piperidin-4-yl, 1-(5-(N-ethyl-N-(cyclohexylmethyl)amino)pentyl)piperidin-4-yl, 1-(4-(N-ethyl-N-(4-fluorobenzyl)amino)butyl)piperidin-4-yl, 1-(5-(N-ethyl-N-(4-fluorobenzyl)-amino)pentyl)piperidin-4-yl, 1-(4-(N-ethyl-N-(4-chlorobenzyl)amino)-butyl)piperidin-4-yl, 1-(5-(N-ethyl-N-(4-chlorobenzyl)amino)pentyl)-piperidin-4-yl, 1-(5-(N-ethyl-N-(4-methylbenzyl)amino)pentyl)piperidin-4-yl, 1-(6-(N-ethyl-N-(4-methylbenzyl)amino)hexyl)piperidin-4-yl, 1-(5-(N-ethyl-N-(4-methoxybenzyl)amino)pentyl)piperidin-4-yl, 1-(6-(N-ethyl-N-(4-methoxybenzyl)amino)hexyl)piperidin-4-yl, 1-(5-(N-ethyl-N-(4-nitrobenzyl)amino)pentyl)piperidin-4-yl, 1-(6-(N-ethyl-N-(4-nitrobenzyl)amino)hexyl)piperidin-4-yl, 1-(3-(N-ethyl-N-(3,4-dichlorobenzyl)amino)propyl)piperidin-4-yl, 1-(4-(N-ethyl-N-(3,4-dichlorobenzyl)amino)butyl)piperidin-4-yl, 1-(5-(N-ethyl-N-(3,4-dichlorobenzyl)amino)pentyl)piperidin-4-yl, 1-(6-(N-ethyl-N-(3,4-dichlorobenzyl)amino)hexyl)piperidin-4-yl, 1-(4-(N -ethyl-N- (2-thienylmethyl)-amino)butyl)piperidin-4-yl, 1-(5-(N-ethyl-N-(2-thienylmethyl)amino)-pentyl)piperidin-4-yl , 1-(6-(N-ethyl -N-(2-thienylmethyl)amino )hexyl)-piperidin-4-yl, 1-(4-(N-ethyl-N-(4-pyridylmethyl)amino)butyl)piperidin-4-yl, 1-(5-(N-ethyl-N-(4-pyridylmethyl)amino)pentyl)piperidin-4-yl, 1-(5-(N-ethyl-N-(1-naphthylmethyl)amino)pentyl)piperidin-4-yl, 1-(6-(N-ethyl-N-(1-naphthylmethyl)amino)hexyl)piperidin-4-yl, 1-(5-(N-ethyl-N-(2-naphthylmethyl)amino)pentyl) piperidin-4-yl, 1-(6-(N-ethyl-N-(2-naphthylmethyl)amino) hexyl)piperidin-4-yl , 1-(5-(N-methyl-N-phenylamino) pentyl)piperidin-4-yl, 1-(6-(N-methyl-N-phenylamino) hexyl)-piperidin-4-yl, 1-(3-phenoxypropyl)piperidin-4-yl, 1-(4-phenoxybutyl)-piperidin-4-yl, 1-(5-phenoxypentyl) piperidin-4-yl, 1-(6-phenoxyhexyl)-piperidin-4-yl, 1-(3-(4-fluorophenoxy)propyl)piperidin-4-yl, 1-(4-(4-fluorophenoxy)butyl)piperidin-4-yl, 1-(5-(4-fluorophenoxy) pentyl)-piperidin-4-yl, 1-(4-(4-chlorophenoxy)butyl) piperidin-4-yl, 1-(5-(4-chlorophenoxy)pentyl)piperidin-4-yl, 1-(4-(4-methylphenoxy)butyl)-piperidin-4-yl, 1-(5-(4-methylphenoxy)pentyl)piperidin-4-yl, 1-(3-benzyloxypropyl)piperidin-4-yl, 1-(4-benzyloxybutyl) piperidin-4-yl, 1-(5-benzyloxypentyl)piperidin-4-yl, 1-(6-benzyloxyhexyl)piperidin-4-yl, 1-(3-phenylthiopropyl) piperidin-4-yl, 1-(4-phenythiobutyl)piperidin-4-yl, 1-(5-phenylthiopentyl)piperidin-4-yl, 1-(6-phenylthiohexyl)-piperidin-4-yl, 1-(3-(4-fluorophenylthio)propyl)piperidin-4-yl, 1-(4-(4-fluorophenylthio)butyl)piperidin-4-yl, 1-(5-(4-fluorophenylthio)-pentyl)piperidin-4-yl, 1-(4-(4-chlorophenylthio)butyl)piperidin-4-yl, 1-(5-(4-chlorophenylthio)pentyl)piperidin-4-yl, 1-(4-(4-methylphenyl-thio)butyl)piperidin-4-yl, 1-(5-(4-methylphenylthio)pentyl)piperidin-4-yl, 1-(3-benzylthiopropyl)piperidin-4-yl, 1-(4-benzylthiobutyl)-piperidin-4-yl, 1-(5-benzylthiopentyl)piperidin-4-yl, 1-(6-benzylthiohexyl)piperidin-4-yl, 1-(5-(4-chlorobenzyloxy) pentyl)piperidin-4-yl, 1-(5-(2-phenylethyloxy)pentyl) piperidin-4-yl, 1-(5-(2-naphthyl-methoxy)pentyl)piperidin-4-yl, 1-(5-cyclohexylmethoxypentyl)piperidin-4-yl, 1-(4-(3-methoxyphenoxy)butyl)piperidin-4-yl, 1-(5-(3-methoxyphenoxy)pentyl)piperidin-4-yl, 1-(4-(3-methoxybenzyloxy)butyl)piperidin-4-yl, 1-(5-(3-methoxybenzyloxy)pentyl)piperidin-4-yl, 1-(4-(3,4-dimethoxyphenoxy)butyl)piperidin-4-yl, 1-(5-(3,4-dimethoxyphenoxy)-pentyl)piperidin-4-yl, 1-(4-(3,4-dimethoxybenzyloxy)butyl)piperidin-4-yl, 1-(5-(3,4-dimethoxybenzyloxy)pentyl)piperidin-4-yl, 1-(4-(3,5-dimethoxyphenoxy)butyl)piperidin-4-yl, 1-(5-(3,5-dimethoxyphenoxy)-pentyl)piperidin-4-yl, 1-(4-(3,5-dimethoxybenzyloxy)butyl)piperidin-4-yl, 1-(5-(3,5-dimethoxybenzyloxy)pentyl)piperidin-4-yl, 1-(5-(4-chlorophenoxy)pentyl)piperidin-4-yl, 1-(5-(4-fluorophenoxy)pentyl)-piperidin-4-yl, 1-(4-(1-naphthyloxy) butyl)piperidin-4-yl, 1-(5-(1-naphthyloxy)pentyl)piperidin-4-yl, 1-(4-(3,4-methylenedioxyphenyl-methoxy)butyl) piperidin-4-yl, 1-(5-(3,4-methylenedioxyphenylmethoxy)-pentyl)piperidin-4-yl, 1-(4-((1,4-benzodioxan-6-yl) methoxy)butyl)-piperidin-4-yl, 1-(5-((1,4-benzodioxan-6-yl)methoxy)pentyl)piperidin-4-yl, 1-(5-(1-naphthylthio) pentyl)piperidin-4-yl, 1-(5-(2-pyrimidinyl-amino)pentyl) piperidin-4-yl, 1-(3-oxo-3-phenylpropyl)piperidin-4-yl, 1-(4-oxo-4-phenylbutyl)piperidin-4-yl, 1-(5-oxo-5-phenylpentyl)-piperidin-4-yl, 1-(6-oxo-6-phenylhexyl) piperidin-4-yl, 1-(7-oxo-7-phenylheptyl)piperidin-4-yl, 1-(8-oxo-8-phenyloctyl)piperidin-4-yl, 1-(6-(2-fluorophenyl)-6-oxohexyl)piperidin-4-yl, 1-(6-(3-fluorophenyl)-6-oxohexyl)piperidin-4-yl, 1-(6-(4-fluorophenyl)-6-oxohexyl)piperidin-4-yl, 1-(6-(2,3-difluorophenyl)-6-oxohexyl)piperidin-4-yl, 1-(6-(2,4-difluorophenyl)-6-oxohexyl)piperidin-4-yl, 1-(6-(2,5-difluorophenyl)-6-oxohexyl)piperidin-4-yl, 1-(6-(2,6-difluorophenyl)-6-oxohexyl)-piperidin-4-yl, 1-(6-(3,4-difluorophenyl)-6-oxohexyl)piperidin-4-yl, 1-(6-(3,5-difluorophenyl)-6-oxohexyl)piperidin-4-yl, 1-(6-(2-chlorophenyl)-6-oxohexyl)piperidin-4-yl, 1-(6-(3-chlorophenyl)-6-oxohexyl)-piperidin-4-yl, 1-(6-(4-chlorophenyl)-6-oxohexyl)piperidin-4-yl, 1-(7-(4-chlorophenyl)-7-oxoheptyl)piperidin-4-yl, 1-(6-(2,3-dichlorophenyl)-6-oxohexyl)piperidin-4-yl, 1-(6-(2,4-dichlorophenyl)-6-oxohexyl)-piperidin-4-yl, 1-(6-(2,5-dichlorophenyl)-6-oxohexyl)piperidin-4-yl, 1-(6-(2,6-dichlorophenyl)-6-oxohexyl)piperidin-4-yl, 1-(6-(3,4-dichlorophenyl)-6-oxohexyl)piperidin-4-yl, 1-(6-(3,5-dichlorophenyl)-6-oxohexyl)piperidin-4-yl, 1-(6-(4-bromophenyl)-6-oxohexyl)piperidin-4-yl, 1-(6-(2-methylphenyl)-6-oxohexyl)piperidin-4-yl, 1-(6-(3-methylphenyl)-6-oxohexyl)piperidin-4-yl, 1-(6-(4-methylphenyl)-6-oxohexyl)piperidin-4-yl, 1-(6-(2-ethylphenyl)-6-oxohexyl)piperidin-4-yl, 1-(6-(3-ethylphenyl)-6-oxohexyl)piperidin-4-yl, 1-(6-(4-ethylphenyl)-6-oxohexyl)-piperidin-4-yl, 1-(6-oxo-6-(2-propylphenyl)hexyl)piperidin-4-yl, 1-(6-oxo-6-(3-propylphenyl)hexyl)piperidin-4-yl, 1-(6-oxo-6-(4-propylphenyl)hexyl)piperidin-4-yl, 1-(6-(2-isopropylphenyl)-6-oxohexyl)-piperidin-4-yl, 1-(6-(3-isopropylphenyl)-6-oxohexyl)piperidin-4-yl, 1-(6-(4-isopropylphenyl)hexyl)piperidin-4-yl, 1-(6-(4-butylphenyl)-6-oxohexyl)piperidin-4-yl, 1-(6-(2,3-dimetthylphenyl)-6-oxohexyl)piperidin-4-yl, 1-(6-(2,4-dimethylphenyl)-6-oxohexyl)piperidin-4-yl, 1-(6-(2,5-dimethylphenyl)-6-oxohexyl)piperidin-4-yl, 1-(6-(2,6-dimethylphenyl)-6-oxohexyl)piperidin-4-yl, 1-(6-(3,4-dimethylphenyl)-6-oxohexyl)piperidin-4-yl, 1-(6-(3,5-dimethylphenyl)-6- oxohexyl)-piperidin-4-yl, 1-(6-(2-methoxyphenyl)-6-oxohexyl)piperidin-4-yl, 1-(6-(3-methoxyphenyl)-6-oxohexyl)piperidin-4-yl, 1-(6-(4-methoxyphenyl)-6-oxohexyl)piperidin-4-yl, 1-(6-(3-fluoro-4-methoxyphenyl)-6-oxohexyl)piperidin-4-yl, 1-(6-(3-chloro-4-methoxyphenyl)-6-oxohexyl)-piperidin-4-yl, 1-(6-(3-bromo-4-methoxyphenyl)-6-oxohexyl)piperidin-4-yl, 1-(6-(3-fluoro-4-methylphenyl)-6-oxohexyl)piperidin-4-yl, 1-(6-(3-chloro-4-methylphenyl)-6-oxohexyl)piperidin-4-yl, 1-(6-(3-bromo-4-methylphenyl)-6-oxohexyl)piperidin-4-yl, 1-(6-(4-methoxy-2-methylphenyl)-6-oxohexyl)piperidin-4-yl, 1-(6-(4-methoxy-3-methylphenyl)-6-oxohexyl)piperidin-4-yl, 1-(6-(3,4-dimethoxyphenyl)-6-oxohexyl)-piperidin-4-yl, 1-(6-(4-hydroxyphenyl)-6-oxohexyl)piperidin-4-yl, 1-(6-(3,4-dihydroxyphenyl)-6-oxohexyl)piperidin-4-yl, 1-(6-(2-aminophenyl)-6-oxohexyl)piperidin-4-yl, 1-(6-(3-aminophenyl)-6-oxohexyl)-piperidin-4-yl, 1-(6-(4-aminophenyl)-6-oxohexyl)piperidin-4-yl, 1-(6-(2-acetaminophenyl)-6-oxohexyl)piperidin-4-yl, 1-(6-(3-acetaminophenyl)-6-oxohexyl)piperidin-4-yl, 1-(6-(4-acetaminophenyl)-6-oxohexyl)piperidin-4-yl, 1-(6-(2-nitrophenyl)-6-oxohexyl)piperidin-4-yl, 1-(6-(3-nitrophenyl)-6-oxohexyl)piperidin-4-yl, 1-(6-(4-nitrophenyl)-6-oxohexyl)piperidin-4-yl, 1-(6-(2-trifluoromethylphenyl)-6-oxohexyl)-piperidin-4-yl, 1-(6-(3-trifluoromethylphenyl)-6-oxohexyl)piperidin-4-yl, 1-(6-(4-trifluoromethylphenyl)-6-oxohexyl)piperidin-4-yl, 1-(6-oxo-6-(2-thienyl)hexyl)piperidin-4-yl, 1-(6-oxo-6-(3-thienyl)hexyl)-piperidin-4-yl, 1-(6-oxo-6-(2-benzo[b]thienyl)hexyl)piperidin-4-yl, 1-(6-oxo-6-(3-benzo[b]thienyl)hexyl)piperidin-4-yl, 1-(6-(1-methyl-1 H-indol-3-yl)-6-oxohexyl)piperidin-4-yl, 1-(6-(1-ethyl-1 H-indol-3-yl)-6-oxohexyl)piperidin-4-yl, 1-(6-(1-propyl-1 H-indol-3-yl)-6-oxohexyl)-piperidin-4-yl, 1-(6-(1-isopropyl-1 H-indol-3-yl)-6-oxohexyl)piperidin-4-yl, 1-(6-(1-benzyl-1 H-indol-3-yl)-6-oxohexyl)piperidin-4-yl, 1-(6-(1-cyclohexylmethyl-1 H-indol-3-yl)-6-oxohexyl)piperidin-4-yl, 1-(6-(1 H-indol-3-yl)-6-oxohexyl)piperidin-4-yl, 1-(7-(1-methyl-1 H-indol-3-yl)-7-oxoheptyl)piperidin-4-yl, 1-(6-(1-naphthyl)-6-oxohexyl)piperidin-4-yl, 1-(6-(2-naphthyl)-6-oxohexyl)piperidin-4-yl, 1-(6-(2-furyl)-6-oxohexyl)piperidin-4-yl, 1-(6-(3-furyl)-6-oxohexyl)piperidin-4-yl, 1-(6-(2-benzo[b]furyl)-6-oxohexyl)piperidin-4-yl, 1-(6-(3-benzo[b]furyl)-6-oxohexyl)piperidin-4-yl, 1-(6-oxo-6-(2-pyridyl)hexyl)piperidin-4-yl, 1-(6-oxo-6-(3-pyridyl)hexyl)piperidin-4-yl, 1-(6-oxo-6-(4-pyridyl)-hexyl)piperidin-4-yl, 1-(6-(3,4-methylenedioxyphenyl)-6-oxohexyl)-piperidin-4-yl, 1-(4-phenylsulfonylbutyl)piperidin-4-yl, 1-(5-phenylsulfonylpentyl)piperidin-4-yl, 1-(6-phenylsulfonylhexyl)piperidin-4-yl, 1-(5-phenylsulfinylpentyl)piperidin-4-yl, 1-(6-(4-amino-5-chloro-2-methoxyphenyl)-6-oxohexyl)piperidin-4-yl, 1-(6-(1,5-dimethyl-1 H-indol-3-yl)-6-oxohexyl)piperidin-4-yl, 1-(6-(5-chloro-1-methyl-1 H-indol-3-yl)-6-oxohexyl)piperidin-4-yl, 1-(6-(5-methoxy-1-methyl-1 H-indol-3-yl)-6-oxohexyl)piperidin-4-yl, 1-(6-(3-benzisothiazolyl)-6-oxohexyl)-piperidin-4-yl, 1-(6-(3-benzisoxazolyl)-6-oxohexyl)piperidin-4-yl, 1-(5-(1-methyl-1 H-indol-3-yl)-5-oxopentyl)piperidin-4-yl, 1-(6-(2-methyl-3-benzo[b]furyl)-6-oxohexyl)-piperidin-4-yl, 1-(6-(3-chlorophenyl)-6-oxohexyl)piperidin-4-yl, 1-(6-(2-chlorophenyl)-6-oxohexyl)piperidin-4-yl, 1-(6-(2-chloro-4-methylphenyl)-6-oxohexyl)piperidin-4-yl, 1-(6-(3-chloro- 4-methylphenyl)-6-oxohexyl)piperidin-4-yl, 1-(6-(2,3-dichlorophenyl)-6-oxohexyl)piperidin-4-yl, 1-(6-(2-methoxyphenyl)-6-oxohexyl)-piperidin-4-yl, 1-(6-(3-methoxyphenyl)-6-oxohexyl)piperidin-4-yl, 1-(6-(2-fluorophenyl)-6-oxohexyl) piperidin-4-yl, 1-(6-(3-fluorophenyl)-6-oxohexyl)piperidin-4-yl, 1-(6-(4-nitrophenyl)-6-oxohexyl)piperidin-4-yl, 1-(6-(1,2-dimethyl-1 H-indol-3-yl)-6-oxohexyl)piperidin-4-yl, 1-(6-(1-butyl-1 H-indol-3-yl)-6-oxohexyl)piperidin-4-yl, 1-(7-(3-chlorophenyl)-7-oxoheptyl)piperidin-4-yl, 4-methoxy-1-(4-(1-naphthylsulfonyl)butyl)piperidin-4-yl, 1-(5-(1-naphthylsulfonyl)pentyl)-piperidin-4-yl, 4-methoxy-1-(4-(1-naphthylmethylsulfonyl)butyl)-piperidin-4-yl, 4-methoxy-1-(5-(1-naphthylmethylsulfonyl)pentyl)-piperidin-4-yl, 1-(7-(1-methyl-1 H-indol-3-yl)-7-oxoheptyl)piperidin-4-yl, 4-hydroxy-1-(6-phenyl-6-oxohexyl)piperidin-4-yl, 4-methoxy-1-(6-phenyl-6-oxohexyl)piperidin-4-yl, 4-methoxy-1-(4-phenylsulfonylbutyl)-piperidin-4-yl, 1-(2-benzylsulfonylethyl)piperidin-4-yl, 1-(3-benzylsulfonylpropyl)piperidin-4-yl, 1-(3-(4-fluorobenzylsulfonyl)-propyl)piperidin-4-yl, 1-(3-(4-chlorobenzylsulfonyl)propyl)piperidin-4-yl, 1-(3-(4-methoxybenzylsulfonyl)propyl)piperidin-4-yl, 1-(2-(2-phenylethylsulfonyl)ethyl)piperidin-4-yl, 1-(5-(4-hydroxyphenyl)-5-oxopentyl)piperidin-4-yl, 1-(3-(4-hydroxyphenyl)-3-oxopropyl)-piperidin-4-yl, 1-(4-(4-hydroxyphenyl)-4-oxobutyl)piperidin-4-yl, 1-(6-(2-hydroxyphenyl)-6-oxohexyl)piperidin-4-yl, 1-(6-(3-hydroxyphenyl)-6-oxohexyl)piperidin-4-yl, 1-(6-(2,4-dihydroxyphenyl)-6-oxohexyl)-piperidin-4-yl, 3-methoxy-1-(6-oxo-6-phenylhexyl)piperidin-4-yl, 1-(6-(4-acetoxyphenyl)-6-oxohexyl)piperidin-4-yl, 3-hydroxy-1-(4-oxo-4-phenylbutyl)piperidin-4-yl, 1-(3-benzyloxypropyl) piperidin-4-yl, 1-(2-benzyloxyethyl)piperidin-4-yl and the like.

Of these, preferred are 1-(4-(1-naphthoylamino)butyl) piperidin-4-yl, 1-(4-(2-naphthoylamino)butyl)piperidin-4-yl, 1-(5-benzoylaminopentyl)piperidin-4-yl, 1-(5-(3-chlorobenzoylamino)pentyl)piperidin-4-yl, 1-(5-(4-methylbenzoylamino)pentyl)piperidin-4-yl, 1-(4-(3-n-propylureido)butyl)piperidin-4-yl, 1-(5-(3-n-propylureido) pentyl)-piperidin-4-yl, 1-(5-(3-(4-chlorophenyl)ureido) pentyl)piperidin-4-yl, 1-(4-((1-methyl-1 H-indol-3-yl) carbonylamino)butyl)piperidin-4-yl, 1-(5-((1-methyl-1 H-indol-3-yl)carbonylamino)pentyl)piperidin-4-yl, 1-(6-(N-benzyl-N-ethylamino)hexyl)piperidin-4-yl, 1-(6-(N-benzylamino)hexyl)piperidin-4-yl, 1-(5-(N-(1-naphthylmethyl)amino)pentyl)-piperidin-4-yl, 1-(5-(N-ethyl-N-(4-fluorobenzyl)amino)pentyl)-piperidin-4-yl, 1-(5-(N-benzyl-N-propylamino)pentyl)piperidin-4-yl, 1-(5-(N-cyclohexylmethylamino)pentyl)piperidin-4-yl, 1-(4-(N-(3,4-dichlorobenzyl)-N-ethylamino)butyl)piperidin-4-yl, I-(6-(N-(3,4-dichlorobenzyl)amino)hexyl)piperidin-4-yl, 1-(6-(N-ethyl-N-(4-methylbenzyl)amino)hexyl)piperidin-4-yl, 1-(6-(N-ethyl-N-(4-nitrobenzyl)-amino)hexyl)piperidin-4-yl, 1-(5-(N-(4-methylbenzyl)amino)pentyl)-piperidin-4-yl, 1-(6-(N-ethyl-N-(2-thienylmethyl)amino)hexyl)piperidin-4-yl, 1-(5-(N-(2-naphthylmethyl)amino)pentyl)piperidin-4-yl, 1-(6-(N-(4-methoxybenzyl)amino)hexyl)piperidin-4-yl, 1-(6-(N-(2-thienylmethyl)-amino)hexyl)piperidin-4-yl, 1-(5-benzylthiopentyl)piperidin-4-yl, 1-(5-benzyloxypentyl)piperidin-4-yl, 1-(5-phenoxypentyl) piperidin-4-yl, 1-(5-phenylthiopentyl)piperidin-4-yl, 1-(5-(4-chlorobenzyloxy)pentyl)-piperidin-4-yl, 1-(4-phenoxybutyl)piperidin-4-yl, 1-(6-phenyl-6-oxohexyl) piperidin-4-yl, 1-(7-phenyl-7-oxoheptyl)piperidin-4-yl, 1-(6-(1-naphthyl)-6-oxohexyl)piperidin-4-yl, 1-(6-(3-fluoro-4-methoxyphenyl)-6-oxohexyl)piperidin-4-yl, 1-(6-(3-chloro-4-methoxyphenyl)-6-oxohexyl)-piperidin-4-yl, 1-(6-(3,4-dimethoxyphenyl)-6-oxohexyl)piperidin-4-yl, 1-(6-(4-hydroxyphenyl)-6-oxohexyl)piperidin-4-yl, 1-(6-(1- naphthyl)-6-oxohexyl)piperidin-4-yl, 1-(6-(1-methyl-1 H-indol-3-yl)-6-oxohexyl)-piperidin-4-yl, 1-(5-(1-methyl-1 H-indol-3-yl)-5-oxopentyl)piperidin-4-yl, 1-(7-(1-methyl-1 H-indol-3-yl)-7-oxoheptyl)piperidin-4-yl, 1-(6-(1-ethyl-1 H-indol-3-yl)- 6-oxohexyl)piperidin-4-yl, 1-(6-(1-isopropyl-1 H-indol-3-yl)-6-oxo-hexyl)piperidin-4-yl, 1-(5-phenyl-5-oxopentyl)-piperidin-4-yl, 1-(6-(1 H-indol-3-yl)-6-oxohexyl)piperidin-4-yl, 1-(4-phenylsulfonylbutyl) piperidin-4-yl, 1-(5-phenylsulfonylpentyl)-piperidin-4-yl and 1-(3-benzylsulfonylpropyl)piperidin-4-yl.

The pharmaceutically acceptable salts of the compound of the present invention are, for example, acid addition salt and quaternary ammonium salt. Examples of the acid addition salt include, for example, hydrochloride, sulfate, hydrobromide, phosphate, nitrate, methanesulfonate, ethanesulfonate, fumarate, maleate, benzoate, citrate, malate, mandelate, p-toluenesulfonate, acetate, succinate, malonate, lactate, salicylate, gallate, picrate, carbonate, ascorbate, trifluoroacetate and tartrate. Examples of quaternary ammonium salt include, for example, quaternary ammonium salts with lower alkyl halide (e.g., methyl iodide, methyl bromide, ethyl iodide, ethyl bromide and the like), lower alkylsulfonate (e.g., methyl methanesulfonate, ethyl methanesulfonate and the like), and lower alkyl arylsulfonate (e.g., methyl p-toluenesulfonate and the like). The N-oxide derivative at substituent A of compound of the formula (I) is also encompassed in the compound of the present invention. The compound of the present invention may be hydrates (e.g., monohydrate, ½ hydrate and ⅔ hydrate) or solvates. For crystallization of compound, oxalic acid may be used.

When the compound of the present invention and pharmaceutically acceptable salts thereof have asymmetric carbon, the compound can be present as optical isomers. The present invention also encompasses such optical isomers and mixtures thereof. In addition, geometric isomers of cis-compounds and trans-compounds, as well as mixtures thereof are also encompassed in the present invention.

The compound of the present invention can be produced by the following methods.

METHOD 1

The compound of the formula (I) can be synthesized by the following route.

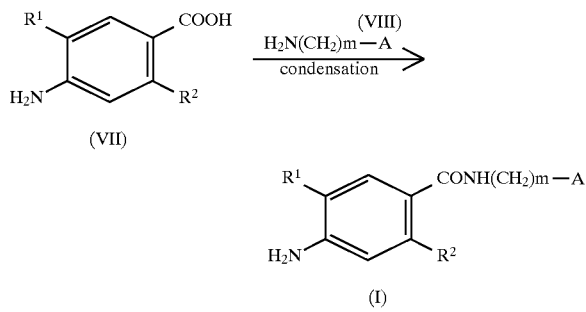

wherein $R_1$, $R_2$, m and A are as defined above.

That is, the compound is produced by reacting carboxylic acid of compound (VII) or reactive derivative thereof with compound (VIII) in a suitable solvent.

When compound (VII) is a free carboxylic acid, the reaction is carried out using a routine condensing agent. Examples of the condensing agent include dicyclohexylcarbodiimide, 1-ethyl-3-(3-dimethylaminopropyl)carbodiimide hydrochloride, carbonyldiimidazole, benzotriazol-1-yloxytris (dimethylamino)phosphonium hexafluorophosphate, N-methyl-2-chloropyridinium iodide and the like. The instant reaction is preferably carried out by condensing in the presence of an organic base such as 1-hydroxybenzotriazole and N-methylmorpholine. The solvent to be used may be, for example, dimethylformamide, dimethyl sulfoxide, methylene chloride, tetrahydrofuran, acetonitrile, dioxane, benzene and toluene. While the reaction temperature varies depending on the kind of solvent to be used, it is generally from −20° C. to 50° C., and the reaction time which varies depending on the kind of reaction temperature is generally 1–24 hr.

When compound (VII) is reactive derivative of carboxylic acid such as acid halide, acid anhydride, mixed acid anhydride and ester, the reaction is carried out in an inert solvent in the presence of a base as necessary. The base to be used as necessary is, for example, sodium carbonate, potassium carbonate, sodium hydrogencarbonate, potassium hydrogencarbonate, sodium hydroxide, potassium hydroxide, triethylamine, diisopropylethylamine or pyridine. Examples of the inert solvent to be used include, for example, methylene chloride, chloroform, ethyl acetate, diethyl ether, tetrahydrofuran, dioxane, acetonitrile, benzene, toluene and mixed solvent thereof.

While the reaction temperature varies depending on the kind of solvent to be used, it is generally from −30° C. to 50° C., and the reaction time which varies depending on reaction temperature is generally 1–24 hr.

METHOD 2

A compound (VIII) wherein A is a group of the formula (II-a)–(II-f), B is a group of the formula —N($R^4$)-$X^1$—$R^5$ and $R^4$ is hydrogen can be synthesized by the following route.

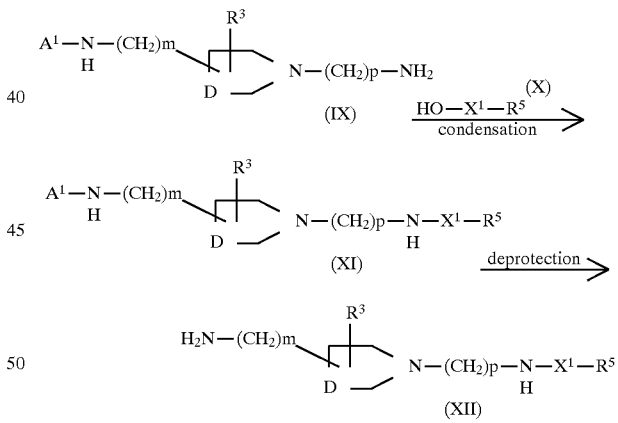

wherein $A^1$ is an urethane type amino-protecting group such as tert-butoxycarbonyl, 1,1-dimethylethoxycarbonyl and isopropyloxycarbonyl, D is —($CH_2$)$_n$— wherein n is an integer of 0–3, and $R^3$, $R^5$, m, p and $X^1$ are as defined above.

That is, the compound is produced by condensing compound (IX) with compound (X) or reactive derivative thereof in a suitable solvent and then deprotecting the obtained compound (XI).

The reaction of compound (IX) and compound (X) can be carried out according to the condensation shown in Method 1.

The compound (XI) can be deprotected by a method generally used for deprotection of amino-protecting group. For example, when $A^1$ is tert-butoxycarbonyl, deprotection is performed by treating with an acid in a suitable solvent as necessary. The acid to be used for this reaction may be any as long as it does not hydrolyze amide bonding, and is exemplified by, for example, hydrogen chloride, sulfuric acid, trifluoroacetic acid and trifluoromethanesulfonic acid. The solvent to be used as necessary may be, for example, methanol, ethanol, propanol, isopropyl alcohol, tetrahydrofuran, acetone, ethyl acetate, methylene chloride, chloroform, dioxane, water and mixed solvents thereof. The reaction temperature is from under ice-cooling to the refluxing temperature of the solvent, preferably at room temperature, and reaction time is from 30 min to 2 hr.

METHOD 3

A compound (VIII) wherein A is a group of the formula (II-a)–(II-f), B is a group of the formula —$N(R^4)$—$X^1$—$R^5$ and $R^4$ is lower alkyl, aralkyl or substituted aralkyl can be synthesized by the following route.

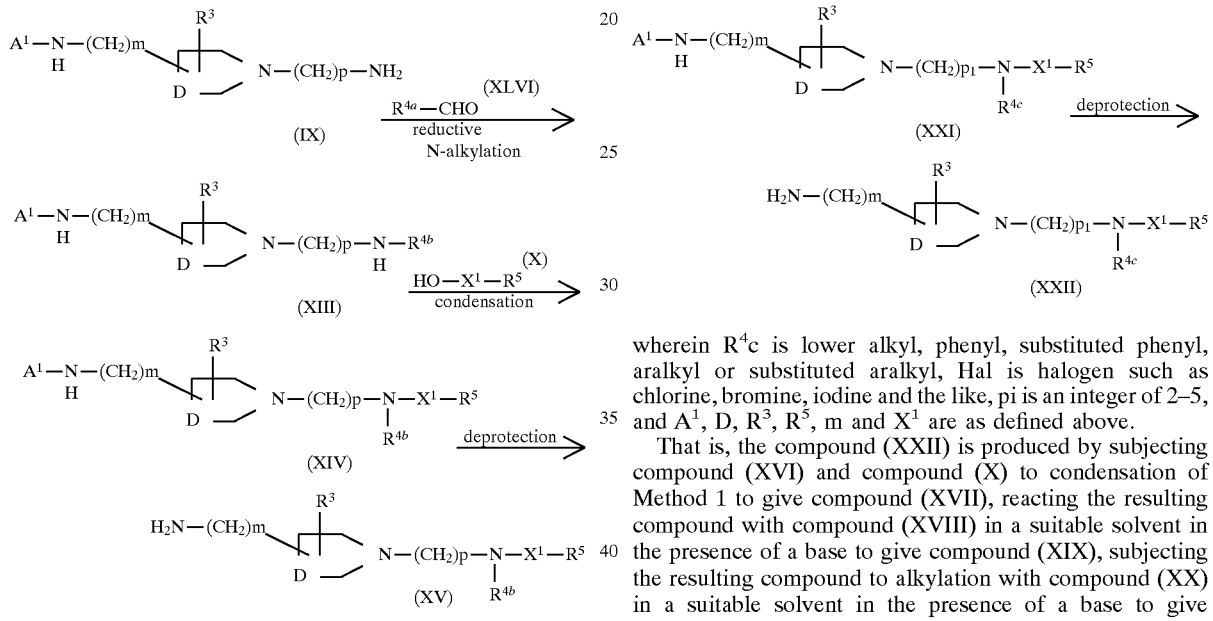

wherein $R^{4a}$ is hydrogen, alkyl having 1 to 5 carbon atoms, aralkyl or substituted aralkyl, $R^{4b}$ is lower alkyl, aralkyl or substituted aralkyl, and $A^1$, D, $R^3$, $R^5$, m, p and $X^1$ are as defined above.

That is, the compound (XV) is produced by subjecting compound (IX) and compound (XLVI) to reductive N-alkylation in a suitable solvent to give compound (XIII), reacting the resultant compound with compound (X) according to Method 2 to give compound (XIV) and deprotection.

The solvent to be used for the reductive N-alkylation includes, for example, methanol, ethanol, propanol, ethyl acetate, tetrahydrofuran, dioxane, dimethylformamide and acetic acid. The reductive N-alkylating agent to be used may be, for example, sodium cyanoborohydride, sodium borohydride, formic acid or sodium formate. While the reaction temperature varies depending on the kind of solvent to be used, it is generally from 0° C. to 30° C., and the reaction time which varies depending on the kind of reaction temperature is generally 1–24 hr.

METHOD 4

A compound (VIII) wherein A is a group of the formula (II-a)–(II-f), B is a group of the formula —$N(R^4)$—$X^1$—$R^5$ and $R^4$ is lower alkyl, phenyl, substituted phenyl, aralkyl or substituted aralkyl can be synthesized by the following route.

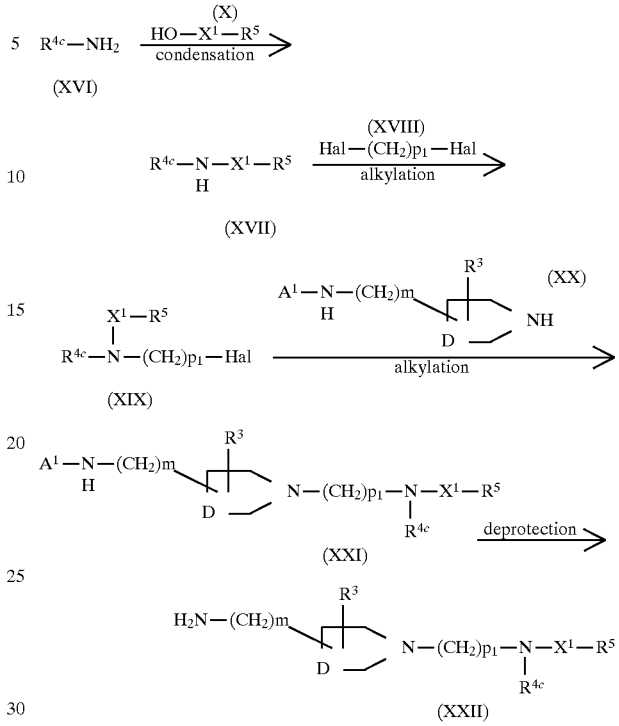

wherein $R^4c$ is lower alkyl, phenyl, substituted phenyl, aralkyl or substituted aralkyl, Hal is halogen such as chlorine, bromine, iodine and the like, pi is an integer of 2–5, and $A^1$, D, $R^3$, $R^5$, m and $X^1$ are as defined above.

That is, the compound (XXII) is produced by subjecting compound (XVI) and compound (X) to condensation of Method 1 to give compound (XVII), reacting the resulting compound with compound (XVIII) in a suitable solvent in the presence of a base to give compound (XIX), subjecting the resulting compound to alkylation with compound (XX) in a suitable solvent in the presence of a base to give compound (XXI) and deprotection according to Method 2.

The solvent to be used for the reaction of compound (XVII) and compound (XVIII) includes, for example, methanol, ethanol, propanol, ethyl acetate, tetrahydrofuran, dioxane, dimethylformamide, dimethyl sulfoxide and toluene. The base to be used may be, for example, sodium carbonate, potassium carbonate, sodium hydrogencarbonate, potassium hydrogencarbonate, sodium hydroxide, potassium hydroxide, sodium hydride, potassium hydride, triethylamine, diisopropylethylamine or pyridine. While the reaction temperature varies depending on the kind of solvent to be used, it is generally from 0° C. to 80° C., and the reaction time which varies depending on the kind of reaction temperature is generally 1–24 hr.

The solvent to be used for the reaction of compound (XIX) and compound (XX) includes, for example, methanol, ethanol, propanol, ethyl acetate, tetrahydrofuran, dioxane, dimethylformamide, dimethyl sulfoxide, toluene and mixed solvents thereof. The base to be used may be, for example, sodium carbonate, potassium carbonate, sodium hydrogencarbonate, potassium hydrogencarbonate, sodium hydroxide, potassium hydroxide, triethylamine, diisopropylethylamine or pyridine. While the reaction temperature varies depending on the kind of solvent to be used, it is generally from 0° C. to 80° C., and the reaction time which varies depending on the kind of reaction temperature is generally 1–24 hr.

METHOD 5

A compound (VIII) wherein A is a group of the formula (II-a)–(II-f), B is a group of the formula —N(R⁴)—X²—N(R⁶)(R⁷) and R⁷ is hydrogen can be synthesized by the following route.

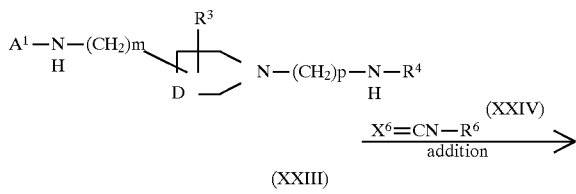

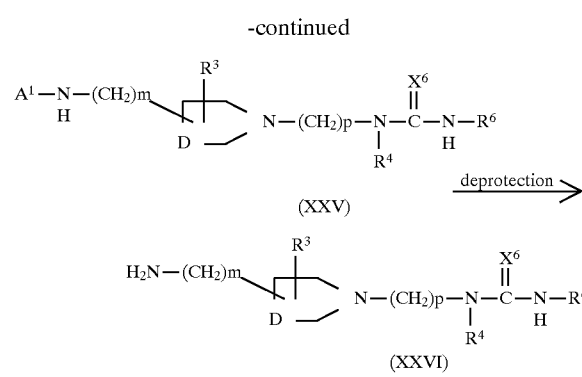

wherein $X^6$ is oxygen atom or sulfur atom, and $A^1$, D, $R^3$, $R^4$, $R^6$, m and p are as defined above.

That is, the compound (XXVI) is produced by reacting compound (XXIII) and compound (XXIV) in a suitable solvent to give compound (XXV), and deprotection according to Method 2.

The solvent to be used for the reaction of compound (XXIII) and compound (XXIV) includes, for example, methylene chloride, chloroform, ethyl acetate, tetrahydrofuran, dioxane, benzene and toluene. The reaction temperature is generally from −30° C. to 40° C., and the reaction time is generally 10 min–5 hr.

METHOD 6

A compound (VIII) wherein A is a group of the formula (II-a)–(II-f), and B is a group of the formula —N(R⁴)—X²—N(R⁶)(R⁷) can be synthesized by the following route.

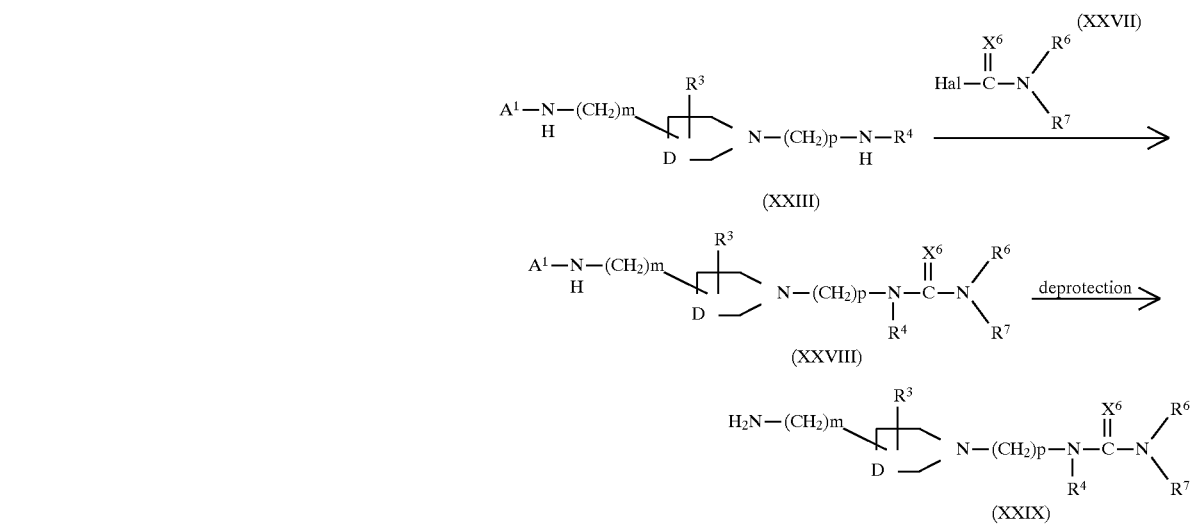

wherein $A^1$, D, $R^3$, $R^4$, $R^6$, $R^7$, m, p, $X^6$ and Hal are as defined above.

That is, the compound (XXIX) is produced by reacting compound (XXIII) and compound (XXVII) in a suitable solvent in the presence of a base to give compound (XXVIII), and deprotection according to Method 2.

The solvent to be used for the reaction of compound (XXIII) and compound (XXVII) includes, for example, dimethylformamide, dimethyl sulfoxide, methylene chloride, chloroform, ethyl acetate, tetrahydrofuran, dioxane, benzene and toluene. The base to be used may be, for example, sodium carbonate, potassium carbonate, sodium hydrogencarbonate, potassium hydrogencarbonate, sodium hydroxide, potassium hydroxide, triethylamine, diisopropylethylamine or pyridine. The reaction temperature is generally from −30° C. to 40° C., and the reaction time is generally 10 min–5 hr.

METHOD 7

The compound (IX) and compound (XX) which are intermediates shown in Method 2–Method 4 can be synthesized by the following route.

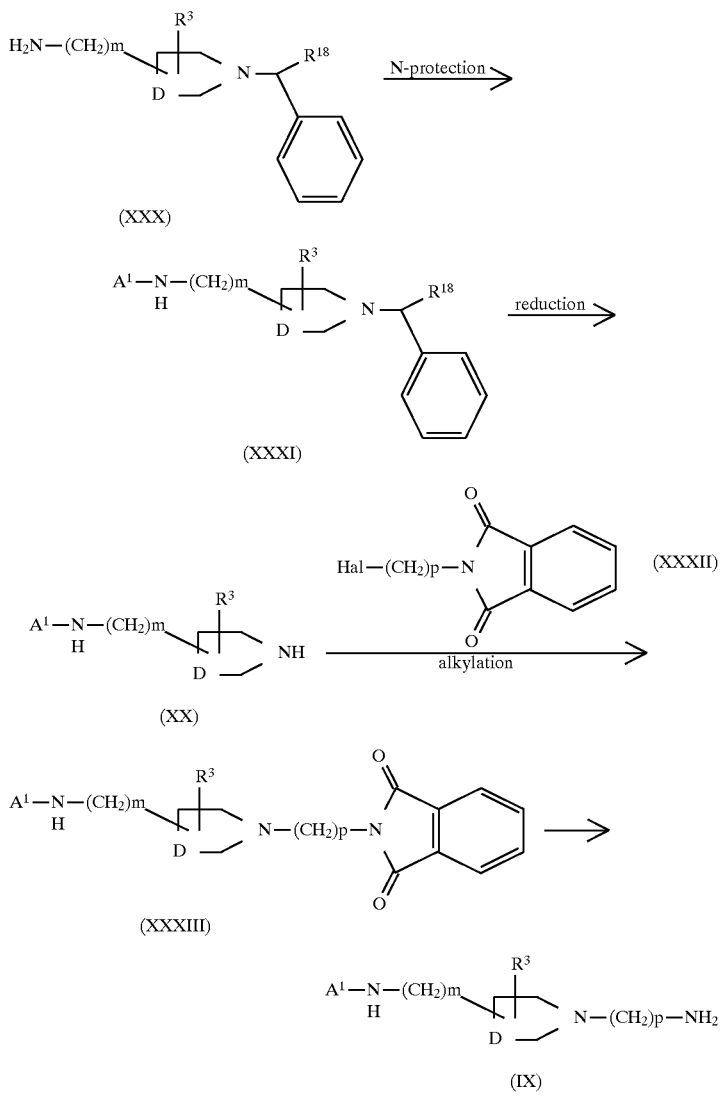

wherein $R^{18}$ is hyrogen or lower alkyl, and $A^1$, D, $R^3$, m, p and Hal are as defined above.

That is, the compound (XX) is produced by reacting a starting compound (XXX) with an amino-protecting reagent in a suitable solvent to give compound (XXXI), and subjecting the resulting compound to reduction in a suitable solvent in the presence of a catalyst under a hydrogen atmosphere or using a suitable hydrogen source. Then, compound (XX) is subjected to alkylation with compound (XXXII) in a suitable solvent in the presence of a base to give compound (XXXIII), and the resulting compound is reacted in a suitable solvent in the presence of a base to give compound (IX).

The amino-protecting reagent to be used for the reaction with compound (XXX) includes, for example, di-tert-butyl dicarbonate and 2-tert-butoxycarbonyloxyimino-2-phenylacetonitrile. The solvent to be used includes, for example, tetrahydrofuran, acetone, ethyl acetate, methylene chloride, chloroform, dioxane, water and mixed solvents thereof. While the reaction temperature varies depending on the kind of solvent to be used, it is generally from −20° C. to 50° C., and the reaction time which varies depending on the kind of reaction temperature is generally 1–24 hr.

The solvent to be used for reduction of compound (XXXI) includes, for example, methanol, ethanol, propanol, isopropyl alcohol, butanol, formic acid, acetic acid, water, tetrahydrofuran, dimethyl sulfoxide and mixed solvents thereof. The catalyst to be used includes, for example, palladium-carbon, Raney-nickel and platinum oxide. The hydrogen source to be used includes, for example, hydrazine hydrate, cyclohexene, 1,4-cyclohexadiene, formic acid and ammonium formate. While the reaction temperature varies depending on the kind of solvent to be used, it is generaly from 0° C. to the boiling point of the solvent to be used, and the reaction time which varies depending on the kind of reaction temperature is generally 1–6 hr.

The solvent to be used for alkylation of compound (XX) includes, for example, methylene chloride, 1,2-dichloroethane, chloroform, methanol, ethanol, propanol, isopropyl alcohol, butanol, tetrahydrofuran, diethyl ether, dioxane, dimethylformamide, dimethyl sulfoxide, benzene, toluene, xylene and mixed solvents thereof. The base to be used may be, for example, sodium carbonate, potassium carbonate, sodium hydrogencarbonate, potassium hydrogencarbonate, sodium hydroxide, potassium hydroxide, triethylamine, diisopropylethylamine or pyridine. While the reaction temperature varies depending on the kind of solvent to be used, it is generally from 0° C. to 140° C., and the reaction time which varies depending on the kind of reaction temperature is generally 1–24 hr.

The solvent to be used for reaction of compound (XXXIII) includes, for example, methanol, ethanol, propanol, isopropyl alcohol and butanol. The base to be used may be, for example, hydrazine hydrate, methylhydrazine, phenylhydrazine and methylamine. While the reaction temperature varies depending on the kind of solvent to be used, it is generally from 50° C. to the boiling point of the solvent to be used, and the reaction time which varies depending on the kind of reaction temperature is generally 1–10 hr.

METHOD 8

The compound (XXXIII) wherein p is 2–5 can be synthesized by the following route.

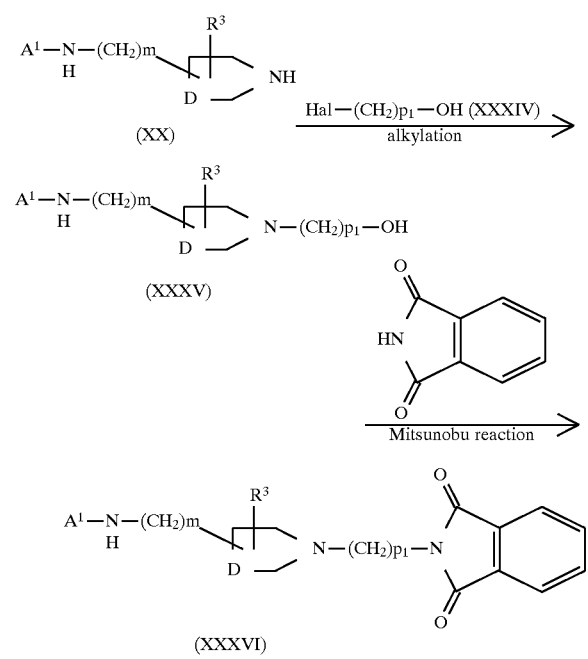

wherein $A^1$, D, $R^3$, m, pi and Hal are as defined above.

That is, the compound (XX) is subjected to alkylation with compound (XXXIV) in a suitable solvent in the presence of a base to give compound (XXXV) and Mitsunobu reaction [Synthesis, p. 1 (1988)] with phthalimide in a suitable solvent to produce compound (XXXVI).

The solvent to be used for alkylation includes, for example, methylene chloride, 1,2-dichloroethane, chloroform, methanol, ethanol, propanol, isopropyl alcohol, butanol, tetrahydrofuran, diethyl ether, dioxane, dimethylformamide, dimethyl sulfoxide, benzene, toluene and xylene. The base to be used may be, for example, sodium carbonate, potassium carbonate, sodium hydrogencarbonate, potassium hydrogencarbonate, sodium hydroxide, potassium hydroxide, triethylamine, diisopropylethylamine or pyridine. While the reaction temperature varies depending on the kind of solvent to be used, it is generally from 0° C. to 140° C., and the reaction time which varies depending on the kind of reaction temperature is generally 1–24 hr.

The solvent to be used for Mitsunobu reaction includes, for example, tetrahydrofuran and dioxane. The reaction temperature is generally 0°–40° C., and the reaction time which varies depending on the kind of reaction temperature is generally 1–24 hr.

METHOD 9

A compound (VIII) wherein A is a group of the formula (II-a)–(II-f), and B is a group of the formula —$X^1$—$N(R^6)$ ($R^7$) can be synthesized by the following route.

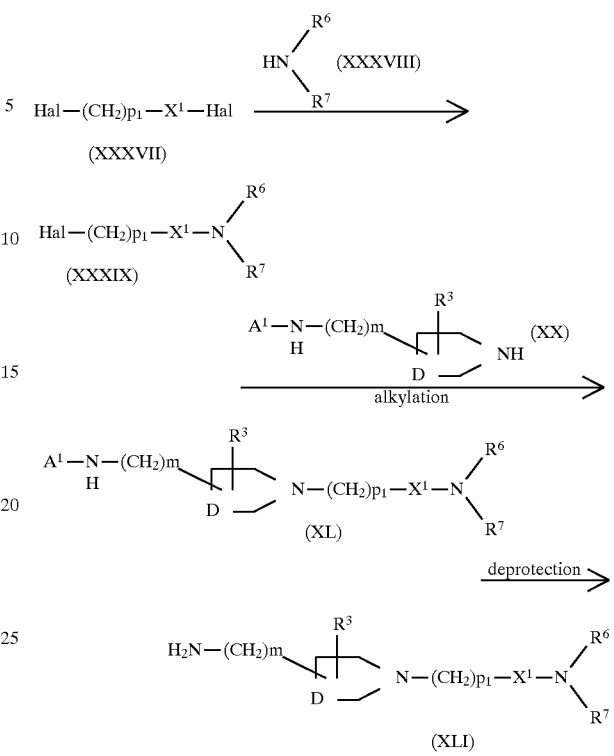

wherein $A^1$, D, $R^3$, $R^6$, $R^7$, m, pi, $X^1$ and Hal are as defined above.

That is, the compound (XLI) is produced by reacting compound (XXXVII) and compound (XXXVIII) in a suitable solvent in the presence of a base to give compound (XXXIX), and subjecting the resulting compound to alkylation with compound (XX) in a suitable solvent in the presence of a base to give compound (XL), followed by deprotection according to Method 2.

The solvent to be used for the reaction of compound (XXXVII) and compound (XXXVIII) includes, for example, methanol, ethanol, propanol, ethyl acetate, tetrahydrofuran, dioxane, dimethylformamide, dimethyl sulfoxide, acetone, methyl ethyl ketone, methylene chloride, chloroform, benzene, toluene and xylene. The base to be used may be, for example, sodium carbonate, potassium carbonate, sodium hydrogencarbonate, potassium hydrogencarbonate, sodium hydroxide, potassium hydroxide, triethylamine, diisopropylethylamine or pyridine. While the reaction temperature varies depending on the kind of solvent to be used, it is generally from −20° C. to 30° C., and the reaction time which varies depending on the kind of reaction temperature is generally 20 min–5 hr.

The solvent to be used for alkylation of compound (XX) includes, for example, methylene chloride, 1,2-dichloroethane, chloroform, methanol, ethanol, propanol, isopropyl alcohol, butanol, tetrahydrofuran, diethyl ether, dioxane, dimethylformamide, dimethyl sulfoxide, benzene, toluene, xylene and mixed solvents thereof. The base to be used may be, for example, sodium carbonate, potassium carbonate, sodium hydrogencarbonate, potassium hydrogencarbonate, sodium hydroxide, potassium hydroxide, triethylamine, diisopropylethylamine or pyridine. While the reaction temperature varies depending on the kind of solvent to be used, it is generally from 0° C. to 140° C., and the reaction time which varies depending on the kind of reaction temperature is generally 1–24 hr.

METHOD 10

A compound (VIII) wherein A is a group of the formula (II-a)–(II-f), and B is a group of the formula –Het can be synthesized by the following route.

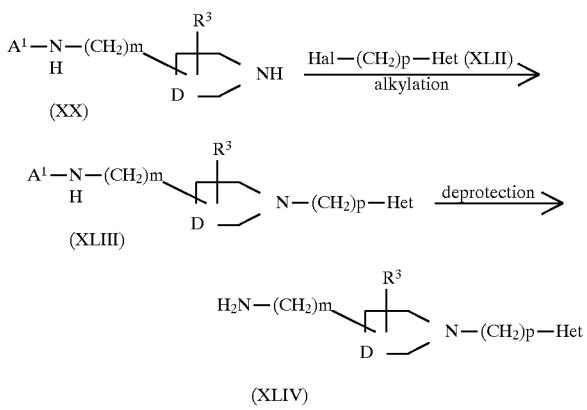

wherein $A^1$, D, $R^3$, m, p, Hal and Het are as defined above.

That is, the compound (XLIV) is produced by subjecting the compound (XX) to alkylation with compound (XLII) in a suitable solvent in the presence of a base to give compound (XLIII) and deprotection according to Method 2.

The solvent to be used for the alkylation includes, for example, methanol, ethanol, propanol, ethyl acetate, tetrahydrofuran, dioxane, dimethylformamide, dimethyl sulfoxide, acetone, methyl ethyl ketone, methylene chloride, chloroform, benzene, toluene, xylene and mixed solvents thereof. The base to be used may be, for example, sodium carbonate, potassium carbonate, sodium hydrogencarbonate, potassium hydrogencarbonate, sodium hydroxide, potassium hydroxide, triethylamine, diisopropylethylamine or pyridine. While the reaction temperature varies depending on the kind of solvent to be used, it is generally from 0° C. to 140° C., and the reaction time which varies depending on the kind of reaction temperature is generally 1–24 hr.

METHOD 11

A compound (VIII) wherein A is a group of the formula (III) can be synthesized in the same manner as in the synthesis of a compound wherein A is expressed by the formula (II-a)–(II-f), by the use of a compound of the formula

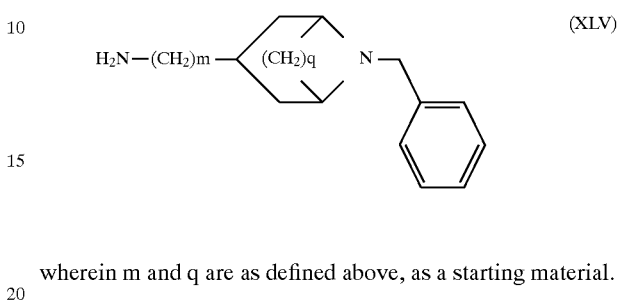

wherein m and q are as defined above, as a starting material.

METHOD 12

The compound of the formula (I) can be also synthesized by the following route.

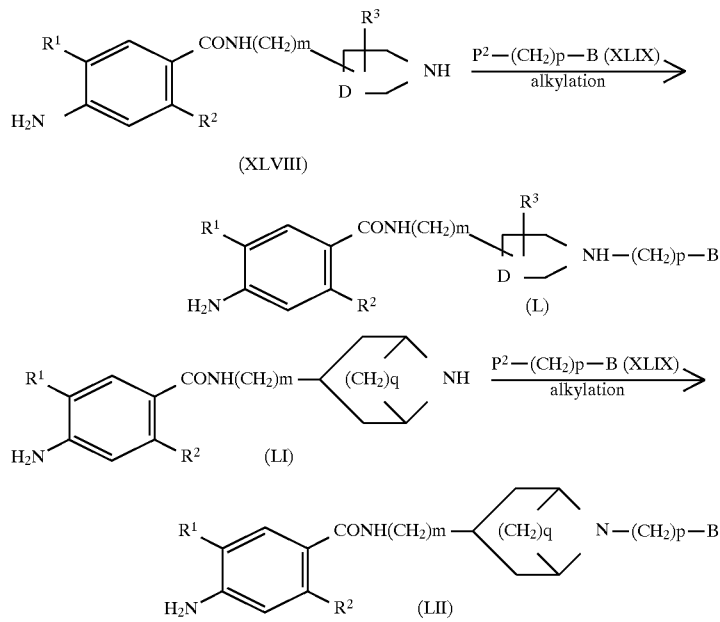

wherein $p^2$ is halogen (e.g., chlorine, bromine, iodine, etc.) or sulfonyloxy (e.g., methanesulfonyloxy, p-toluenesulfonyloxy, trifluoromethanesulfonyloxy, etc.), and D, $R^1$, $R^2$, $R^3$, m, p, q, B and Hal are as defined above.

That is, the compound is produced by reacting intermediates of compound (XLVIII) and compound (LI) with compound (XLIX) in a suitable solvent in the presence of a base.

The solvent to be used for the alkylation includes, for example, methylene chloride, 1,2-dichloroethane, chloroform, methanol, ethanol, propanol, isopropyl alcohol, butanol, tetrahydrofuran, diethyl ether, dioxane, dimethylformamide, dimethyl sulfoxide, benzene, toluene and xylene. The base to be used may be, for example, sodium carbonate, potassium carbonate, sodium hydrogencarbonate, potassium hydrogencarbonate, sodium hydroxide, potassium hydroxide, triethylamine, diisopropylethylamine or pyridine. While the reaction temperature varies depending on the kind of solvent to be used, it is generally from 0° C. to 140° C., and the reaction time which varies depending on the kind of reaction temperature is generally 1–24 hr.

The intermediates of compound (XLVIII) and compound (LI) can be produced according to Japanese Patent Unexamined Publication Nos. 211685/1992, 262724/1993 and others.

METHOD 13

The compound of the formula (I) can be also synthesized by the following route.

The solvent to be used for the alkylation of compound (XLVIII) includes, for example, methylene chloride, 1,2-dichloroethane, chloroform, methanol, ethanol, propanol, isopropyl alcohol, butanol, tetrahydrofuran, diethyl ether, dioxane, dimethylformamide, dimethyl sulfoxide, benzene, toluene, xylene and mixed solvents thereof. The base to be used may be, for example, sodium carbonate, potassium carbonate, sodium hydrogencarbonate, potassium hydrogencarbonate, sodium hydroxide, potassium hydroxide, triethylamine, diisopropylethylamine or pyridine. While the reaction temperature varies depending on the kind of solvent to be used, it is generally from 0° C. to 140° C., and the reaction time which varies depending on the kind of reaction temperature is generally 1–24 hr.

The solvent to be used for the reaction from compound (LIII) to compound (LIV) includes, for example, methanol,

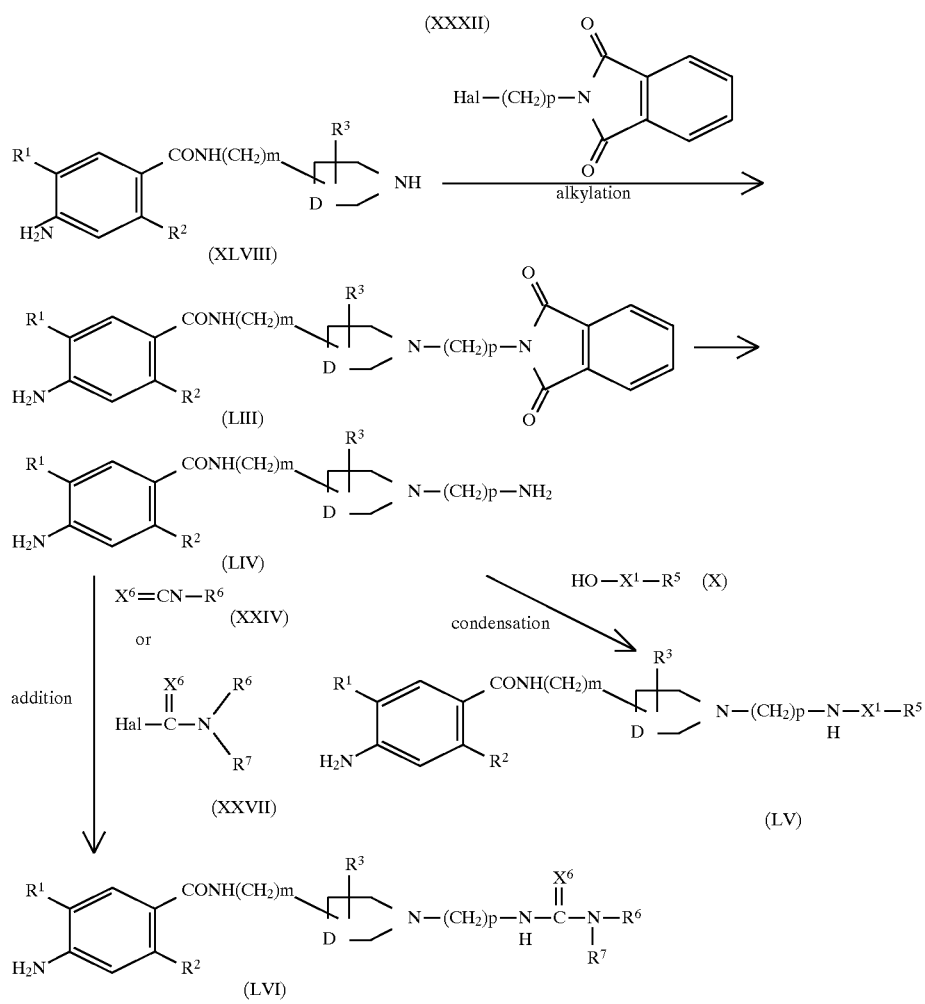

wherein D, $R^1$, $R^2$, $R^3$, $R^5$, $R^6$, $R^7$, $X^1$, $X^6$, m, p and Hal are as defined above.

That is, the compound (XLVIII) is subjected to alkylation with compound (XXXII) in a suitable solvent in the presence of a base to give compound (LIII) and reacting the obtained compound in a suitable solvent in the presence of a base to give compound (LIV). Then, the compound is reacted with compound (X), compound (XXIV), compound (XXVII) and the like to give compound (LV) or compound (LVI).

ethanol, propanol, isopropyl alcohol and butanol. The base to be used may be, for example, hydrazine hydrate, methylhydrazine, phenylhydrazine and methylamine. While the reaction temperature varies depending on the kind of solvent to be used, it is generally from 50° C. to the boiling point of the solvent to be used, and the reaction time which varies depending on the kind of reaction temperature is generally 1–10 hr.

The reaction with compound (X) is carried out according to Method 2, and the reaction with compound (XXIV) or compound (XXVII) is carried out according to Method 5 or Method 6, whereby compound (LV) or compound (LVI) can be produced, respectively.

METHOD 14

The compound of the formula (I) can be also synthesized by the following route.

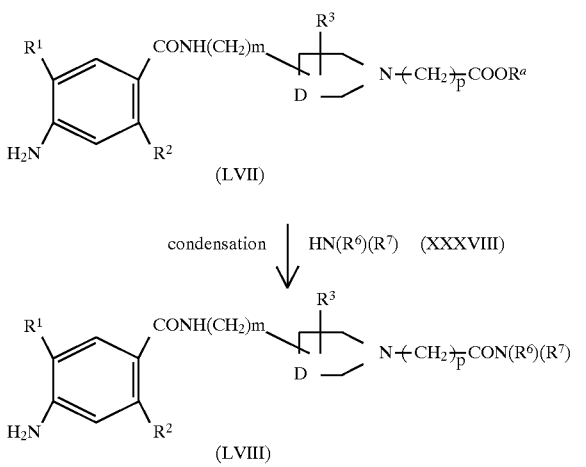

(LVII)

condensation ↓ HN(R⁶)(R⁷)  (XXXVIII)

(LVIII)

wherein $R^a$ is hydrogen or lower alkyl, and D, $R^1$, $R^2$, $R^3$, $R^6$, $R^7$, m and p are as defined above.

That is, the compound can be obtained by reacting carboxylic acid represented by compound (LVII) or a reactive derivative thereof with compound (XXXVIII) in a suitable solvent.

When compound (LVII) is a free carboxylic acid, the reaction is carried out using a routine condensing agent. Examples of the condensing agent include dicyclohexylcarbodiimide, 1-ethyl-3-(3-dimethylaminopropyl)carbodiimide hydrochloride, carbonyldiimidazole, benzotriazol-1-yloxytris(dimethylamino)phosphonium hexafluorophosphate, N-methyl-2-chloropyridinium iodide and the like. The instant reaction is preferably carried out by condensing in the presence of an organic base such as 1-hydroxybenzotriazole and N-methylmorpholine. The solvent to be used may be, for example, dimethylformamide, dimethyl sulfoxide, methylene chloride, tetrahydrofuran, acetonitrile, dioxane and benzene. While the reaction temperature varies depending on the kind of solvent to be used, it is generally from −20° C. to 50° C., and the reaction time which varies depending on the kind of reaction temperature is generally 1–24 hr.

When compound (LVII) is reactive derivative of carboxylic acid such as acid halide, acid anhydride, mixed acid anhydride and ester, the reaction is carried out in an inert solvent in the presence of a base as necessary. The base to be used as necessary is, for example, sodium carbonate, potassium carbonate, sodium hydrogencarbonate, potassium hydrogencarbonate, sodium hydroxide, potassium hydroxide, triethylamine, diisopropylethylamine or pyridine. Examples of the inert solvent to be used include, for example, methylene chloride, chloroform, ethyl acetate, diethyl ether, tetrahydrofuran, dioxane, acetonitrile, benzene, toluene and mixed solvent thereof. While the reaction temperature varies depending on the kind of solvent to be used, it is generally from −30° C. to 50° C., and the reaction time which varies depending on the kind of reaction temperature is generally 1–24 hr.

The compound (LVII) can be produced according to Japanese Patent Unexamined Publication No. 262724/1993.

METHOD 15

A quaternary ammonium salt of compound of the formula (I) can be synthesized by the following route.

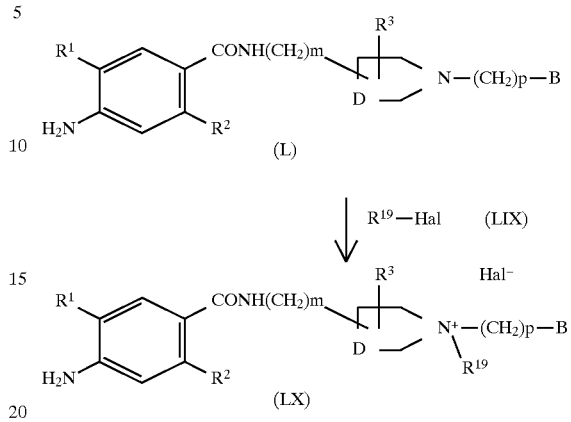

wherein $R^{19}$ is lower alkyl, and D, $R^1$, $R^2$, $R^3$, m, p, B and Hal are as defined above.

That is, the salt can be produced, for example, by reacting compound (L) and compound (LIX) in a suitable solvent.

The solvent to be used includes, for example, methylene chloride, 1,2-dichloroethane, chloroform, methanol, ethanol, propanol, isopropyl alcohol, butanol, tetrahydrofuran, diethyl ether, dioxane, benzene, toluene and xylene. While the reaction temperature varies depending on the kind of solvent to be used, it is generally 0°–40° C., and the reaction time which varies depending on the kind of reaction temperature is generally 1–24 hr.

The compound of the formula (I) thus obtained can be separated and purified from reaction mixture by a method known per se, such as recrystallization, column chromatography, and the like.

METHOD 16

The compound (VII) can be produced according to the method described in Journal of Medicinal Chemistry, vol. 34, pp. 616–624 (1991).

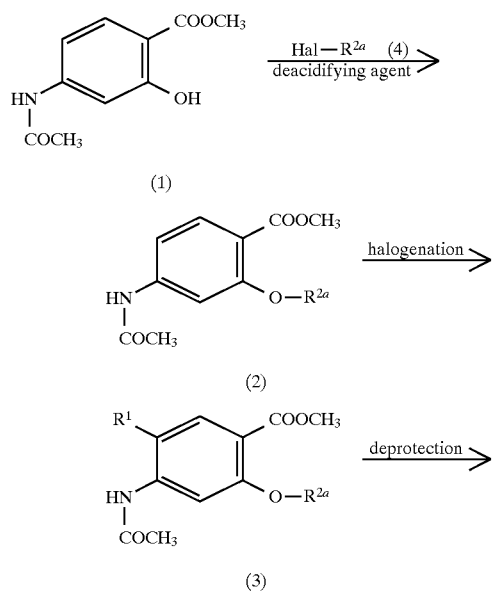

-continued

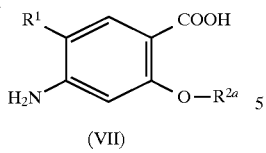

(VII)

wherein $R^{2a}$ is lower alkyl, substituted lower alkyl, cycloalkyl or cycloalkylalkyl, and $R^1$ and Hal are as defined above.

That is, compound (1) is reacted with compound (4) to give compound (2). This compound is halogenated to give compound (3), which is subjected to deprotection to give compound (VII).

The deacidifying agent to be used for the reaction of compound (1) and compound (4) is exemplified by potassium carbonate, sodium carbonate and the like. The solvent to be used for this reaction may be, for example, dimethylformamide or dimethyl sulfoxide. The reaction temperature is from room temperature to 100° C., and the reaction time is 2–10 hr.

Examples of halogenating agent to be used for halogenation of compound (2) include, for example, N-bromosuccinimide and N-chlorosuccinimide. The solvent to be used for the instant reaction includes, for example, dimethylformamide, dimethyl sulfoxide, toluene and acetonitrile. The reaction temperature is from room temperature to 100° C., and the reaction time is 1–10 hr.

The reagent to be used for deprotection of compound (3) may be, for example, aqueous sodium hydroxide solution and aqueous potassium hydroxide solution. This reaction may be carried out in a solvent such as methanol, ethanol, isopropyl alcohol and the like. The reaction temperature is the refluxing temperature of solvent to be used, and the reaction time is 3–10 hr.

When the compound of the formula (I) of the present invention and pharmaceutically acceptable salts thereof have asymmetric carbon, they are generally produced as racemates which can be optically resolved into optical isomers by a conventional method such as preparative recrystallization and chromatography. Also, the use of optically active starting compound results in optical isomers. When compound has two or more asymmetric carbons, they can be obtained as individual diastereomers or mixtures thereof which can be separated by a conventional method such as preparative recrystallization and chromatography.

When the cyclic amine of the formula (II) of the compound of the present invention is that of the formula (II-b), its optical isomer(s) can be produced, for example, from optically active carboxylate obtained by the method described in Journal of Medicinal Chemistry, vol. 33, pp. 71–77 (1990) and the like, or by the route shown in the following Method 17.

METHOD 17

A compound (VIII) wherein m is 1, A is a group of the formula (II-b) and the absolute configuration at the 3-position of pyrrolidine is R-configuration can be synthesized by the following route.

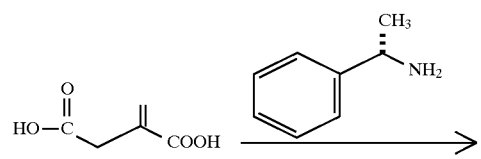

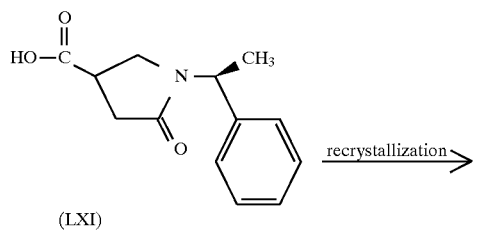
(LXI)

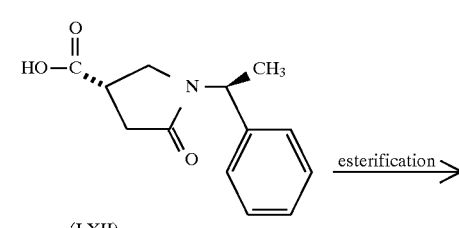
(LXII)

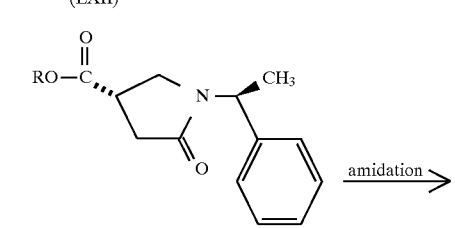
(LXIII)

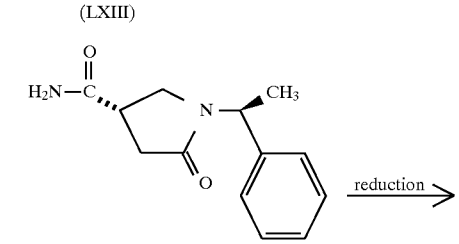
(LXIV)

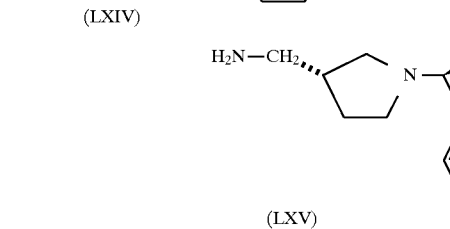
(LXV)

wherein R is lower alkyl.

That is, itaconic acid is used as a starting compound and reacted with (S)-1-phenylethylamine without solvent or in a suitable solvent to give compound (LXI), followed by repetitive recrystallization in a suitable solvent to give optically pure diastereomer compound (LXII). This compound is reacted in an alcohol solvent in the presence of an acid catalyst to give compound (LXIII), which is subjected to amidation in a suitable solvent in the presence of ammonia gas to give compound (LXIV), followed by reaction with a suitable reducing agent in a suitable solvent to give compound (LXV).

The solvent to be used for the reaction of itaconic acid and (S)-1-phenylethylamine is exemplified by methanol, ethanol, propanol, acetone, ethyl acetate, benzene, toluene, tetrahydrofuran, dioxane, 1,3-dimethylimidazolidinone, dimethylformamide, dimethyl sulfoxide and the like. While the reaction temperature varies depending on the kind of solvent to be used, it is generally from 30° C. to the refluxing temperature of the solvent, and the reaction time which varies depending on the kind of reaction temperature is generally 1–24 hr.

The solvent to be used for the recrystallization of compound (LXI) is exemplified by water, methanol, ethanol, propanol, isopropyl alcohol, butanol, acetone, ethyl acetate, benzene, toluene, dioxane, mixed solvents thereof and the like.

The alcohol solvent to be used for the esterification of compound (LXII) is exemplified by methanol, ethanol, propanol, butanol and the like. The acid catalyst to be used may be, for example, hydrochloric acid, sulfuric acid, The optically active compound (VIII) thus obtained can be separated and purified from reaction mixture by a method known per se, such as recrystallization, column chromatography, and the like.

METHOD 18

A compound (I) wherein A is a group of the formula (II-a)–(II-f), and B is a group of the formula —N($R^{10}$)($R^{11}$) wherein $R^{10}$ is lower alkyl, cycloalkyl, cycloalkylalkyl, aralkyl, substituted aralkyl, heteroarylalkyl or substituted heteroarylalkyl, and $R^{11}$ is hydrogen, can be synthesized by the following route.

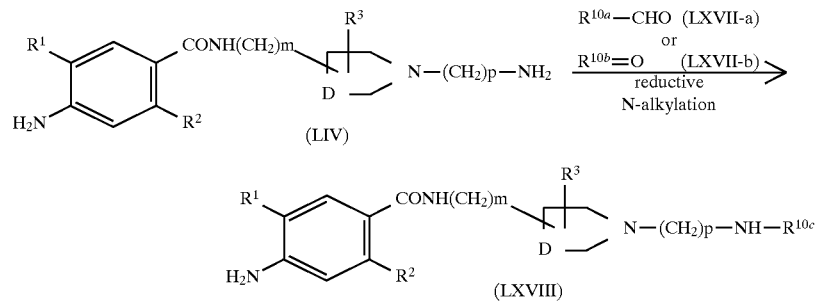

p-toluenesulfonic acid or thionyl chloride. The reaction temperature is generally from 0° C. to the refluxing temperature of the solvent, and the reaction time which varies depending on the kind of reaction temperature is generally 1–24 hr.

The solvent to be used for the amidation of compound (LXIII) includes, for example, methanol, ethanol, propanol, isopropyl alcohol, butanol, ethyl acetate, benzene, toluene and dioxane. The reaction temperature is generally from −20° C. to 50° C., and the reaction time which varies depending on the kind of reaction temperature is generally 1–24 hr.

The solvent to be used for the reduction of compound (LXIV) includes, for example, methanol, ethanol, propanol, isopropyl alcohol, benzene, toluene, tetrahydrofuran, dioxane and diethyl ether. The reducing agent to be used includes, for example, lithium aluminum hydride, diborane, diisobutylaluminum hydride, sodium borohydride-sulfuric acid and sodium borohydride-boron trifluoride. The reaction temperature is generally from −30° C. to the refluxing temperature of the solvent, and the reaction time which varies depending on the kind of reaction temperature is generally 1–24 hr.

The compound wherein the absolute configuration at the 3-position of pyrrolidine is S can be synthesized in the same manner as above using itaconic acid and (R)-1-phenylethylamine as starting compounds.

wherein $R^{10\ a}$ is hydrogen, alkyl having 1 to 5 carbon atoms, cycloalkylalkyl, aralkyl, substituted aralkyl, heteroarylalkyl or substituted heteroarylalkyl, $R^{10\ b}$ is alkyl having 1 to 6 carbon atoms or cycloalkyl, $R^{10\ c}$ is alkyl having 1 to 6 carbon atoms, cycloalkyl, cycloalkylalkyl, aralkyl, substituted aralkyl, heteroarylalkyl or substituted heteroarylalkyl, and D, $R^1$, $R^2$, $R^3$, m and p are as defined above.

That is, compound (LXVIII) can be produced by subjecting compound (LIV) to reductive N-alkylation with compound (LXVII-a) or compound (LXVII-b) in a suitable solvent.

The solvent to be used for the reductive N-alkylation includes, for example, water, methanol, ethanol, propanol, ethyl acetate, tetrahydrofurn, dioxane, dimethylformamide and acetic acid. The reductive N-alkylating agent to be used includes, for example, sodium cyanoborohydride, sodium borohydride, formic acid and sodium formate. While the reaction temperature varies depending on the kind of solvent, it is from 0° C. to 80° C., and the reaction time which varies depending on the reaction temperature is generally 1–24 hr.

METHOD 19

A compound (I) wherein A is a group of the formula (II-a)–(II-f), B is a group of the formula —N($R^{10}$)($R^{11}$), and $R^{10}$ and $R^{11}$ are the same or different and each is lower alkyl, cycloalkyl, cycloalkylalkyl, aralkyl, substituted aralkyl, heteroarylalkyl or substituted heteroarylalkyl can be synthesized by the following route.

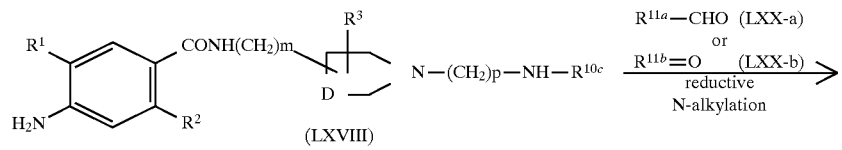

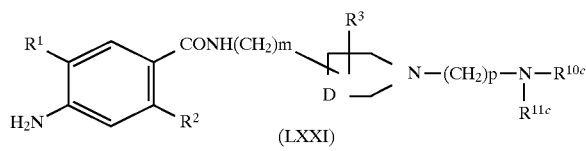

(LXXI)

wherein $R^{11\ a}$ is hydrogen, alkyl having 1 to 5 carbon atoms, cycloalkylalkyl, aralkyl, substituted aralkyl, heteroarylalkyl or substituted heteroarylalkyl, $R^{11\ b}$ is alkyl having 1 to 6 carbon atoms or cycloalkyl, $R^{11\ c}$ is alkyl having 1 to 6 carbon atoms, cycloalkyl, cycloalkylalkyl, aralkyl, substituted aralkyl, heteroarylalkyl or substituted heteroarylalkyl, and D, $R^1$, $R^2$, $R^3$, $R^{10\ c}$, m and p are as defined above.

That is, compound (LXXI) can be produced by subjecting compound (LXVIII) to reductive N-alkylation with compound (LXX-a) or compound (LXX-b) in a suitable solvent.

The solvent to be used for the reductive N-alkylation includes, for example, water, methanol, ethanol, propanol, ethyl acetate, tetrahydrofuran, dioxane, dimethylformamide and acetic acid. The reductive N-alkylating agent to be used includes, for example, sodium cyanoborohydride, sodium borohydride, formic acid and sodium formate. While the reaction temperature varies depending on the kind of solvent, it is from 0° C. to 80° C., and the reaction time which varies depending on the reaction temperature is generally 1–24 hr.

METHOD 20

The compound (XLVIII) which is an intermediate shown in Method 12 can be synthesized by the following route.

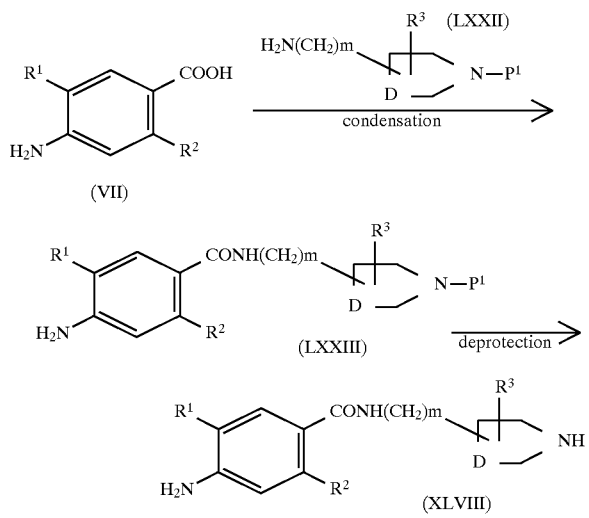

wherein $P^1$ is an urethane type amino-protecting group such as tert-butoxycarbonyl, benzyloxycarbonyl, isopropyloxycarbonyl and the like, and D, $R^1$, $R^2$, $R^3$ and m are as defined above.

That is, compound (XLVIII) can be produced by condensing a carboxylic acid represented by compound (VII) or its reactive derivative with compound (LXXII) in a suitable solvent to give compound (LXXIII) and deprotection.

When compound (VII) is a free carboxylic acid, condensation is carried out using a routine condensing agent. Examples of the condensing agent include, for example, dicyclohexylcarbodiimide, 1-ethyl-3-(3-dimethylaminopropyl)carbodiimide hydrochloride, carbonyldiimidazole and N-methyl-2-chloropyridinium iodide. This reaction is preferably carried out in the presence of an organic base such as 1-hydroxybenzotriazole, N-methylmorpholine and the like. The solvent to be used includes, for example, dimethylformamide, dimethyl sulfoxide, methylene chloride, tetrahydrofuran, acetonitrile, dioxane and benzene. While the reaction temperature varies depending on the kind of solvent, it is generally from −20° C. to 50° C., and the reaction time which varies depending on the reaction temperature is generally 1–24 hr.

When compound (VII) is a reactive derivative of carboxylic acid such as acid halide, acid anhydride, mixed acid anhydride and ester, condensation is generally carried out in a suitable solvent in the presence of a base as necessary. Examples of the base to be used as necessary include, for example, sodium carbonate, potassium carbonate, sodium hydrogencarbonate, potassium hydrogencarbonate, sodium hydroxide, potassium hydroxide, triethylamine, diisopropylethylamine and pyridine. The solvent to be used includes, for example, methylene chloride, chloroform, ethyl acetate, diethyl ether, tetrahydrofuran, dioxane, acetonitrile, benzene, toluene and mixed solvents thereof. While the reaction temperature varies depending on the kind of solvent, it is generally from −30° C. to 50° C., and the reaction time which varies depending on the reaction temperature is generally 1–24 hr.

The deprotection of compound (LXXIII) can be carried out by a method generally used for removing amino-protecting group. For example, when $P^1$ is tert-butoxycarbonyl, the compound is treated with an acid in a suitable solvent as necessary. The acid to be used in this reaction may be any as long as amide bonding is not hydrolyzed, and may be, for example, hydrogen chloride, sulfuric acid, trifluoroacetic acid or trifluoromethanesulfonic acid. The solvent to be used as necessary includes, for example, methanol, ethanol, propanol, isopropyl alcohol, tetrahydrofuran, acetone, ethyl acetate, methylene chloride, chloroform, dioxane, water and mixed solvents thereof. The reaction temperature is from ice-cooling to refluxing temperature of solvent, preferably room temperature, and the reaction time is from 30 min to 5 hr.

METHOD 21

The compound (LIII) can be also synthesized by the following route.

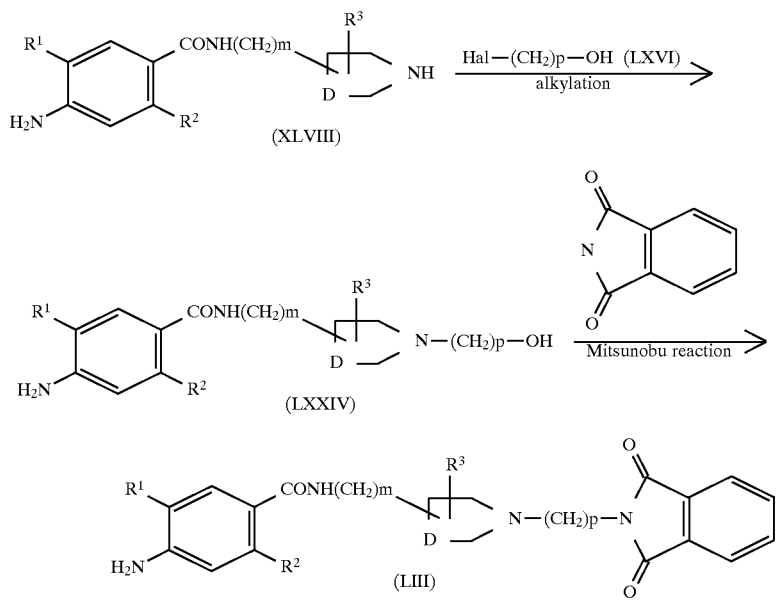

wherein D, $R^1$, $R^2$, $R^3$, m, p and Hal are as defined above.

That is, compound (LIII) can be produced by subjecting compound (XLVIII) and compound (LXVI) to alkylation in a suitable solvent in the presence of a base to give compound (LXXIV) and subjecting this compound to Mitsunobu reaction [Synthesis, p. 1 (1981)] with phthalimide in a suitable solvent.

The solvent to be used for the alkylation includes, for example, methylene chloride, 1,2-dichloroethane, chloroform, methanol, ethanol, propanol, isopropyl alcohol, butanol, tetrahydrofuran, diethyl ether, dioxane, dimethylformamide, dimethyl sulfoxide, benzene, toluene and xylene. Examples of the base to be used include sodium carbonate, potassium carbonate, sodium hydrogencarbonate, potassium hydrogencarbonate, sodium hydroxide, potassium hydroxide, triethylamine, diisopropylethylamine, pyridine and the like. While the reaction temperature varies depending on the kind of solvent, it is generally from 0° C. to 140° C., and the reaction time which varies depending on the reaction temperature is generally 1–24 hr.

The reagent used for the Mitsunobu reaction includes, for example, azodicarboxylate (e.g., ethyl azodicarboxylate and the like)-triphenylphosphine.

The solvent to be used for the Mitsunobu reaction includes, for example, tetrahydrofuran and dioxane. The reaction temperature is generally from −20° C. to 40° C., and the reaction time which varies depending on the reaction temperature is generally 1–24 hr.

METHOD 22

The compound (XLIX) which is an intermediate shown in Method 12 can be synthesized by the following route.

$$P^2-(CH_2)p-P^2 \xrightarrow{H-B \ (LXXVI)} P^2-(CH_2)p-B$$
(LXXV) \hspace{4em} (XLIX)

wherein $P^2$, p and B are as defined above.

That is, compound (XLIX) can be produced by reacting compound (LXXV) with compound (LXXVI) in a suitable solvent in the presence of a base.

The solvent to be used for the reaction includes, for example, methylene chloride, 1,2-dichloroethane, chloroform, methanol, ethanol, propanol, isopropyl alcohol, butanol, tetrahydrofuran, diethyl ether, dioxane, dimethylformamide, dimethyl sulfoxide, benzene, toluene and xylene. Examples of the base to be used include, for-example, sodium hydride, sodium carbonate, potassium carbonate, sodium hydrogencarbonate, potassium hydrogencarbonate, sodium hydroxide, potassium hydroxide, triethylamine, diisopropylethylamine and pyridine. While the reaction temperature varies depending on the kind of solvent, it is generally from 0° C. to 140° C., and the reaction time which varies depending on the reaction temperature is generally 1–24 hr.

METHOD 23

A compound (VIII) wherein A is a group of the formula (II-a)–(II-f), and B is a group of the formula —NH($R^{10}$) or —N($R^{10}$)($R^{11}$) wherein $R^{10}$ and $R^{11}$ are the same or different and each is lower alkyl, cycloalkyl, cycloalkylalkyl, aralkyl, substituted aralkyl, heteroarylalkyl or substituted heteroarylalkyl, can be synthesized by the following route.

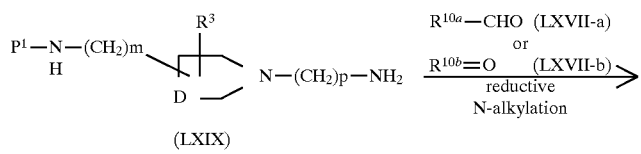

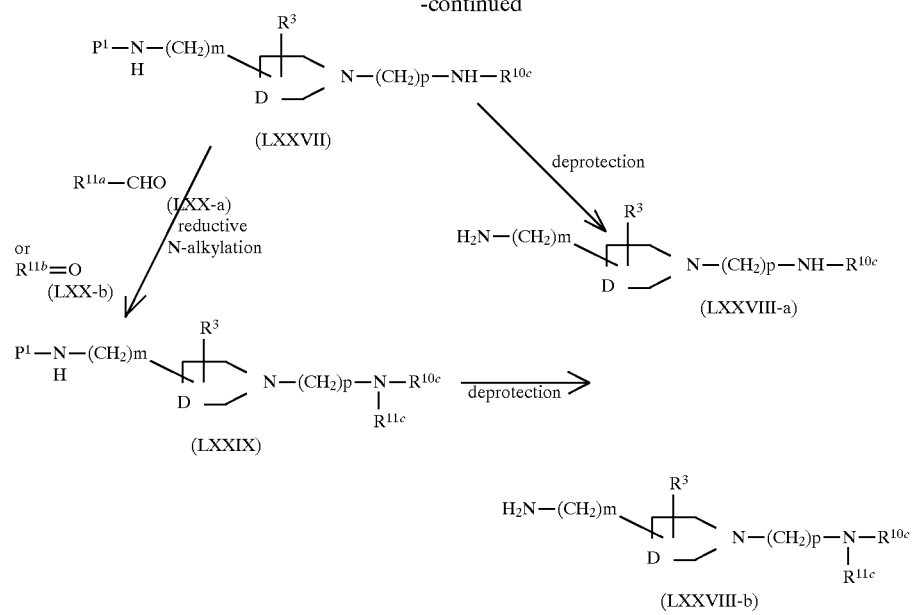

wherein D, $R^3$, $R^{10\ a}$, $R^{10\ b}$, $R^{10\ c}$, $R^{11\ a}$, $R^{11\ b}$, $R^{11\ c}$, m, $P^1$ and p are as defined above.

That is, compound (LXXVIII-a) can be produced by subjecting compound (LXIX) to reductive N-alkylation with compound (LXVII-a) or compound (LXVII-b) in a suitable solvent to give compound (LXXVII) and then deprotection. Also, compound (LXXVIII-b) can be produced by subjecting compound (LXXVII) to reductive N-alkylation with compound (LXX-a) or compound (LXX-b) in a suitable solvent to give compound (LXXIX) and then deprotection.

The solvent to be used for the reductive N-alkylation of compound (LXIX) and compound (LXXVII) includes, for example, water, methanol, ethanol, propanol, ethyl acetate, tetrahydrofuran, dioxane, dimethylformamide and acetic acid. The reductive N-alkylating agent to be used includes, for example, sodium cyanoborohydride, sodium borohydride, formic acid and sodium formate. While the reaction temperature varies depending on the kind of solvent, it is from 0° C. to 80° C., and the reaction time which varies depending on the reaction temperature is generally 1–24 hr.

The amino deprotection of compound (LXXVII) and compound (LXXIX) can be carried out by a method generally used for removing amino-protecting group. For example, when $P^1$ is tert-butoxycarbonyl, the compound is treated with an acid in a suitable solvent as necessary. The acid to be used in this reaction may be any as long as amide bonding is not hydrolyzed, and may be, for example, hydrogen chloride, sulfuric acid, trifluoroacetic acid or trifluoromethanesulfonic acid. The solvent to be used as necessary includes, for example, methanol, ethanol, propanol, isopropyl alcohol, tetrahydrofuran, acetone, ethyl acetate, methylene chloride, chloroform, dioxane, water and mixed solvents thereof. The reaction temperature is from ice-cooling to refluxing temperature of solvent, preferably room temperature, and the reaction time is from 30 min to 5 hr.

METHOD 24

A compound (VIII) wherein A is a group of the formula (II-a)–(II-f), and B is a group of the formula —$X^3$—$R^{12}$ can be synthesized by the following route.

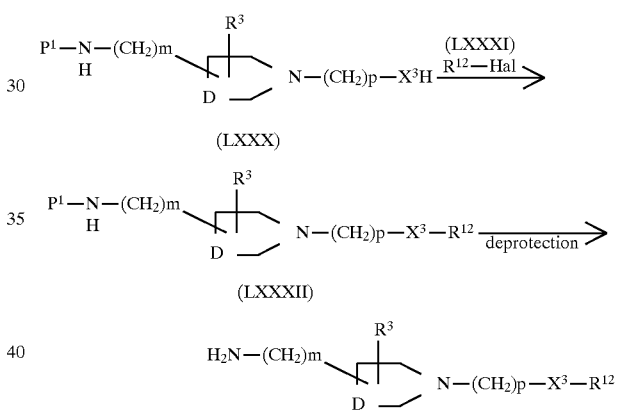

wherein D, $R^3$, $R^{12}$, m, p, $X^3$, $P^1$ and Hal are as defined above.

That is, compound (LXXXIII) can be produced by reacting compound (LXXX) with compound (LXXXI) in a suitable solvent in the presence of a base to give compound (LXXXII) and deprotection thereof.

The solvent to be used for the reaction includes, for example, methylene chloride, 1,2-dichloroethane, chloroform, methanol, ethanol, propanol, isopropyl alcohol, butanol, tetrahydrofuran, diethyl ether, dioxane, dimethylformamide, dimethyl sulfoxide, benzene, toluene and xylene. Examples of the base to be used include, for example, sodium hydride, sodium carbonate, potassium carbonate, sodium hydrogencarbonate, potassium hydrogencarbonate, sodium hydroxide, potassium hydroxide, triethylamine, diisopropylethylamine and pyridine. While the reaction temperature varies depending on the kind of solvent, it is generally from 0° C. to 140° C., and the reaction time which varies depending on the reaction temperature is generally 1–24 hr.

The deprotection of amino of compound (LXXXII) can be carried out by a method generally used for removing amino-protecting group. For example, when $P^1$ is tert-butoxycarbonyl, the compound is treated with an acid in a suitable solvent as necessary. The acid to be used in this reaction may be any as long as amide bonding is not hydrolyzed, and may be, for example, hydrogen chloride, sulfuric acid, trifluoroacetic acid or trifluoromethanesulfonic acid. The solvent to be used as necessary includes, for example, methanol, ethanol, propanol, isopropyl alcohol, tetrahydrofuran, acetone, ethyl acetate, methylene chloride, chloroform, dioxane, water and mixed solvents thereof. The reaction temperature is from ice-cooling to refluxing temperature of solvent, preferably room temperature, and the reaction time is from 30 min to 5 hr.

METHOD 25

The compound (LXXX) which is a starting compound used in Method 24 can be also synthesized by the following route.

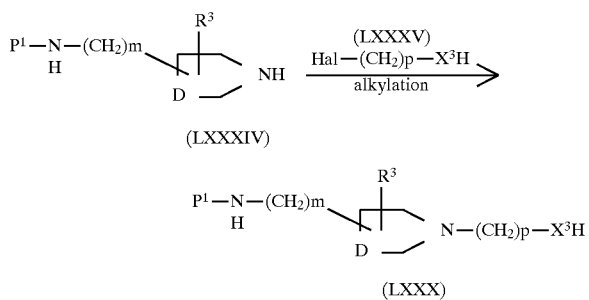

wherein D, $R^3$, m, p, $X^3$, $P^1$ and Hal are as defined above.

That is, compound (LXXX) can be produced by subjecting compound (LXXXIV) and compound (LXXXV) to alkylation in a suitable solvent in the presence of a base.

The solvent to be used for the alkylation includes, for example, methylene chloride, 1,2-dichloroethane, chloroform, methanol, ethanol, propanol, isopropyl alcohol, butanol, tetrahydrofuran, diethyl ether, dioxane, dimethylformamide, dimethyl sulfoxide, benzene, toluene and xylene. Examples of the base to be used include, for example, sodium carbonate, potassium carbonate, sodium hydrogencarbonate, potassium hydrogencarbonate, sodium hydroxide, potassium hydroxide, triethylamine, diisopropylethylamine and pyridine. While the reaction temperature varies depending on the kind of solvent, it is generally from 0° C. to 140° C., and the reaction time which varies depending on the reaction temperature is generally 1–24 hr.

METHOD 26

A compound (VIII) wherein A is a group of the formula (II-a)–(II-f) can be synthesized by the following route.

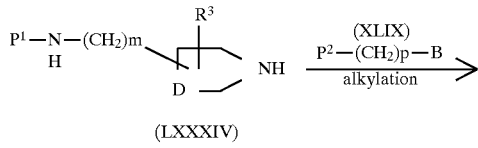

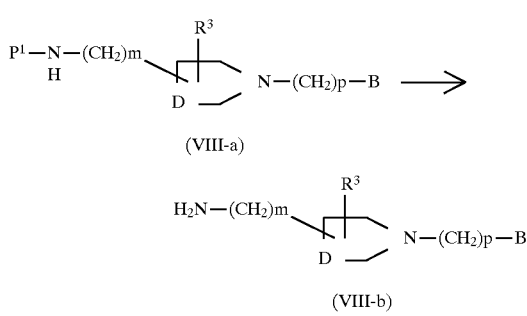

wherein D, $R^3$, p, m, $p^2$, $P^1$ and B are as defined above.

That is, compound (VIII-b) can be produced by subjecting compound (LXXXIV) to alkylation with compound (XLIX) in a suitable solvent in the presence of a base to give compound (VIII-a) and deprotection.

The solvent to be used for the alkylation includes, for example, methylene chloride, 1,2-dichloroethane, chloroform, methanol, ethanol, propanol, isopropyl alcohol, butanol, tetrahydrofuran, diethyl ether, dioxane, dimethylformamide, dimethyl sulfoxide, benzene, toluene and xylene. Examples of the base to be used include, for example, sodium carbonate, potassium carbonate, sodium hydrogencarbonate, potassium hydrogencarbonate, sodium hydroxide, potassium hydroxide, triethylamine, diisopropylethylamine and pyridine. While the reaction temperature varies depending on the kind of solvent, it is generally from 0° C. to 140° C., and the reaction time which varies depending on the reaction temperature is generally 1–24 hr.

The deprotection of amino of compound (VIII-a) can be carried out by a method generally used for removing amino-protecting group. For example, when $P^1$ is tert-butoxycarbonyl, the compound is treated with an acid in a suitable solvent as necessary. The acid to be used in this reaction may be, for example, hydrogen chloride, sulfuric acid, trifluoroacetic acid or trifluoromethanesulfonic acid. The solvent to be used as necessary includes, for example, methanol, ethanol, propanol, isopropyl alcohol, tetrahydrofuran, acetone, ethyl acetate, methylene chloride, chloroform, dioxane, water and mixed solvents thereof. The reaction temperature is from ice-cooling to refluxing temperature of solvent, preferably room temperature, and the reaction time is from 30 min to 5 hr.

METHOD 27

A compound (I) wherein A is a group of the formula (II-a)–(II-f) and B is a group of the formula —CS—$R^{13}$ can be synthesized by the following route.

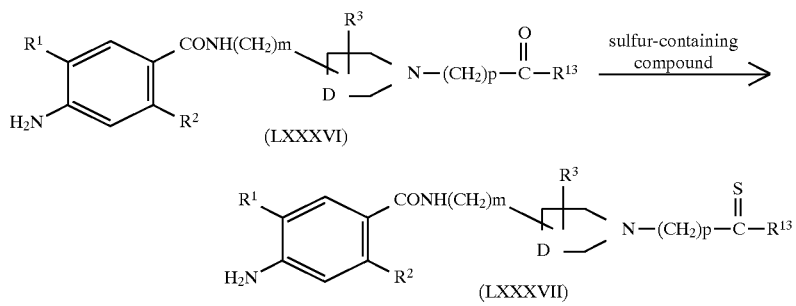

wherein D, $R^1$, $R^2$, $R^3$, $R^{13}$, m and p are as defined above.

That is, compound (LXXXVII) can be produced by reacting compound (LXXXVI) with sulfur-containing compound in a suitable solvent in the presence of an acid or base as necessary.

Examples of the sulfur-containing compound include, for example, hydrogen sulfide, phosphorus pentasulfide, sodium sulfide, potassium sulfide and Lawesson's reagent. The solvent to be used includes, for example, methanol, ethanol, acetic acid, dimethylformamide, dimethyl sulfoxide, methylene chloride, chloroform, ethyl acetate, diethyl ether, tetrahydrofuran, dioxane, acetonitrile, benzene, toluene and mixed solvents thereof. The acid to be used as necessary includes, for example, hydrochloric acid, acetic acid, sulfuric acid, phosphoric acid and hydrofluoric acid. Examples of the base to be used as necessary include, for example, ammonia, methylamine, ethylamine, dimethylamine, diethylamine, pyrrolidine, piperidine, piperazine and morpholine. While the reaction temperature varies depending on the kind of solvent, it is generally from −30° C. to 100° C., and the reaction time which varies depending on the reaction temperature is generally 1–24 hr.

METHOD 28

A compound (I) wherein A is a group of the formula (II-a)–(II-f) and B is a group of the formula —SO—$R^{13}$ or —$SO_2$—$R^{13}$ can be synthesized by the following route.

wherein D, $R^1$, $R^2$, $R^3$, $R^{13}$, m and p are as defined above.

That is, compound (LXXXIX-a) or compound (LXXXIX-b) can be produced by reacting compound (LXXXVIII) with 1 or 2 equivalent(s) of an oxidizing agent in a suitable solvent in the presence of an acid as necessary.

The oxidizing agent to be used for the reaction includes, for example, ruthenium tetraoxide, chromic acid, permanganate, m-chloroperbenzoic acid and aqueous hydrogen peroxide solution. The solvent to be used for oxidation includes, for example, formic acid, acetic acid, methylene chloride, 1,2-dichloroethane, chloroform, methanol, ethanol, propanol, isopropyl alcohol, butanol, tetrahydrofuran, diethyl ether, dioxane, dimethylformamide, dimethyl sulfoxide, benzene, toluene and xylene. Examples of the acid to be used as necessay include, for example, hydrochloric acid, sulfuric acid, p-toluenesulfonic acid and benzoic acid. While the reaction temperature varies depending on the kind of oxidizing agent to be used, it is generally from 0° C. to 140° C., and the reaction time which varies depending on the reaction temperature is generally 1–24 hr.

METHOD 29

Of the intermediate compound (XLIX) shown in Method 12, the compound of the following formula

(XC)

wherein $R^{13\ a}$ is phenyl or substituted phenyl, and p and $P^2$ are as defined above, can be particularly synthesized by the following route.

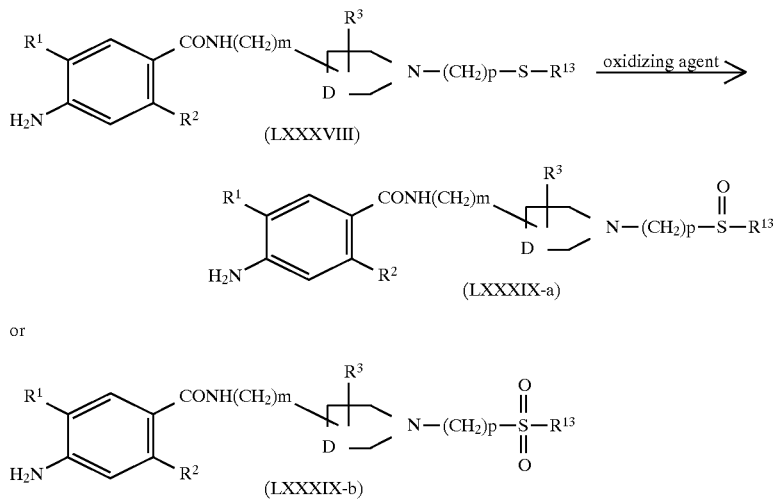

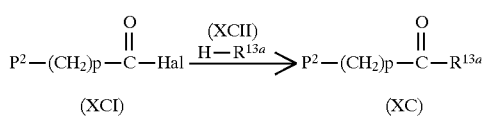

wherein $R^{13a}$, p, $P^2$ and Hal are as defined above.

That is, compound (XC) can be produced by subjecting compound (XCI) derived from carboxylic acid and compound (XCII) to Friedel-Crafts reaction in the presence of an acid.

The acid to be used for Friedel-Crafts reaction includes, for example, aluminum chloride, aluminum bromide, titanium chloride, sulfuric acid, zinc chloride, iron chloride, hydrogen fluoride and phosphoric acid. The organic solvent to be used for Friedel-Crafts reaction includes, for example, tetrahydrofuran, diethyl ether, ethylene glycol dimethyl ether, dimethylformamide, dimethyl sulfoxide, methylene chloride, 1,2-dichloroethane, chloroform, acetonitrile, nitromethane and carbon disulfide. The reaction may be carried out without solvent on demand. While the reaction temperature varies depending on the kind of solvent to be used, it is generally from −20° C. to 100° C., and the reaction time which varies depending on the reaction temperature is generally 1–24 hr.

METHOD 30

Of the intermediate compound (XLIX) shown in Method 12, the compound of the following formula

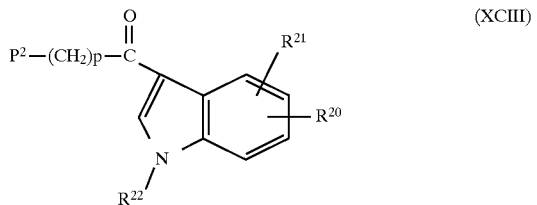

wherein $R^{20}$ and $R^{21}$ are the same or different and each is hydrogen, halogen, lower alkyl, lower alkoxy, nitro and the like, $R^{22}$ is hydrogen, lower alkyl, cycloalkylalkyl, aralkyl and the like, and p and $P^2$ are as defined above, can be particularly synthesized by the following route.

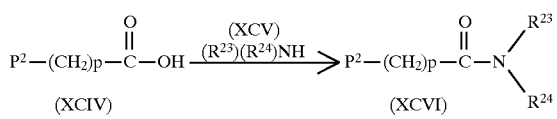

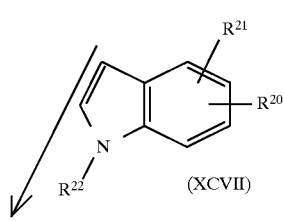

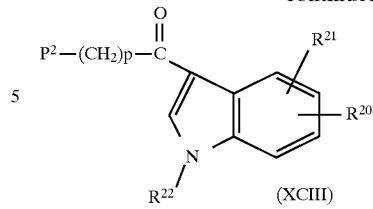

wherein $R^{23}$ and $R^{24}$ are respectively lower alkyl or form a ring such as piperidine and the like together with the adjacent nitrogen atom, and $R^{20}$, $R^{21}$, $R^{22}$, p and $P^2$ are as defined above.

That is, compound (XCIII) can be produced by reacting compound (XCV) and a carboxylic acid represented by compound (XCIV) or its reactive derivative thereof in a suitable solvent to give compound (XCVI) and reacting this compound with compound (XCVII) in a suitable solvent in the presence of phosphorus oxychloride.

When compound (XCIV) is a free carboxylic acid, the reaction is carried out using a routine condensing agent. Examples of the condensing agent include, for example, dicyclohexylcarbodiimide, 1-ethyl-3-(3-dimethylaminopropyl)carbodiimide hydrochloride, carbonyldiimidazole and N-methyl-2-chloropyridinium iodide. This reaction is preferably carried out in the presence of an organic base such as 1-hydroxybenzotriazole, N-methylmorpholine and the like. The solvent to be used includes, for example, dimethylformamide, dimethyl sulfoxide, methylene chloride, tetrahydrofuran, acetonitrile, dioxane and benzene. While the reaction temperature varies depending on the kind of solvent, it is generally from −20° C. to 50° C., and the reaction time which varies depending on the reaction temperature is generally 1–24 hr.

When compound (XCIV) is a reactive derivative of carboxylic acid, such as acid halide, acid anhydride, mixed acid anhydride and ester, condensation is generally carried out in a suitable solvent in the presence of a base as necessary. Examples of the base to be used as necessary include, for example, sodium carbonate, potassium carbonate, sodium hydrogencarbonate, potassium hydrogencarbonate, sodium hydroxide, potassium hydroxide, triethylamine, diisopropylethylamine and pyridine. The solvent to be used includes, for example, methylene chloride, chloroform, ethyl acetate, diethyl ether, tetrahydrofuran, dioxane, acetonitrile, benzene, toluene and mixed solvents thereof. While the reaction temperature varies depending on the kind of solvent, it is generally from −30° C. to 50° C., and the reaction time which varies depending on the reaction temperature is generally 1–24 hr.

The reaction of compound (XCVI) and compound (XCVII) is carried out according to the Vilsmeier reaction described in Journal of Organic Chemistry, vol. 30, p. 2534 (1965). The solvent to be used for the reaction includes, for example, chloroform, methylene chloride and dichloroethane. While the reaction temperature varies depending on the kind of solvent, it is generally from room temperature to refluxing temperature of solvent, and the reaction time which varies depending on the reaction temperature is generally 1–12 hr.

METHOD 31

Of the intermediate compound (XLIX) shown in Method 12, the compound of the following formula

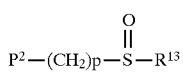

(XCVIII-a)

or

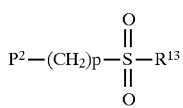

(XCVIII-b)

wherein $R^{13}$ $^a$, p and $P^2$ are as defined above, can be particularly synthesized by the following route.

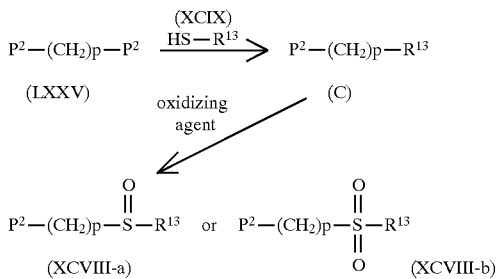

wherein $R^{13}$, p and $P^2$ are as defined above.

That is, compound (XCVIII-a) or compound (XCVIII-b) can be produced by reacting compound (LXXV) with compound (XCIX) in a-suitable solvent in the presence of a base to give compound (C) and oxidizing the compound using 1 or 2 equivalent(s) of an oxidizing agent in the presence of an acid as necessary.

The solvent to be used for the reaction of compound (LXXV) and compound (XCIX) includes, for example, methylene chloride, 1,2-dichloroethane, chloroform, methanol, ethanol, propanol, isopropyl alcohol, butanol, tetrahydrofuran, diethyl ether, dioxane, dimethylformamide, dimethyl sulfoxide, benzene, toluene and xylene. Examples of the base to be used include, for example, sodium hydride, sodium carbonate, potassium carbonate, sodium hydrogencarbonate, potassium hydrogencarbonate, sodium hydroxide, potassium hydroxide, triethylamine, diisopropylethylamine and pyridine. While the reaction temperature varies depending on the kind of solvent to be used, it is generally from 0° C. to 140° C., and the reaction time which varies depending on the reaction temperature is generally 1–24 hr.

The oxydizing agent to be used for the oxidation includes, for example, ruthenium tetraoxide, chromic acid, permanganate, m-chloroperbenzoic acid and aqueous hydrogen peroxide solution. The solvent to be used for oxidation includes, for example, formic acid, acetic acid, methylene chloride, 1,2-dichloroethane, chloroform, methanol, ethanol, propanol, isopropyl alcohol, butanol, tetrahydrofuran, diethyl ether, dioxane, dimethylformamide, dimethyl sulfoxide, benzene, toluene and xylene. Examples of the acid to be used as necessay include, for example, hydrochloric acid, sulfuric acid, p-toluenesulfonic acid and benzoic acid. While the reaction temperature varies depending on the kind of oxidizing agent to be used, it is generally from 0 ° C. to 140° C., and the reaction time which varies depending on the reaction temperature is generally 1–24 hr.

METHOD 32

A compound (I) wherein A is a group of the formula (II-a)–(II-f), B is a group of the formula —NH($R^{10}$) or —N($R^{10}$)($R^{11}$), and $R^{10}$ and $R^{11}$ are the same or different and each is lower alkyl, cycloalkyl, cycloalkylalkyl, aryl, substituted aryl, aralkyl, substituted aralkyl, heteroaryl, substituted heteroaryl, heteroarylalkyl or substituted heteroarylalkyl, can be synthesized by the following route.

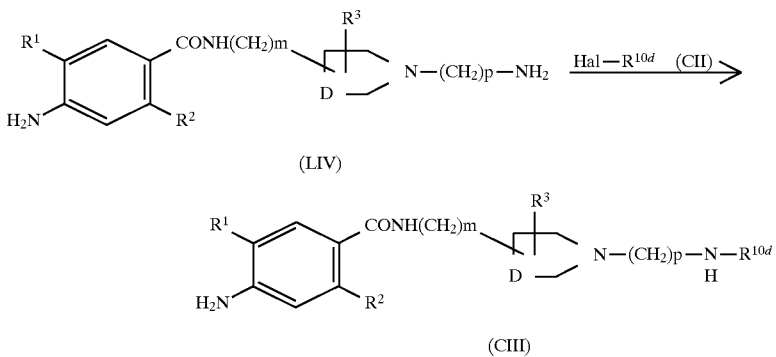

wherein $R^{10}$ $^d$ is lower alkyl, cycloalkyl, cycloalkylalkyl, aryl, substituted aryl, aralkyl, substituted aralkyl, heteroaryl, substituted heteroaryl, heteroarylalkyl or substituted heteroarylalkyl, and D, $R^1$, $R^2$, $R^3$, m, p and Hal are as defined above.

That is, the compound (CIII) can be produced by subjecting compound (LIV) and compound (CII) to alkylation.

The solvent to be used for this reaction includes, for example, methylene chloride, 1,2-dichloroethane, chloroform, methanol, ethanol, propanol, isopropyl alcohol, butanol, tetrahydrofuran, diethyl ether, dioxane, dimethylformamide, dimethyl sulfoxide, benzene, toluene and xylene. Examples of the base to be used include, for example, sodium carbonate, potassium carbonate, sodium hydrogencarbonate, potassium hydrogencarbonate, sodium hydroxide, potassium hydroxide, triethylamine, diisopropylethylamine and pyridine. While the reaction temperature varies depending on the kind of solvent to be used, it is generally from 0° C. to 140° C., and the reaction time which varies depending on the reaction temperature is generally 1–24 hr.

By then reacting the obtained compound (CIII) and Hal-$R^{11}$ $^d$ under the above-mentioned conditions, compound (CIV) of the formula (CIV)

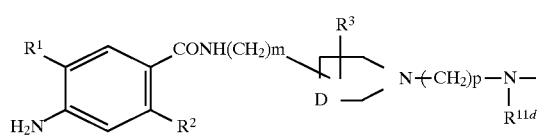

wherein $R^{11\ d}$ is lower alkyl, cycloalkyl, cycloalkylalkyl, aryl, substituted aryl, aralkyl, substituted aralkyl, heteroaryl, substituted heteroaryl, heteroarylalkyl or substituted heteroarylalkyl, and D, $R^1$, $R^2$, $R^3$, $R^{10\ d}$, m and p are as defined above, can be obtained.

METHOD 33

A compound (LXXII) which is represented by the formula

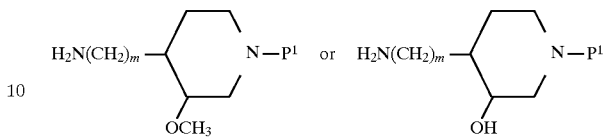

wherein $P^1$ is as defined above, and m is 1, can be synthesized by the following route.

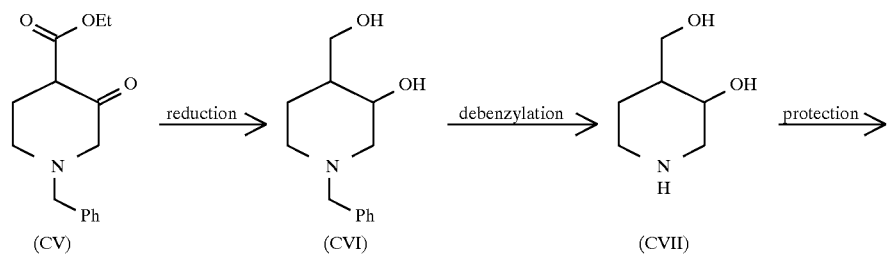

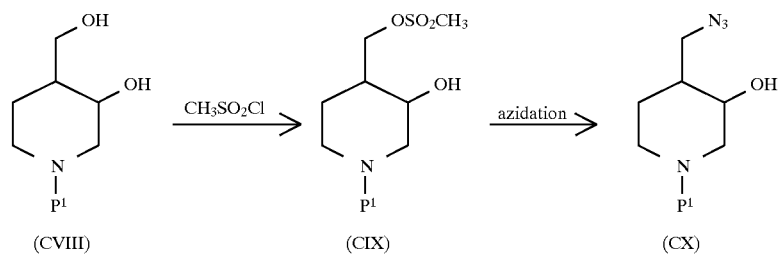

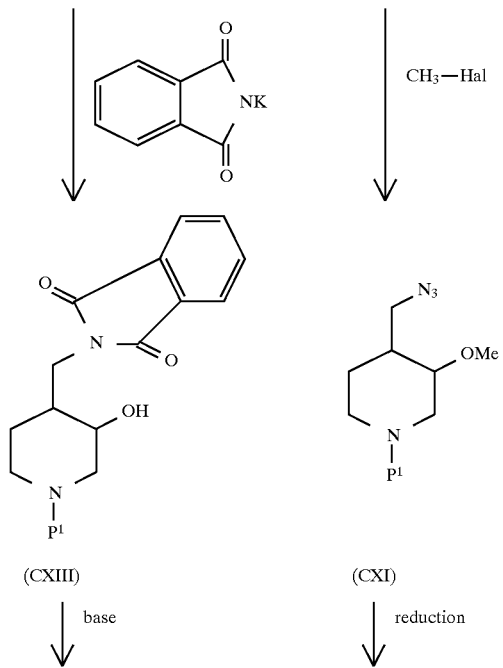

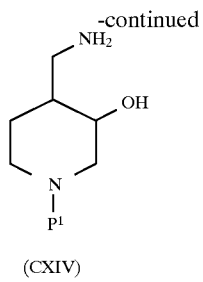

(CXIV)

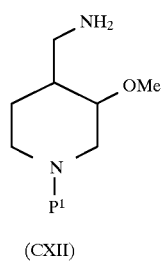

(CXII)

That is, compound (CV) is reduced to give compound (CVI), which is debenzylated to give compound (CVII). The amino group of compound (CVII) is protected to give compound (CVIII), and compound (CVIII) is reacted with methanesulfonyl chloride in the presence of a suitable base to give compound (CIX). Then, compound (CIX) is treated with azidation agent to give compound (CX), then reacted with methyl halide such as methyl iodide to give compound (CXI), which is followed by reduction to give compound (CXII). The compound (CIX) is treated with potassium phthalimide to give compound (CXIII) and then with a base to give compound (CXIV).

The solvent to be used for reduction of compound (CV) includes, for example, methanol, ethanol, tert-butyl alcohol, tetrahydrofuran, diethyl ether and ethylene glycol dimethyl ether. The reducing agent to be used is exemplified by diborane and metal reducing agent such as sodium borohydride, lithium borohydride and lithium aluminum hydride. While the reaction temperature differs depending on the kind of solvent to be used, it is generally from −100° C. to 80° C. and the reaction period, which also differs depending on the reaction temperature, is generally from 30 min to 24 hr.

Examples of the solvent to be used for debenzylation of compound (CVI) include methanol, ethanol, propanol, isopropyl alcohol, butanol, formic acid, acetic acid, water, tetrahydrofuran, dimethyl sulfoxide and mixed solvents thereof. The catalyst to be used is exemplified by palladium carbon, Raney nickel, platinum oxide and the like. The hydrogen source to be used may be hydrazine hydrates, cyclohexene, 1,4-cyclohexadiene, formic acid, ammonium formate and the like. While the reaction temperature differs depending on the kind of solvent to be used, it is generally from 0° C. to the boiling point of the solvent used and the reaction period, which also differs depending on the reaction temperature, is generally 1–6 hr.

The amino-protecting reagent to be used for protecting compound (CVII) includes, for example, di-tert-butyl dicarbonate, 2-tert-butoxycarbonyloxyimino-2-phenylacetonitrile, benzyloxycarbonyl chloride and the like. The solvent to be used include, for example, tetrahydrofuran, acetone, ethyl acetate, methylene chloride, chloroform, dioxane, dimethylformamide, water and mixed solvents thereof. While the reaction temperature differs depending on the kind of solvent to be used, it is generally from −20° C. to 50° C. and the reaction period, which also differs depending on the reaction temperature, is generally 1–24 hr.

Examples of the solvent to be used for methanesulfonylation of compound (CVIII) include methylene chloride, 1,2-dichloroethane, chloroform, methanol, ethanol, propanol, isopropyl alcohol, butanol, tetrahydrofuran, diethyl ether, dioxane, dimethylformamide, dimethyl sulfoxide, benzene, toluene, xylene and the like. The base to be used is exemplified by sodium hydride, sodium carboate, potassium carbonate, sodium hydrogencarbonate, potassium hydrogencarbonate, sodium hydroxide, potassium hydroxide, triethylamine, diisopropylethylamine, pyridine and the like. While the reaction temperature differs depending on the kind of solvent to be used, it is generally from 0° C. to 140° C. and the reaction period, which also differs depending on the reaction temperature, is generally 1–24 hr. The obtained compound (CIX) can be separated into cis compound and trans compound by column chromatography.

Examples of the solvent to be used for azidation of compound (CIX) include methylene chloride, chloroform, methanol, ethanol, diethylene glycol monomethyl ether, diethylene glycol dimethyl ether, water, tetrahydrofuran, diethyl ether, dimethylformamide, dimethyl sulfoxide and mixtures thereof. The azidation agent to be used includes, for example, sodium azide, lithium azide and the like. Where necessary, ammonium chloride, trimethylsilyl chloride and the like may be added. While the reaction temperature differs depending on the kind of solvent to be used, it is generally from −20° C. to 80° C. and the reaction period, which also differs depending on the reaction temperature, is generally 1–24 hr.

Examples of the solvent to be used for the reaction of compound (CX) with methyl halide include methylene chloride, 1,2-dichloroethane, chloroform, methanol, ethanol, propanol, isopropyl alcohol, butanol, tetrahydrofuran, diethyl ether, dioxane, dimethylformamide, dimethyl sulfoxide, benzene, toluene, xylene and the like. The base to be used is exemplified by sodium hydride, sodium carboate, potassium carbonate, sodium hydrogencarbonate, potassium hydrogencarbonate, sodium hydroxide, potassium hydroxide, triethylamine, diisopropylethylamine, pyridine and the like. While the reaction temperature differs depending on the kind of solvent to be used, it is generally from 0° C. to 140° C. and the reaction period, which also differs depending on the reaction temperature, is generally 1–24 hr.

The reducing agent to be used for reduction of compound (CXI) is exemplified by metal reducing reagent such as sodium borohydride, lithium borohydride and lithium aluminum hydride, palladium carbon, palladium carbon hydroxide, Raney nickel, platinum oxide and the like. While the instant reaction is generally carried out under a hydrogen stream, a hydrogen source such as hydrazine hydrate, cyclohexene, 1,4-cyclohexadiene, formic acid, ammonium formate and the like may be also used. While the reaction temperature differs depending on the kind of solvent to be used, it is generally from 0C to the boiling point of the solvent used and the reaction period, which also differs depending on the reaction temperature, is generally 1–6 hr.

Examples of the solvent to be used for the reaction of compound (CIX) with potassium phthalimide include methylene chloride, 1,2-dichloroethane, chloroform, methanol, ethanol, propanol, isopropyl alcohol, butanol, tetrahydrofuran, diethyl ether, dioxane, dimethylformamide, dimethyl sulfoxide, benzene, toluene, xylene and the like. While the reaction temperature differs depending on the kind of solvent to be used, it is generally from 0° C. to 140° C. and the reaction period, which also differs depending on the reaction temperature, is generally 1–24 hr.

Examples of the solvent to be used for treating compound (CXIII) with a base include methanol, ethanol, propanol, isopropyl alcohol, butanol and the like. The base to be used is exemplified by hydrazine hydrate, methyl hydrazine, phenyl hydrazine, methylamine and the like. While the reaction temperature differs depending on the kind of solvent to be used, it is generally from 50° C. to the boiling point of the solvent used and the reaction period, which also differs depending on the reaction temperature, is generally 1–10 hr.

The compound of the formula (I) thus obtained can be separated and purified from reaction mixtures by a method known Per se, such as recrystallization and column chromatography.

When the compound of the formula (I) of the present invention and pharmaceutically acceptable salts thereof have asymmetric carbon, they are generally produced as racemates which can be optically resolved into optical isomers by a conventional method such as preparative recrystallization and chromatography. Also, the use of optically active starting compound results in optical isomers. When a compound has two or more asymmetric carbons, they can be obtained as individual diastereomers or mixtures thereof which can be separated by a conventional method such as preparative recrystallization and chromatography.

The compound of the formula (I) can be converted to acid addition salt by treating the compound with an acid such as hydrochloric acid, sulfuric acid, hydrobromic acid, phosphoric acid, nitric acid, methanesulfonic acid, ethanesulfonic acid, fumaric acid, maleic acid, benzoic acid, citric acid, malic acid, mandelic acid, p-toluenesulfonic acid, acetic acid, succinic acid, malonic acid, lactic acid, salicylic acid, gallic acid, piclinic acid, carbonic acid, ascorbic acid, trifluoroacetic acid and tartaric acid in a suitable solvent such as methanol and ethanol.

The compound of the formula (I) can be converted to N-oxide compound by oxidation using 1 to 10 equivalents, preferably from monoequivalent to a slightly excess, of an oxidizing agent such as m-chloroperbenzoic acid, perbenzoic acid, peracetic acid, trifluoroperacetic acid, permaleic acid, sodium bromite, sodium hypochlorite and hydrogen peroxide, in a suitable solvent such as chloroform, methylene chloride, tetrahydrofuran, dioxane, dimethylformamide, acetic acid, water and mixed solvents thereof, at −50° C. to room temperature for 5 min to 24 hr. This oxidation reaction can be also carried out in the presence of a catalyst such as sodium tungstate.

When the crystals of the obtained compound of the present invention are anhydrides, the crystals can be converted to hydrates or solvates by a treatment with water, aqueous solvent or other solvent.

The Experimental Examples are shown in the following, to which the present invention is not limited.

EXPERIMENTAL EXAMPLE 1

5-HT$_4$ Receptor Binding Test

According to the method of C. J. Grossman et al. [British Journal of Pharmacology, vol. 109, pp. 618–624 (1993)], a specific 5-HT$_4$ receptor binding test was run using, as a tracer ligand, 1-methyl-1 H-indole-3-carboxylic acid. 1-(2-methylsulfonylaminoethyl)-piperidin-4-ylmethyl ester substituted by tritium (hereinafter to be referred to as [3H] GR113808). Specifically, crude synapse membrane sample was prepared from guinea pig striatum, suspended in 50 mM HEPES buffer (pH 7.4) and used for testing. The test compound having several different concentrations and [3H] GR113808 (final concentration 0.1 nM) were added to this suspension and allowed to react at 37° C. Thirty minutes later, the reaction mixture was filtered by suction with cell harvester. The filter was washed with 50 mM HEPES buffer, and the radioactivity on the filter was counted by liquid scintillation counter. The non-specific binding was determined in the presence of 1 μM GR113808. The concentration of the test compound necessary for 50% inhibition (IC$_{50}$) and Ki value were determined from graph.

EXPERIMENTAL EXAMPLE 2

5-HT$_3$ Receptor Binding Test

According to the method of Nelson and Thomas [Biochemical Pharmacology, vol. 38, pp. 1693–1695 (1989)], a specific 5-HT$_3$ receptor binding test was run using, as a tracer ligand, endo-1-methyl-N-(9-methyl-9-azabicyclo [3.3.1]non-3-yl)-1 H-indazole-3-carboxamide substituted by tritium (hereinafter to be referred to as [3 H] Granisetron). Specifically, crude synapse membrane sample was prepared from rat cerebral cortex, suspended in 50 mM HEPES buffer (pH 7.4) and used for testing. The test compound having several different concentrations and [3 H]Granisetron (final concentration 1.0 nM) were added to this suspension and allowed to react at 25° C. Thirty minutes later, the reaction mixture was filtered by suction with cell harvester. The filter was washed with 50 mM Tris buffer (pH 7.4), and the radioactivity on the filter was counted using liquid scintillation counter or β-plate. The non-specific binding was determined in the presence of 1 μM Tropisetron. The concentration of the test compound necessary for 50% inhibition (IC$_{50}$) and Ki value were determined from graph.

The results of the above-mentioned Experimental Examples 1 and 2 are shown in Table A, wherein * shows IC$_{50}$.

TABLE A

| | Affinity for receptor (Ki value, nM) | |
|---|---|---|
| Example | 5-HT$_4$ | 5-HT$_3$ |
| 11 | 6.2 | >1000* |
| 13 | 3.1 | >1000* |
| 17 | 3.1 | >1000* |
| 19 | 4.4 | >1000* |
| 22 | 1.3 | >1000* |
| 24 | 1.6 | >1000* |
| 25 | 1.4 | >1000* |
| 27 | 2.2 | >1000* |
| 29 | 1.7 | >1000* |
| 30 | 0.81 | >1000* |
| 31 | 2.3 | >1000* |
| 45 | 5.5 | >1000* |
| 46 | 1.5 | >1000* |
| 48 | 2.1 | >1000* |
| 56 | 0.65 | >1000* |
| 59 | 1.1 | 190 |
| 70 | 7.4 | >1000* |
| 71 | 7.4 | >1000* |
| 78 | 1.4 | 370 |
| 85 | 0.44 | 260 |
| 88 | 1.2 | 350 |
| 90 | 0.43 | >1000* |
| 94 | 3.5 | >1000* |
| 95 | 1.2 | >1000* |

TABLE A-continued

| Example | Affinity for receptor (Ki value, nM) | |
|---|---|---|
| | 5-HT$_4$ | 5-HT$_3$ |
| 98 | 1.6 | >1000* |
| 100 | 5.3 | >1000* |
| 127 | 0.51 | >1000* |
| 130 | 0.97 | >1000* |
| 141 | 0.94 | >1000* |
| 149 | 0.84 | >1000* |
| 158 | 0.62 | >1000* |
| 160 | 0.67 | >1000* |
| 163 | 2.7 | >1000* |
| 169 | 3.5 | 370 |
| 170 | 1.6 | 340 |
| 173 | 2.4 | >1000* |
| 174 | 1.5 | >1000* |
| 189 | 1.8 | >1000* |
| 190 | 5.1 | >1000* |
| 191 | 1.5 | >1000* |
| 193 | 0.34 | >1000* |
| 197 | 0.50 | >1000* |
| 200 | 1.4 | >1000* |
| 209 | 0.47 | >1000* |
| 285 | 1.5 | >1000* |

EXPERIMENTAL EXAMPLE 3

Contraction of the Isolated Guinea Pig Ascending Colon

About 3 cm long ascending colon segment was taken from male Hartley Guinea pig and suspended in 10 ml of a Tyrode solution ventilated with a mixed gas of oxygen (95%) and $CO_2$ (5%) at 37° C. with the load of 2 g. The contraction was isotonically measured via ransducer. After an equibilium period of about 30 min, the test compound was administered non-cumulatively from lower concentrations, and concentration-dependent contraction was measured. The test compound was administered at 15 minutes intervals. Then, contraction by the test compound in the presence of a 5-HT$_4$ receptor antagonist, 4-amino-3-chloro-6-methoxybenzoic acid- 2-diethylamino-ethyl ester (0.3 $\mu$M, hereinafter to be referred to as SDZ 205-557) mined, and antagonistic effect on the reaction by SDZ 205-557 was confirmed.

The contraction by the test compound was evaluated based on the ratio of reaction relative to mean contraction induced by methacholine (30 $\mu$M) administered before and after each determination of concentration-dependent contraction. The contraction was prohibit-converted using the maximum value of concentration-response curve as 100, and expressed by EC$_{50}$ as determined from linear regression.

The results of the above-mentioned Experimental Example are shown in Table B.

TABLE B

| Example | Contraction of removed colon (EC$_{50}$, nM) |
|---|---|
| 22 | 3.3 |
| 24 | 3.9 |
| 25 | 4.6 |
| 27 | 5.3 |
| 29 | 3.7 |
| 30 | 1.6 |
| 46 | 6.9 |
| 48 | 4.8 |
| 56 | 1.0 |

TABLE B-continued

| Example | Contraction of removed colon (EC$_{50}$, nM) |
|---|---|
| 70 | 6.7 |
| 85 | 1.2 |
| 88 | 1.4 |
| 90 | 0.9 |
| 98 | 4.0 |

EXPERIMENTAL EXAMPLE 4

Promotion of Postcibal Enterokinesis of Dog Without Anesthesia

According to the method of Ito et al. [Journal of Smooth Muscle Research, vol. 13, pp. 33–43 (1976)], male and female adult mongrel dogs are subjected to laparotomy under pentobarbital anesthesia, and force transducer is sutured to the serous membrane of various sites of gastrointestinal tract in the direction of circular muscle. After about two weeks' recovery period, posteibal gastrointestinal motility is measured in vigilance.

EXPERIMENTAL EXAMPLE 5

Bioavailability in Rats

Female SD rats (3 per group) are administered with 2.5 mg/kg (i.v.) and 10 mg/kg (p.o.) of the drug. The blood is taken with the passage of time, and concentration of the drug in plasma is measured with high performance liquid chromatography. The bioavailability is calculated from the following formula wherein AUC means area under plasma concentration time curve.

$$\frac{AUC \text{ by oral administration}}{AUC \text{ by intravenous administration}} \times$$

$$\frac{\text{Dose of intravenous administration}}{\text{Dose of oral administration}} \times 100(\%)$$

EXPERIMENTAL EXAMPLE 6

Absorption by Small Intestine in Rat

Male SD rats (3 per group) fasted overnight are subjected to laparotomy under ether anesthesia, and the upper part of small intestine is ligated to form a loop (15–20 cm in length). The drug is dissolved in 5% glucose to the drug concentration of 5 mg/10 ml, and 10 ml/kg thereof is injected into the loop. At 2 hours from the drug injection, the loop is removed, washed with 100 ml of 0.1N hydrochloric acid-methanol (3:7), and the drug concentration is determined by high performance liquid chromatography. The absorption ratio is calculated according to the following formula, and the value is expressed by mean±standard deviation.

$$\frac{\text{Injected amount (mg)} - \text{drug concentration in loop (mg/ml)} \times 100 \text{ (ml)}}{\text{Injected amount (mg)}} \times 100(\%)$$

EXPERIMENTAL EXAMPLE 7

Stimulation of Defecation in Mouse

Male ddY mice were placed in partition box, and the number and wet weight of feces excreted for 2 hours from immediately after oral administration of the compound of Example 173 were measured.

| Compound | mg/kg p.o. | n | number | promotion (%) | wet weight (mg) | promotion (%) |
|---|---|---|---|---|---|---|
| Vehicle | — | 20 | 2.0 ± 0.3 | | 35.1 ± 5.4 | |
| Example 173 | 0.1 | 20 | 3.4 ± 0.3 | 70 | 59.2 ± 6.95 | 69 |
| | 0.3 | 20 | 4.7 ± 0.5** | 135 | 82.7 ± 11.5** | 136 |
| | 1 | 20 | 4.6 ± 0.6 | 130 | 77.2 ± 11.9** | 120 |
| | 3 | 20 | 4.7 ± 0.5** | 135 | 81.6 ± 10.4** | 132 |

**;P < 0.01

EXPERIMENTAL EXAMPLE 8

Promotion of Colonic Transit in Guinea Pig

Male Hartley guinea pigs were subjected to laparotomy under ether anesthesia, and a polyethylene tube was inserted into the beginning of colon. The other end was passed under the skin to be exposed from the neck and fixed there. At day 5 postoperation, Evans blue solution was injected into the colon through the polyethylene tube. One hour later, the colon was removed, and the range of the Evans blue solution was measured, which was calculated relative to the entire length of the colon and expressed as transit ratio. The compound of Example 173 was orally administered one hour before injection of the Evans blue solution.

| Compound | mg/kg p.o. | n | ratio of colonic transit (%) | promotion (%) |
|---|---|---|---|---|
| Vehicle | — | 13 | 44.2 ± 7.7 | |
| Example 173 | 0.1 | 16 | 54.5 ± 8.0 | 23 |
| | 0.3 | 16 | 54.7 ± 5.9 | 24 |
| | 1 | 15 | 71.8 ± 6.9* | 62 |
| | 3 | 14 | 73.2 ± 6.3* | 66 |

*;P < 0.05

EXPERIMENTAL EXAMPLE 9

Promotion of Gastric Emptying in Rats

Barium pellets (ca. 1 mm diameter) coated with polystyrene was intragastrically administered to male Wistar rats. One hour later, stomach was removed, and the remaining pellets were counted. The compound of Example 173 was orally administered one hour before administration of the pellets. The promotion ratio was calculated from the comparison of the number of remaining pellets and the number thereof in the group administered with vehicle.

| Compound | mg/kg p.o. | number of pellets | promotion (%) |
|---|---|---|---|
| Vehicle | — | 28.1 ± 1.8 | |
| Example 173 | 0.3 | 28.2 ± 1.3 | 0 |
| | 1 | 24.3 ± 2.5 | 14 |
| | 3 | 19.0 ± 2.6* | 32 |
| | 10 | 13.3 ± 3.0** | 53 |

*;P < 0.05, **;P < 0.01

As demonstrated in the above tests, the compound of the present invention and pharmaceutically acceptable salts thereof have selective and high affinity for $5\text{-HT}_4$ receptors, and are useful as superior digestive function stimulators for the prophylaxis and treatment of various gastrointestinal diseases selected from reflux esophagitis; gastroesophageal reflux such as that accompanying cystic fibrosis; Barrett syndrome; intestinal pseudoileus; acute or chronic gastritis; gastric or duodenal ulcer; Crohn's disease; non-ulcer dyspepsia; ulcerative colitis; postgastrectomy syndrome; postoperative digestive function failure; delayed gastric emptying caused by gastric neurosis, gastroptosis, diabetes, and the like; gastrointestinal disorders such as indigestion, meteorism, abdominal indefinite complaint, and the like; constipation such as atonic constipation, chronic constipation, and that caused by spinal cord injury, pelvic diaphragm failure and the like; and irritable bowel syndrome. They are also useful for the prophylaxis and treatment of diseases in which $5\text{-HT}_4$ receptors are involved, such as central nervous disorders (e.g., schizophrenia, depression, anxiety, disturbance of memory and dementia); cardiac function disorders (e.g., cardiac failure and myocardial ischemia); and urinary diseases (e.g., dysuria caused by urinary obstruction, ureterolith, prostatomegaly, spinal cord injury, pelvic diaphragm failure, etc).

The compound of the present invention also has antinociceptive action, and is useful as an anti-nociceptor for analgesic use which increases threshold of pain. In addition, the compound of the present invention wherein (thio) carbonyl, sulfinyl or sulfonyl is substituted at the alkyl moiety bound to nitrogen atom of cyclic amine of the formulas (II-a)–(II-f) and (III) particularly shows superior absorption by oral administration.

When the compound of the present invention and pharmaceutically acceptable salts thereof are used as medicaments, they can be administered as they are or upon formulation into pharmaceutical compositions such as tablets, buccal, pills, capsules, powders, fine granules, granules, liquids, oral liquids inclusive of syrups, injections, inhalants, suppositories, transdermal liquids, ointments, transdermal plasters, transmucosal plasters (e.g., intraoral plaster), transmucosal liquids (e.g. nasal liquid), and the like, using pharmaceutically acceptable carriers, excipients, extenders, diluents and other additives, orally or parenterally to the patients in need of treatment. Examples of the pharmaceutically acceptable carriers, excipients, extenders, diluents and other additives are solid or liquid nontoxic pharmaceutical substances, such as lactose, magnesium stearate, starch, talc, gelatin, agar, pectin, gum arabic, olive oil, sesame oil, cacao butter, ethylene glycol and other conventional ones. While the clinical dose of the compound of the present invention varies depending on the compound to be selected, disease, symptom, body weight, age, sex and the like of the patients who will undergo treatment, administration route and the like, it is generally 1–2000 mg, preferably 10–300 mg, daily for an adult by oral administration which is given in a sigle dose or 2–4 doses.

BEST MODE FOR EMBODYING THE INVENTION

The present invention is specifically described by Preparation Examples and Examples, to which the invention is not limited. When the compound to be obtained is an optical isomer, it can be confirmed by its optical rotation and high performance liquid chromatography. When the optical isomer is crystal, the absolute configuration thereof can be confirmed by X-ray diffraction.

PREPARATION EXAMPLE 1

Itaconic acid (650 g) and (S)-1-phenylethylamine (605 g) were suspended in 1,3-dimethylimidazolidinone (650 ml), and the suspension was stirred at 80° C. for 1 hr with heating, and further at 120° C. for 3 hr with heating. The mixture was cooled to room temperature, and water (4 l) was added. The precipitated crystals were collected by filtration and dried to give 950 g of 1-((S)-1-phenylethyl)-5-oxo-3-pyrrolidinecarboxylic acid. The crystals were recrystallized 3 times with isopropyl alcohol to give 156 g of (3S)-1-((S)-1-phenylethyl)-5-oxo-3-pyrrolidinecarboxylic acid.
m.p. 209°–211° C., $[\alpha]_D^{25}=-69.1$ (c=1.0, dimethylformamide), optical purity: not less than 99%

The compound of the following Preparation Example 2 was produced in the same manner as in Preparation Example 1.

PREPARATION EXAMPLE 2

(3R)-1-((R)-1-phenylethyl)-5-oxo-3-pyrrolidinecarboxylic acid, m.p. 207°–210° C., $[\alpha]_D^{25}=+68.4$ (c=1.0, dimethylformamide), optical purity: not less than 99%

PREPARATION EXAMPLE 3

(3S)-1-((S)-1-Phenylethyl)-5-oxo-3-pyrrolidinecarboxylic acid (666 g, optical purity not less than 99%) was dissolved in methanol (6 l), and conc. sulfuric acid (15 ml) was added at room temperature. The mixture was stirred at refluxing temperature for 7 hr. Methanol was evaporated, and the residue was extracted with ethyl acetate. The organic layer was washed with sodium hydrogencarbonate, dried over magnesium sulfate and concentrated under reduced pressure to give 738 g of methyl (3S)-1-((S)-1-phenylethyl)-5-oxo-3-pyrrolidinecarboxylate.
$^1$H-NMR (CDCl$_3$,ppm) δ: 1.47–1.53(3 H,d,J=7.3 Hz), 2.72–2.83(2 H,m), 3.03–3.23(2 H,m), 3.50–3.61(1 H,m), 3.74(3 H,s), 5.44–5.59(1 H,q,J=7.3 Hz), 7.20–7.41 (5 H,m)

In the same manner as in Preparation Example 3, the compound of the following Preparation Example 4 was produced.

PREPARATION EXAMPLE 4

Methyl (3R)-1-((R)-1-phenylethyl)-5-oxo-3-pyrrolidinecarboxylate $^1$H-NMR (CDCl$_3$,ppm) δ: 1.48–1.54(3 H,d,J=7.3 Hz), 2.70–2.83(2 H,m), 3.05–3.25(2 H,m), 3.61–3.71(1 H,m), 3.75(3 H,s), 5.43–5.58(1 H,q,J=7.3 Hz), 7.22–7.41(5 H,m), $[\alpha]_D^{25}=+55.5$ (c=2.1, ethyl acetate)

PREPARATION EXAMPLE 5

Methyl (3S)-1-((S)-1-phenylethyl)-5-oxo-3-pyrrolidinecarboxylate (738 g) was dissolved in methanol (3.5 l). The solution was stirred for 8 hr under ice-cooling while blowing in ammonia gas, and concentrated under reduced pressure to give 537 g of (3S)-1-((S)-1-phenylethyl)-5-oxo-3-pyrrolidinecarboxamide.
m.p. 149°~150° C., $[\alpha]_D^{25}=-58.2$ (c=1.0, chloroform)

In the same manner as in Preparation Example 5, the compound of the following Preparation Example 6 was produced.

PREPARATION EXAMPLE 6

(3R)-1-((R)-1-phenylethyl)-5-oxo-3-pyrrolidinecarboxamide,
m.p. 151°~153° C.

PREPARATION EXAMPLE 7

(3S)-1-((S)-1-Phenylethyl)-5-oxo-3-pyrrolidinecarboxamide (150 g) was dissolved in tetrahydrofuran (2.5 l), and sodium borohydride (138 g) was added with stirring. Conc. sulfuric acid (130 ml) was dropwise added under ice-cooling. The mixture was stirred for 1 hr at room temperature, and further at refluxing temperature for 10 hr. 6N Hydrochloric acid (300 ml) was dropwise added under ice-cooling, and the mixture was stirred at refluxing temperature for 4 hr. The solvent was evaporated under reduced pressure, a 3N sodium hydroxide solution was added to make same alkaline, and the mixture was extracted with chloroform. The extract was dried over magnesium sulfate, concentrated under reduced pressure and distilled under reduced pressure to give 95 g of (3R)-3-aminomethyl-1-((S)-1-phenylethyl)pyrrolidine.
$^1$H-NMR (CDCl$_3$,ppm) δ: 1.27–1.42(3 H,d,J=6.6 Hz), 1.30–1.52(3 H,m), 1.85–2.03(1 H,m), 2.05–2.30(2 H,m), 2.35–2.59(2 H,m), 2.60–2.67(2 H,d,J=7.2 Hz), 2.73–2.83(1 H,m), 3.13–3.23(1 H,q,J=6.6 Hz), 7.18–7.41(5 H,m), $[\alpha]_D^{25}=-56.6$ (c=1.0, chloroform)

In the same manner as in Preparation Example 7, the compound of the following Preparation Example 8 was produced.

PREPARATION EXAMPLE 8

(3S)-3-aminomethyl-1-((R)-1-phenylethyl) pyrrolidine $^1$H-NMR (CDCl$_3$,ppm) δ: 1.27–1.42(3 H,d,J=6.6 Hz), 1.30–1.52(3 H,m), 1.85–2.03(1 H,m), 2.05–2.30(2 H,m), 2.35–2.59(2 H,m), 2.60–2.67(2 H,d,J=7.2 Hz), 2.73–2.83(1 H,m), 3.13–3.23(1 H,q,J=6.6 Hz), 7.18–7.41(5 H,m)

PREPARATION EXAMPLE 9

Methylene chloride (1000 ml) was added to (1-benzylpyrrolidin-3-ylmethyl)amine (112 g), and a solution of di-tert-butyl dicarbonate (141 g) in methylene chloride was dropwise added at 0° C. with stirring. The mixture was stirred at room temperature for 8 hr. Aqueous potassium carbonate solution was added and the mixture was extracted with chloroform. The mixture dried over magnesium sulfate, and concentrated under reduced pressure to give 171 g of 1-benzyl-3-(tert-butoxycarbonylaminomethyl)pyrrolidine.
m.p. 51°~54° C.

In the same manner as in Preparation Example 9, the compounds of the following Preparation Examples 10–12 were produced.

PREPARATION EXAMPLE 10

1-benzyl-4-(tert-butoxycarbonylaminomethyl) piperidine $^1$H-NMR (CDCl$_3$,ppm) δ: 1.20–1.35(3 H,m), 1.43(9 H,s), 1.55–1.73(2 H,m), 1.85–1.99(2 H,m), 2.80–3.03(4 H,m), 3.48(2 H,s), 4.53–4.65(1 H,br), 7.20–7.35(5 H,m)

PREPARATION EXAMPLE 11

(3R)-3-(tert-butoxycarbonylaminomethyl)-1-((S)-1-phenylethyl)-pyrrolidine $^1$H-NMR (CDCl$_3$,ppm)δ: 1.35(3 H,d,J=6.6 Hz), 1.45(9 H,s), 1.45–1.50(1 H,m), 1.90–2.03(1 H,m), 2.18–2.36(3 H,m), 2.48–2.57(1 H,m), 2.73–2.86(1 H,m), 3.03–3.10(2 H,m), 3.10–3.18(1 H,q,J=6.6 Hz), 5.10–5.21(1 H,br), 7.18–7.33(5 H,m), $[\alpha]_D^{25}=-11.9$ (c=1.0, chloroform)

PREPARATION EXAMPLE 12

(3S)-3-(tert-butoxycarbonylaminomethyl)-1-((R)-1-phenylethyl)-pyrrolidine $^1$H-NMR (CDCl$_3$,ppm) δ: 1.35(3 H,d,J=6.6 Hz), 1.45(9 H,s), 1.45–1.50(1 H,m), 1.90–2.03(1 H,m), 2.18–2.36(3

H,m), 2.48–2.57(1 H,m), 2.73–2.86(1 H,m), 3.03–3.10(2 H,m), 3.10–3.18(1 H,q,J=6.6 Hz), 5.10–5.21(1 H,br), 7.18–7.33(5 H,m), [α]$_D^{25}$=+11.1 (c=1.0, chloroform)

PREPARATION EXAMPLE 13

Ethanol (1700 ml) and 10% palladium-carbon (34 g, M type) were added to 1-benzyl-3-(tert-butoxycarbonylaminomethyl)pyrrolidine (171 g), and hydrazine hydrate (29 ml) was dropwise added at room temperature with stirring and the mixture was refluxed with stirring at 80° C. for 2 hr. 10% Palladium-carbon was filtered off, and the filtrate was concentrated under reduced pressure to give 116 g of 3-tert-butoxycarbonylaminomethyl) pyrrolidine.

$^1$H-NMR (CDCl$_3$,ppm) δ: 1.35–1.50(10 H,m), 1.89–1.97(1 H,m), 2.21–2.28(2 H,m), 2.58–2.66(1 H,m), 2.83–3.12(5 H,m), 4.82–4.92(1 H,br)

In the same manner as in Preparation Example 13, the compounds of the following Preparation Examples 14–16 were produced.

PREPARATION EXAMPLE 14

4-(tert-butoxycarbonylaminomethyl)piperidine $^1$H-NMR (CDCl$_3$,ppm) δ: 1.20–1.35(3 H,m), 1.44(9 H,s), 1.55–1.80(2 H,m), 2.60–2.73(2 H,m), 2.95–3.28(4 H,m), 4.73–4.83(1 H,br)

PREPARATION EXAMPLE 15

(3S)-3-(tert-butoxycarbonylaminomethyl)pyrrolidine $^1$H-NMR (CDCl$_3$,ppm) δ: 1.35–1.52(10 H,m), 1.85–1.97(1 H,m), 2.16–2.32(2 H,m), 2.56–2.67(1 H,m), 2.82–3.15(5 H,m), 4.74–4.89(1 H,br), [α]$_D^{25}$=−9.2 (c=1.0, chloroform)

PREPARATION EXAMPLE 16

(3R)-3-(tert-butoxycarbonylaminomethyl)pyrrolidine $^1$H-NMR (CDCl$_3$,ppm) δ: 1.35–1.52(10 H,m), 1.91–1.95(1 H,m), 2.07–2.31(2 H,m), 2.55–2.67(1 H,m), 2.83–3.15(5 H,m), 4.72–4.85(1 H,br), [α]$_D^{25}$=+8.3 (c=1.0, chloroform)

PREPARATION EXAMPLE 17

Dimethylformamide (200 ml) was added to 3-(tert-butoxycarbonylaminomethyl)pyrrolidine (14 g), and potassium carbonate (30 g) and N-(3-bromopropyl)phthalimide (18 g) were added at room temperature with stirring, and the mixture was stirred at room temperature for 8 hr. The reaction mixture was concentrated under reduced pressure, and aqueous potassium carbonate solution was added to the residue. The mixture was extracted with ethyl acetate. The mixture was dried over magnesium sulfate, and concentrated under reduced pressure. The obtained residue was purified by silica gel chromatography to give 17 g of 2-(3-(3-tert-butoxycarbonylaminomethylpyrrolidin-1-yl)propyl)-2,3-dihydro-1 H-isoindole-1,3-dione.

$^1$H-NMR (CDCl$_3$,ppm) δ: 1.43(9 H,s), 1.54–1.73(1 H,m), 1.82–2.14(3 H,m), 2.25–2.69(7 H,m), 3.01–3.09(2 H,m), 3.70–3.86(2 H,m), 4.90–5.04(1 H,br), 7.69–7.73(2 H,m), 7.81–7.86(2 H,m)

In the same manner as in Preparation Example 17, the compounds of the following Preparation Examples 18–39 were produced.

PREPARATION EXAMPLE 18

2-(2-(3-tert-butoxycarbonylaminomethylpyrrolidin-1-yl)ethyl)-2,3-dihydro-1 H-isoindole-1,3-dione oxalate m.p. 141°–143° C.

PREPARATION EXAMPLE 19

2-(2-((3R)-3-tert-butoxycarbonylaminomethylpyrrolidin-1-yl)ethyl)-2,3-dihydro-1H-isoindole-1,3-dione $^1$H-NMR (CDCl$_3$,ppm) δ: 1.44–1.52(10 H,m), 1.81–2.08(1 H,m), 2.15–2.60(7 H,m), 2.88–3.11(2 H,m), 3.82–3.86(2 H,m), 4.95–5.09(1 H,br), 7.65–7.74(2 H,m), 7.82–7.89(2 H,m)

PREPARATION EXAMPLE 20

2-(3-((3R)-3-tert-butoxycarbonylaminomethylpyrrolidin-1-yl)propyl)-2,3-dihydro-1 H-isoindole-1,3-dione $^1$H-NMR (CDCl$_3$,ppm) δ: 1.42–1.52(10 H,m), 1.81–2.08(3 H,m), 2.20–2.65(7 H,m), 2.97–3.12(2 H,m), 3.82–3.85(2 H,m), 4.90–5.04(1 H,br), 7.68–7.76(2 H,m), 7.81–7.88(2 H,m)

PREPARATION EXAMPLE 21

2-(3-((3S)-3-tert-butoxycarbonylaminomethylpyrrolidin-1-yl)propyl)-2,3-dihydro-1 H-isoindole-1,3-dione $^1$H-NMR (CDCl$_3$,ppm) δ: 1.42–1.52(10 H,m), 1.81–2.08(3 H,m), 2.20–2.65(7 H,m), 2.97–3.12(2 H,m), 3.82–3.85(2 H,m), 4.90–5.04(1 H,br), 7.68–7.76(2 H,m), 7.81–7.88(2 H,m)

PREPARATION EXAMPLE 22

2-(4-(3-tert-butoxycarbonylaminomethylpyrrolidin-1-yl)butyl)-2,3-dihydro-1 H-isoindole-1,3-dione $^1$H-NMR(CDCl$_3$,ppm) δ: 1.40(9 H,s),1.55–1.62(3 H,m), 1.70–1.81(2 H,m), 1.91–2.05(1 H,m),2.35–2.44(2 H,m), 2.45–2.60(3 H,m),2.62–2.73(2 H,m), 3.06–3.18(2 H,m), 3.71–3.83(2 H,m),4.95–5.01(1 H,br),7.68–7.72(2 H,m), 7.79–7.83(2 H,m)

PREPARATION EXAMPLE 23

2-(4-(4-tert-butoxycarbonylaminomethylpiperidin-1-yl)butyl)-2,3-dihydro-1 H-isoindole-1,3-dione $^1$H-NMR(CDCl$_3$,ppm) δ: 1.15–1.35(3 H,m), 1.43(9 H,s), 1.43–1.73(6 H,m), 1.83–1.97(2 H,m), 2.27–2.38(2 H,m), 2.82–3.06(4 H,m), 3.65–3.73(2 H,m), 4.53–4.67(1 H,br), 7.79–7.89(4 H,m)

PREPARATION EXAMPLE 24

2-(4-((3R)-3-tert-butoxycarbonylaminomethylpyrrolidin-1-yl)butyl)-2,3-dihydro-1 H-isoindole-1,3-dione $^1$H-NMR(CDCl$_3$,ppm) δ: 1.35–1.60(12 H,m), 1.62–1.81(2 H,m), 1.87–2.05(1 H,m), 2.06–2.68(7 H,m), 3.00–3.18(2 H,m), 3.65–3.79(2 H,m), 4.93–5.05(1 H,br), 7.67–7.89(4 H,m)

PREPARATION EXAMPLE 25

2-(4-((3S)-3-tert-butoxycarbonylaminomethylpyrrolidin-1-yl)butyl)-2,3-dihydro-1 H-isoindole-1,3-dione $^1$H-NMR(CDCl$_3$,ppm) δ: 1.35–1.60(12 H,m), 1.62–1.81(2 H,m), 1.87–2.05(1 H,m), 2.06–2.68(7 H,m), 3.00–3.18(2 H,m), 3.65–3.79(2 H,m), 4.93–5.05(1 H,br), 7.67–7.89(4 H,m)

PREPARATION EXAMPLE 26

2-(5-(3-tert-butoxycarbonylaminomethylpyrrolidin-1-yl)pentyl)-2,3-dihydro-1 H-isoindole-1,3-dione $^1$H-NMR(CDCl$_3$,ppm) δ: 1.31–1.79(7 H,m),1.42(9 H,s), 1.89–2.05(1 H,m), 2.30–2.69(7 H,m),3.05–3.16(2 H,m), 3.61–3.75(2 H,m),4.92–5.05(1 H,br), 7.66–7.75(2 H,m), 7.79–7.86(2 H,m)

PREPARATION EXAMPLE 27

2-(5-((3R)-3-tert-butoxycarbonylaminomethylpyrrolidin-1-yl)pentyl)-2,3-dihydro-1 H-isoindole-1,3-dione $^1$H-NMR(CDCl$_3$,ppm) δ: 1.32–1.80(7 H,m), 1.41(9 H,s), 1.90–2.05(1 H,m), 2.30–2.70(7 H,m), 3.06–3.16(2 H,m), 3.65–3.79(2 H,m), 4.95–5.06(1 H,br), 7.65–7.75(2 H,m), 7.78–7.87(2 H,m)

PREPARATION EXAMPLE 28

2-(5-((3S)-3-tert-butoxycarbonylaminomethylpyrrolidin-1-yl)pentyl)-2,3-dihydro-1 H-isoindole-1,3-dione $^1$H-NMR(CDCl$_3$,ppm) δ: 1.32–1.80(7 H,m), 1.41(9 H,s), 1.90–2.05(1 H,m), 2.30–2.70(7 H,m), 3.06–3.16(2 H,m), 3.65–3.79(2 H,m), 4.95–5.06(1 H,br), 7.65–7.75(2 H,m), 7.78–7.87(2 H,m)

PREPARATION EXAMPLE 29

2-(6-((3R)-3-tert-butoxycarbonylaminomethylpyrrolidin-1-yl)hexyl)-2,3-dihydro-1 H-isoindole-1,3-dione $^1$H-NMR(CDCl$_3$,ppm) δ: 1.28–2.40(19 H,m), 2.75–3.79 (11 H,m), 5.66–5.73(1 H,br), 7.68–7.92(4 H,m)

PREPARATION EXAMPLE 30

2-(6-((3S)-3-tert-butoxycarbonylaminomethylpyrrolidin-1-yl)hexyl)-2,3-dihydro-1 H-isoindole-1,3-dione $^1$H-NMR(CDCl$_3$,ppm) δ: 1.28–2.40(19 H,m), 2.75–3.79 (11 H,m), 5.66–5.73(1 H,br), 7.68–7.92(4 H,m)

PREPARATION EXAMPLE 31

2-(5-(4-tert-butoxycarbonylaminomethylpiperidin-1-yl)pentyl)-2,3-dihydro-1 H-isoindole-1,3-dione $^1$H-NMR(CDCl$_3$,ppm) δ: 1.35–1.52(12 H,m), 1.55–1.91(8 H,m), 2.30–2.51(2 H,m), 2.61–2.73(2 H,m), 3.03–3.09(2 H,m), 3.18–3.33(2 H,m), 3.62–3.70(2 H,m), 4.75–4.85(1 H,br), 7.68–7.88(4 H,m)

PREPARATION EXAMPLE 32

4-(3-tert-butoxycarbonylaminomethylpyrrolidin-1-yl)-N-phenylbutylamide $^1$H-NMR(CDCl$_3$,ppm) δ: 1.44(9 H,s), 1.82–2.20(5 H,m), 2.25–2.81(8 H,m), 2.85–3.23(2 H,m), 4.98–5.10(1 H,br), 6.96–7.70(5 H,m), 8.65–8.82(1 H,br)

PREPARATION EXAMPLE 33

4-(3-tert-butoxycarbonylaminomethylpyrrolidin-1-yl)-N-(4-methylphenyl)butylamide $^1$H-NMR(CDCl$_3$,ppm) δ: 1.44(9 H,s), 1.82–2.10(5 H,m), 2.30(3 H,s), 2.25–2.80(8 H,m), 2.85–3.23(2 H,m), 5.05–5.15(1 H,br), 7.05–7.60(4 H,m), 8.55–8.64(1 H,br)

PREPARATION EXAMPLE 34

4-(3-tert-butoxycarbonylaminomethylpyrrolidin-1-yl)-N-(3-chlorophenyl)butylamide $^1$H-NMR(CDCl$_3$,ppm) δ: 1.44(9 H,s), 1.83–2.20(5 H,m), 2.25–2.80(8 H,m), 2.90–3.25(2 H,m), 4.95–5.12(1 H,br), 7.00–7.70(4 H,m), 9.02–9.19(1 H,br)

PREPARATION EXAMPLE 35

2-(4-(4-(2-hydroxyethyl)piperidin-1-yl)butyl)-2,3-dihydro-1 H-isoindole-1,3-dione $^1$H-NMR(CDCl$_3$,ppm) δ: 1.18–1.95(13 H,m), 2.25–2.38(2 H,m), 2.80–2.94(2 H,m), 3.60–3.78(4 H,m), 7.67–7.90(4 H,m)

PREPARATION EXAMPLE 36

3-tert-butoxycarbonylaminomethyl-1-(2-methylsulfonylaminoethyl)-pyrrolidine $^1$H-NMR(CDCl$_3$,ppm) δ: 1.44(9 H,s), 1.44–1.53(1 H,m), 1.90–2.20(1 H,m), 2.29–2.78(7 H,m), 2.98(3 H,s), 3.05–3.26(4 H,m), 4.70–4.80(1 H,br), 5.00–5.17(1 H,br)

PREPARATION EXAMPLE 37

3-tert-butoxycarbonylaminomethyl-1-(3-(1,1,3-trioxo-2,3-dihyro-1,2-benzisothiazol-2-yl)propyl) pyrrolidine $^1$H-NMR(CDCl$_3$,ppm) δ: 1.40(9 H,s),1.45–1.55(1 H,m), 1.91–2.20(1 H,m), 2.20–2.27(2 H,m),2.30–2.73(7 H,m), 3.04–3.18(2 H,m),3.80–3.92(2 H,m), 5.02–5.10(1 H,br), 7.80–7.92(3 H,m),8.05–8.09(1 H,m)

PREPARATION EXAMPLE 38

3-tert-butoxycarbonylaminomethyl-1-(3-(2,3-dihydro-2-oxobenzimidazol-1 -yl) propyl) pyrrolidine $^1$H-NMR(CDCl$_3$,ppm) δ: 1.40(9 H,s), 1.45–1.50(3 H,m), 1.93–2.08(1 H,m), 2.45–2.78(7 H,m), 3.47(2 H,t,J=6.3 Hz), 3.84(3 H,s), 3.91(2 H,t,J=6.9 Hz), 4.40(2 H,s), 6.98–7.14(4 H,m), 9.10–9.10(1 H,br)

PREPARATION EXAMPLE 39

N-(4-(3-tert-butoxycarbonylaminomethylpyrrolidin-1-yl)butyl)-N-methylbenzamide $^1$H-NMR(CDCl$_3$,ppm) δ: 1.43(9 H,s), 1.45–1.99(5 H,m), 2.01–2.25(1 H,m), 2.45–3.33(12 H,m), 3.45–3.55(2 H,m), 5.01–5.20(1 H,br), 7.25–7.50(5 H,m)

PREPARATION EXAMPLE 40

Ethanol (200 ml) was added to 2-(3-(3-tert-butoxycarbonylamino-methylpyrrolidin-1-yl)propyl)-2,3-dihydro-1 H-isoindole-1,3-dione (17 g) and hydrazine hydrate (4.5 ml) was added at room temperature with stirring and the mixture was refluxed with stirring for 8 hr. The precipitated crystals were filtered off, and the filtrate was concentrated under reduced pressure to give 11 g of 3-(3-tert-butoxycarbonylaminomethylpyrrolidin-1-yl) propylamine.

$^1$H-NMR(CDCl$_3$,ppm) δ: 1.44(9 H,s),1.53–1.73(3 H,m), 1.87–2.06(1 H,m), 2.30–3.27(13 H,m),5.06–5.22(1 H,br)

In the same manner as in Preparation Example 40, the compounds of the following Preparation Examples 41–54 were produced.

PREPARATION EXAMPLE 41

2-(3-tert-butoxycarbonylaminomethylpyrrolidin-1-yl)ethylamine $^1$H-NMR(CDCl$_3$,ppm) δ: 1.45(9 H,s),1.48–1.50(1 H,m), 1.80–1.93(1 H,m), 2.25–2.61(7 H,m),3.06–3.43(4 H,m), 4.96–5.10(1 H,br)

PREPARATION EXAMPLE 42

2-((3R)-3-tert-butoxycarbonylaminomethylpyrrolidin-1-yl)ethylamine $^1$H-NMR(CDCl$_3$,ppm) δ: 1.44(9 H,s), 1.48–1.50(1 H,m), 1.85–2.02(1 H,m), 2.15–2.55(7 H,m), 2.88–3.13(2 H,m), 3.82–3.86(2 H,m), 4.95–5.09(1 H,br)

PREPARATION EXAMPLE 43

3-((3R)-3-tert-butoxycarbonylaminomethylpyrrolidin-1-yl)propylamine $^1$H-NMR(CDCl$_3$,ppm) δ: 1.44(9 H,s), 1.50–1.70(3 H,m), 1.88–2.04(1 H,m), 2.20–2.69(7 H,m), 2.74–2.83(2 H,m), 3.02–3.17(2 H,m), 5.06–5.16(1 H,br)

PREPARATION EXAMPLE 44

3-((3S)-3-tert-butoxycarbonylaminomethylpyrrolidin-1-yl)propylamine $^1$H-NMR(CDCl$_3$,ppm) δ: 1.44(9 H,s), 1.50–1.70(3 H,m), 1.88–2.04(1 H,m), 2.20–2.69(7 H,m), 2.74–2.83(2 H,m), 3.02–3.17(2 H,m), 5.06–5.16(1 H,br)

PREPARATION EXAMPLE 45

4-(3-tert-butoxycarbonylaminomethylpyrrolidin-1-yl)butylamine $^1$H-NMR(CDCl$_3$,ppm) δ: 1.45(9 H,s),1.48–1.75(5 H,m), 1.90–2.06(1 H,m), 2.31–2.80(7 H,m),3.06–3.17(2 H,m), 3.22–3.43(2 H,m),5.04–5.15(1 H,br)

PREPARATION EXAMPLE 46

4-((3R)-3-tert-butoxycarbonylaminomethylpyrrolidin-1-yl)butylamine $^1$H-NMR(CDCl$_3$,ppm) δ: 1.45(9 H,s), 1.40–1.57(5 H,m), 1.87–2.03(1 H,m), 2.28–2.79(7 H,m), 3.05–3.13(2 H,m), 3.38–3.52(2 H,m), 5.12–5.23(1 H,br)

PREPARATION EXAMPLE 47

4-((3S)-3-tert-butoxycarbonylaminomethylpyrrolidin-1-yl)butylamine $^1$H-NMR(CDCl$_3$,ppm) δ: 1.45(9 H,s), 1.40–1.57(5 H,m), 1.87–2.03(1 H,m), 2.28–2.79(7 H,m), 3.05–3.13(2 H,m), 3.38–3.52(2 H,m), 5.12–5.23(1 H,br)

PREPARATION EXAMPLE 48

5-(3-tert-butoxycarbonylaminomethylpyrrolidin-1-yl)pentylamine $^1$H-NMR(CDCl$_3$,ppm) δ: 1.45(9 H,s), 1.48–1.60(7 H,m), 1.95–2.07(1 H,m), 2.25–2.78(7 H,m), 3.10–3.20(2 H,m), 3.25–3.45(2 H,m), 5.00–5.09(1 H,br)

PREPARATION EXAMPLE 49

5-((3R)-3-tert-butoxycarbonylaminomethylpyrrolidin-1-yl)pentylamine $^1$H-NMR(CDCl$_3$+CD$_3$OD,ppm) 67 :1.28–1.59(7 H,m), 1.44(9 H,s), 1.90–2.04(1 H,m), 2.22–2.80(7 H,m), 3.05–3.13(2 H,m), 3.55–3.59(2 H,m)

PREPARATION EXAMPLE 50

5-((3S)-3-tert-butoxycarbonylaminomethylpyrrolidin-1-yl)pentylamine $^1$H-NMR(CDCl$_3$+CD$_3$OD,ppm) δ: 1.28–1.59(7 H,m), 1.44(9 H,s), 1.90–2.04(1 H,m), 2.22–2.80(7 H,m), 3.05–3.13(2 H,m), 3.55–3.59(2 H,m)

PREPARATION EXAMPLE 51

6-((3R)-3-tert-butoxycarbonylaminomethylpyrrolidin-1-yl)hexylamine $^1$H-NMR(CDCl$_3$+CD$_3$OD,ppm) δ: 1.20–1.78(9 H,m), 1.44(9 H,s), 1.90–2.05(1 H,m), 2.22–2.85(7 H,m), 3.20–3.41(2 H,m), 3.53–3.59(2 H,m)

PREPARATION EXAMPLE 52

6-((3S)-3-tert-butoxycarbonylaminomethylpyrrolidin-1-yl)hexylamine $^1$H-NMR(CDCl$_3$+CD$_3$OD,ppm) δ: 1.20–1.78(9 H,m), 1.44(9 H,s), 1.90–2.05(1 H,m), 2.22–2.85(7 H,m), 3.20–3.41(2 H,m), 3.53–3.59(2 H,m)

PREPARATION EXAMPLE 53

4-(4-tert-butoxycarbonylaminomethylpiperidin-1-yl)butylamine $^1$H-NMR(CDCl$_3$,ppm) δ: 1.15–1.35(3 H,m), 1.43(9 H,s), 1.43–1.72(6 H,m), 1.80–1.95(2 H,m), 2.24–2.38(2 H,m), 2.82–3.05(6 H,m), 4.70–4.92(1 H,br)

PREPARATION EXAMPLE 54

5-(4-tert-butoxycarbonylaminomethylpiperidin-1-yl)pentylamine $^1$H-NMR(CDCl$_3$,ppm) δ: 1.25–1.77(20 H,m), 1.95–2.12(2 H,m), 2.38–2.45(2 H,m), 2.75–2.85(2 H,m), 2.95–3.10(2 H,m), 4.38–4.55(2 H,m), 4.73–4.84(1 H,br)

PREPARATION EXAMPLE 55

3-(3-tert-Butoxycarbonylaminomethylpyrrolidin-1-yl) propylamine (5 g) was dissolved in dimethylformamide (50 ml) and 4-amino-5-chloro-2-methoxybenzoic acid (3.9 g)

and 1-hydroxybenzotriazole (3.2 g) were added. The mixture was stirred at 0° C. for 15 min and 1-ethyl-3-(3-dimethylaminopropyl)carbodiimide (4.5 g) was added, followed by stirring at room temperature for 10 hr. The reaction mixture was concentrated under reduced pressure, and aqueous potassium carbonate solution was added to the residue. The mixture was extracted with ethyl acetate, dried over magnesium sulfate, and concentrated under reduced pressure. The obtained residue was purified by silica gel chromatography to give 3.4 g of 4-amino-N-(3-(3-tert-butoxycarbonylaminomethylpyrrolidin- 1-yl)propyl)-5-chloro-2-methoxybenzamide.

$^1$H-NMR (CDCl$_3$,ppm) δ: 1.43(9 H,s), 1.43–1.62(1 H,m), 1.80–2.10(3 H,m), 2.36–2.82(7 H,m), 3.03–3.18(2 H,m), 3.44–3.56(2 H,m), 3.90(3 H,s), 4.38(2 H,s), 5.03–5.15(1 H,br), 6.30(1 H,s), 7.75–7.87(1 H,br), 8.09(1 H,s)

In the same manner as in Preparation Example 55, the compounds of the following Preparation Examples 56–80 were produced.

PREPARATION EXAMPLE 56

4-amino-N-(2-(3-tert-butoxycarbonylaminomethylpyrrolidin-1-yl)-ethyl)-5-chloro-2-methoxybenzamide $^1$H-NMR (CDCl$_3$,ppm) δ: 1.43(9 H,s), 1.43–1.66(1 H,m), 1.92–2.10(1 H,m), 2.30–2.82(7 H,m), 3.07–3.20(2 H,m), 3.50–3.63(2 H,m), 3.89(3 H,s), 4.35(2 H,s), 4.68–4.83(1 H,br), 6.28(1 H,s), 8.01–8.14(1 H,br), 8.10(1 H,s)

PREPARATION EXAMPLE 57

4-amino-N-(4-(3-tert-butoxycarbonylaminomethylpyrrolidin-1-yl)-butyl)-5-chloro-2-methoxybenzamide $^1$H-NMR (CDCl$_3$,ppm) δ: 1.43(9 H,s), 1.45–1.70(5 H,m), 1.90–2.04(1 H,m), 2.32–2.72(7 H,m), 3.05–3.16(2 H,m), 3.36–3.46(2 H,m), 3.89(3 H,s), 6.30(1 H,s), 7.65–7.73(1 H,br), 8.10(1 H,s)

PREPARATION EXAMPLE 58

4-amino-N-(4-((3R)-3-tert-butoxycarbonylaminomethylpyrrolidin-1-yl)butyl)-5-chloro-2-methoxybenzamide $^1$H-NMR (CDCl$_3$,ppm) δ: 1.43(9 H,s), 1.45–1.68(5 H,m), 1.90–2.07(1 H,m), 2.31–2.68(7 H,m), 3.03–3.14(2 H,m), 3.36–3.44(2 H,m), 3.89(3 H,s), 6.29(1 H,s), 7.65–7.73(1 H,br), 8.09(1 H,s)

PREPARATION EXAMPLE 59

4-amino-N-(5-((3R)-3-tert-butoxycarbonylaminomethylpyrrolidin-1-yl)pentyl)-5-chloro-2-methoxybenzamide $^1$H-NMR (CDCl$_3$,ppm) δ: 1.42(9 H,s), 1.30–1.80(7 H,m), 1.95–2.10(1 H,m), 2.20–2.71(7 H,m), 3.04–3.15(2 H,m), 3.38–3.48(2 H,m), 3.89(3 H,s), 6.30(1 H,s), 7.64–7.70(1 H,br), 8.08(1 H,s)

PREPARATION EXAMPLE 60

N-(3-(3-tert-butoxycarbonylaminomethylpyrrolidin-1-yl)propyl)-4-pyridinecarboxamide $^1$H-NMR (CDCl$_3$,ppm) δ: 1.35–1.60(10 H,m), 1.75–2.20(4 H,m),2.30–2.45(2 H,m), 2.55–2.90(4 H,m), 3.03–3.18(2 H,m),3.51–3.68(2 H,m),4.71–4.85(1 H,br), 7.58–7.66(2 H,m),8.55–8.65(1 H,br),8.65–8.79(2 H,m)

PREPARATION EXAMPLE 61

N-(2-(3-tert-butoxycarbonylaminomethylpyrrolidin-1-yl)ethyl)-6-chloro-4-methyl-3,4-dihydro-2H-1,4-benzoxazine-8-carboxamide $^1$H-NMR (CDCl$_3$,ppm) δ: 1.42(9 H,s), 1.45–1.62(1 H,m), 1.92–2.08(1 H,m), 2.30–2.83(7 H,m), 2.90(3 H,s), 3.06–3.18(2 H,m), 3.30–3.38(2 H,m), 3.52–3.64(2 H,m), 4.35–4.41(2 H,m), 4.75–4.87(1 H,br), 6.66(1 H,d,J=2.64 Hz), 7.42(1 H,d,J=2.64 Hz), 8.04–8.16(1 H,br)

PREPARATION EXAMPLE 62

N-(3-(3-tert-butoxycarbonylaminomethylpyrrolidin-1-yl)propyl)-6-chloro-4-methyl-3,4-dihydro-2H-1,4-benzoxazine-8-carboxamide $^1$H-NMR (CDCl$_3$,ppm) δ: 1.43(9 H,s), 1.43–1.57(1 H,m), 1.77–2.10(3 H,m), 2.62–2.74(7 H,m), 2.90(3 H,s), 3.05–3.14(2 H,m), 3.32–3.38(2 H,m), 3.42–3.56(2 H,m), 4.35–4.43(2 H,m), 5.00–5.10(1 H,br), 6.67(1 H,d,J=1.98 Hz), 7.40(1 H,d,J=1.98 Hz), 7.81–7.90(1 H,br)

PREPARATION EXAMPLE 63

N-(4-(3-tert-butoxycarbonylaminomethylpyrrolidin-1-yl)butyl)-6-chloro-4-methyl-3,4-dihydro-2H-1,4-benzoxazine-8-carboxamide $^1$H-NMR (CDCl$_3$,ppm)δ: 1.40(9 H,s),1.45–1.81(5 H,m), 1.90–2.07(1 H,m), 2.31–2.49(2 H,m),2.50–2.64(3 H,m), 2.65–2.78(2 H,m),2.89(3 H,s), 3.06–3.17(2 H,m), 3.34–3.41(2 H,m),3.41–3.48(2 H,m),4.35–4.41(2 H,m), 5.03–5.10(1 H,br),6.67(1 H,d,J=2.64 Hz),7.42(1 H,d,J=2.64 Hz), 7.74–7.83(1 H,br)

PREPARATION EXAMPLE 64

N-(2-(3-tert-butoxycarbonylaminomethylpyrrolidin-1-yl)ethy)-1-methyl-1 H-indole-3-carboxamide $^1$H-NMR (CDCl$_3$,ppm) δ: 1.43(9 H,s), 1.42–1.60(1 H,m), 1.90–2.04(1 H,m), 2.29–2.80(7 H,m), 3.23–3.31(2 H,m), 3.66–3.78(2 H,m), 3.79(3 H,s), 4.95–5.12(1 H,br), 7.22–7.41(4 H,m), 7.70(1 H,s), 8.03–8.07(1 H,m)

PREPARATION EXAMPLE 65

N-(3-(3-tert-butoxycarbonylaminomethylpyrrolidin-1-yl)propyl)-1-methyl- 1 H-indole-3-carboxamide $^1$H-NMR (CDCl$_3$,ppm) δ: 1.42(9 H,s), 1.42–1.60(1 H,m), 1.80–2.04(3 H,m), 2.33–2.47(2 H,m), 2.66–2.90(5 H,m), 3.00–3.13(2 H,m), 3.54–3.65(2 H,m), 3.81(3 H,s), 4.76–4.87(1 H,br), 7.20–7.37(4 H,m), 7.70(1 H,s), 8.00–8.05(1 H, m)

PREPARATION EXAMPLE 66

N-(4-(3-tert-butoxycarbonylaminomethylpyrrolidin-1-yl)butyl)-1-methyl-1 H-indole-3-carboxamide $^1$H-NMR (CDCl$_3$,ppm) δ: 1.41(9 H,s),1.45–1.80(5 H,m) ,1.91–2.05(1 H,m), 2.31–2.82(7 H,m),3.05–3.16(2 H,m), 3.45–3.56(2 H,m),3.80(3 H,s), 4.95–5.03(1 H,br), 7.20–7.36(4 H,m),7.69(1 H,s),7.88–7.99(1 H,br)

PREPARATION EXAMPLE 67

N-(4-((3R)-3-tert-butoxycarbonylaminomethylpyrrolidin-1-yl)butyl)-1-methyl-1 H-indole-3-carboxamide $^1$H-NMR(CDCl$_3$,ppm) δ: 1.41(9 H,s), 1.42–1.70(5 H,m), 1.96–2.07(1 H,m), 2.25–2.73(7 H,m), 3.06–3.16(2 H,m),

PREPARATION EXAMPLE 68

N-(4-((3S)-3-tert-butoxycarbonylaminomethylpyrrolidin-1-yl)butyl)-1-methyl-1 H-indole-3-carboxamide $^1$H-NMR(CDCl$_3$,ppm) δ: 1.41(9 H,s), 1.42–1.70(5 H,m), 1.96–2.07(1 H,m), 2.25–2.73(7 H,m), 3.06–3.16(2 H,m), 3.45–3.53(2 H,m), 3.78(3 H,s), 4.91–4.99(1 H,br), 7.23–7.38(4 H,m), 7.70(1 H,s), 7.83–7.96(1 H,br)

PREPARATION EXAMPLE 69

N-(5-(3-tert-butoxycarbonylaminomethylpyrrolidin-1-yl)pentyl)-1-methyl-1 H-indole-3-carboxamide $^1$H-NMR(CDCl$_3$,ppm) δ: 1.15–1.70(7 H,m), 1.41(9 H,s), 1.90–2.10(1 H,m), 2.31–2.875(7 H,m), 3.01–3.11(2 H,m), 3.40–3.51(2 H,m), 3.81(3 H,s), 4.95–5.00(1 H,br), 7.15–7.31(4 H,m), 7.67(1 H,s), 7.84–7.95(1 H,br)

PREPARATION EXAMPLE 70

N-(5-((3R)-3-tert-butoxycarbonylaminomethylpyrrolidin-1-yl)pentyl)-1-methyl-1 H-indole-3-carboxamide $^1$H-NMR(CDCl$_3$,ppm) δ: 1.17–1.72(7 H,m), 1.42(9 H,s), 2.00–2.14(1 H,m), 2.45–3.22(9 H,m), 3.38–3.54(2 H,m), 3.80(3 H,s), 5.00–5.10(1 H,br), 7.20–7.37(4 H,m), 7.75(1 H,s), 7.93–7.99(1 H,br)

PREPARATION EXAMPLE 71

N-(5-((3S)-3-tert-butoxycarbonylaminomethylpyrrolidin-1-yl)pentyl)-1-methyl-1 H-indole-3-carboxamide $^1$H-NMR(CDCl$_3$,ppm) δ: 1.17–1.72(7 H,m), 1.42(9 H,s), 2.00–2.14(1 H,m), 2.45–3.22(9 H,m), 3.38–3.54(2 H,m), 3.80(3 H,s), 5.00–5.10(1 H,br), 7.20–7.37(4 H,m), 7.75(1 H,s), 7.93–7.99(1 H,br)

PREPARATION EXAMPLE 72

N-(6-((3R)-3-tert-butoxycarbonylaminomethylpyrrolidin-1-yl)hexyl)-1-methyl-1 H-indole-3-carboxamide $^1$H-NMR(CDCl$_3$,ppm) δ: 1.17–1.62(18 H,m), 1.72–1.85(1 H,m), 1.95–2.12(1 H,m), 2.45–2.85(4 H,m), 2.95–3.20(2 H,m), 3.26–3.41(2 H,m), 3.47(3 H,s), 3.60–3.70(2 H,m), 6.45–6.60(1 H,br), 7.12–7.35(4 H,m), 7.85–7.92(1 H,m), 8.08–8.18(1 H,m)

PREPARATION EXAMPLE 73

N-(6-((3S)-3-tert-butoxycarbonylaminomethylpyrrolidin-1-yl)hexyl)-1-methyl-1 H-indole-3-carboxamide $^1$H-NMR(CDCl$_3$,ppm) δ: 1.17–1.62(18 H,m), 1.72–1.85(1 H,m), 1.95–2.12(1 H,m), 2.45–2.85(4 H,m), 2.95–3.20(2 H,m), 3.26–3.41(2 H,m), 3.47(3 H,s), 3.60–3.70(2 H,m), 6.45–6.60(1 H,br), 7.12–7.35(4 H,m), 7.85–7.92(1 H,m), 8.08–8.18(1 H,m)

PREPARATION EXAMPLE 74

N-(4-((3R)-3-tert-butoxycarbonylaminomethylpyrrolidin-1-yl)butyl)-1-methyl-1 H-indole-3-carboxamide $^1$H-NMR(CDCl$_3$,ppm) δ: 1.43(9 H,s), 1.42–1.80(5 H,m), 1.88–2.07(1 H,m), 2.28–2.75(7 H,m), 3.03–3.16(2 H,m), 3.38–3.53(2 H,m), 4.05(3 H,s), 4.82–4.96(1 H,br), 6.80–6.88(1 H,br), 7.08–7.40(4 H,m), 7.55–7.66(1 H,m)

PREPARATION EXAMPLE 75

N-(4-((3R)-3-tert-butoxycarbonylaminomethylpyrrolidin-1-yl)butyl)-1-isopropyl-1 H-indole-3-carboxamide $^1$H-NMR(CDCl$_3$,ppm) δ: 1.42(9 H,s), 1.55(6 H,d,J=6.6 Hz), 1.60–1.92(5 H,m), 2.03–2.19(1 H,m), 2.54–3.33(9 H,m), 3.44–3.59(2 H,m), 4.62–4.78(1 H,m), 5.08–5.18(1 H,br), 6.75–6.88(1 H,br), 7.18–7.43(3 H,m), 8.08–8.18(2 H,m)

PREPARATION EXAMPLE 76

N-(4-((3R)-3-tert-butoxycarbonylaminomethylpyrrolidin-1-yl)butyl)-1-benzyl-1 H-indole-3-carboxamide $^1$H-NMR(CDCl$_3$,ppm) δ: 1.42(9 H,s), 1.44–1.80(5 H,m), 1.88–2.05(1 H,m), 2.29–2.85(7 H,m), 3.01–3.17(2 H,m), 3.40–5.58(2 H,m), 4.95–5.08(1 H,br), 5.30(2 H,s), 6.47–6.62(1 H,br), 7.08–7.35(8 H,m), 7.73–7.85(1 H,s), 8.00–8.18(1 H,m)

PREPARATION EXAMPLE 77

N-(4-(4-tert-butoxycarbonylaminomethylpiperidin-1-yl)butyl)-1-methyl-1 H-indole-3-carboxamide $^1$H-NMR(CDCl$_3$,ppm) δ: 1.15–1.30(3 H,m), 1.44(9 H,s), 1.55–1.75(6 H,m), 1.83–2.10(3 H,m), 2.35–2.45(2 H,m), 2.88–3.05(3 H,m), 3.44–3.55(2 H,m), 3.82(3 H,s), 4.53–4.64(1 H,br), 6.14–6.25(1 H,br), 7.18–7.38(3 H,m), 7.65(1 H,s), 7.85–7.93(1 H,m)

PREPARATION EXAMPLE 78

N-(3-((3R)-3-tert-butoxycarbonylaminomethylpyrrolidin-1-yl)propyl)-3-phenylpropylamide $^1$H-NMR(CDCl$_3$,ppm) δ: 1.44(9 H,s), 1.46–1.53(1 H,m), 1.59–1.70(2 H,m), 1.90–2.04(1 H,m), 2.30–2.70(9 H,m), 2.90–3.00(2 H,m), 3.05–3.14(2 H,m), 3.25–3.36(2 H,m), 4.88–4.98(1 H,br), 6.75–6.84(1 H,br), 7.14–7.33(5 H,m)

PREPARATION EXAMPLE 79

N-(2-((3R)-3-tert-butoxycarbonylaminomethylpyrrolidin-1-yl)ethyl)-4-phenylbutylamide $^1$H-NMR(CDCl$_3$,ppm) δ: 1.40–1.55(10 H,m), 1.88–2.04(3 H,m), 2.14–2.78(11 H,m), 3.05–3.50(4 H,m), 4.78–4.92(1 H,br), 6.31–6.45(1 H,br), 7.10–7.33(5 H,m)

PREPARATION EXAMPLE 80

N-(5-(4-tert-butoxycarbonylaminomethylpiperidin-1-yl)pentyl)-1-methyl-1 H-indole-3-carboxamide $^1$H-NMR(CDCl$_3$,ppm) δ: 1.18–1.72(11 H,m), 1.43(9 H,s), 1.85–2.02(2 H,m), 2.30–2.39(2 H,m), 2.85–3.05(4 H,m), 3.44–3.55(2 H,m), 3.79(3 H,s), 4.60–4.74(1 H,br), 6.05–6.13(1 H,br), 7.20–7.38(3 H,m), 7.66(1 H,s), 7.92–7.98(1 H,m)

PREPARATION EXAMPLE 81

4-Aminomethyl-1-tert-butoxycarbonylpiperidine (10.0 g) was dissolved in dimethylformamide and 4-amino-5-chloro- 2-methoxybenzoic acid (9.4 g) and 1-hydroxybenzotriazole (6.6 g) were added. After stirring at 0° C. for 40 min, 1-ethyl-3-(3-dimethylaminopropyl)-carbodiimide hydrochloride (9.4 g) was added, and the mixture was stirred at room temperature for 24 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 19.0 g of 4-amino-5-chloro-N-(1-tert-butoxycarbonylpiperidin-4-ylmethyl)-2-methoxybenzamide.

$^1$H-NMR(CDCl$_3$,ppm) δ: 1.05–1.26(1 H,m), 1.45(9 H,s), 1.65–1.89(2 H,m), 2.63–2.89(2 H,m), 2.88(2 H,s), 2.95(2 H,s), 3.28–3.38(2 H,m), 3.89(3 H,s), 4.05–4.20(2 H,brs), 6.32(1 H,s), 7.73–7.82(1 H,br), 8.09(1 H,s)

PREPARATION EXAMPLE 82

4-amino-5-chloro-N-(1-tert-butoxycarbonylpiperidin-4-ylmethyl)-2-methoxybenzamide (18.9 g) was dissolved in 4N hydrochloric acid-dioxane solution (150 ml). The mixture was stood at room temperature for 2 hr and the precipitated crystals were collected by filtration to give 15.3 g of 4-amino-5-chloro-2-methoxy-N-(piperidin-4-ylmethyl)-benzamide hydrochloride.
m.p. 208°~211° C.

PREPARATION EXAMPLE 83

4-Amino-5-chloro-2-methoxy-N-(piperidin-4-ylmethyl) benzamide hydrochloride (15.0 g) was dissolved in dimethylformamide (100 ml) and toluene (150 ml), and potassium carbonate (18.6 g) and 4-bromobutylphthalimide (12.7 g) were added. The mixture was stirred at 70° C. for 2 hr. The reaction mixture was concentrated under reduced pressure and the residue was extracted with ethyl acetate. The extract was dried over magnesium sulfate and concentrated under reduced pressure. The obtained residue was purified by silica gel chromatography to give 13.6 g of 4-amino-5-chloro-N-(1-(4-(2,3-dihydro-1,3-dioxo-1 H-isoindol-2-yl)butyl) piperidin-4-ylmethyl)-2-methoxybenzamide.

$^1$H-NMR(CDCl$_3$,ppm) δ: 1.20–1.39(2 H,m), 1.55–1.98(9 H,m), 2.28–2.41(2 H,m), 2.85–2.97(2 H,m), 3.25–3.37(2 H,m), 3.66–3.78(2 H,m), 3.89(3 H,s), 4.42(2 H,s), 6.29(1 H,s), 7.65–7.86(4 H,m), 8.09(1 H,s)

In the same manner as in Preparation Example 83, the compounds of the following Preparation Examples 84–86 were produced.

PREPARATION EXAMPLE 84

4-amino-5-chloro-N-(1-(3-(2,3-dihydro-1,3-dioxo-1 H-isoindol-2-yl)-propyl)piperidin-4-ylmethyl)-2-methoxybenzamide $^1$H-NMR (CDCl$_3$,ppm) δ: 1.05–1.22(2 H,m), 1.41–1.70(3 H,m), 1.75–1.95(4 H,m), 2.33–2.45(2 H,m), 2.80–2.93(2 H,m), 3.18–3.25(2 H,m), 3.72–3.80(2 H,m), 3.88(3 H,s), 4.43(2 H,s), 6.30(1 H,s), 7.65–7.88(4 H,m), 8.08(1 H,s)

PREPARATION EXAMPLE 85

4-amino-5-chloro-N-(1-(5-(2,3-dihydro-1,3-dioxo-1H-isoindol-2-yl)-pentyl)piperidin-4-ylmethyl)-2-methoxybenzamide $^1$H-NMR (CDCl$_3$,ppm)δ: 1.20–1.98(11 H,m), 2.00–2.11(2 H,m), 2.30–2.40(2 H,m), 2.85–2.97(2 H,m), 3.25–3.37(2 H,m), 3.66–3.78(2 H,m), 3.89(3 H,s), 4.42(2 H,s), 6.29(1 H,s), 7.63–7.85(4 H,m), 8.09(1 H,s)

PREPARATION EXAMPLE 86

4-amino-5-chloro-N-(1-(6-(2,3-dihydro-1,3-dioxo-1H-isoindol-2-yl)-hexyl)piperidin-4-ylmethyl)-2-methoxybenzamide $^1$H-NMR (CDCl$_3$,ppm)δ: 1.30–1.82(13 H,m), 1.95–2.08(2 H,m), 2.33–2.42(2 H,m), 2.95–3.05(2 H,m), 3.25–3.38(2 H,m), 3.64–3.75(2 H,m), 89(3 H,s), 4.48(2 H,s), 6.32(1 H,s), 7.68–7.82(4 H,m), 8.08(1 H,s)

PREPARATION EXAMPLE 87

4-Amino-5-chloro-N-(1-(4-(2,3-dihydro-1,3-dioxo-1H-isoindol-2-yl)butyl)piperidin-4-ylmethyl)-2-methoxybenzamide (8.3 g) was dissolved in ethanol (100 ml) and hydrazine hydrate (1.1 ml) was added at room temperature with stirring. The mixture was refluxed with stirring for 3 hr. The precipitated crystals were filtered off and the filtrate was concentrated under reduced pressure to give 4.4 g of 4-amino-N-(1-(4-aminobutyl)piperidin-4-ylmethyl)-5-chloro-2-methoxybenzamide.

$^1$H-NMR(CDCl$_3$+CD$_3$OD,ppm) δ: 1.25–1.41(2 H,m), 1.45–1.79(7 H,m), 1.91–2.07(2 H,m), 2.28–2.45(2 H,m), 2.73–2.83(2 H,m), 2.95–3.03(2 H,m), 3.25–3.33(2 H,m), 3.89(3 H,s), 6.35(1 H,s), 7.82–7.90(1 H,br), 7.99(1 H,s)

In the same manner as in Preparation Example 87, the compounds of the following Preparation Examples 88–90 were produced.

PREPARATION EXAMPLE 88

4-amino-N-(1-(3-aminopropyl)piperidin-4-ylmethyl) -5-chloro-2-methoxybenzamide $^1$H-NMR (CDCl$_3$+CD$_3$OD,ppm) δ: 1.20–1.41(2 H,m), 1.50–2.05(7 H,m), 2.38–2.48(2 H,m), 2.78–2.85(2 H,m), 2.92–3.03(2 H,m), 3.25–3.35(2 H,m), 3.90(3 H,s), 6.40(1 H,s), 7.82–7.95(1 H,br), 8.00(1 H,s)

PREPARATION EXAMPLE 89

4-amino-N-(1-(5-aminopentyl)piperidin-4-ylmethyl) -5-chloro-2-methoxybenzamide $^1$H-NMR (CDCl$_3$+CD$_3$OD,ppm) δ: 1.20–1.85(11 H,m), 1.90–2.07(2 H,m), 2.28–2.42(2 H,m), 2.66–2.78(2 H,m), 2.88–3.03(2 H,m), 3.25–3.42(2 H,m), 3.48(3 H,s), 6.36(1 H,s), 7.83–7.95(1 H,br), 8.01(1 H,s)

PREPARATION EXAMPLE 90

4-amino-N-(1-(6-aminohexyl)piperidin-4-ylmethyl)-5-chloro-2-methoxybenzamide $^1$H-NMR (CDCl$_3$+CD$_3$OD,ppm) δ: 1.25–1.88(13 H,m), 1.96–2.18(2 H,m), 2.32–2.48(2 H,m), 2.73–2.85(2 H,m), 2.95–3.10(2 H,m), 3.25–3.40(2 H,m), 3.90(3 H,s), 6.36(1 H,s), 7.87–7.95(1 H,br), 8.00(1 H,s)

PREPARATION EXAMPLE 91

60% Sodium hydride (1.4 g) was suspended in dimethylformamide (40 ml), and phenol (3 g) was added under ice-cooilng with stirring. The mixture was stirred at room temperature for 1 hr. The mixture was again ice-cooled, and 1-bromo-5-chloropentane (5.9 g) was added, which was followed by stirring at room temperature for 1.5 hr. Water was added to the reaction mixture and the mixture was extracted with ethyl acetate. The organic layer was washed with brine, dried and the solvent was evaporated under reduced pressure to give 5.9 g of 5-phenoxypentyl chloride.

$^1$H-NMR (CDCl$_3$,ppm) δ: 1.55–1.67(2 H,m), 1.75–1.89(4 H,m), 3.55(2 H,t,J=6.6 Hz), 3.95(2 H,t,J=6.6 Hz), 6.86–6.95(3 H,m), 7.22–7.31 (2 H,m)

PREPARATION EXAMPLE 92

60% Sodium hydride (1.33 g) was suspended in dimethylformamide (40 ml), and benzyl alcohol (3 g) was added under ice-cooilng with stirring. The mixture was stirred at room temperature for 1 hr. The mixture was again ice-cooled, and 1,5-dibromopentane (6.4 g) was added, which was followed by stirring at room temperature for 3 hr. Water was added to the reaction mixture and the mixture was extracted with ethyl acetate. The organic layer was washed with brine, dried and the solvent was evaporated under reduced pressure to give 7.2 g of 5-benzyloxypentyl bromide.

$^1$H-NMR (CDCl$_3$,ppm) δ: 1.48–1.91(6 H,m), 3.37–3.51(4 H,m), 4.49(2 H,s), 7.22–7.37(5 H,m)

PREPARATION EXAMPLE 93

Potassium carbonate (5 g) and 1-bromo-5-chloropentane (4.9 g) were added to a solution of benzylmercaptan (3 g) in dimethylformamide (40 ml), and the mixture was stirred at 70–80° C. for 2 hr. Water was added to the reaction mixture and the mixture was extracted with ethyl acetate. The organic layer was washed with brine, dried and the solvent was evaporated under reduced pressure to give 3 g of 5-benzylthiopentyl chloride.

$^1$H-NMR (CDCl$_3$,ppm) δ: 1.42–1.91 (6 H,m), 2.41 (2 H,t,J=7.3 Hz), 3.49(2 H,t,J=6.6 Hz), 3.70(2 H,s), 7.19–7.37(5 H,m)

PREPARATION EXAMPLE 94

6-Chlorohexyl alcohol (1.4 g), N-methylaniline (1.1 g) and sodium carbonate (1.1 g) were heated at 120° C. for 9 hr. Water was added to the reaction mixture and the mixture was extracted with ethyl acetate. The organic layer was washed with brine, dried and the solvent was evaporated under reduced pressure. The obtained residue was purified by silica gel column chromatography to give 1.1 g of 6-(N-methy-N-phenylamino)hexyl alcohol.

$^1$H-NMR (CDCl$_3$,ppm) δ: 1.31–1.42(4 H,m), 1.51–1.63(4 H,m), 2.91(3 H,s), 3.30(2 H,t,J=7.9 Hz), 3.63(2 H,t,J=6.6 Hz), 6.64–6.70(3 H,m), 7.18–7.21(2 H,m) 6-(N-Methy-N-phenylamino)hexyl alcohol (1.1 g) and triphenylphosphine (1.3 g) were dissolved in methylene chloride (40 ml), and N-chlorosuccinylimide (0.71 g) was added, which was followed by stirring at room temperature for 1 hr 20 min. The organic layer was washed with brine, dried and the solvent was evaporated under reduced pressure. The obtained residue was purified by silica gel column chromatography to give 0.90 g of 6-(N-methy-N-phenylamino)hexyl chloride.

$^1$H-NMR (CDCl$_3$,ppm) δ: 1.31–1.64(6 H,m), 1.72–1.82(2 H,m), 2.91(3 H,s), 3.00(2 H,t,J=7.3 Hz), 3.52(2 H,t,J=6.6 Hz), 6.69(3 H,d,J=8.0 Hz), 7.21(2 H,dd,J=1.3,7.2 Hz)

PREPARATION EXAMPLE 95

60% Sodium hydride (1.16 g) was suspended in dimethylformamide (40 ml), and phenol (3 g) was added under ice-cooilng with stirring. The mixture was stirred at room temperature for 1 hr. The mixture was again ice-cooled, and a solution of 1,6-dibromohexane (7.78 g) in dimethylformamide (10 ml) was dropwise added, which was followed by stirring at room temperature for 2 hr. Water was added to the reaction mixture and the mixture was extracted with ethyl acetate. The organic layer was washed with brine, dried and the solvent was evaporated under reduced pressure to give 8.2 g of 6-phenoxyhexyl bromide.

$^1$H-NMR (CDCl$_3$,ppm)δ: 1.42–1.58(4 H,m), 1.70–1.93(4 H,m), 3.36–3.42(2 H,m), 3.92–3.98(2 H,m), 6.86–6.94(3 H,m), 7.26(2 H,t,J=7.3 Hz)

PREPARATION EXAMPLE 96

60% Sodium hydride (1.2 g) was suspended in tetrahydrofuran (30 ml), and benzyl alcohol (3.0 g) was added under ice-cooling with stirring. The mixture was stirred at room temperature for 30 min, and again ice-cooled. 1,4-Dibromobutane (6.0 g) was added and the mixture was stirred for 3 hr. Water was added to the reaction mixture and the mixture was extracted with ethyl acetate. The organic layer was washed with brine, dried and the solvent was evaporated under reduced pressure to give 3.8 g of 4-benzyloxybutyl bromide.

$^1$H-NMR (CDCl$_3$,ppm) δ: 2.00–2.06(4 H,m), 3.40–3.46(4 H,m), 4.67(2 H,s), 7.27–7.36(5 H,m)

PREPARATION EXAMPLE 97

4-Chlorobenzyl alcohol (4.3 g), 60% sodium hydride (1.8 g) and 1-bromo-5-chloropentane (6.0 g) were reacted and treated in the same manner as in Example 96 to give 3.6 g of 5-(4-chlorobenzyloxy)pentyl chloride.

$^1$H-NMR (CDCl$_3$,ppm) δ: 0.80–0.92(2 H,q), 1.43–1.72(4 H,m), 1.88–1.92(2 H,m), 3.41–3.48(2 H,m), 3.48(2 H,s), 7.26(2 H,dd), 7.30(2 H,dd)

PREPARATION EXAMPLE 98

60% Sodium hydride (1.16 g) was suspended in dimethylformamide (40 ml), and a solution of cyclohexanemethanol (0.3 g) in dimethylformamide (10 ml) was dropwise added under ice-cooling with stirring, which was followed by stirring at room temperature for 1 hr. The mixture was again ice-cooled, and a solution of 1-bromo-5-chloropentane (4.88 g) in dimethylformamide (10 ml) was dropwise added, which was followed by stirring at room temperature for 2.5 hr. Water was added to the reaction mixture and the mixture was extracted with ethyl acetate. The organic layer was washed successively with water and brine, dried and the solvent was evaporated under reduced pressure. The obtained residue was purified by silica gel column chromatography (hexane:ethyl acetate=10:1) to give 2.9 g of 5-(cyclohexylmethoxy)pentyl bromide.

$^1$H-NMR (CDCl$_3$,ppm) δ: 0.83–1.94(17 H,m), 3.19(2 H,d,J=6.6 Hz), 3.39(2 H,t,J=6.6 Hz), 3.54(2 H,t,J=7.3 Hz)

PREPARATION EXAMPLE 99

Potassium carbonate (5.64 g) and 1,4-dibromobutane (5.88 g) were added to a solution of thiophenol (3 g) in dimethylformamide (40 ml), and the mixture was stirred at 50° C. for 3 hr. Water was added to the reaction mixture and the mixture was extracted with ethyl acetate. The organic layer was washed with brine, dried and the solvent was evaporated under reduced pressure to give 6.67 g of 4-phenylthiobutyl bromide.

$^1$H-NMR (CDCl$_3$,ppm) δ: 1.74–1.85(2 H,m), 1.97–2.04(2 H,m), 2.94(2 H,t,J=6.6 Hz), 3.40(2 H,t,J=6.6 Hz), 7.14–7.35(5 H,m)

PREPARATION EXAMPLE 100

Thiophenol (3 g), potassium carbonate (5.64 g) and 1,6-dibromohexane (6.64 g) were reacted and treated in the same manner as in Preparation Example 99 to give 7.4 g of 6-phenylthiohexyl bromide.

$^1$H-NMR (CDCl$_3$,ppm) δ: 1.40–1.49(4 H,m), 1.59–1.72(2 H,m), 1.81–1.89(2 H,m), 2.93(2 H,t,J=6.6 Hz), 3.40(2 H,t, J=6.6 Hz), 7.15–7.34(5 H,m)

In the same manner as in the above-mentioned Preparation Example 92, the following compounds were obtained.

PREPARATION EXAMPLE 101

6-Benzyloxyhexyl chloride $^1$H-NMR (CDCl$_3$,ppm) δ: 1.38–1.80(8 H,m), 3.47(2 H,t, J=6.3 Hz), 3.53(2 H,t,J=7.0 Hz), 4.50(2 H,s), 7.26–7.35(5 H,m)

PREPARATION EXAMPLE 102

5-(2-phenylethyloxy)pentyl chloride $^1$H-NMR (CDCl$_3$,ppm)δ: 1.41–1.85(6 H,m), 1.88(2 H,t, J=7.3 Hz), 3.44(2 H,t,J=6.3 Hz), 3.51(2 H,t,J=6.6 Hz), 3.62(2 H,t,J=7.2 Hz), 7.19–7.31(5 H,m)

PREPARATION EXAMPLE 103

5-(2-naphthylmethoxy)pentyl chloride $^1$H-NMR (CDCl$_3$,ppm) δ: 1.49–1.93(6 H,m), 3.49–3.55(4 H,m), 4.66(2 H,s), 7.42–7.84(7 H,m)

In the same manner as in the above-mentioned Preparation Example 99, the following compounds were obtained.

PREPARATION EXAMPLE 104

5-phenylthiopentyl bromide $^1$H-NMR (CDCl$_3$,ppm)δ: 1.49–1.89(6 H,m), 2.92(2 H,t, J=7.2 Hz), 3.51(2 H,t,J=6.6 Hz), 7.13–7.34(5 H,m)

PREPARATION EXAMPLE 105

6-Bromohexanoyl chloride (16.2 g) was dissolved in methylene chloride (50 ml), and aluminum chloride (10.6 g) was added, which was followed by stirring at room temperature for 30 min. The reaction mixture was ice-cooled, and benzene (5.0 g) was dropwise added, which was followed by stirring for 4 hr. Water was added to the reaction mixture and the mixture was extracted with ethyl acetate. The organic layer was washed with brine, dried and the solvent was evaporated under reduced pressure. The obtained residue was purified by silica gel column chromatography (hexane:ethyl acetate=3:1) to give 18.2 g of 6-bromo-1-phenyl-1-hexanone.
m.p. 35°–36° C.

PREPARATION EXAMPLE 106

Aluminum chloride (1.23 g) was added to a solution of 7-bromoheptanoyl chloride (2 g) in benzene (20 ml) under ice-cooling, which was followed by stirring at room temperature for 1 hr. Ice water and conc. hydrochloric acid were added to the reaction mixture, and the mixture was extracted with ethyl acetate. The organic layer was washed with water and brine, dried and the solvent was evaporated. The obtained residue was purified by silica gel column chromatography to give 0.93 g of 7-bromo-1-phenyl-1-heptanone.

$^1$H-NMR (CDCl$_3$,ppm) δ: 1.35–1.56(4 H,m), 1.71–1.93(4 H,m), 2.98(2 H,t,J=7.3 Hz), 3.41(2 H,t,J=6.6 Hz), 7.43–7.49(2 H,m), 7.53–7.59(1 H,m), 7.95(2 H,d,J=7.3 Hz)

PREPARATION EXAMPLE 107

Aluminum chloride (1.74 g) was added to a solution of 8-bromooctanoyl chloride (3 g) in benzene (20 ml), and the mixture was stirred at room temperature for 1.5 hr. Ice water and conc. hydrochloric acid were added to the reaction mixture, and the mixture was extracted with ethyl acetate. The organic layer was washed with water and brine, dried and the solvent was evaporated under reduced pressure. The obtained residue was purified by silica gel column chromatography to give 1.36 g of 8-bromo-1-phenyl-1-octanone.

$^1$H-NMR (CDCl$_3$,ppm) δ: 1.30–1.51(6 H,m), 1.70–1.91(4 H,m), 2.97(2 H,t,J=7.3 Hz), 3.40(2 H,t,J=6.6 Hz), 7.43–7.49(2 H,m), 7.52–7.58(1 H,m), 7.95(2 H,d,J=7.3 Hz)

PREPARATION EXAMPLE 108

Aluminum chloride (1.3 g) was added to a solution of 6-bromohexanoyl chloride (2 g) in toluene (20 ml) under ice-cooling, and the mixture was stirred at room temperature for 2 hr. Ice water and conc. hydrochloric acid were added to the reaction mixture, and the mixture was extracted with ethyl acetate. The organic layer was washed with water and brine, dried and the solvent was evaporated under reduced pressure to give 2.76 g of 6-bromo-1-(4-methylphenyl)-1-hexanone.

$^1$H-NMR (CDCl$_3$,ppm) δ: 1.47–1.58(2 H,m), 1.74–1.82(2 H,m), 1.86–1.97(2 H,m), 2.41(3 H,s), 2.96(2 H,t,J=7.3 Hz), 3.42(2 H,t,J=6.6 Hz), 7.25(2 H,d,J=8.6 Hz), 7.85(2 H,d,J=8.6 Hz)

PREPARATION EXAMPLE 109

6-Bromohexanoyl chloride (2.0 g) was added to o-xylene (20 ml), and aluminum chloride (1.4 g) was added at −20° C., which was followed by stirring for 30 min. Water was added to the reaction mixture and the mixture was extracted with ethyl acetate. The organic layer was washed with brine, dried and the solvent was evaporated under reduced pressure to give 2.6 g of 6-bromo-1-(3,4-dimethylphenyl)-1-hexanone.
m.p. 61°–63° C.

PREPARATION EXAMPLE 110

Anisole (1.16 g), 6-bromohexanoyl chloride (2.3 g) and aluminum chloride (1.5 g) were reacted and treated in the same manner as in Preparation Example 105 to give 3.07 g of 6-bromo-1-(4-methoxyphenyl)-1-hexanone.
m.p. 40°–41° C.

PREPARATION EXAMPLE 111

6-Bromohexanoyl chloride (1.83 g), 1,2-dimethylcatechol (1.08 g) and aluminum chloride (1.83 g) were reacted and treated in the same manner as in Preparation Example 105 to give 2.62 g of 6-bromo-1-(3,4-dimethoxyphenyl)-1-hexanone.
m.p. 38–40° C.

PREPARATION EXAMPLE 112

Aluminum chloride (1.3 g) was added to a solution of 6-bromohexanoyl chloride (2 g) in chlorobenzene (20 ml) under ice-cooling and the mixture was stirred at room temperature for 2 hr. Ice water and conc. hydrochloric acid were added to the reaction mixture, and the mixture was extracted with ethyl acetate. The organic layer was washed with water and brine, dried and the solvent was evaporated under reduced pressure. The obtained residue was purified by silica gel column chromatography to give 1.38 g of 6-bromo-1-(4-chlorophenyl)-1-hexanone.

$^1$H-NMR (CDCl$_3$,ppm) δ: 1.47–1.59(2 H,m), 1.71–1.82(2 H,m), 1.87–1.97(2 H,m), 2.96(2 H,t,J=6.6 Hz), 3.43(2 H,t, J=6.6 Hz), 7.43(2 H,d,J=8.6 Hz), 7.89(2 H,d,J=8.6 Hz)

PREPARATION EXAMPLE 113

7-Bromoheptanoyl chloride (3.2 g) was added to chlorobenzene (30 ml), and aluminum chloride (1.6 g) was added under ice-cooling, which was followed by stirring for 3 hr. Water was added to the reaction mixture and the mixture was extracted with ethyl acetate. The organic layer was washed with brine, dried and the solvent was evaporated under reduced pressure. The obtained residue was purified by silica gel column chromatography to give 2.2 g of 7-bromo-1-(4-chlorophenyl)-1-heptanone.

$^1$H-NMR (CDCl$_3$,ppm) δ: 1.24–1.92(4 H,m), 2.30(2 H,t, J=7.2 Hz), 2.94(2 H,t,J=7.2 Hz), 3.37–3.43(4 H,m), 7.43(2 H,dd,J=2.0,4.0 Hz), 7.89(2 H,dd,J=2.0,4.0 Hz)

PREPARATION EXAMPLE 114

Aluminum chloride (1.31 g) was added to a solution of 6-bromohexanoyl chloride (2 g) in 1,2-dichlorobenzene (20 ml) under ice-cooling and the mixture was stirred at 60°–70° C. for 1.5 hr. Ice water and conc. hydrochloric acid were added to the reaction mixture, and the mixture was extracted with ethyl acetate. The organic layer was washed with water and brine, dried and the solvent was evaporated under reduced pressure. The obtained residue was purified by silica gel column chromatography to give 0.47 g of 6-bromo-1-(3,4-dichlorophenyl)-1-hexanone.

$^1$H-NMR (CDCl$_3$,ppm) δ: 1.47–1.58(2 H,m), 1.72–1.97(4 H,m), 2.96(2 H,t,J=7.3 Hz), 3.42(2 H,t,J=6.6 Hz), 7.55(1 H,d,J=8.6 Hz), 7.78(1 H,dd,J=2.0,8.6 Hz), 8.03(1 H,d,J=2.0 Hz)

PREPARATION EXAMPLE 115

Aluminum chloride (1.3 g) was added to a solution of 6-bromohexanoyl chloride (2 g) in fluorobenzene (20 ml) under ice-cooling and the mixture was stirred at room temperature for 2 hr. Ice water and conc. hydrochloric acid were added to the reaction mixture, and the mixture was extracted with ethyl acetate. The organic layer was washed with water and brine, dried and the solvent was evaporated under reduced pressure to give 2.47 g of 6-bromo-1-(4-fluorophenyl)-1-hexanone.

$^1$H-NMR (CDCl$_3$,ppm) δ: 1.48–1.59(2 H,m), 1.72–1.83(2 H,m), 1.87–1.97(2 H,m), 2.97(2 H,t,J=7.3 Hz), 3.43(2 H,t, J=6.6 Hz), 7.10–7.16(2 H,m), 7.95–8.01(2 H,m)

PREPARATION EXAMPLE 116

Aluminum chloride (1.31 g) was added to a solution of 6-bromohexanoyl chloride (2 g) in 1,3-difluorobenzene (20 ml) under ice-cooling and the mixture was stirred at room temperature for 2 hr. Ice water and conc. hydrochloric acid were added to the reaction mixture, and the mixture was extracted with ethyl acetate. The organic layer was washed with water and brine, dried and the solvent was evaporated under reduced pressure. The obtained residue was purified by silica gel column chromatography to give 1.16 g of 6-bromo-1-(2,4-difluorophenyl)-1-hexanone.

$^1$H-NMR (CDCl$_3$,ppm)δ: 1.46–1.59(2 H,m), 1.72–1.79(2 H,m), 1.86–1.97(2 H,m), 2.94–3.00(2 H,m), 3.43(2 H,t,J= 6.6 Hz), 6.83–6.99(2 H,m), 7.88–7.97(1 H,m)

PREPARATION EXAMPLE 117

6-Bromohexanoyl chloride (2.0 g), 2-chloroanisole (1.17 g) and aluminum chloride (1.12 g) were reacted and treated in the same manner as in Preparation Example 105 to give 0.86 g of 6-bromo-1-(3-chloro-4-methoxyphenyl)-1-hexanone.
m.p. 104°–106° C.

PREPARATION EXAMPLE 118

2-Fluoroanisole (1.18 g), 6-bromohexanoyl chloride (2.0 g) and aluminum chloride (1.31 g) were reacted and treated in the same manner as in Preparation Example 105 to give 2.65 g of 6-bromo-1-(3-fluoro-4-methoxyphenyl)-1-hexanone.
m.p. 47°–48° C.

PREPARATION EXAMPLE 119

Phenol (0.88 g), 6-bromohexanoyl chloride (2.0 g) and aluminum chloride (1.4 g) were reacted and treated in the same manner as in Preparation Example 105 to give 0.51 g of 6-bromo-1-(4-hydroxyphenyl)-1-hexanone.

$^1$H-NMR (CDCl$_3$,ppm) δ: 1.45–1.60(2 H,m), 1.71–1.85(2 H,m), 1.88–2.00(2 H,m), 2.94(2 H,t), 3.41(2 H,t), 5.74(1 H,s), 6.89(2 H,d), 7.90(2 H,d)

PREPARATION EXAMPLE 120

6-Bromohexanoyl chloride (2.1 g) and thiophene (0.84 g) were dissolved in benzene (20 ml) and tin chloride (1.3 ml) was added under ice-cooling, which was followed by stirring for 1 hr. Water was added to the reaction mixture and the mixture was extracted with ethyl acetate. The organic layer was washed with brine, dried and the solvent was evaporated under reduced pressure to give 3.1 g of 6-bromo-1-(2-thienyl)-1-hexanone.

$^1$H-NMR (CDCl$_3$,ppm) δ: 1.46–2.08(6 H,m), 2.93(2 H,t, J=7.2 Hz), 3.42(2 H,t,J=7.2 Hz), 7.13(1 H,t,J=4.6 Hz), 7.64(1 H,d,J=4.6 Hz), 7.73(1 H,d,J=4.0 Hz)

PREPARATION EXAMPLE 121

1-Methyl-1 H-indol (1.0 g) and N,N-dimethyl-5-bromopentylamide (1.7 g) were dissolved in chloroform (20 ml) and phosphorus oxychloride (0.85 ml) was added, which was followed by refluxing under heating for 7 hr. Saturated aqueous sodium hydrogencarbonate solution was added to the reaction mixture and the mixture was extracted with chloroform. The organic layer was washed with brine, dried and the solvent was evaporated under reduced pressure to give 1.2 g of 6-bromo-1-(1-methyl-1 H-indol-3-yl)-1-hexanone.

$^1$H-NMR (CDCl$_3$,ppm)δ: 1.48–1.60(2 H,m), 1.75–2.00(4 H,m), 2.83–2.90(2 H,t), 3.50(2 H,dt), 3.82(3 H,s), 7.27–7.32(3 H,m), 7.69(1 H,s), 8.35–8.39(1 H,m)

PREPARATION EXAMPLE 122

6-Bromohexanoyl chloride (2 g) and benzo[b]thiophene (1.26 g) were dissolved in methylene chloride (20 ml), and aluminum chloride (1.31 g) was added under ice-cooling, which was followed by stirring at room temperature for 1.5 hr. Ice water and conc. hydrochloric acid were added to the reaction mixture, and the mixture was extracted with ethyl acetate. The organic layer was washed with water and brine, dried and the solvent was evaporated under reduced pressure. The obtained residue was purified by silica gel column chromatography and recrystallized from ethyl acetate-hexane to give 0.45 g of 6-bromo-1-(2-benzo[b]thienyl)-1-hexanone.

$^1$H-NMR (CDCl$_3$,ppm) δ: 1.51–1.63(2 H,m), 1.77–1.99(4 H,m), 3.03(2 H,t,J=7.3 Hz), 3.43(2 H,t,J=6.6 Hz), 7.38–7.50(2 H,m), 7.86–7.91 (2 H,m), 7.96(1 H,s)

PREPARATION EXAMPLE 123

The mother liquor of recrystallization of Preparation Example 122 was concentrated under reduced pressure. The obtained residue was recrystallized from ethyl acetate-hexane to give 0.42 g of 6-bromo-1-(3-benzo[b]thienyl)-1-hexanone.

$^1$H-NMR (CDCl$_3$,ppm) δ: 1.51–1.62(2 H,m), 1.77–1.99(4 H,m), 3.02(2 H,t,J=7.3 Hz), 3.44(2 H,t,J=6.6 Hz), 7.39–7.52(2 H,m), 7.87(1 H,d,J=7.9 Hz), 8.28(1 H,s), 8.77(1 H,d,J=7.9 Hz)

PREPARATION EXAMPLE 124

1,2-Methylenedioxybenzene (1.18 g), 6-bromohexanoyl chloride (2.0 g) and aluminum chloride (1.31 g) were reacted and treated in the same manner as in Preparation Example 105 to give 1.22 g of 6-bromo-1-(3,4-methylenedioxyphenyl)-1-hexanone.

$^1$H-NMR (CDCl$_3$,ppm) δ: 1.46–1.98(6 H,m), 2.91(2 H,t, J=6.6 Hz), 3.42(2 H,t,J=7.3 Hz), 6.03(2 H,s), 6.85(1 H,d,J= 7.9 Hz), 7.43(1 H,d,J=2.0 Hz), 7.56(1 H,dd,J=2.0,7.9 Hz)

PREPARATION EXAMPLE 125

Naphthalene (1.0 g), 6-bromohexanoyl chloride (1.8 g) and aluminum chloride (1.18 g) and carbon disulfide as solvent were reacted and treated in the same manner as in Preparation Example 105 to give 0.84 g of 6-bromo-1-(1-naphthyl)-1-hexanone as an oily substance.

$^1$H-NMR (CDCl$_3$,ppm) δ: 1.47–1.98(6 H,m), 3.07(2 H,t, J=7.3 Hz), 3.43(2 H,t,J=6.6 Hz), 7.46–7.61(3 H,m), 7.82–7.99(3 H,m), 8.55(1 H,d)

PREPARATION EXAMPLE 126

30% Aqueous hydrogen peroxide solution (27.6 ml) was dropwise added under ice-cooling to a solution of 4-phenylthiobutyl chloride (22.2 g) obtained in the same manner as in Preparation Example 99 in formic acid (150 ml), which was followed by stirring at room temperature for 1 hr. The reaction mixture was poured into ice water, neutralized with sodium hydroxide solution and extracted with chloroform. The organic layer was washed with brine, dried and the solvent was evaporated under reduced pressure. The obtained residue was purified by silica gel column chromatography (chloroform) and further recrystallized from hexane to give 21 g of 4-phenylsulfonylbutyl chloride. m.p. 54°–55° C.

PREPARATION EXAMPLE 127

Benzenethiol (3.0 g), 1-bromo-5-chloropentane (5.7 g) and potassium carbonate (4.15 g) were suspended in N,N-dimethylformamide (50 ml), and the mixture was stirred at 50° C. for 5 hr. After cooling, water was added to the reaction mixture, and the mixture was extracted with ethyl acetate. The organic layer was washed with brine, dried and the solvent was evaporated under reduced pressure. Thus, 5-phenylthiopentyl chloride was obtained. This compound was dissolved in formic acid (50 ml) and 2 equivalents of 30% aqueous hydrogen peroxide solution was added thereto, and the mixture was stirred at room temperature for 6 hr.

Water was added to the reaction mixture, and the mixture was extracted with ethyl acetate. The organic layer was washed with brine, dried and the solvent was evaporated under reduced pressure to give 2.11 g of 5-phenylsulfonylpentyl chloride.

$^1$H-NMR (CDCl$_3$,ppm) δ: 1.47–1.84(6 H,m), 3.09(2 H,t, J=6.0 Hz), 3.50(2 H,t,J=6.6 Hz), 7.55–7.94(5H,m)

PREPARATION EXAMPLE 128

5-Phenylthiopentyl chloride (1.84 g) was dissolved in dichloromethane (50 ml), and one equivalent of m-chloroperbenzoic acid was added thereto, which was followed by stirring at room temperature for 6 hr. Water was added to the reaction mixture, and the mixture was extracted with ethyl acetate. The organic layer was washed with brine, dried and the solvent was evaporated under reduced pressure. The obtained residue was purified by silica gel column chromatography to give 1.20 g of 5-phenylsulfinylpentyl chloride.

$^1$H-NMR (CDCl$_3$,ppm) δ: 1.49–1.87(6H,m), 2.80(2 H,t, J=6.0 Hz), 3.51 (2 H,t,J=6.6 Hz), 7.49–7.64(5H,m)

PREPARATION EXAMPLE 129

1-Methyl-1 H-indol (3.5 g), N, N-dimethyl-4-bromobutylamide (4.4 g) and phosphorus oxychloride (6 ml) were reacted and treated in the same manner as in Preparation Example 121 to give 3.73 g of 5-bromo-1-(1-methyl-1 H-indol-3-yl) -1-pentanone.

$^1$H-NMR (CDCl$_3$,ppm)δ: 1.84–2.00(4 H,m), 2.87(2 H,t, J=6.6 Hz), 3.58(2 H,t,J=5.9 Hz), 3.84(3 H,s), 7.28–7.35(3 H,m), 7.71(1 H,s), 8.35–8.39 (1 H, m)

PREPARATION EXAMPLE 130

Tin tetrachloride (1.15 ml) was added to a solution of 6-bromohexanoyl chloride (2 g) and 2-methylbenzo[b]furan (1.24 g) in carbon disulfide (30 ml) under ice-cooling, the mixture was stirred at room temperature for 3 hr. Ice water and conc. hydrochloric acid were added to the reaction mixture, and the mixture was extracted with ethyl acetate. The organic layer was washed with water and brine, dried and the solvent was evaporated under reduced pressure. The obtained residue was purified by silica gel column chromatography to give 2.2 g of 6-bromo-1-(2-methyl-3-benzo[b] furyl)-1-hexanone.

$^1$H-NMR (CDCl$_3$,ppm) δ: 1.52–1.63(2 H,m), 1.76–2.04(4 H,m), 2.78(3 H,s), 2.97(2 H,t,J=7.3 Hz), 3.44(2 H,t,J=6.6 Hz), 7.29–7.36(2 H,m), 7.42–7.47(1 H,m), 7.88–7.92(1 H,m)

PREPARATION EXAMPLE 131

A solution (30 ml) of 1-bromo-5-chloropentane (7.0 g) in tetrahydrofuran was gently added dropwise under refluxing to a suspension (30 ml) of magnesium (0.92 g) in tetrahydrofuran. After confirmation of disappearance of magnesium, a solution (30 ml) of 3-chlorobenzaldehyde (5.3 g) in tetrahydrofuran was dropwise added. After cooling, water was added to the reaction mixture, and the mixture was extracted with ethyl acetate. The organic layer was washed with brine, dried and the solvent was evaporated under reduced pressure. The obtained residue was purified by silica gel column chromatography to give 6-bromo-1-(3-chlorophenyl)-1-hexanol, which was dissolved in chloroform (50 ml). Thereto was added 15 equivalents of manganese dioxide, and the mixture was stirred at room temperature for 48 hr. The reaction mixture was filtered, and the residue was purified by silica gel column chromatography to give 6-bromo-1-(3-chlorophenyl)-1-hexanone.

$^1$H-NMR (CDCl$_3$,ppm) δ: 1.47–1.86(6 H,m), 2.97(2 H,t, J=7.3 Hz), 3.56(2 H,t,J=6.6 Hz), 7.37–7.92(4 H,m)

PREPARATION EXAMPLE 132

1-Methyl-1 H-indol (2.80 g) and N,N-dimethyl-6-bromohexylamide (1.56 g) were reacted and treated in the same manner as in Preparation Example 121 to give 0.94 g of 7-bromo-1-(1-methyl-
$^1$H-indol-3-yl)-1-heptanone.

$^1$H-NMR (CDCl$_3$,ppm) δ: 1.35–1.99(8 H,m), 2.85(2 H,t, J=7.2 Hz), 3.53(2 H,t,J=7.0 Hz), 3.85(1 H,s), 7.28–7.35(3 H,m), 7.72(1 H,s), 8.37–8.39(1 H,m)

PREPARATION EXAMPLE 133

$^1$H-Indole (2.3 g) and N,N-dimethyl-5-bromopentylamide (4.3 g) were dissolved in chloroform (40 ml) and phosphorus oxychloride (2.3 ml) was added, which was followed by refluxing under heating for 12 hr. Saturated aqueous sodium hydrogencarbonate solution was added to the reaction mixture and the mixture was extracted with chloroform. The organic layer was washed with brine, dried and the solvent was evaporated under reduced pressure. The obtained residue was purified by silica gel column chromatography (hexane:ethyl acetate=5:1) to give 0.9 g of 6-bromo-1-(1 H-indol-3-yl)-1-hexanone.
m.p. 156°–158° C.

PREPARATION EXAMPLE 134

1-Ethyl-1 H-indol (3.26 g) and N,N-dimethyl-5-bromopentylamide (5.0 g) were reacted and treated in the same manner as in Preparation Example 121 to give 2.77 g of 6-bromo-1-(1-ethyl-1 H-indol-3-yl)-1-hexanone.

$^1$H-NMR (CDCl$_3$,ppm)δ: 1.54(3 H,t,J=7.2 Hz), 1.76–1.95(6 H,m), 2.87(2 H,t,J=7.2 Hz), 3.43(2 H,t,J=6.5 Hz), 4.22(2 H,q,J=7.3 Hz), 7.25–7.39(3 H,m), 7.78(1 H,s), 8.36–8.39(1 H,m)

PREPARATION EXAMPLE 135

1-Isopropyl-1 H-indol (1.4 g), N,N-dimethyl-5-bromopentylamide (1.95 g) and phosphorus oxychloride (1.63 ml) were reacted and treated in the same manner as in Preparation Example 121 to give 1.96 g of 6-bromo-1-(1-isopropyl-1 H-indol-3-yl)-1-hexanone.

$^1$H-NMR (CDCl$_3$,ppm) δ: 1.50–1.58(2 H,m), 1.59(6 H,d, J=6.6 Hz), 1.77–1.99(4 H,m), 2.90(2 H,t,J=7.3 Hz), 3.43(2 H,t,J=6.6 Hz), 4.71(1 H,m), 7.26–7.33(2 H,m), 7.37–7.42(1 H,m), 7.87(1 H,s), 8.35–8.40(1 H,m)

PREPARATION EXAMPLE 136

6-Bromohexanoyl chloride (2 g), 1,3-difluorobenzene (20 ml) and aluminum chloride (1.31 g) were reacted and treated in the same manner as in Preparation Example 105 to give 1.16 g of 6-bromo-1-(2,4-difluorophenyl)-1-hexanone.

$^1$H-NMR (CDCl$_3$,ppm) δ: 1.47–1.97(6 H,m), 2.93–2.30(2 H,m), 3.43(2 H,t,J=6.6 Hz), 6.83–6.99(2 H,m), 7.88–7.97(1 H,m)

PREPARATION EXAMPLE 137

1-Butyl-1 H-indol (3.5 g), N,N-dimethyl-5-bromopentylamide (4.49 g) and phosphorus oxychloride (3.75 ml) were reacted and treated in the same manner as in Preparation Example 121 to give 2.59 g of 6-bromo-1-(1-butyl-1 H-indol-3-yl)-1-hexanone.

$^1$H-NMR (CDCl$_3$,ppm) δ: 0.97(3 H,t,J=7.3 Hz), 1.34–1.98(10 H,m), 2.87(2 H,t,J=7.3 Hz), 3.39–3.45(2 H,m), 4.16(2 H,t,J=6.6 Hz), 7.26–7.39(3 H,m), 7.75(1 H,s), 8.35–8.41(1 H,m)

PREPARATION EXAMPLE 138

(1) 6-Bromo-1-phenyl-1-hexanone (2.9 g) and potassium carbonate (3 g) were added to a solution of 4-hydroxy-4-tert-butoxycarbonylaminomethylpiperidine (2.5 g) in dimethylformamide (40 ml), and the mixture was stirred at 60° C. for 2 hr. Water was added to the reaction mixture, and the mixture was extracted with chloroform. The organic layer was washed with brine, dried and the solvent was evaporated under reduced pressure. The obtained residue was purified by silica gel column chromatography (chloroform:methanol=10:1) to give 3.74 g of 4-hydroxy-1-(6-oxo-6-phenylhexyl)-4-tert-butoxycarbonylaminomethylpiperidine.

$^1$H-NMR (CDCl$_3$,ppm) δ: 1.36–1.82(20 H,m), 2.36–2.88(4 H,m), 2.60–2.67(2 H,m), 2.97(2 H,t,J=7.3 Hz), 3.14(2 H,d,J=6.6 Hz), 5.01(1 H,br), 7.42–7.59(3 H,m), 7.93–7.97(2 H,m) (2) 4-Hydroxy-1-(6-oxo-6-phenylhexyl)-4-tert-butoxycarbonylaminomethylpiperidine (3.6 g) was dissolved in isopropyl alcohol (30 ml) and 15% hydrochloric acid-isopropyl alcohol (10 ml) was added under ice-cooling, which was followed by stirring at 60° C. for 3 hr. The solvent was evaporated under reduced pressure to give 2.92 g of 4-aminomethyl-4-hydroxy-1-(6-oxo-6-phenylhexyl) piperidine dihydrochloride.

$^1$H-NMR (DMSO-d$_6$,ppm) δ: 1.33–1.41(2 H,m), 1.59–1.97(8 H,m), 2.80–2.83(2 H,m), 3.01–3.09(8 H,m), 5.54(1 H,br), 7.50–7.67(3 H,m), 7.96–7.99(2 H,m), 8.13(3 H,br), 10.61(1 H,br)

PREPARATION EXAMPLE 139

(1) 4-Methoxy-4-tert-butoxycarbonylaminomethylpiperidine (2.3 g), 6-bromo-1-phenyl-1-hexanone (2.52 g) and potassium carbonate (2.6 g) were reacted and treated in the same manner as in Preparation Example 138(1) to give 3.35 g of 4-methoxy-1-(6-oxo-6-phenylhexyl)-4-tert-butoxycarbonylaminomethylpiperidine.

$^1$H-NMR (CDCl$_3$,ppm) δ: 1.34–1.81(19 H,m), 2.26–2.39(4 H,m), 2.51–2.59(2 H,m), 2.92–2.97(2 H,m), 3.16(3 H,s), 3.18–3.21(2 H,m), 4.69(1 H,br), 7.42–7.56(3 H,m), 7.93–7.96(2 H,m) (2) 4-Methoxy-1-(6-oxo-6-phenylhexyl)-4-tert-butoxycarbonylaminomethylpiperidine (3.35 g) and 15% hydrochloric acid-isopropyl alcohol (15 ml) were reacted and treated in the same manner as in Preparation Example 138(2) to give 2.25 g of 4-aminomethyl-4-methoxy-1-(6-oxo-6-phenylhexyl) piperidine dihydrochloride.

$^1$H-NMR (DMSO-d$_6$,ppm) δ:1.32–2.07(10 H,m), 2.52–3.19(13 H,m), 7.53(2 H,t,J=7.3 Hz), 7.61–7.64(1 H,m), 7.96(2 H,d,J=9.3 Hz), 8.13(2 H,br), 8.83(1 H,br), 10.85(1 H,br)

PREPARATION EXAMPLE 140

(1) 4-Methoxy-4-tert-butoxycarbonylaminomethylpiperidine (1.43 g), 4-phenylsulfonylbutyl bromide (1.7 g) and potassium carbonate (1.6 g) were reacted and treated in the same manner as in Preparation Example 138(1) to give 2.58 g of 4-methoxy-1-(4-phenylsulfonylbutyl)-4-tert-butoxycarbonylaminomethylpiperidine.

$^1$H-NMR (CDCl$_3$,ppm)δ: 1.42–1.86(17 H,m), 2.22–2.50(6 H,m), 3.09–3.19(7 H,m), 4.68(1 H,br), 7.54–7.70(3 H,m), 7.89–7.93(2 H,m) (2) 4-Methoxy-1-(4-phenylsulfonylbutyl)-4-tert-butoxycarbonylaminomethylpiperidine (2.58 g) and 15% hydrochloric acid-isopropyl alcohol (15 ml) were reacted and treated in the same manner as in Preparation Example 138(2) to give 2.2 g of 4-aminomethyl-4-methoxy-1-(4-phenylsulfonylbutyl)piperidine dihydrochloride.

$^1$H-NMR (DMSO-d$_6$,ppm)δ: 1.32–2.12(8 H,m), 2.71–3.42(13 H,m), 7.65–7.83(3 H,m), 7.86–7.97(2 H,m), 8.18(2 H,br), 8.83(1 H,br)

In the same manner as in Preparation Example 105, the following compounds were produced.

PREPARATION EXAMPLE 141

6-bromo-1-(4-ethylphenyl)-1-hexanone $^1$H-NMR (CDCl$_3$,ppm) δ: 1.26(3 H,t,J=7.6 Hz), 1.48–2.04(6 H,m), 2.71(2 H,q,J=7.2 Hz), 2.97(2 H,t,J=7.3 Hz), 3.43(2 H,t,J=7.0 Hz), 7.28(1 H,d,J=8.6 Hz), 7.88(1 H,d,J=8.6 Hz)

PREPARATION EXAMPLE 142

6-bromo-1-(2-naphthyl)-1-hexanone
m.p. 68°–70° C.

In the same manner as in Preparation Example 131, the following compound was produced.

PREPARATION EXAMPLE 143

7-bromo-1-(3-chlorophenyl)-1-heptanone $^1$H-NMR (CDCl$_3$,ppm) δ: 1.38–1.85(8 H,m), 2.95(2 H,t, J=7.3 Hz), 3.54(2 H,t,J=6.6 Hz), 7.40–7.92(4 H,m)

In the same manner as in Preparation Example 116, the following compound was produced.

PREPARATION EXAMPLE 144

6-bromo-1-(2,4-dichlorophenyl)-1-hexanone $^1$H-NMR (CDCl$_3$,ppm) δ: 1.45–1.79(2 H,m), 1.83–1.89(2 H,m), 1.91–1.94(2 H,m), 2.33(2 H,t,J=7.2 Hz), 2.94(2 H,t, J=7.2 Hz), 7.30(1 H,dd,J=2.0,8.6 Hz), 7.42(1 H,d,J=8.6 Hz), 7.48(1 H,d,J=2.0 Hz)

In the same manner as in Preparation Example 121, the following compounds were produced.

PREPARATION EXAMPLE 145

6-bromo-1-(1-benzyl-1 H-indol-3-yl)-1-hexanone $^1$H-NMR (CDCl$_3$,ppm) δ: 1.47–1.62(2 H,m), 1.74–1.95(4 H,m), 2.85(2 H,t,J=8.8 Hz), 3.41(2 H,t,J=8.8 Hz), 5.34(2 H,s), 7.13–7.16(2 H,m) 7.23–7.33(6 H,m), 7.76(1 H,s), 8.38–8.42(1 H,m)

PREPARATION EXAMPLE 146

6-bromo-1-(1,2-dimethyl-1 H-indol-3-yl)-1-hexanone
m.p. 54°–56° C.

PREPARATION EXAMPLE 147

4-(Aminomethyl)piperidine (137 g) was dissolved in toluene (1200 ml), and benzaldehyde (127 g) was added, and the mixture was stirred at refluxing temperature for 6.5 hr. The reaction mixture was cooled to room temperature, and di-tert-butyl dicarbonate (288 g) was dropwise added, and the mixture was stirred at room temperature for 1 hr. The reaction mixture was concentrated under reduced pressure, and 1N potassium hydrogensulfate (1200 ml) was added to the obtained residue, which was followed by stirring at room temperature for 4 hr. The reaction mixture was washed 3 times with isopropyl ether and made alkaline with 10% sodium hydroxide solution. The mixture was extracted with chloroform. The organic layer was washed with saturated aqueous sodium chloride solution, dried over sodium sulfate and concentrated under reduced pressure to give 236.5 g of 4-aminomethyl-1-(tert-butoxycarbonyl)piperidine.

$^1$H-NMR (CDCl$_3$,ppm) δ: 1.01–1.30(5 H,m), 1.45(9 H,s), 1.65–1.75(2 H,m), 4.07–4.16(2 H,m)

PREPARATION EXAMPLE 148

To a solution of 4-aminomethyl-1-(tert-butoxycarbonyl)piperidine (236.5 g) in dimethylformamide (1200 ml) were added 4-amino-5-chloro-2-methoxybenzoic acid (130 g) and 1-hydroxybenzotriazole (91.4 g). 1-Ethyl-3-(3-dimethylaminopropyl)carbodiimide hydrochloride (129.6 g) was added under ice-cooling, and the mixture was stirred at room temperature for 1 hr. The reaction mixture was concentrated under reduced pressure, and water was added to the obtained residue, which was followed by extraction with chloroform. The organic layer was washed successively with 10% aqueous potassium carbonate solution and saturated aqueous sodium chloride solution and dried. The solvent was evaporated under reduced pressure and the obtained residue was purified by silica gel column chromatography (chloroform) to give 272 g of 4-amino-5-chloro-2-methoxy-N-((l-tert-butoxycarbonyl)piperidin-4-ylmethyl)benzamide.

$^1$H-NMR (CDCl$_3$,ppm) δ: 1.10–1.27(2 H,m), 1.45(9 H,s), 1.65–1.85(3 H,m), 2.62–2.75(2 H,m), 3.27–3.37(2 H,m), 3.88(3 H,s), 4.61(2 H,s), 6.34(1 H,s), 7.72–7.82(1 H,m), 8.07(1 H,s)

PREPARATION EXAMPLE 149

4.25M Hydrochloric acid-dioxane (1000 ml) was dropwise added to a solution (600 ml) of 4-amino-5-chloro-2-methoxy-N-((1-tert-butoxycarbonyl)piperidin-4-ylmethyl)benzamide (272 g) in 1,4-dioxane, and the mixture was stirred at room temperature for 2 hr. The precipitated crystals were collected by filtration and recrystallized from methanol-isopropyl ether to give 211 g of 4-amino-5-chloro-2-methoxy-N-(piperidin-4-ylmethyl)benzamide dihydrochloride.
m.p. 235°–239° C.

PREPARATION EXAMPLE 150

N-(5-Bromopentyl)phthalimide (60 g) was added to a solution of 4-amino-5-chloro-2-methoxy-N-(piperidin-4-ylmethyl)benzamide dihydrochloride (75.1 g) and potassium carbonate (112 g) in dimethylformamide (800 ml), and the mixture was stirred at 75°–80° C. for 8 hr. Insoluble matter was filtered off and the solvent was evaporated under reduced pressure. The obtained residue was purified by silica gel column chromatography (chloroform:methanol=10:1) to give 60.2 g of 4-amino-5-chloro-N-(1-(5-(2,3-dihydro-1,3-dioxo-1H-isoindol-2-yl)pentyl)piperidin-4-ylmethyl)-2-methoxybenzamide.
m.p. 58–61° C.

PREPARATION EXAMPLE 151

4-Amino-5-chloro-2-methoxy-N-(piperidin-4-ylmethyl)benzamide dihydrochloride (11.1 g) and N-(3-bromopropyl)

phthalimide (8.0 g) were reacted and treated in the same manner as in Preparation Example 150 to give 7.7 g of 4-amino-5-chloro-N-(1-(3-(2,3-dihydro-1,3-dioxo-1 H-isoindol-2-yl)propyl)piperidin-4-ylmethyl)-2-methoxybenzamide.

$^1$H-NMR (CDCl$_3$,ppm) δ: 1.03–1.95(9 H,m), 2.39(2 H,t, J=7.3 Hz), 2.83–2.90(2 H,m), 3.21(2 H,t,J=6.6 Hz), 3.75(2 H,t,J=7.3 Hz), 3.89(3 H,s), 4.41(2 H,s), 6.29(1 H,s), 7.66–7.75(3 H,m), 7.80–7.86(2 H,m), 8.09(1 H,s)

PREPARATION EXAMPLE 152

4-Amino-5-chloro-2-methoxy-N-(piperidin-4-ylmethyl) benzamide dihydrochloride (17.0 g) and N-(4-bromobutyl) phthalimide (15.8 g) were reacted and treated in the same manner as in Preparation Example 150 to give 9.3 g of 4-amino-5-chloro-N-(1-(4-(2,3-dihydro-1,3-dioxo-1 H-isoindol-2-yl)butyl)piperidin-4-ylmethyl)-2-methoxybenzamide.

$^1$H-NMR (CDCl$_3$,ppm)δ: 1.23–1.38(2 H,m), 1.47–1.75(7 H,m), 1.84–1.96(2 H,m), 2.29–2.38(2 H,m), 2.86–2.95(2 H,m), 3.31(2 H,t,J=6.6 Hz), 3.70(2 H,t,J=6.6 Hz), 3.89(3 H,s), 4.42(2 H,s), 6.29(1 H,s), 7.67–7.76(3 H,m), 7.80–7.84(2 H,m), 8.09(1 H,s)

PREPARATION EXAMPLE 153

4-Amino-5-chloro-2-methoxy-N-(piperidin-4-ylmethyl) benzamide dihydrochloride (17.0 g) and N-(6-bromohexyl) phthalimide (17.4 g) were reacted and treated in the same manner as in Preparation Example 150 to give 17.0 g of 4-amino-5-chloro-N-(1-(6-(2,3-dihydro-1,3-dioxo-1 H-isoindol-2-yl)hexyl)piperidin-4-ylmethyl)-2-methoxybenzamide.

$^1$H-NMR (CDCl$_3$,ppm) δ: 1.23–1.81(13 H,m), 2.03–2.15(2 H,m), 2.40–2.48(2 H,m), 3.02–3.09(2 H,m), 3.32(2 H,t,J=5.9 Hz), 3.67(2 H,t,J=6.6 Hz), 3.90(3 H,s), 4.45(2 H,s), 6.32(1 H,s), 7.67–7.87(5 H,m), 8.08(1 H,s)

In the same manner as in the above-mentioned Preparation Examples, the following compounds were obtained.

PREPARATION EXAMPLE 154

5-(3,4-dimethoxyphenoxy)pentyl chloride $^1$H-NMR (CDCl$_3$,ppm) δ: 1.56–1.68(2 H,m), 1.75–1.91(4 H,m), 3.57(2 H,t,J=6.6 Hz), 3.83(3 H,s), 3.85(3 H,s), 3.92(2 H,t,J=6.6 Hz), 6.38(1 H,dd,J=2.6,8.6 Hz), 6.51(1 H,d,J=2.6 Hz), 6.77(1 H,d,J=8.6 Hz)

PREPARATION EXAMPLE 155

5-(1-naphthyloxy)pentyl chloride $^1$H-NMR (CDCl$_3$,ppm) δ: 1.64–1.76(2 H,m), 1.83–1.99(4 H,m), 3.57(2 H,t,J=6.6 Hz), 4.11(2 H,t,J=5.9 Hz), 6.75–6.78(1 H,m), 7.31–7.51(4 H,m), 7.74–7.81(1 H,m), 8.24–8.29(1 H,m)

PREPARATION EXAMPLE 156

4-(benzylthio)butyl chloride $^1$H-NMR (CDCl$_3$,ppm) δ: 1.66–1.88(4 H,m), 2.42(2 H,t, J=7.3 Hz), 3.49(2 H,t,J=5.9 Hz), 3.70(2 H,s), 7.19–7.36(5 H,m)

PREPARATION EXAMPLE 157

4-(benzylsulfonyl)butyl chloride
m.p. 100°–101° C.

PREPARATION EXAMPLE 158

5-((1,4-benzodioxan-6-yl)methoxy)pentyl chloride $^1$H-NMR (CDCl$_3$,ppm)δ: 1.50–1.99(6 H,m), 3.44(2 H,t, J=6.3 Hz), 3.53(2 H,t,J=7.0 Hz), 4.24(4 H,s), 4.37(2 H,s), 6.80–6.90(3 H,m)

PREPARATION EXAMPLE 159

5-(3-methoxyphenoxy)pentyl chloride $^1$H-NMR (CDCl$_3$,ppm)δ: 1.57–1.92(6 H,m), 3.56(2 H,t, J=6.6 Hz), 3.78(3 H,s), 3.95(2 H,t,J=6.3 Hz), 6.44–6.51(3 H,m), 7.11–7.19(1 H,m)

PREPARATION EXAMPLE 160

5-bromo-1-(1-naphthyl)-1-pentanone $^1$H-NMR (CDCl$_3$,ppm) δ: 1.86–2.02(4 H,m), 3.07(2 H,t, J=6.6 Hz), 3.44(2 H,t,J=6.8 Hz), 7.44–7.61(3 H,m), 7.81–8.01(3 H,m), 8.56(1 H,d,J=8.7 Hz)

PREPARATION EXAMPLE 161

5-benzylsulfonylpentyl chloride
m.p. 91°–92° C.

PREPARATION EXAMPLE 162

5-(4-fluorophenoxy)pentyl bromide $^1$H-NMR (DMSO-d$_6$,ppm) δ: 1.49–1.58(2 H,m), 1.70–1.77(2 H,m), 1.80–1.89(2 H,m), 3.55(2 H,t,J=6.1 Hz), 3.93(2 H,t,J=6.1 Hz), 6.90–6.95(2 H,m), 7.05–7.13(2 H,m)

PREPARATION EXAMPLE 163

5-(4-chlorophenoxy)pentyl bromide $^1$H-NMR (CDCl$_3$,ppm)δ: 1.56–1.67(2 H,m), 1.73–1.86(2 H,m), 1.87–1.99(2 H,m), 3.43(2 H,t,J=6.0 Hz), 3.93(2 H,t, J=6.0 Hz), 6.79–6.82(2 H,m), 7.20–7.23(2 H,m)

PREPARATION EXAMPLE 164

5-(3,5-dimethoxyphenoxy)pentyl chloride $^1$H-NMR (CDCl$_3$,ppm) δ: 1.55–1.63(2 H,m), 1.77–1.87(4 H,m), 3.56(2 H,t,J=6.6 Hz), 3.76(6 H,s), 3.95(2 H,t,J=6.6 Hz), 6.07(3 H,s)

PREPARATION EXAMPLE 165

3-(phenoxy)propyl chloride $^1$H-NMR (CDCl$_3$,ppm) δ: 2.23(2 H,t,J=6.4 Hz), 3.74(2 H,t,J=6.7 Hz), 4.11(2 H,t,J=5.9 Hz), 6.78–7.32(5 H,m)

PREPARATION EXAMPLE 166

3-(phenylthio)propyl chloride $^1$H-NMR (CDCl$_3$,ppm) δ: 2.01–2.18(2 H,m), 3.07(2 H,t, J=7.2 Hz), 3.68(2 H,t,J=6.4 Hz), 7.11–7.40(5 H,m)

PREPARATION EXAMPLE 167

3-(phenylsulfonyl)propyl chloride $^1$H-NMR (CDCl$_3$,ppm) δ: 2.20–2.35(2 H,m), 3.29(2 H,t, J=7.7 Hz), 3.62(2 H,t,J=5.7 Hz), 7.65–7.99(5 H,m)

PREPARATION EXAMPLE 168

3-bromo-1-phenyl-1-propanone
m.p. 50°–51° C.

PREPARATION EXAMPLE 169 p-Toluenesulfonic acid in a catalytic amount and ethylene glycol (2.9 g) were added to a solution of 3-bromo-1-phenyl-1-propanone (10 g) in benzene (100 ml), and the mixture was stirred at refluxing temperature for 70 hr. The reaction mixture was washed successively with 10% aqueous potassium carbonate solution and brine, and dried. The solvent was evaporated under reduced pressure, and the obtained residue was purified by silica gel column chromatography to give 6.0 g of 3,3-ethylenedioxy-3-phenylpropyl bromide. m.p. 57°–58° C.

In the same manner as in the above-mentioned Preparation Examples, the following compounds were obtained.

PREPARATION EXAMPLE 170

4-bromo-1-phenyl-1-butanone $^1$H-NMR (CDCl$_3$,ppm) δ: 2.27–2.36(2 H,m), 3.19(2 H,t, J=6.6 Hz), 3.55(2 H,t,J=6.6 Hz), 7.44–7.48(2 H,m), 7.50–7.60(1 H,m), 7.96–8.00(2 H,m)

PREPARATION EXAMPLE 171

2-(phenylsulfonyl)ethyl bromide
m.p. 58°–59° C.

PREPARATION EXAMPLE 172

2-(phenylthio)ethyl bromide $^1$H-NMR (CDCl$_3$,ppm) δ: 3.25–3.31(2 H,m), 3.42–3.49(2 H,m), 7.16–7.41 (5 H,m)

PREPARATION EXAMPLE 173

60% Sodium hydride (0.6 g) was suspended in dimethylformamide (10 ml), and piperonyl alcohol (1.5 g) was added under ice-cooilng with stirring. The mixture was stirred at room temperature for 1 hr. The mixture was again ice-cooled, and 1-bromo-5-chloropentane(1.8 g) was added, which was followed by stirring at room temperature for 1.5 hr. Water was added to the reaction mixture and the mixture was extracted with ethyl acetate. The organic layer was washed with brine, dried and the solvent was evaporated under reduced pressure to give 0.6 g of 5-((3,4-methylenedioxyphenyl)methoxy)pentyl chloride.

$^1$H-NMR (CDCl$_3$,ppm) δ: 1.42–1.68(4 H,m), 1.72–1.82(2 H,m), 3.44(2 H,t,J=4.3 Hz), 3.53(2 H,t,J=6.6 Hz), 4.39(2 H,s), 5.94(2 H,s), 6.77(2 H,s), 6.84(1 H,s)

In the same manner as in the foregoing Preparation Examples, the following compounds were produced.

PREPARATION EXAMPLE 174

2-benzylsulfonylethyl chloride
m.p. 98°–101° C.

PREPARATION EXAMPLE 175

3-benzylsulfonylpropyl chloride
m.p. 108°–110° C.

PREPARATION EXAMPLE 176

3-(4-fluorobenzylsulfonyl)propyl chloride
m.p. 132°–133° C.

PREPARATION EXAMPLE 177

3-(4-chlorobenzylsulfonyl)propyl chloride
m.p. 149°–150° C.

PREPARATION EXAMPLE 178

3-(4-methoxybenzylsulfonyl)propyl chloride
m.p. 93°–94° C.

PREPARATION EXAMPLE 179

2-(2-phenylethyl)sulfonylethyl chloride
m.p. 111°–112° C.

PREPARATION EXAMPLE 180

5-bromo-1-(4-hydroxyphenyl)-1-pentanone
m. p. 99°–101° C.

PREPARATION EXAMPLE 181

To a solution of 4-(tert-butoxycarbonylaminomethyl) piperidine (9.70 g) in toluene (160 ml) were added 3-ethylenedioxy-3-(4-methoxyphenyl)propyl bromide (13.0 g) and potassium carbonate (18.8 g), and the resulting mixture was stirred at 80° C. for 16.5 hr. The solvent was evaporated under reduced pressure, and the residue was purified by silica gel chromatography (chloroform:methanol=20:1) to give 14.7 g of 1-(3-ethylenedioxy-3-(4-methoxyphenyl)propyl)-4-(tert-butoxycarbonylaminomethyl)piperidine.

$^1$H-NMR (CDCl$_3$,ppm) δ: 1.14–1.30(3 H,m), 1.42(9 H,s), 1.58–1.69(2 H,m), 1.83–1.98(2 H,m), 2.07–2.13(2 H,m), 2.36–2.42(2 H,m), 2.83–3.03(4 H,m), 3.72–3.78(2 H,m), 3.80(3 H,s), 3.96–4.01(2 H,m), 4.59(1 H,Br), 6.85(2 H,d,J=9.2 Hz), 7.34(2 H,d,J=9.2 Hz)

PREPARATION EXAMPLE 182

4-(tert-Butoxycarbonylaminomethyl)piperidine (10.0 g) as a starting compound, 4-ethylenedioxy-4-(4-methoxyphenyl)butyl chloride (12.0 g) and potassium carbonate (19.3 g) were reacted and treated in the same manner as in Preparation Example 181 to give 7.65 g of 1-(4-ethylenedioxy-4-(4-methoxyphenyl)butyl)-4-(tert-butoxycarbonylaminomethyl)piperidine.

$^1$H-NMR (CDCl$_3$,ppm)δ: 1.14–1.67(16 H,m), 1.80–1.92(4 H,m), 2.23–2.29(2 H,m), 2.83–3.01(4 H,m), 3.73–3.78(2 H,m), 3.80(3 H,s), 3.96–4.01(2 H,m), 4.58(1 H,Br), 6.84(2 H,d,J=9.2 Hz), 7.34(2 H,d,J=9.2 Hz)

PREPARATION EXAMPLE 183

To 1-(3-ethylenedioxy-3-(4-methoxyphenyl)propyl)-4-(tert-butoxycarbonylaminomethyl)piperidine (13.2 g) was added 47% aqueous hydrogen bromide solution (150 ml), and the resulting mixture was stirred at 100° C. for 4 hr. The solvent was evaporated under reduced pressure, and the residue was crystalized from ethanol to give 9.00 g of 3-(1-(4-aminomethylpiperidin-1-yl))-1-(4-hydroxyphenyl)-1-propanone•dihydrobromide, m.p. 241°–242° C.

PREPARATION EXAMPLE 184

1-(4-Ethylenedioxy-4-(4-methoxyphenyl)butyl)-4-(tert-butoxycarbonylaminomethyl)piperidine (7.65 g) as a starting compound and 47% aqueous hydrogen bromide solution (100 ml) were reacted and treated in the same manner as in Preparation Example 183 to give 3.68 g of 4-(1-(4- aminomethylpiperidin-1-yl))-1-(4-hydroxyphenyl)-1-butanone•dihydrobromide, m.p. 253°–255° C.

PREPARATION EXAMPLE 185

Tin chloride (8.18 g) and 6-bromohexanoic acid were stirred at 120° C. Thereto was added resorcinol (5.50 g), and the resulting mixture was stirred for 20 min. The reaction mixture was poured into ice-water and the mixture was extracted with ethyl acetate ester. The organic layer was washed with brine and dried, followed by evaporation of the solvent under reduced pressure. The residue was purified by silica gel chromatography (chloroform:methanol=30:1) to give 3.70 g of 6-bromo-1-(2,4-dihydroxyphenyl)-1-hexanone.

$^1$H-NMR (CDCl$_3$,ppm) δ: 1.47–1.97(6 H,m), 2.93(2 H,t, J=6.6 Hz), 3.51–3.58(2 H,m), 6.38–6.42(2 H,m), 7.63–7.67(1 H,m), 12.80(1 H,s)

PREPARATION EXAMPLE 186

To cis-4-amino-5-chloro-2-methoxy-N-((1-tert-butoxycarbonyl-3-methoxypiperidin-4-yl)methyl)benzamide (2.10 g) was added 15% hydrogen chloride isopropyl alcohol solution, and the resulting mixture was stirred at 50° C. for 6 hr. The solvent was evaporated and the residue was crystalized from isopropyl alcohol to give 0.88 g of cis-4-amino-5-chloro-2-methoxy-N-((3-methoxypiperidin-4-yl)methyl)-benzamide•dihydrochloride, m.p. 192°–195° C.

PREPARATION EXAMPLE 187

(1) To a solution of cis-4-aminomethyl-3-hydroxy-1-(tert-butoxycarbonyl)piperidine (1.75 g) in dimethylformamide (30 ml) were added 4-amino-5-chloro-2-methoxybenzoic acid (1.34 g) and 1-hydroxybenztriazole (0.94 g), and 1-ethyl-3-(3-dimethylaminopropyl)-carbodiimide•hydrochloride (1.34 g) was further added under ice-cooling. The resulting mixture was stirred at room temperature for 2 hr. The solvent was evaporated under reduced pressure, and water was added to the residue, which was followed by extraction with chloroform. The organic layer was washed successively with 10% aqueous potassium carbonate solution and brine and dried, followed by evaporation of the solvent under reduced pressure. The residue was purified by silica gel chromatography (chloroform:methanol=30:1) to give 1.70 g of cis-4-amino-5-chloro-N-((3-hydroxy-1-tert-butoxycarbonyl)piperidin-4-ylmethyl)-2-methoxybenzamide.

$^1$H-NMR (CDCl$_3$,ppm) δ: 1.31–1.48(10 H,m), 1.67–1.76(2 H,m), 2.61–3.20(4 H,m), 3.65–3.80(2 H,m), 3.90(3 H,s), 4.12–4.31(2 H,m), 4.50(2 H,br), 6.31(1 H,s), 7.92–8.03(1 H,m), 8.09(1 H,s)

(2) To a solution of cis-4-amino-5-chloro-N-((3-hydroxy-1-tert-butoxycarbonyl)piperidin-4-ylmethyl)-2-methoxybenzamide (1.7 g) in isopropyl alcohol (15 ml) were added 15% hydrochloric acid-isopropyl alcohol (5 ml), and the resulting mixture was stirred at 60° C. for 1.5 hr. The solvent was evaporated under reduced pressure, and the obtained crystals were recrystalized from isopropyl alcohol to give 0.99 g of cis-4-amino-5-chloro-N-((3-hydroxy)piperidin-4-ylmethyl)-2-methoxybenzamide•dihydrochloride, m.p. 227°–230° C.

PREPARATION EXAMPLE 188

4,4-ethylenedioxy-4-phenylbutyl bromide m.p. 51°–53° C.

PREPARATION EXAMPLE 189

To a solution of 2-benzyloxyethanol (11.7 g) and pyridine (6.08 g) in dichloromethane (50 ml) was added thionyl chloride (6.7 ml) under ice-cooling, and the resulting mixture was stirred at refluxing temperature for 2.5 hr. Ice-water was added to the reaction mixture, and the organic layer was washed with water and dried. The solvent was evaporated under reduced pressure, and the obtained residue was purified by silica gel column chromatography (chloroform) to give 10.3 g of 2-benzyloxyethyl chloride.

$^1$H-NMR (CDCl$_3$,ppm) δ: 3.62(2 H,t,J=6.3 Hz), 3.72(2 H,t,J=6.3 Hz), 4.57(2 H,s), 7.26–7.39(5 H,m)

PREPARATION EXAMPLE 190

(1) To a solution of ethyl 1-benzyl-3-oxo-4-piperidinecarboxylate (21 g) in ethanol (20 ml) was added sodium borohydride (9.1 g) under ice-cooling, and the resulting mixture was stirred at room temperature for 9 hr. Water was added to the reaction mixture, and the mixture was extracted with chloroform. The organic layer was washed with brine and dried. The solvent was evaporated under reduced pressure, and the obtained residue was purified by silica gel column chromatography to give 10.55 g of 1-benzyl-3-hydroxy-4-hydroxymethylpiperidine.

$^1$H-NMR (CDCl$_3$,ppm) δ: 1.17–2.19(3 H,m), 2.77–3.06(4 H,m), 3.46–3.97(5 H,m), 7.19–7.42(5 H,m)

(2) To a solution of 1-benzyl-3-hydroxy-4-hydroxymethylpiperidine (7.1 g) and hydrazine monohydrate (1.56 ml) in ethanol was added 10% palladium carbon (3 g), and the resulting mixture was stirred at refluxing temperature for 5 hr. 10% Palladium carbon was filtered off and the solvent was evaporated under reduced pressure to give 4.51 g of 3-hydroxy-4-hydroxymethylpiperidine.

$^1$H-NMR(CD$_3$OD, ppm) δ: 1.22–1.92(3 H,m), 2.31–3.21(4 H,m), 3.35–3.99(3 H,m)

(3) To a solution of 3-hydroxy-4-hydroxymethylpiperidine (4.21 g) in dimethylformamide (100 ml) was added di-tert-butyl-dicarbonate, and the resulting mixture was stirred at room temperature for 22 hr. The solvent was evaporated under reduced pressure and the residue was purified by silica gel column chromatography (chloroform:methanol=10:1) to give 6.5 g of 1-tert-butoxycarbonyl-3-hydroxy-4-hydroxymethylpiperidine.

$^1$H-NMR(CDCl$_3$, ppm) δ: 1.46(9 H,s), 1.47–1.90(3 H,m), 2.65–2.93(4 H,m), 3.66–3.76(1 H,m), 4.04–4.27(2 H,m)

(4) To a solution of 1-tert-butoxycarbonyl-3-hydroxy-4-hydroxymethylpiperidine (6.5 g) and triethylamine (5.87 ml) in dichloromethane (100 ml) was added dropwise methanesulfonyl chloride (3.54 g) under ice-cooling, and the resulting mixture was stirred at room temperature for 6 hr. Water was added to the reaction mixture and the mixture was extracted with chloroform. The organic layer was washed with brine and dried. The solvent was evaporated under reduced pressure and the residue was purified by silica gel column chromatography (chloroform:methanol=40:1) to give 4.44 g of cis-1-tert-butoxycarbonyl-3-hydroxy-4-methanesulfonyloxymethylpiperidine and 0.93 g of trans-1-tert-butoxycarbonyl-3-hydroxy-4-methanesulfonyloxymethylpiperidine.

cis compound: m.p. 115°–118° C.

$^1$H-NMR(CDCl$_3$, ppm) δ: 1.46(9 H,s), 1.47–1.90(2 H,m), 1.93–2.07(1 H,m), 2.66–2.90(2 H,m), 3.03(3 H,s), 3.98(1 H,br), 4.07–4.33(4 H,m)

trans compound:

$^1$H-NMR(CDCl$_3$, ppm) δ: 1.46(9 H,s), 1.65–1.84(3 H,m), 2.46–2.85(2 H,m), 3.04(3 H,s), 3.46–3.57(1 H,m), 4.07–4.35(3 H,m), 4.43–4.52(1 H,m)

(5) To a solution of cis-1-tert-butoxycarbonyl-3-hydroxy-4-methanesulfonyloxymethylpiperidine (4.44 g) in dimethylformamide (60 ml) were added sodium azide (1.4 g) and ammonium chloride (1.15 g), and the resulting mixture was stirred at 60° C. for 6 hr. Water was added to the reaction mixture and the mixture was extracted with chloroform. The organic layer was washed with brine and dried. The solvent was evaporated under reduced pressure and the residue was purified by silica gel column chromatography (chloroform:methanol=40:1) to give 3.4 g of cis-4-azidomethyl-1-tert-butoxycarbonyl-3-hydroxypiperidine.

$^1$H-NMR(CDCl$_3$, ppm) δ: 1.46(9 H,s), 1.47–1.80(2 H,m), 2.16–2.23(1 H,m), 2.65–2.88(2 H,m), 3.19–3.27(1 H,m), 3.42–3.49(1 H,m), 3.92–3.96(1 H,m), 4.10–4.28(2 H,m)

(6) To a solution of 60% sodium hydride (0.58 g) in dimethylformamide (10 ml) was added dropwise a solution of cis-4-azidomethyl-1-tert-butoxycarbonyl-3-hydroxypiperidine (3.4 g) in dimethylformamide (50 ml), and the resulting mixture was stirred at room temperature for 1 hr. Methyl iodide (1.24 ml) was added to the mixture with stirring, and the resulting mixture was stirred at room temperature for 15 hr. Water was added to the reaction mixture and the mixture was extracted with chloroform. The organic layer was washed with brine and dried. The solvent was evaporated under reduced pressure and the residue was purified by silica gel column chromatography (chloroform) to give 1.5 g of cis-4-azidomethyl-1-tert-butoxycarbonyl-3-methoxypiperidine.

$^1$H-NMR(CDCl$_3$, ppm) δ: 1.46(9 H,s), 1.47–1.82(2 H,m), 2.16–2.23(1 H,m), 2.57–2.82(2 H,m), 3.13–3.22(1 H,m), 3.27–3.45(4 H,m), 3.90–4.50(3 H,m)

(7) To a solution of cis-4-azidomethyl-1-tert-butoxycarbonyl-3-methoxypiperidine (1.5 g) in methanol (50 ml) was added 20% palladium carbon hydroxide (0.6 g), and the resulting mixture was stirred at room temperature under hydrogen atmosphere for 2 hr. 20% Palladium carbon hydroxide was filtered off and the solvent was evaporated under reduced pressure to give 1.2 g of cis-4-aminomethyl-1-tert-butoxycarbonyl-3-methoxypiperidine.

$^1$H-NMR(DMSO-d$_6$, ppm) δ: 1.38(9 H,s), 1.39–1.70(3 H,m), 2.51–2.95(4 H,m), 3.19–4.30(6 H,m)

PREPARATION EXAMPLE 191

(1) To a solution of cis-1-tert-butoxycarbonyl-3-hydroxy-4-methanesulfonyloxymethylpiperidine (2.0 g) in dimethylformamide (40 ml) was added potassium phthalimide (1.44 g), and the resulting mixture was stirred at 60° C. for 7 hr. Water was added to the reaction mixture and the mixture was extracted with ethyl acetate. The organic layer was washed successively with saturated aqueous sodium hydrogencarbonate solution and brine, and dried. The solvent was evaporated under reduced pressure and the residue was purified by silica gel column chromatography to give 2.4 g of cis-1-tert-butoxycarbonyl-4-(2,3-dihydro-1,3-dioxo-1 H-isoindol-2-yl)methyl-3-hydroxypiperidine.

$^1$H-NMR(CDCl$_3$, ppm) δ: 1.46(9 H,s), 1.66–2.02(2 H,m), 2.64–2.95(3 H,m), 3.68–3.76(3 H,m), 4.13–4.33(2 H,m), 7.72–7.78(2 H,m), 7.82–7.89(2 H,m)

(2) To a solution of cis-l-tert-butoxycarbonyl-4-(2,3-dihydro-1,3-dioxo-1 H-isoindol-2-yl)methyl-3-hydroxypiperidine (2.4 g) in ethanol (35 ml) was added hydrazine monohydrate (0.48 ml), and the resulting mixture was stirred at refluxing temperature for 1 hr. The resulting crystals were filtered off and the solvent was evaporated under reduced pressure to give 1.7 g of cis-4-aminomethyl-1-tert-butoxycarbonyl-3-hydroxypiperidine.

$^1$H-NMR(DMSO-d$_6$, ppm) δ: 1.38(9 H,s), 1.39–1.69(3 H,m), 2.51–2.92(4 H,m), 3.73–3.89(3 H,m), 4.50(3 H,br)

PREPARATION EXAMPLE 192

4-aminomethyl-1-(6-(2-hydroxyphenyl)-6-oxohexyl) piperidine dihydrochloride m.p. 221°–223° C.

PREPARATION EXAMPLE 193

6-bromo-1-(3-hydroxyphenyl)-1-hexanone $^1$H-NMR(CDCl$_3$, ppm) δ: 1.46–1.96(7 H,m), 2.96(2 H,t, J=7.3 Hz), 3.42(2 H,t,J=6.6 Hz), 7.07(1 H,dd,J=2.6,7.9 Hz), 7.31(1 H,t,J=7.9 Hz), 7.46–7.48(2 H,m)

EXAMPLE 1

2-(3-tert-Butoxycarbonylaminomethylpyrrolidin-1-yl) ethylamine (1 g) was dissolved in methylene chloride (10 ml) and triethylamine (0.86 ml) was added. Then, a solution of acetyl chloride (0.29 ml) in methylene chlride was dropwise added under ice-cooling. The mixture was stirred at room temperature for 1 hr, and the reaction mixture was concentrated under reduced pressure to give 1-(2-acetylaminoethyl)-3-tert-butoxycarbonylaminomethylpyrrolidine.

The obtained compound was dissolved in a solution (15 ml) of 4N hydrochloric acid-dioxane and the mixture was stood at room temperature for 30 min. The reaction mixture was concentrated under reduced pressure. Dimethylformamide (15 ml) was added to the residue and the mixture was neutralized with triethylamine. 4-Amino-5-chloro-2-methoxybenzoic acid (0.83 g) and 1-hydroxybenzotriazole (0.61 g) were added, and the mixture was stirred at 0° C. for 15 min. Then, 1-ethyl-3-(3-dimethylaminopropyl)carbodiimide hydrochloride (0.86 g) was added, and the mixture was stirred at room temperature for 8 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.56 g of N-(1-(2-acetylaminoethyl)pyrrolidin-3-ylmethyl)-4-amino-5-chloro-2-methoxybenzamide.

$^1$H-NMR (CDCl$_3$,ppm) δ: 1.48–1.64(1 H,m), 1.98(3 H,s) ,1.94–2.17(1 H,m), 2.36–2.78(7 H,m), 3.18–3.62(4 H,m), 3.90(3 H,s), 4.44(2 H,s), 6.31(1 H,s), 6.30–6.44(1 H,br), 7.75–7.88(1 H,br), 8.08(1 H,s)

EXAMPLE 2

4-(3-tert-Butoxycarbonylaminomethylpyrrolidin-1-yl) butylamine (1.05 g) as starting compound was reacted and treated in the same manner as in Example 1 using acetyl chloride (0.30 ml) and 4-amino-5-chloro-2-methoxybenzoic acid (0.78 g) to give N-(1-(4-acetylaminobutyl)pyrrolidin-3-ylmethyl)-4-amino-5-chloro-2-methoxybenzamide.

$^1$H-NMR (CDCl$_3$,ppm) δ: 1.48–1.72(5 H,m),1.96(3 H,s) ,2.02–2.14(1 H,m), 2.41–2.87(7 H,m),3.20–3.30(2 H,m), 3.35–3.57(2 H,m),3.92(3 H,s),4.45(2 H,s), 6.31(1 H,s), 6.30–6.40(1 H,br),7.79–7.90(1 H,br),8.10(1 H,s)

EXAMPLE 3

5-(3-tert-Butoxycarbonylaminomethylpyrrolidin-1-yl) pentylamine (0.99 g) as starting compound was reacted and treated in the same manner as in Example 1 using acetyl chloride (0.25 ml) and 4-amino-5-chloro-2-methoxybenzoic acid (0.71 g) to give N-(1-(5-acetylaminopentyl)pyrrolidin-3-ylmethyl)-4-amino-5-chloro-2-methoxybenzamide.

¹H-NMR (CDCl₃,ppm) δ: 1.30–2.12(8 H,m),1.97(3 H,s) ,2.35–2.76(7 H,m), 3.18–3.57(4 H,m),3.89(3 H,s),4.39(2 H,s),5.60–5.77(1 H,br),6.30(1 H,s), 7.76–7.90(1 H,br), 8.08(1 H,s)

EXAMPLE 4

2-(3-tert-Butoxycarbonylaminomethylpyrrolidin-1-yl) ethylamine (1.00 g) as starting compound was reacted and treated in the same manner as in Example 1 using cyclohexanecarbonyl chloride (0.64 g) and 4-amino-5-chloro-2-methoxybenzoic acid (0.84 g) to give 4-amino-5-chloro-N-(1-(2-cyclohexanecarbonylaminoethyl)pyrrolidin-3-ylmethyl)-2-methoxybenzamide.

¹H-NMR (CDCl₃,ppm) : 1.04–2.18(16 H,m),2.34–2.76(6 H,m),3.21–3.81(2 H,m), 3.88(3 H,s),4.39(2 H,s), 6.06–6.24(1 H,br),6.30(1 H,s),7.72–7.90(1 H,br), 8.10(1 H,s)

EXAMPLE 5

3-(3-tert-Butoxycarbonylaminomethylpyrrolidin-1-yl) propylamine (0.98g) as starting compound was reacted and treated in the same manner as in Example 1 using cyclohexanecarbonyl chloride (0.54 ml) and 4-amino-5-chloro-2-methoxybenzoic acid (0.77 g) to give 4-amino-5-chloro-N-(1-(3-cyclohexanecarbonylaminopropyl)pyrrolidin-3-ylmethyl)-2-methoxybenzamide.

¹H-NMR (CDCl₃,ppm) δ: 1.07–2.15(18 H,m), 2.40–2.95(6 H,m),3.27–3.57(2 H,m), 3.90(3 H,s),4.37(2 H,s),6.31(1 H,s),6.78–6.91(1 H,br),7.74–7.90(1 H,br), 8.10(1 H,s)

EXAMPLE 6

4-(3-tert-Butoxycarbonylaminomethylpyrrolidin-1-yl) butylamine (1.00 g) as starting compound was reacted and treated in the same manner as in Example 1 using cyclohexanecarbonyl chloride (0.49 ml) and 4-amino-5-chloro-2-methoxybenzoic acid (0.74 g) to give 4-amino-5-chloro-N-(1-(4-cyclohexanecarbonylaminobutyl)pyrrolidin-3-ylmethyl)-2-methoxybenzamide.

¹H-NMR (CDCl₃,ppm) δ: 1.10–1.89(18 H,m), 1.97–2.12(2 H,m),2.41–2.81(6 H,m), 3.18–3.31(2 H,m), 3.38–3.62(2 H,m),3.93(3 H,s),4.41(2 H,s),5.97–6.08(1 H,br), 6.31(1 H,s),7.79–7.88(1 H,br),8.12(1 H,s)

EXAMPLE 7

5-((3R)-3-tert-Butoxycarbonylaminomethylpyrrolidin-1-yl)pentylamine (1.00 g) as starting compound was reacted and treated in the same manner as in Example 1 using cyclohexanecarbonyl chloride (0.52 ml) and 4-amino-5-chloro-2-methoxybenzoic acid (0.70 g) to give 4-amino-5-chloro-N-((3R)-1-(5-cyclohexanecarbonylaminopentyl) pyrrolidin-3-ylmethyl)-2-methoxybenzamide.

¹H-NMR (CDCl₃,ppm)δ: 1.15–2.15(18 H,m), 2.08–2.75(7 H,m), 3.15–3.27(2 H,m), 3.31–3.50(2 H,m), 3.89(3 H,s), 4.39(2 H,s), 5.48–5.59(1 H,br), 6.30(1 H,s), 7.77–7.89(1 H,br), 8.08(1 H,s)

EXAMPLE 8

4-((3R)-3-tert-Butoxycarbonylaminomethylpyrrolidin-1-yl)butylamine (1.20 g) as starting compound was reacted and treated in the same manner as in Example 1 using 1-adamantanecarbonyl chloride (0.98 g) and 4-amino-5-chloro-2-methoxybenzoic acid (0.85 g) to give N-((3R)-1-(4-(1-adamantanecarbonylamino)butyl)pyrrolidin-3-ylmethyl)-4-amino-5-chloro-2-methoxybenzamide.

¹H-NMR (CDCl₃,ppm) δ: 1.42–2.10(21 H,m), 2.30–2.81(7 H,m), 3.17–3.30(2 H,m), 3.36–3.48(2 H,m), 3.89(3 H,s), 4.38(2 H,s), 5.75–5.84(1 H,br), 6.30(1 H,s), 7.76–7.87(1 H,br), 8.09(1 H,s)

EXAMPLE 9

2-(3-tert-Butoxycarbonylaminomethylpyrrolidin-1-yl) ethylamine (1 g) as starting compound was reacted and treated in the same manner as in Example 1 using benzoyl chloride (0.47 ml) and 4-amino-5-chloro-2-methoxybenzoic acid (0.83 g) to give ⁴-amino-N-(1-(2-benzoylaminoethyl) pyrrolidin-3-ylmethyl)-5-chloro-2-methoxybenzamide.

¹H-NMR (CDCl₃,ppm)δ: 1.48–1.68(1 H,m),1.94–2.10(1 H,m), 2.38–2.86(7 H,m), 3.32–3.70(4 H,m), 3.84(3 H,s), 4.41(2 H,s), 6.22(1 H,s), 6.92–7.06(1 H,br), 7.32–7.52(3 H,m), 7.73–7.91(3 H,m), 8.08(1 H,s)

EXAMPLE 10

3-(3-tert-Butoxycarbonylaminomethylpyrrolidin-1-yl) propylamine (1.1 g) as starting compound was reacted and treated in the same manner as in Example 1 using benzoyl chloride (0.50 ml) and 4-amino-5-chloro-2-methoxybenzoic acid (0.15 g) to give 4-amino-N-(1-(3-benzoylaminopropyl) pyrrolidin-3-ylmethyl)-5-chloro-2-methoxybenzamide.

¹H-NMR (CDCl₃,ppm)δ: 1.61–1.74(1 H,m), 1.86–1.92(2 H,m), 2.06–2.16(1 H,m), 2.57–2.70(2 H,m), 2.83–3.10(5 H,m), 3.37–3.48(2 H,m), 3.50–3.64(2 H,m), 3.86(3 H,s), 4.44(2 H,s), 6.28(1 H,s), 7.35–7.50(3 H,m), 7.77–7.85(3 H,m), 8.06(1 H,s), 8.12–8.20(1 H,br)

EXAMPLE 11

3-((3R)-3-tert-Butoxycarbonylaminomethylpyrrolidin-1-yl)propylamine (1.50 g) was dissolved in methylene chloride (30 ml) and triethylamine (1.2 ml) was added. Then, a soution of benzoyl chloride (0.68 ml) in methylene chlride was dropwise added under ice-cooling. The mixture was stirred at room temperature for 1 hr, and the reaction mixture was concentrated under reduced pressure. The residue was dissolved in 4N hydrochloric acid-dioxane solution (10 ml) and the mixture was stood at room temperature for 30 min. The reaction mixture was concentrated under reduced pressure. Dimethylformamide (10 ml) was added to the residue and the mixture was neutralized with triethylamine (1.7 ml). 4-Amino-5-chloro-2-methoxybenzoic acid (0.80 g) and benzotriazol-1-yloxytris(dimethylamino)phosphonium hexafluorophosphate (1.93 g) were added, and the mixture was stirred at room temperature for 8 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.12 g of 4-amino-N-((3R)-1-(3-benzoylaminopropyl)pyrrolidin-3-ylmethyl)-5-chloro-2-methoxybenzamide.

¹H-NMR (CDCl₃,ppm) δ: 1.45–1.62(1 H,m), 1.72–1.84(2 H,m), 1.94–2.08(1 H,m), 2.30–2.85(7 H,m), 3.34–3.48(2 H,m), 3.50–3.63(2 H,m), 3.86(3 H,s), 4.45(2 H,s), 6.29(1 H,s), 7.35–7.50(3 H,m), 7.65–7.83(3 H,m), 8.08(1 H,s), 8.17–8.28(1 H,br)

EXAMPLE 12

3-((3S)-3-tert-Butoxycarbonylaminomethylpyrrolidin-1-yl)propylamine (1.50 g) as starting compound was reacted and treated in the same manner as in Example 1 using benzoyl chloride (0.68 ml) and 4-amino-5-chloro-2-methoxybenzoic acid (1.17 g) to give 4-amino-N-((3S)-1-(3-benzoylaminopropyl)pyrrolidin-3-ylmethyl)-5-chloro-2-methoxybenzamide.

$^1$H-NMR (CDCl$_3$,ppm) 67 : 1.45–1.62(1 H,m), 1.72–1.84(2 H,m), 1.94–2.08(1 H,m), 2.30–2.85(7 H,m), 3.34–3.48(2 H,m), 3.50–3.63(2 H,m), 3.86(3 H,s), 4.45(2 H,s), 6.29(1 H,s), 7.35–7.50(3 H,m), 7.65–7.83(3 H,m), 8.08(1 H,s), 8.17–8.28(1 H,br)

EXAMPLE 13

3-(3-tert-Butoxycarbonylaminomethylpyrrolidin-1-yl)propylamine (1.00 g) as starting compound was reacted and treated in the same manner as in Example 1 using 4-chlorobenzoyl chloride (0.54 ml) and 4-amino-5-chloro-2-methoxybenzoic acid (0.86 g) to give 4-amino-5-chloro-N-(1-(3-(4-chlorobenzoylamino)propyl)pyrrolidin-3-ylmethyl)-2-methoxybenzamide.

$^1$H-NMR (CDCl$_3$,ppm) δ: 1.51–2.17(4 H,m), 2.36–2.95(7 H,m), 3.30–3.65(4 H,m), 3.90(3 H,s), 4.40(2 H,s), 6.30(1 H,s), 7.31–7.44(2 H,m), 7.60–7.65(1 H,br), 7.70–7.80(2 H,m), 8.08(1 H,s), 8.35–8.45(1 H,br)

EXAMPLE 14

3-(3-tert-Butoxycarbonylaminomethylpyrrolidin-1-yl)propylamine (1.00 g) was dissolved in methylene chloride (20 ml) and triethylamine (0.81 ml) was added. Then, a solution (10 ml) of 3-chlorobenzoyl chloride (0.75 g) in methylene chlride was dropwise added under ice-cooling. The mixture was stirred at room temperature for 3 hr, and the reaction mixture was concentrated under reduced pressure. The residue was dissolved in 4N hydrochloric acid-dioxane solution (20 ml) and the mixture was stood at room temperature for 30 min. The reaction mixture was concentrated under reduced pressure. Dimethylformamide (20 ml) was added to the residue and the mixture was neutralized with triethylamine. 4-Amino-5-chloro-2-methoxybenzoic acid (0.86 g) and benzotriazol-1-yloxytris(dimethylamino)phosphonium hexafluorophosphate (1.89 g) were added thereto, and the mixture was stirred at room temperature for 22 hr. The reaction mixture was concentrated under reduced pressure. Aqueous potassium carbonate solution was added to the residue and the mixture was extracted with chloroform. The extract was dried over magnesium sulfate and concentrated under reduced pressure. The obtained residue was purified by silica gel chromatography to give 0.28 g of 4-amino-5-chloro-N-(1-(3-(3-chlorobenzoylamino)propyl)pyrrolidin-3-ylmethyl)-2-methoxybenzamide.

$^1$H-NMR (CDCl$_3$,ppm) δ: 1.55–1.69(1 H,m), 1.70–1.85(2 H,m), 1.95–2.12(1 H,m), 2.25–2.35(1 H,m), 2.43–2.95(6 H,m), 3.30–3.55(4 H,m), 3.88(3 H,s), 4.39(2 H,s), 6.28(1 H,s), 7.32–7.48(3 H,m), 7.55–7.60(1 H,m), 7.61–7.75(1 H,br), 8.06(1 H,s)

EXAMPLE 15

3-(3-tert-Butoxycarbonylaminomethylpyrrolidin-1-yl)propylamine (1.00 g) was dissolved in methylene chloride (20 ml) and triethylamine (0.81 ml) was added. Then, a solution (10 ml) of 2-chlorobenzoyl chloride (0.75 g) in methylene chlride was dropwise added under ice-cooling. The mixture was stirred at room temperature for 6 hr, and the reaction mixture was concentrated under reduced pressure. The residue was dissolved in 4N hydrochloric acid-dioxane solution (20 ml) and the mixture was stood at room temperature for 2 hr. The reaction mixture was concentrated under reduced pressure. Dimethylformamide (20 ml) was added to the residue and the mixture was neutralized with triethylamine. 4-Amino-5-chloro-2-methoxybenzoic acid (0.86 g) and benzotriazol-1-yloxytris(dimethylamino)phosphonium hexafluorophosphate (1.89 g) were added, and the mixture was stirred at room temperature for 17 hr. The reaction mixture was concentrated under reduced pressure. Aqueous potassium carbonate solution was added to the residue and the mixture was extracted with chloroform. The extract was dried over magnesium sulfate and concentrated under reduced pressure. The obtained residue was purified by silica gel chromatography to give 0.25 g of 4-amino-5-chloro-N-(1-(3-(2-chlorobenzoylamino)propyl)pyrrolidin-3-ylmethyl)-2-methoxybenzamide.

$^1$H-NMR (CDCl$_3$,ppm) δ: 1.35–1.50(1 H,m), 1.73–1.98(3 H,m), 2.30–2.72(7 H,m), 3.18–3.25(2 H,m), 3.48–3.60(2 H,m), 3.89(3 H,s), 4.39(2 H,s), 6.29(1 H,s), 7.22–7.40(2 H,m), 7.69–7.85(3 H,m), 8.09(1 H,s), 8.66–8.79(1 H,br)

EXAMPLE 16

3-(3-tert-Butoxycarbonylaminomethylpyrrolidin-1-yl)propylamine (1.10 g) was dissolved in methylene chloride (10 ml) and triethylamine (0.89 ml) was added. Then, a solution of 4-nitrobenzoyl chloride (0.80 g) in methylene chlride was dropwise added under ice-cooling. The mixture was stirred at room temperature for 5 hr, and the reaction mixture was concentrated under reduced pressure. The residue was dissolved in 4N hydrochloric acid-dioxane solution (10 ml) and the mixture was stood at room temperature for 30 min. The reaction mixture was concentrated under reduced pressure. Dimethylformamide (10 ml) was added to the residue and the mixture was neutralized with triethylamine (0.92 ml). 4-Amino-5-chloro-2-methoxybenzoic acid (0.44 g) and benzotriazol-1-yloxytris(dimethylamino)phosphonium hexafluorophosphate (1.06 g) were added, and the mixture was stirred at room temperature for 8 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.29 g of 4-amino-5-chloro-2-methoxy-N-(1-(3-(4-nitrobenzoylamino)propyl)pyrrolidin-3-ylmethyl)benzamide.

$^1$H-NMR (CDCl$_3$+CD$_3$OD,ppm) δ: 1.60–1.79(1 H,m), 1.83–1.99(2 H,m), 2.05–2.20(1 H,m), 2.53–3.08(5 H,m), 3.17–3.57(6 H,m), 3.91(3 H,s), 4.37(2 H,s), 6.35(1 H,s), 7.94–8.03(3 H,m), 8.25–8.32(2 H,m)

EXAMPLE 17

3-(3-tert-Butoxycarbonylaminomethylpyrrolidin-1-yl)propylamine (1.08 g) as starting compound was reacted and treated in the same manner as in Example 1 using 4-methylbenzoyl chloride (0.56 ml) and 4-amino- 5-chloro-2-methoxybenzoic acid (0.48 g) to give 4-amino-5-chloro-2-methoxy-N-(1-(3-(4-methylbenzoylamino)propyl)pyrrolidin-3-ylmethyl)benzamide.

$^1$H-NMR (CDCl$_3$+CD$_3$OD,ppm) δ: 1.82–2.07(3 H,m), 2.20–2.32(1 H,m), 2.39(3 H,s), 2.78–3.90(11 H,m), 3.92(3 H,s), 6.37(1 H,s), 7.20–7.28(2 H,m), 7.65–7.72(2 H,m), 7.96(1 H,s)

EXAMPLE 18

3-(3-tert-Butoxycarbonylaminomethylpyrrolidin-1-yl)propylamine (1.03 g) as starting compound was reacted and treated in the same manner as in Example 1 using 4-methoxybenzoyl chloride (0.68 g) and 4-amino-5-chloro-2-methoxybenzoic acid (0.41 g) to give 4-amino-5-chloro-2-methoxy-N-(1-(3-(4-methoxybenzoylamino)propyl) pyrrolidin-3-ylmethyl)benzamide.

$^1$H-NMR (CDCl$_3$+CD$_3$OD,ppm) δ: 1.82–2.07(3 H,m), 2.20–2.32(1 H,m), 2.39(3 H,s), 2.78–3.90(11 H,m), 3.92(3 H,s), 6.37(1 H,s), 7.20–7.28(2 H,m), 7.65–7.72(2 H,m), 7.96(1 H,s)

EXAMPLE 19

3-(3-tert-Butoxycarbonylaminomethylpyrrolidin-1-yl) propylamine (1.05 g) as starting compound was reacted and treated in the same manner as in Example 1 using 2-thiophenecarbonyl chloride (0.48 ml) and 4-amino-5-chloro-2-methoxybenzoic acid (0.82 g) to give 4-amino-5-chloro-2-methoxy-N-(1-(3-(2-thiophenecarbonylamino) propyl)pyrrolidin-3-ylmethyl)benzamide.

$^1$H-NMR (CDCl$_3$,ppm) δ: 1.56–1.72(1 H,m), 1.75–1.91(2 H,m), 2.00–2.15(1 H,m), 2.47–3.05(7 H,m), 3.40–3.61(4 H,m), 3.86(3 H,s), 4.45(2 H,brs), 6.30(1 H,s), 7.02–7.08(1 H,m), 7.40–7.48(1 H,m), 7.53–7.64(1 H,m), 7.78–7.85(1 H,br), 8.08(1 H,s),8.10–8.18(1 H,br)

EXAMPLE 20

4-(3-tert-Butoxycarbonylaminomethylpyrrolidin-1-yl) butylamine (1 g) as starting compound was reacted and treated in the same manner as in Example 1 using benzoyl chloride (0.43 ml) and 4-amino-5-chloro-2-methoxybenzoic acid (0.74 g) to give 4-amino-N-(1-(4-benzoylaminobutyl) pyrrolidin-3-ylmethyl)-5-chloro-2-methoxybenzamide.

$^1$H-NMR (CDCl$_3$,ppm) δ: 1.45–1.75(5 H,m),1.90–2.13(1 H,m),2.37-2.76(7 H,m),3.33–3.52(4 H,m),3.85(3 H,s), 4.38(2 H,brs),6.27(1 H,s), 7.12(1 H,br),7.31–7.50(3 H,m), 7.71–7.86(3 H,m),8.08(1 H,s)

EXAMPLE 21

4-Amino-N-(1-(4-aminobutyl)piperidin-4-ylmethyl)-5-chloro-2-methoxybenzamide (0.8 g) was dissolved in dimethylformamide (10 ml), and benzoic acid (0.25 g) and 1-ethyl-3-(3-dimethylaminopropyl)-carbodiimide hydrochloride (0.44 g) were added. The mixture was stirred at room temperature for 12 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.2 g of 4-amino-N-(1-(4-benzoylaminobutyl)piperidin-4-ylmethyl)-5-chloro-2-methoxybenzamide.
Melting point 165°~168° C.

EXAMPLE 22

4-((3R)-3-tert-Butoxycarbonylaminomethylpyrrolidin-1-yl)butylamine (1.00 g) was dissolved in methylene chloride (20 ml) and potassium carbonate (0.56 g) was added. Then, a solution of 1-naphthoyl chloride (0.6 g) in methylene chloride was dropwise added under ice-cooling. The mixture was stirred at room temperature for 1 hr, and the reaction mixture was concentrated under reduced pressure. The residue was dissolved in 4N hydrochloric acid-dioxane solution (10 ml) and the mixture was stood at room temperature for 30 min. The reaction mixture was concentrated under reduced pressure. Dimethylformamide (10 ml) was added to the residue and the mixture was neutralized with triethylamine. 4-Amino-5-chloro-2-methoxybenzoic acid (0.39 g) and 1-hydroxybenzotriazole (0.27 g) were added, and the mixture was stirred at 0° C. for 15 min. Then, 1-ethyl-3-(3-dimethylaminopropyl)carbodiimide hydrochloride (0.38 g) was added and the mixture was stirred at room temperature for 8 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.50 g of 4-amino-5-chloro-2-methoxy-N-((3R)-1-(4-(1-naphthoylamino)butyl)pyrrolidin-3-ylmethyl)benzamide.

$^1$H-NMR (CDCl$_3$,ppm) δ: 1.25–1.39(1 H,m), 1.57–1.78(4 H,m), 2.11–2.34(2 H,m), 2.42–2.69(6 H,m), 3.13–3.33(2 H,m), 3.39–3.52(2 H,m), 3.79(3 H,s), 4.54(2 H,s), 6.26(1 H,s), 7.33–7.89(8 H,m), 8.01(1 H,s), 8.20–8.27(1 H,br)

EXAMPLE 23

4-((3R)-3-tert-Butoxycarbonylaminomethylpyrrolidin-1-yl)butylamine (1.05 g) was dissolved in methylene chloride (30 ml) and triethylamine (0.81 ml) was added. Then, 2-naphthoyl chloride (0.74 g) was added under ice-cooling. The mixture was stirred at room temperature for 5 hr, and the reaction mixture was concentrated under reduced pressure. The residue was dissolved in 4N hydrochloric acid-dioxane solution (10 ml) and the mixture was stood at room temperature for 30 min. The reaction mixture was concentrated under reduced pressure. Dimethylformamide (30 ml) was added to the residue and the mixture was neutralized with triethylamine (0.66 ml). 4-Amino-5-chloro-2-methoxybenzoic acid (0.32 g) and 1-hydroxybenzotriazole (0.23 g) were added, and the mixture was stirred at 0° C. for 15 min. Then, 1-ethyl-3-(3-dimethylaminopropyl) carbodiimide hydrochloride (0.33 g) was added and the mixture was stirred at room temperature for 8 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.25 g of 4-amino-5-chloro-2-methoxy-N-((3R)-1-(4-(2-naphthoylamino)butyl)pyrrolidin-3-ylmethyl)benzamide.

$^1$H-NMR (CDCl$_3$,ppm)δ: 1.50–1.85(5 H,m), 1.90–2.28(2 H,m), 2.35–2.85(6 H,m), 3.33–3.62(4 H,m), 3.82(3 H,s), 4.34(2 H,s), 6.23(1 H,s), 7.25–7.36(1 H,br), 7.40–7.60(2 H,m), 7.71–7.93(5 H,m), 8.06(1 H,s), 8.25–8.34(1 H,m)

EXAMPLE 24

4-Amino-N-(1-(4-aminobutyl)piperidin-4-ylmethyl)-5-chloro-2-methoxybenzamide (0.80 g) was dissolved in dichloromethane (30 ml), and potassium carbonate (0.60 g) was added. Then, a solution of 1-naphthoyl chloride (0.33 ml) in methylene chloride was dropwise added under ice-cooling. The mixture was stirred at room temperature for 1 hr, and the insoluble matter was filtered off. The filtrate was concentrated under reduced pressure. The obtained residue was purified by silica gel chromatography to give 0.45 g of 4-amino-5-chloro-2-methoxy-N-(1-(4-(1-naphthoylamino) butyl)piperidin-4-ylmethyl)benzamide.
Melting point 138°~141° C. (0.5 fumarate)

EXAMPLE 25

4-Amino-N-(1-(4-aminobutyl)piperidin-4-ylmethyl)-5-chloro-2-methoxybenzamide (1.10 g) was dissolved in dichloromethane (30 ml), and potassium carbonate (0.82 g) was added. Then, a solution of 2-naphthoyl chloride (0.33 ml) in methylene chloride was dropwise added under ice-cooling. The mixture was stirred at room temperature for 1 hr, and the insoluble matter was filtered off. The filtrate was concentrated under reduced pressure. The obtained residue was purified by silica gel chromatography to give 0.25 g of 4-amino-5-chloro-2-methoxy-N-(1-(4-(2-naphthoylamino)butyl)piperidin-4-ylmethyl)benzamide.
Melting point 179°~181° C.

EXAMPLE 26

4-((3R)-3-tert-Butoxycarbonylaminomethylpyrrolidin-1-yl)butylamine (1.00 g) as starting compound was reacted and treated in the same manner as in Example 1 using phenylacetyl chloride (0.50 ml) and 4-amino-5-chloro-2-methoxybenzoic acid (0.54 g) to give 4-amino-5-chloro-2-methoxy-N-((3R)-1-(4-phenylacetylaminobutyl)pyrrolidin-3-ylmethyl)benzamide.

$^1$H-NMR (CDCl$_3$,ppm) δ: 1.33–1.82(5 H,m), 1.88–2.05(1 H,m), 2.25–2.70(7 H,m), 3.14–3.69(2 H,m), 3.51(2 H,s), 3.81(3 H,s), 4.81(2 H,s), 6.35(1 H,s), 6.55–6.66(1 H,br), 7.14–7.35(5 H,m), 7.80–7.95(1 H,br), 8.02(1 H,s)

EXAMPLE 27

5-((3R)-3-tert-Butoxycarbonylaminomethylpyrrolidin-1-yl)pentylamine (1.15 g) was dissolved in methylene chloride (10 ml) and triethylamine (0.84 ml) was added. Then, a solution of benzoyl chloride (0.47 ml) in methylene chloride was dropwise added under ice-cooling. The mixture was stirred at room temperature for 1 hr, and the reaction mixture was concentrated under reduced pressure. The residue was dissolved in 4N hydrochloric acid-dioxane solution (10 ml) and the mixture was stood at room temperature for 30 min. The reaction mixture was concentrated under reduced pressure. Dimethylformamide (30 ml) was added to the residue and the mixture was neutralized with triethylamine (1.1 ml). 4-Amino-5-chloro-2-methoxybenzoic acid (0.55 g) and 1-hydroxybenzotriazole (0.40 g) were added, and the mixture was stirred at 0C for 15 min. Then, 1-ethyl-3-(3-dimethylaminopropyl)carbodiimide hydrochloride (0.57 g) was added and the mixture was stirred at room temperature for 8 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.48 g of 4-amino-N-((3R)-1-(5-benzoylaminopentyl)pyrrolidin-3-ylmethyl)-5-chloro-2-methoxybenzamide.

$^1$H-NMR (CDCl$_3$,ppm)δ: 1.35–1.69(7 H,m), 1.97–2.13(1 H,m), 2.47–2.88(7 H,m), 3.35–3.50(4 H,m), 3.88(3 H,s), 4.47(2 H,s), 6.31(1 H,s), 6.45–6.55(1 H,br), 7.35–7.52(3 H,m), 7.75–7.89(3 H,m), 8.06(1 H,s)

EXAMPLE 28

5-((3R)-3-tert-Butoxycarbonylaminomethylpyrrolidin-1-yl)pentylamine (1.51 g) was dissolved in methylene chloride (15 ml) and triethylamine (1.11 ml) was added. Then, a solution of 4-chlorobenzoyl chloride (0.67 ml) in methylene chloride was dropwise added under ice-cooling. The mixture was stirred at room temperature for 5 hr, and the reaction mixture was concentrated under reduced pressure. The residue was dissolved in 4N hydrochloric acid-dioxane solution (10 ml) and the mixture was stood at room temperature for 30 min. The reaction mixture was concentrated under reduced pressure. Dimethylformamide (30 ml) was added to the residue and the mixture was neutralized with triethylamine (2.22 ml). 4-Amino-5-chloro-2-methoxybenzoic acid (1.07 g) and 1-hydroxybenzotriazole (0.79 g) were added, and the mixture was stirred at 0C for 15 min. Then, 1-ethyl-3-(3-dimethylaminopropyl)carbodiimide hydrochloride (1.12 g) was added and the mixture was stirred at room temperature for 8 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 1.39 g of 4-amino-5-chloro-N-((3R)-1-(5-(4-chlorobenzoylamino)-pentyl)pyrrolidin-3-ylmethyl)-2-methoxybenzamide.

$^1$H-NMR (CDCl$_3$,ppm) δ: 1.35–1.69(7 H,m), 1.97–2.12(1 H,m), 2.45–2.83(7 H,m), 3.33–3.52(4 H,m), 3.88(3 H,s), 4.44(2 H,s), 6.30(1 H,s), 6.55–6.70(1 H,br), 7.35–7.43(2 H,m), 7.73–7.79(2 H,m), 7.80–7.89(1 H,br), 8.05(1 H,s)

EXAMPLE 29

5-(4-tert-Butoxycarbonylaminomethylpiperidin-1-yl) pentylamine (1.2 g) was dissolved in methylene chloride (20 ml) and potassium carbonate (1.66 g) was added. Then, a solution of benzoyl chloride (0.47 ml) in methylene chloride was dropwise added under ice-cooling. The mixture was stirred at room temperature for 1 hr, and the reaction mixture was concentrated under reduced pressure. The residue was dissolved in 4N hydrochloric acid-dioxane solution (30 ml) and the mixture was stood at room temperature for 30 min. The reaction mixture was concentrated under reduced pressure. Dimethylformamide (30 ml) was added to the residue and the mixture was neutralized with triethylamine (1.1 ml). 4-Amino-5-chloro-2-methoxybenzoic acid (0.81 g) and 1-hydroxybenzotriazole (0.60 g) were added, and the mixture was stirred at 0° C. for 20 min. Then, 1-ethyl-3-(3-dimethylaminopropyl)carbodiimide hydrochloride (0.85 g) was added and the mixture was stirred at room temperature for 8 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.68 g of 4-amino-N-(1-(5-benzoylaminopentyl)piperidin-4-ylmethyl)-5-chloro-2-methoxybenzamide.
Melting point 138°~140° C.

EXAMPLE 30

5-(4-tert-Butoxycarbonylaminomethylpiperidin-1-yl) pentylamine (1.50 g) was dissolved in methylene chloride (30 ml) and triethylamine (1.0 ml) was added. Then, a solution (20 ml) of 3-chlorobenzoyl chloride (0.75 ml) in methylene chloride was dropwise added under ice-cooling. The mixture was stirred at room temperature for 30 hr, and the reaction mixture was concentrated under reduced pressure. The residue was dissolved in 4N hydrochloric acid-isopropyl alcohol solution (80 ml) and the mixture was stood at room temperature for 24 hr. The reaction mixture was concentrated under reduced pressure. Dimethylformamide (40 ml) was added to the residue and the mixture was neutralized with triethylamine (2.30 ml). 4-Amino-5-chloro-2-methoxybenzoic acid (1.01 g) and 1-hydroxybenzotriazole (0.75 g) were added, and the mixture was stirred at 0° C. for 15 min. Then, 1-ethyl-3-(3- dimethylaminopropyl)carbodiimide hydrochloride (1.06 g) was added and the mixture was stirred at room temperature for 20 hr. The reaction mixture was concentrated under reduced pressure. Aqueous potassium carbonate solution was added to the residue and the mixture was extracted with chloroform. The extract was dried over magnesium sulfate and concentrated under reduced pressure. The obtained residue was purified by silica gel chromatography to give 0.65 g of 4-amino-5-chloro-N-(1-(5-(3-chlorobenzoylamino)pentyl)piperidin-4-ylmethyl)-2-methoxybenzamide.
Melting point 139°~142° C.

EXAMPLE 31

5-(4-tert-Butoxycarbonylaminomethylpiperidin-1-yl) pentylamine (1.50 g) was dissolved in methylene chloride (30 ml) and triethylamine (1.04 ml) was added. Then, a solution (20 ml) of 4-methylbenzoyl chloride (0.73 ml) in methylene chloride was dropwise added under ice-cooling. The mixture was stirred at room temperature for 27 hr, and the reaction mixture was concentrated under reduced pressure. The residue was dissolved in 4N hydrochloric acid-isopropyl alcohol solution (80 ml) and the mixture was stood at room temperature for 24 hr. The reaction mixture was concentrated under reduced pressure. Dimethylformamide (40 ml) was added to the residue and the mixture was neutralized with triethylamine (2.30 ml). 4-Amino-5-chloro-2-methoxybenzoic acid (1.01 g) and 1-hydroxybenzotriazole (0.75 g) were added, and the mixture was stirred at 0° C. for 15 min. Then, 1-ethyl-3-(3-dimethylaminopropyl)carbodiimide hydrochloride (1.06 g) was added and the mixture was stirred at room temperature for 24 hr. The reaction mixture was concentrated under reduced pressure. Aqueous potassium carbonate solution was added to the residue and the mixture was extracted with chloroform. The extract was dried over magnesium sulfate and concentrated under reduced pressure. The obtained residue was purified by silica gel chromatography to give 0.55 g of 4-amino-5-chloro-N-(1-(5-(4-methylbenzoylamino)pentyl)piperidin-4-ylmethyl)-2-methoxybenzamide.
Melting point 142°~146° C.

EXAMPLE 32

5-((3R)-3-tert-Butoxycarbonylaminomethylpyrrolidin-1-yl)pentylamine (1.00 g) as starting compound was reacted and treated in the same manner as in Example 1 using 4-benzenesulfonyl chloride (0.49 ml) and 4-amino-5-chloro-2-methoxybenzoic acid (0.70 g) to give 4-amino-N-((3R)-1-(5-benzenesulfonylaminopentyl)pyrrolidin-3-ylmethyl)-5-chloro-2-methoxybenzamide.

$^1$H-NMR (CDCl$_3$,ppm)δ: 1.22–1.63(7 H,m), 1.95–2.10(1 H,m), 2.30–2.70(7 H,m), 2.88–2.98(2 H,m), 3.31–3.54(2 H,m), 3.89(3 H,s), 4.38(2 H,s), 5.08–5.20(1 H,br), 6.30(1 H,s), 7.45–7.60(3 H,m), 7.79–7.89(3 H,m), 8.09(1 H,s)

EXAMPLE 33

4-((3R)-3-tert-Butoxycarbonylaminomethylpyrrolidin-1-yl)butylamine (1.00 g) as starting compound was reacted and treated in the same manner as in Example 1 using 1-morpholinecarbonyl chloride (0.48 ml) and 4-amino-5-chloro-2-methoxybenzoic acid (0.74 g) to give 4-amino-5-chloro-N-((3R)-1-(4-(1-morpholine)carbonylaminobutyl)-pyrrolidin-3-ylmethyl)-2-methoxybenzamide.

$^1$H-NMR (CDCl$_3$,ppm) δ: 1.45–1.79(5 H,m), 1.90–2.06(1 H,m), 2.28–2.72(7 H,m), 3.20–3.48(8 H,m), 3.60–3.75(4 H,m), 3.89(3 H,s), 4.37(2 H,s), 4.88–4.97(1 H,br), 6.29(1 H,s), 7.73–7.85(1 H,br), 8.09(1 H,s)

EXAMPLE 34

2-(3-tert-Butoxycarbonylaminomethylpyrrolidin-1-yl) ethylamine (1 g) was dissolved in methylene chloride (10 ml) and a solution of methyl isocyanate (0.24 ml) in methylene chloride was dropwise added under ice-cooling. The mixture was stirred at room temperature for 1 hr, and the reaction mixture was concentrated under reduced pressure to give 1-(2-(3-methylureido)ethyl)-3-tert-butoxycarbonylaminomethylpyrrolidine.

This compound was dissolved in 4N hydrochloric acid-dioxane solution and the mixture was stood at room temperature for 30 min. The reaction mixture was concentrated under reduced pressure. Dimethylformamide was added to the residue and the mixture was neutralized with triethylamine. 4-Amino-5-chloro-2-methoxybenzoic acid (0.83 g) and 1-hydroxybenzotriazole (0.61 g) were added thereto, and the mixture was stirred at 0° C. for 15 min. Then, 1-ethyl-3-(3-dimethylaminopropyl)carbodiimide hydrochloride (0.86 g) was added and the mixture was stirred at room temperature for 8 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.51 g of 4-amino-5-chloro-2-methoxy-N-(1-(2-(3-methylureido)ethyl)pyrrolidin-3-ylmethyl) benzamide.

$^1$H-NMR (CDCl$_3$,ppm) δ: 1.45–1.62(1 H,m),1.92–2.08(1 H,m), 2.27(3 H,s), 2.36–2.92(7 H,m), 3.12–3.45(4 H,m), 3.91(3 H,s), 4.51(2 H,s), 5.20–5.32(1 H,br), 5.42–5.57(1 H,br), 6.33(1 H,s), 7.79–7.91(1 H,br), 8.02(1 H,s)

EXAMPLE 35

3-(3-tert-Butoxycarbonylaminomethylpyrrolidin-1-yl) propylamine (1.12 g) as starting compound was reacted and treated in the same manner as in Example 34 using methyl isocyanate (0.38 ml) and 4-amino-5-chloro-2-methoxybenzoic acid (0.96 g) to give 4-amino-5-chloro-2-methoxy-N-(1-(3-(3-methylureido)propyl)pyrrolidin-3-ylmethyl)-benzamide.

$^1$H-NMR (CDCl$_3$+CD$_3$OD,ppm) δ: 1.80–2.00(3 H,m), 2.17–2.38(1 H,m), 2.70(3 H,s), 2.91–3.80(11 H,m), 3.93(3 H,s), 6.38(1 H,s), 7.98(1 H,s)

EXAMPLE 36

4-(3-tert-Butoxycarbonylaminomethylpyrrolidin-1-yl) butylamine (1.00 g) as starting compound was reacted and treated in the same manner as in Example 34 using methyl isocyanate (0.24 ml) and 4-amino-5-chloro-2-methoxybenzoic acid (0.74 g) to give 4-amino-5-chloro-2-methoxy-N-(1-(4-(3-methylureido)butyl)pyrrolidin-3-ylmethyl)benzamide.

$^1$H-NMR (CDCl$_3$,ppm) δ: 1.45–1.72(5 H,m),1.98–2.15(1 H,m), 2.51–2.88(7 H,m), 2.85(3 H,d,J=4.62 Hz), 3.12–3.25(2 H,m), 3.36–3.62(2 H,m), 3.92(3 H,s), 4.45(2 H,s), 4.80–4.93(1 H,br), 5.05–5.17(1 H,br), 6.31(1 H,s), 7.82–7.94(1 H,br), 8.08(1 H,s)

EXAMPLE 37

5-(3-tert-Butoxycarbonylaminomethylpyrrolidin-1-yl) pentylamine (0.84 g) as starting compound was reacted and treated in the same manner as in Example 34 using methyl isocyanate (0.26 ml) and 4-amino-5-chloro-2-methoxybenzoic acid (0.58 g) to give 4-amino-5-chloro-2-methoxy-N-(1-(5-(3-methylureido)pentyl)pyrrolidin-3-ylmethyl)-benzamide.

1H-NMR (CDCl₃+CD₃OD,ppm) δ: 1.32–1.81(7 H,m), 2.08–2.25(1 H,m), 2.35(3 H,s), 2.63–3.50(11 H,m), 3.93(3 H,s), 6.39(1 H,s), 7.97(1 H,s)

EXAMPLE 38

5-((3R)-3-tert-Butoxycarbonylaminomethylpyrrolidin-1-yl)-pentylamine (2.0 g) was dissolved in methylene chloride (20 ml) and a solution of ethyl isocyanate (0.55 ml) in methylene chloride was dropwise added under ice-cooling. The mixture was stirred at room temperature for 0.25 hr, and the reaction mixture was concentrated under reduced pressure to give (3R)-3-tert-butoxycarbonylaminomethyl-1-(5-(3-ethylureido)pentyl)pyrrolidine.

This compound was dissolved in 4N hydrochloric acid-dioxane solution (10 ml) and the mixture was stood at room temperature for 2 days. The reaction mixture was concentrated under reduced pressure. Dimethylformamide (10 ml) was added to the residue and the mixture was neutralized with triethylamine (1.0 ml). 4-Amino-5-chloro-2-methoxybenzoic acid (0.57 g) and 1-hydroxybenzotriazole (0.4 g) were added thereto, and the mixture was stirred at 0° C. for 15 min. Then, dicyclohexylcarbodiimide (0.56 g) was added and the mixture was stirred at room temperature for 14 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.2 g of 4-amino-5-chloro-N-(( 3R)-1-(5-(3-ethylureido)pentyl)pyrrolidin-3-ylmethyl)-2-methoxybenzamide.

¹H-NMR (CDCl₃,ppm) δ: 1.05–1.82(12 H,m), 1.90–2.13(1 H,m), 2.20–2.80(7 H,m), 3.10–3.65(4 H,m), 3.85(3 H,s), 4.84(2 H,s), 6.37(1 H,s), 7.90–7.95(1 H,br), 8.05(1 H,s)

EXAMPLE 39

5-((3R)-3-tert-Butoxycarbonylaminomethylpyrrolidin-1-yl)pentylamine (2.0 g) was dissolved in methylene chloride (20 ml) and a solution of isopropyl isocyanate (0.69 ml) in methylene chloride was dropwise added under ice-cooling. The mixture was stirred at room temperature for 0.25 hr, and the reaction mixture was concentrated under reduced pressure to give (3R)-3-tert-butoxycarbonylaminomethyl-1-(5-(3-isopropylureido)pentyl)pyrrolidine.

This compound was dissolved in 4N hydrochloric acid-dioxane solution (10 ml) and the mixture was stood at room temperature for 14 hr. The reaction mixture was concentrated under reduced pressure. Dimethylformamide (10 ml) was added to the residue and the mixture was neutralized with triethylamine (1.0 ml). 4-Amino-5-chloro-2-methoxybenzoic acid (0.54 g) and 1-hydroxybenzotriazole (0.38 g) were added thereto, and the mixture was stirred at 0° C. for 15 min. Then, dicyclohexylcarbodiimide (0.54 g) was added and the mixture was stirred at room temperature for 12 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.50 g of 4-amino-5-chloro-N-((3R)-1-(5-(3-isopropylureido)pentyl)pyrrolidin-3-ylmethyl)-2-methoxybenzamide.

¹H-NMR (CDCl₃,ppm) δ: 1.12(6 H,d,J=4.06 Hz), 1.15–1.69(6 H,m), 1.90–2.10(1 H,m), 2.21–2.79(7 H,m), 3.05–3.60(4 H,m), 3.88(3 H,s), 4.56(2 H,s), 4.70–4.80(1 H,m), 4.90–5.01(1 H,br), 6.33(1 H,s), 7.80–7.95(1 H,br), 8.04(1 H,s)

EXAMPLE 40

2-(3-tert-Butoxycarbonylaminomethylpyrrolidin-1-yl) ethylamine (1 g) as starting compound was reacted and treated in the same manner as in Example 34 using n-propyl isocyanate (0.38 ml) and 4-amino-5-chloro-2-methoxybenzoic acid (0.83 g) to give 4-amino-5-chloro-2-methoxy-N-(1-(2-(3-n-propylureido)ethyl)pyrrolidin-3-ylmethyl)-benzamide.

¹H-NMR (CDCl₃,ppm) δ: 0.91(3 H,t,J=7.5 Hz), 1.38–1.62(5 H,m), 1.88–2.08(1 H,m), 2.28–2.88(7 H,m), 3.07–3.41(4 H,m), 3.90(3 H,s), 4.55(2 H,s), 5.25–5.40(1 H,br), 5.42–5.53(1 H,br), 6.33(1 H,s), 7.80–7.91(1 H,br), 8.03(1 H,s)

EXAMPLE 41

3-(3-tert-Butoxycarbonylaminomethylpyrrolidin-1-yl) propylamine (1.1 g) as starting compound was reacted and treated in the same manner as in Example 34 using n-propyl isocyanate (0.40 ml) and 4-amino-5-chloro-2-methoxybenzoic acid (0.87 g) to give 4-amino-5-chloro-2-methoxy-N-(1-(3-(3-n-propylureido)propyl)pyrrolidin-3-ylmethyl)benzamide.

¹H-NMR (CDCl₃,ppm) δ: 0.91(3 H,t,J=7.26 Hz), 1.50–1.77(5 H,m), 1.92–2.08(1 H,m), 2.38–2.86(7 H,m), 3.11–3.44(6 H,m), 3.91(3 H,s), 4.46(2 H,s), 5.15–5.80(1 H,br), 5.36–5.48(1 H,br), 6.32(1 H,s), 7.77–7.86(1 H,br), 8.06(1 H,s)

EXAMPLE 42

4-(3-tert-Butoxycarbonylaminomethylpyrrolidin-1-yl) butylamine (1.10 g) as starting compound was reacted and treated in the same manner as in Example 34 using n-propyl isocyanate (0.42 ml) and 4-amino-5-chloro-2-methoxybenzoic acid (0.82 g) to give 4-amino-5-chloro-2-methoxy-N-(1-(4-(3-n-propylureido)butyl)pyrrolidin-3-ylmethyl)benzamide.

¹H-NMR (CDCl₃,ppm) δ: 0.90(3 H,t,J=7.26 Hz), 1.43–1.70(7 H,m), 1.97–2.13(1 H,m), 2.46–2.81(7 H,m), 3.09–3.25(4 H,m), 3.31–3.59(2 H,m), 3.90(3 H,s), 4.43(2 H,s), 4.78–6.85(1 H,br), 4.90–5.05(1 H,br), 6.31(1 H,s), 7.83–7.92(1 H,br), 8.08(1 H,s)

EXAMPLE 43

4-((3R)-³-tert-Butoxycarbonylaminomethylpyrrolidin-1-yl)butylamine (2.00 g) as starting compound was reacted and treated in the same manner as in Example 34 using n-propyl isocyanate (0.76 ml) and 4-amino-5-chloro-2-methoxybenzoic acid (1.49 g) to give 4-amino-5-chloro-2-methoxy-N-((3R)-1-(4-(3-n-propylureido)butyl)pyrrolidin-3-ylmethyl)benzamide.

¹H-NMR (CDCl₃,ppm) δ: 0.87(3 H,t,J=7.26 Hz), 1.40–1.60(7 H,m), 1.92–2.08(1 H,m), 2.34–2.71(7 H,m), 3.05–3.25(4 H,m), 3.25–3.55(2 H,m), 3.88(3 H,s), 4.53(2 H,s), 4.95–5.03(1 H,br), 5.03–5.28(1 H,br), 6.32(1 H,s), 7.83–7.92(1 H,br), 8.04(1 H,s)

EXAMPLE 44

4-((3S)-3-tert-Butoxycarbonylaminomethylpyrrolidin-1-yl)butylamine (1.50 g) as starting compound was reacted and treated in the same manner as in Example 34 using n-propyl isocyanate (0.57 ml) and 4-amino-5-chloro-2-methoxybenzoic acid (1.11 g) to give 4-amino-5-chloro-2-methoxy-N-((3S)-1-(4-(3-n-propylureido)butyl)pyrrolidin-3-ylmethyl)benzamide.

$^1$H-NMR (CDCl$_3$,ppm) δ: 0.87(3 H,t,J=7.26 Hz), 1.40–1.60(7 H,m), 1.92–2.08(1 H,m), 2.34–2.71(7 H,m), 3.05–3.25(4 H,m), 3.25–3.55(2 H,m), 3.88(3 H,s), 4.53(2 H,s), 4.95–5.03(1 H,br), 5.03–5.28(1 H,br), 6.32(1 H,s), 7.83–7.92(1 H,br), 8.04(1 H,s)

EXAMPLE 45

4-Amino-N-(1-(4-aminobutyl)piperidin-4-ylmethyl)-5-chloro-2-methoxybenzamide (1.0 g) was dissolved in dimethylformamide (10 ml) and n-propyl isocyanate (0.26 ml) was dropwise added under ice-cooling. The mixture was stirred at room temperature for 1 hr, and the reaction mixture was concentrated under reduced pressure. The obtained residue was purified by silica gel chromatography to give 0.2 g of $^4$-amino-5-chloro-2-methoxy-N-(1-(4-(3-n-propylureido)butyl)-piperidin-4-ylmethyl)benzamide. Melting point 114°~115° C.

EXAMPLE 46

5-((3R)-3-tert-Butoxycarbonylaminomethylpyrrolidin-1-yl)-pentylamine (1.50 g) was dissolved in methylene chloride (15 ml) and a solution of n-propyl isocyanate (0.49 ml) in methylene chloride was dropwise added under ice-cooling. The mixture was stirred at room temperature for 1 hr. The reaction mixture was concentrated under reduced pressure. This compound was dissolved in 4N hydrochloric acid-dioxane solution (10 ml) and the mixture was stood at room temperature for 30 min. The reaction mixture was concentrated under reduced pressure. Dimethylformamide (30 ml) was added to the residue and the mixture was neutralized with triethylamine (2.2 ml). 4-Amino-5-chloro-2-methoxybenzoic acid (1.06 g) and 1-hydroxybenzotriazole (0.78 g) were added thereto, and the mixture was stirred at 0° C. for 15 min. Then, 1-ethyl-3-(3-dimethylaminopropyl)carbodiimide hydrochloride (1.11 g) was added and the mixture was stirred at room temperature for 8 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.27 g of 4-amino-5-chloro-2-methoxy-N-((3R)-1-(5-(3-n-propylureido)pentyl)pyrrolidin-3-ylmethyl)benzamide.

$^1$H-NMR (CDCl$_3$,ppm) δ: 0.90(3 H,t,J=7.26 Hz), 1.28–1.67(9 H,m), 1.98–2.14(1 H,m), 2.25–2.81(7 H,m), 3.04–3.25(4 H,m), 3.25–3.58(2 H,m), 3.90(3 H,s), 4.47(2 H,s), 4.80–4.93(2 H,m), 6.32(1 H,s), 7.83–7.91(1 H,br), 8.05(1 H,s)

EXAMPLE 47

5-((3S)-3-tert-Butoxycarbonylaminomethylpyrrolidin-1-yl)pentylamine (1.50 g) as starting compound was reacted and treated in the same manner as in Example 34 using n-propyl isocyanate (0.49 ml) and 4-amino-5-chloro-2-methoxybenzoic acid (0.61 g) to give 4-amino-5-chloro-2-methoxy-N-((3S)-1-(5-(3-n-propylureido)pentyl)pyrrolidin-3-ylmethyl)benzamide.

$^1$H-NMR (CDCl$_3$,ppm) δ: 0.90(3 H,t,J=7.26 Hz), 1.28–1.67(9 H,m), 1.98–2.14(1 H,m), 2.25–2.81(7 H,m), 3.04–3.25(4 H,m), 3.25–3.58(2 H,m), 3.90(3 H,s), 4.47(2 H,s), 4.80–4.93(2 H,m), 6.32(1 H,s), 7.83–7.91(1 H,br), 8.05(1 H,s)

EXAMPLE 48

5-(4-tert-Butoxycarbonylaminomethylpiperidin-1-yl) pentylamine (1.1 g) was dissolved in methylene chloride (20 ml) and a solution of n-propyl isocyanate (0.34 ml) in methylene chloride was dropwise added under ice-cooling. The mixture was stirred at room temperature for 1 hr, and the reaction mixture was concentrated under reduced pressure to give 4-tert-butoxycarbonylaminomethyl-1-(5-(3-n-propylureido)pentyl)piperidine.

This compound was dissolved in 4N hydrochloric acid-dioxane solution (30 ml) and the mixture was stood at room temperature for 60 min. The reaction mixture was concentrated under reduced pressure. Dimethylformamide (30 ml) was added to the residue and the mixture was neutralized with triethylamine (1.22 ml). 4-Amino-5-chloro-2-methoxybenzoic acid (0.89 g) and 1-hydroxybenzotriazole (0.66 g) were added thereto, and the mixture was stirred at 0° C. for 15 min. Then, dicyclohexylcarbodiimide (1.00 g) was added and the mixture was stirred at room temperature for 8 hr. The precipitated crystals were filtered off and the filtrate was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.39 g of 4-amino-5-chloro-2-methoxy-N-(1-(5-(3-n-propylureido)-pentyl)piperidin-4-ylmethyl)benzamide. Melting point 144°~147° C.

EXAMPLE 49

6-((3R)-3-tert-Butoxycarbonylaminomethylpyrrolidin-1-yl)hexylamine (1.50 g) as starting compound was reacted and treated in the same manner as in Example 34 using n-propyl isocyanate (0.50 ml) and 4-amino-5-chloro-2-methoxybenzoic acid (1.01 g) to give 4-amino-5-chloro-2-methoxy-N-((3R)-1-(6-(3-n-propylureido)hexyl)pyrrolidin-3-ylmethyl)benzamide.

$^1$H-NMR (CDCl$_3$+CD$_3$OD,ppm) δ: 0.90(3 H,t,J=7.26 Hz), 1.25–1.75(11 H,m), 1.95–2.12(1 H,m), 2.25–2.42(1 H,m), 2.93–3.75(12 H,m), 3.95(3 H,s), 6.42(1 H,s), 7.92(1 H,s)

EXAMPLE 50

6-((3S)-3-tert-Butoxycarbonylaminomethylpyrrolidin-1-yl)hexylamine (1.00 g) as starting compound was reacted and treated in the same manner as in Example 34 using n-propyl isocyanate (0.33 ml) and 4-amino-5-chloro-2-methoxybenzoic acid (0.67 g) to give 4-amino-5-chloro-2-methoxy-N-((3S)-1-(6-(3-n-propylureido)hexyl)pyrrolidin-3-ylmethyl)benzamide.

$^1$H-NMR (CDCl$_3$+CD$_3$OD,ppm) δ: 0.90(3 H,t,J=7.26 Hz), 1.25–1.75(11 H,m), 1.95–2.12(1 H,m), 2.25–2.42(1 H,m), 2.93–3.75(12 H,m), 3.95(3 H,s), 6.42(1 H,s), 7.92(1 H,s)

EXAMPLE 51

5-((3R)-3-tert-Butoxycarbonylaminomethylpyrrolidin-1-yl)pentylamine (2.00 g) as starting compound was reacted and treated in the same manner as in Example 34 using n-butyl isocyanate (0.79 ml) and 4-amino-5-chloro-2-methoxybenzoic acid (0.54 g) to give 4-amino-N-((3R)-1-(5-(3-n-butylureido)pentyl)pyrrolidin-3-ylmethyl)-5-chloro-2-methoxybenzamide.

$^1$H-NMR (CDCl$_3$,ppm) δ: 0.85–0.95(3 H,t,J=7.26 Hz), 1.25–1.63(9 H,m), 1.94–2.09(1 H,m), 2.35–2.71(7 H,m), 3.07–3.21(4 H,m), 3.25–3.58(2 H,m), 3.89(3 H,s), 4.46(2 H,s), 4.70–4.83(2 H,m), 6.32(1 H,s), 7.83–7.90(1 H,br), 8.06(1 H,s)

EXAMPLE 52

2-(3-tert-Butoxycarbonylaminomethylpyrrolidin-1-yl) ethylamine (1 g) as starting compound was reacted and treated in the same manner as in Example 34 using phenyl isocyanate (0.40 ml) and 4-amino-5-chloro-2-methoxybenzoic acid (0.83 g) to give 4-amino-5-chloro-2-methoxy-N-(1-(2-(3-phenylureido)ethyl)pyrrolidin-3-ylmethyl)benzamide.

$^1$H-NMR (CDCl$_3$,ppm)δ: 1.55–1.72(1 H,m),2.01–2.18(1 H,m), 2.43–3.22(7 H,m), 3.28–3.61(4 H,m), 3.90(3 H,s), 4.39(2 H,s), 6.29(1 H,s), 6.31–6.43(1 H,br), 6.92–7.47(5 H,m), 7.62–7.72(1 H,br), 7.85–7.93(1 H,br), 8.06(1 H,s)

EXAMPLE 53

3-(3-tert-Butoxycarbonylaminomethylpyrrolidin-1-yl) propylamine (0.74 g) as starting compound was reacted and treated in the same manner as in Example 34 using phenyl isocyanate (0.33 ml) and 4-amino-5-chloro-2-methoxybenzoic acid (0.58 g) to give 4-amino-5-chloro-2-methoxy-N-(1-(3-(3-phenylureido)propyl)pyrrolidin-3-ylmethyl)-benzamide.

$^1$H-NMR (CDCl$_3$+CD$_3$OD,ppm) δ: 1.82–2.08(3 H,m), 2.19–2.38(1 H,m), 2.97–3.74(11 H,m), 3.91(3 H,s), 6.35(1 H,s), 6.91–7.01(1 H,m), 7.18–7.45(4 H,m), 7.97(1 H,s)

EXAMPLE 54

4-(3-tert-Butoxycarbonylaminomethylpyrrolidin-1-yl) butylamine (0.92 g) as starting compound was reacted and treated in the same manner as in Example 34 using phenyl isocyanate (0.37 ml) and 4-amino-5-chloro-2-methoxybenzoic acid (0.68 g) to give 4-amino-5-chloro-2-methoxy-N-(1-(4-(3-phenylureido)butyl)pyrrolidin-3-ylmethyl)-benzamide.

$^1$H-NMR (CDCl$_3$,ppm) δ: 1.43–1.69(5 H,m), 1.95–2.17(1 H,m), 2.35–2.85(7 H,m), 3.15–3.41(4 H,m), 3.90(3 H,s), 4.43(2 H,s), 5.78–5.92(1 H,br), 6.30(1 H,s), 6.93–7.03(1 H,br), 7.20–7.44(5 H,m), 7.85–7.94(1 H,br), 8.10(1 H,s)

EXAMPLE 55

5-(3-tert-Butoxycarbonylaminomethylpyrrolidin-1-yl) pentylamine (0.87 g) as starting compound was reacted and treated in the same manner as in Example 34 using phenyl isocyanate (0.33 ml) and 4-amino-5-chloro-2-methoxybenzoic acid (0.63 g) to give 4-amino-5-chloro-2-methoxy-N-(1-(5-(3-phenylureido)pentyl)pyrrolidin-3-ylmethyl)-benzamide.

$^1$H-NMR (CDCl$_3$+CD$_3$OD,ppm) δ: 1.35–1.96(7 H,m), 2.12–2.38(1 H,m), 2.72–3.30(11 H,m), 3.93(3 H,s), 6.38(1 H,s), 6.95–7.02(1 H,m), 7.20–7.29(2 H,m), 7.29–7.38(2 H,m), 7.95(1 H,s)

EXAMPLE 56

5-((3R)-3-tert-Methoxycarbonylaminomethylpyrrolidin-1-yl)pentylamine (1.50 g) was dissolved in methylene chloride (15 ml) and a solution of phenyl isocyanate (0.58 ml) in methylene chloride was dropwise added under ice-cooling. The mixture was stirred at room temperature for 1 hr, and the reaction mixture was concentrated under reduced pressure. This compound was dissolved in 4N hydrochloric acid-dioxane solution (10 ml), and the mixture was stood at room temperature for 30 min. The reaction mixture was concentrated under reduced pressure. Dimethylformamide (30 ml) was added to the residue and the mixture was neutralized with triethylamine (2.2 ml). 4-Amino-5-chloro-2-methoxybenzoic acid (1.06 g) and 1-hydroxybenzotriazole (0.78 g) were added thereto, and the mixture was stirred at 0° C. for 15 min. Then, 1-ethyl-3-(3-dimethylaminopropyl) carbodiimide hydrochloride (1.11 g) was added and the mixture was stirred at room temperature for 8 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.50 g of 4-amino-5-chloro-2-methoxy-N-((3R)-1-(5-(3-phenylureido)pentyl)pyrrolidin-3-ylmethyl)benzamide.

$^1$H-NMR (CDCl$_3$,ppm) δ: 1.35–1.63(7 H,m), 1.90–2.04(1 H,m), 2.05–2.80(7 H,m), 3.12–3.38(3 H,m), 3.55–3.69(1 H,m), 3.88(3 H,s), 4.47(2 H,s), 5.58–5.68(1 H,br), 6.31(1 H,s), 6.91–7.00(1 H,br), 7.18–7.40(5 H,m), 7.86–7.94(1 H,br), 8.05(1 H,s)

EXAMPLE 57

5-((3S)-3-tert-Butoxycarbonylaminomethylpyrrolidin-1-yl)-pentylamine (1.52 g) as starting compound was reacted and treated in the same manner as in Example 34 using phenyl isocyanate (0.58 ml) and 4-amino-5-chloro-2-methoxybenzoic acid (0.75 g) to give 4-amino-5-chloro-2-methoxy-N-((3S)-1-(5-(3-phenylureido)pentyl)pyrrolidin-3-ylmethyl)benzamide.

$^1$H-NMR (CDCl$_3$,ppm) δ: 1.35–1.63(7 H,m), 1.90–2.04(1 H,m), 2.05–2.80(7 H,m), 3.12–3.38(3 H,m), 3.55–3.69(1 H,m), 3.88(3 H,s), 4.47(2 H,s), 5.58–5.68(1 H,br), 6.31(1 H,s), 6.91–7.00(1 H,br), 7.18–7.40(5 H,m), 7.86–7.94(1 H,br), 8.05(1 H,s)

EXAMPLE 58

5-(4-tert-Butoxycarbonylaminomethylpiperidin-1-yl) pentylamine (2.00 g) was dissolved in methylene chloride (80 ml) and phenyl isocyanate (0.80 ml) was dropwise added under ice-cooling. The mixture was stirred at room temperature for 15 hr, and the reaction mixture was concentrated under reduced pressure to give 4-tert-butoxycarbonylaminomethyl-1-(5-(3-phenylureido)pentyl) piperidine.

This compound was dissolved in 4N hydrochloric acid-isopropyl alcohol solution (60 ml) and the mixture was stood at room temperature for 18 hr. The reaction mixture was concentrated under reduced pressure. Dimethylformamide (60 ml) was added to the residue and the mixture was neutralized with triethylamine (2.50 ml). 4-Amino-5-chloro-2-methoxybenzoic acid (1.11 g) and 1-hydroxybenzotriazole (0.82 g) were added thereto, and the mixture was stirred at 0° C. for 15 min. Then, 1-ethyl-3-(3-dimethylaminopropyl) carbodiimide hydrochloride (1.16 g) was added and the mixture was stirred at room temperature for 20 hr. The reaction mixture was concentrated under reduced pressure. Aqueous potassium carbonate solution was added to the residue and the mixture was extracted with chloroform. The extract was dried over magnesium sulfate and concentrated under reduced pressure. The obtained residue was purified by silica gel chromatography to give 1.25 g of 4-amino-5-chloro-2-methoxy-N-(1-(5-(3-phenylureido)pentyl) piperidin-4-ylmethyl)benzamide.
m.p. 214°~217° C.

EXAMPLE 59

5-(4-tert-Butoxycarbonylaminomethylpiperidin-1-yl) pentylamine (2.00 g) was dissolved in methylene chloride (80 ml) and a solution of 4-chlorophenyl isocyanate (1.13 g) in methylene chloride was dropwise added under ice-cooling. The mixture was stirred at room temperature for 15 hr, and the reaction mixture was concentrated under reduced pressure to give 4-tert-butoxycarbonylaminomethyl-1-(5-(3-(4-chlorophenyl)ureido)pentyl)piperidine.

This compound was dissolved in 4N hydrochloric acid-dioxane solution (60 ml) and the mixture was stood at room temperature for 14 hr. The reaction mixture was concentrated under reduced pressure. Dimethylformamide (40 ml) was added to the residue and the mixture was neutralized with triethylamine (2.5 ml). 4-Amino-5-chloro-2-methoxybenzoic acid (1.11 g) and 1-hydroxybenzotriazole (0.82 g) were added thereto, and the mixture was stirred at 0° C. for 15 min. Then, 1-ethyl-3-(3-dimethylaminopropyl) carbodiimide hydrochloride (1.16 g) was added and the mixture was stirred at room temperature for 17 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.76 g of 4-amino-5-chloro-N-(1-(5-(3-(4-chlorophenyl)ureido)-pentyl)piperidin-4-ylmethyl)-2-methoxybenzamide.
m.p. 204°~206° C.

EXAMPLE 60

6-((3R)-3-tert-Butoxycarbonylaminomethylpyrrolidin-1-yl)-hexylamine (1.50 g) as starting compound was reacted and treated in the same manner as in Example 34 using phenyl isocyanate (0.57 ml) and 4-amino-5-chloro-2-methoxybenzoic acid (1.01 g) to give 4-amino-5-chloro-2-methoxy-N-((3R)-1-(6-(3-phenylureido)hexyl)pyrrolidin-3-ylmethyl)benzamide.

$^1$H-NMR (CDCl$_3$+CD$_3$OD,ppm) δ: 1.35–1.75(9 H,m), 1.90–2.04(1 H,m), 2.20–2.36(1 H,m), 2.91–3.85(10 H,m), 3.93(3 H,s), 6.44(1 H,s), 6.90–6.99(1 H,m), 7.15–7.46(4 H,m), 7.91(1 H,s), 8.20–8.30(1 H,br)

EXAMPLE 61

6-((3S)-3-tert-Butoxycarbonylaminomethylpyrrolidin-1-yl)hexylamine (1.00 g) as starting compound was reacted and treated in the same manner as in Example 34 using phenyl isocyanate (0.38 ml) and 4-amino-5-chloro-2-methoxybenzoic acid (0.67 g) to give 4-amino-5-chloro-2-methoxy-N-((3S)-1-(6-(3-phenylureido)hexyl)pyrrolidin-3-ylmethyl)benzamide.

$^1$H-NMR (CDCl$_3$+CD$_3$OD,ppm) δ: 1.35–1.75(9 H,m), 1.90–2.04(1 H,m), 2.20–2.36(1H,m), 2.91–3.85(10 H,m), 3.93(3 H,s), 6.44(1 H,s), 6.90–6.99(1 H,m), 7.15–7.46(4 H,m), 7.91(1 H,s), 8.20–8.30(1 H,br)

EXAMPLE 62

2-(3-tert-Butoxycarbonylaminomethylpyrrolidin-1-yl) ethylamine (1 g) as starting compound was reacted and treated in the same manner as in Example 34 using methyl isothiocyanate (0.25 ml) and 4-amino-5-chloro-2-methoxybenzoic acid (0.83 g) to give 4-amino-5-chloro-2-methoxy-N-(1-(2-(3-methylthioureido)ethyl)pyrrolidin-3-ylmethyl)-benzamide.

$^1$H-NMR (CDCl$_3$,ppm) δ: 1.53–1.71(1H,m),1.98–2.16(1 H,m), 2.42–3.28(7 H,m), 3.06(3 H,d,J=5.3 Hz), 3.50–3.87(4 H,m), 3.92(3 H,s), 4.41(2 H,s), 6.30(1 H,s), 6.98–7.14(1 H,br), 7.22–7.30(1 H,br), 7.80–7.90(1 H,br), 8.00(1 H,s)

EXAMPLE 63

3-(3-tert-Butoxycarbonylaminomethylpyrrolidin-1-yl) propylamine (1.06 g) as starting compound was reacted and treated in the same manner as in Example 34 using methyl isothiocyanate (0.32 ml) and 4-amino-5-chloro-2-methoxybenzoic acid (0.91 g) to give 4-amino-5-chloro-2-methoxy-N-(1-(3-(3-methylthioureido)propyl)pyrrolidin-3-ylmethyl)benzamide.

$^1$H-NMR (CDCl$_3$,ppm) δ: 1.05–2.87(4 H,m),2.93–3.01(3 H,br),3.31–3.71(11 H,m), 3.91(3 H,s),4.41(2 H,s),6.30(1 H,s),7.75–7.94(1 H,br),8.07(1 H,s)

EXAMPLE 64

4-(3-tert-Butoxycarbonylaminomethylpyrrolidin-1-yl) butylamine (1.01 g) as starting compound was reacted and treated in the same manner as in Example 34 using methyl isothiocyanate (0.28 ml) and 4-amino-5-chloro-2-methoxybenzoic acid (0.82 g) to give 4-amino-5-chloro-2-methoxy-N-(1-(4-(3-methylthioureido)butyl)pyrrolidin-3-ylmethyl)benzamide.

$^1$H-NMR (CDCl$_3$,ppm) δ: 1.62–1.80(5 H,m), 2.08–2.21(1 H,m), 2.63–3.05(7 H,m), 3.05(3 H,d,J=4.62 Hz), 3.38–3.63(4 H,m), 3.92(3 H,s), 4.44(2 H,s), 6.31(1 H,s), 6.69–6.90(1 H,br), 6.90–7.05(1 H,br), 7.85–7.94(1 H,br), 8.07(1 H,s)

EXAMPLE 65

2-(3-tert-Butoxycarbonylaminomethylpyrrolidin-1-yl) ethylamine (1 g) as starting compound was reacted and treated in the same manner as in Example 34 using phenyl isothiocyanate (0.49 ml) and 4-amino-5-chloro-2-methoxybenzoic acid (0.83 g) to give 4-amino-5-chloro-2-methoxy-N-(1-(2-(3-phenylthioureido)ethyl)pyrrolidin-3-ylmethyl)benzamide.

$^1$H-NMR (DMSO-D$_6$,ppm) δ: 1.41–1.57(1 H,m), 1.82–1.98(1 H,m), 2.32–2.80(7 H,m), 3.14–3.66(4 H,m), 3.82(3 H,s), 5.91(2 H,s), 6.45(1 H,s), 7.05–7.43(5 H,m), 7.55–7.62(1 H,br), 7.82–7.90(1 H,br), 7.94–8.02(1 H,br), 8.31 (1 H,s)

EXAMPLE 66

4-(3-tert-Butoxycarbonylaminomethylpyrrolidin-1-yl) butylamine (1.00 g) as starting compound was reacted and treated in the same manner as in Example 34 using phenyl isothioanate (0.44 ml) and 4-amino-5-chloro-2-methoxybenzoic acid (0.74 g) to give 4-amino-5-chloro-2-methoxy-N-(1-(4-(3-phenylthioureido)butyl)pyrrolidin-3-ylmethyl)benzamide.

$^1$H-NMR (CDCl$_3$,ppm) δ: 1.43–1.69(5 H,m),1.95–2.17(1 H,m), 2.35–2.85(7 H,m), 3.15–3.41(4 H,m), 3.90(3 H,s), 4.43(2 H,s), 5.78–5.92(1 H,br), 6.30(1 H,s), 6.93–7.03(1 H,br), 7.20–7.44(5 H,m), 7.85–7.94(1 H,br), 8.10(1 H,s)

EXAMPLE 67

2-(4-(3-tert-Butoxycarbonylaminomethylpyrrolidin-1-yl) butyl)-2,3-dihydro-1 H-isoindole-1,3-dione (1.1 g) was dissolved in trifluoroacetic acid (10 ml) and the mixture was stood at room temperature for 30 min. The reaction mixture was concentrated under reduced pressure. Dimethylformamide (10 ml) was added to the residue and the mixture was neutralized with triethylamine (0.8 ml). 4-Amino-5-chloro-2-methoxybenzoic acid (0.51 g) and 1-hydroxybenzotriazole (0.40 g) were added thereto, and the mixture was stirred at 0° C. for 15 min. Then, 1-ethyl-3-(3-dimethylaminopropyl)carbodiimide hydrochloride (0.57 g) was added and the mixture was stirred at room temperature for 8 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.62 g of 4-amino-5-chloro-N-(1-(4-(2,3-dihydro-1,3-dioxo-1 H-isoindol-2-yl)butyl)pyrrolidin-3-ylmethyl)-2-methoxybenzamide.

$^1$H-NMR (CDCl$_3$,ppm) δ: 1.50–1.61(3 H,m),1.65–1.76(2 H,m),1.96–2.08(1 H,m), 2.34–2.42(2 H,m),2.45–2.66(3 H,m),2.72–2.78(2 H,m),3.40(2 H,m), 3.65–3.72(2 H,m), 3.86(3 H,s),4.50(2 H,s),6.30(1 H,s),7.65–7.74(2 H,m), 7.78–7.86(2 H,m),8.08(1 H,s)

EXAMPLE 68

2-(2-(3-tert-Butoxycarbonylaminomethylpyrrolidin-1-yl) ethyl)-2,3-dihydro-1 H-isoindole-1,3-dione (1.5 g) as starting compound was reacted and treated in the same manner as in Example 67 using 4-amino-5-chloro-2-methoxybenzoic acid (0.81 g) to give 4-amino-5-chloro-N-(1-(2-(-2,3-dihydro-1 ,3-dioxo-1 H-isoindol-2-yl)ethyl) pyrrolidin-3-ylmethyl)-2-methoxybenzamide.

$^1$H-NMR (CDCl$_3$,ppm) δ: 1.42–1.62(1 H,m),1.88–2.06(1 H,m), 2.43–2.97(7 H,m), 3.17–3.50(4 H,m), 3.88(3 H,s), 4.33(2 H,s), 6.21(1 H,s), 7.62–7.72(2 H,m), 7.75–7.85(2 H,m), 7.90–8.02(1 H,br), 8.07(1 H,s)

EXAMPLE 69

2-(3-(3-tert-Butoxycarbonylaminomethylpyrrolidin-1-yl) propyl)-2,3-dihydro-1 H-isoindole-1,3-dione (1 g) as starting compound was reacted and treated in the same manner as in Example 67 using 4-amino-5-chloro-2-methoxybenzoic acid (0.50 g) to give 4-amino-5-chloro-N-(1-(3-(2,3-dihydro-1,3-dioxo-1 H-isoindol-2-yl)propyl)-pyrrolidin-3-ylmethyl)-2-methoxybenzamide.

$^1$H-NMR (CDCl$_3$,ppm) δ: 1.62–1.74(1 H,m), 1.98–2.17(3 H,m), 2.61–3.14(7 H,m), 3.34–3.48(4 H,m), 3.73(2 H,s), 3.93(3 H,s), 6.37(1 H,s), 7.25–7.36(1 H,br), 7.72–7.79(2 H,m), 7.82–7.87(2 H,m), 7.95(1 H,s)

EXAMPLE 70

2-(5-(3-tert-Butoxycarbonylaminomethylpyrrolidin-1-yl) pentyl)-2,3-dihydro-1 H-isoindole-1,3-dione (0.50 g) was dissolved in 4N hydrochloric acid-dioxane solution (10 ml) and the mixture was stood at room temperature for 30 min. The reaction mixture was concentrated under reduced pressure. Dimethylformamide (10 ml) was added to the residue and the mixture was neutralized with triethylamine (0.50 ml). 4-Amino-5-chloro-2-methoxybenzoic acid (0.24 g) and benzotriazol-1-yloxytris(dimethylamino)phosphonium hexafluorophosphate (0.58 g) were added thereto, and the mixture was stirred at room temperature for 8 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.16 g of 4-amino-5-chloro-N-(1-(5-(2,3-dihydro-1,3-dioxo-1 H-isoindol-2-yl)pentyl)pyrrolidin-3-ylmethyl)-2-methoxybenzamide.

$^1$H-NMR (CDCl$_3$,ppm) δ: 1.65–1.85(7 H,m), 2.12–2.28(1 H,m), 2.65–3.23(7 H,m), 3.44–3.79(4 H,m), 3.91(3 H,s), 4.43(2 H,s), 6.31(1 H,s), 7.65–7.90(4 H,m), 7.99(1 H,s), 7.98–8.13(1 H,br)

EXAMPLE 71

4-(3-tert-Butoxycarbonylaminomethylpyrrolidin-1-yl)-N-phenylbutylamide (0.99 g) was dissolved in 4N hydrochloric acid-dioxane solution (10 ml) and the mixture was stood at room temperature for 30 min. The reaction mixture was concentrated under reduced pressure. Dimethylformamide (10 ml) was added to the residue and the mixture was neutralized with triethylamine (1.2 ml). 4-Amino-5-chloro-2-methoxybenzoic acid (0.55 g) and benzotriazol-1-yloxytris(dimethylamino)phosphonium hexafluorophosphate (1.33 g) were added thereto, and the mixture was stirred at room temperature for 8 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.35 g of 4-amino-5-chloro-2-methoxy-N-(1-(3-phenylcarbamoylpropyl)pyrrolidin-3-ylmethyl)benzamide.

$^1$H-NMR (CDCl$_3$+CD$_3$OD,ppm) δ: 1.80–2.10(3 H,m), 2.15–2.32(1 H,m), 2.50–2.59(2 H,t,J=6.6 Hz), 3.75–3.90(1 H,m), 3.05–3.52(8 H,m), 3.92(3 H,s), 6.38(1 H,s), 7.02–7.53(5 H,m), 7.95(1 H,br)

EXAMPLE 72

4-(3-tert-Butoxycarbonylaminomethylpyrrolidin-1-yl)-N-(4-methylphenyl)butylamide (2.04 g) as starting compound was reacted and treated in the same manner as in Example 67 using 4-amino-5-chloro-2-methoxybenzoic acid (1.10 g) to give 4-amino-5-chloro-2-methoxy-N-(1-(3-(4-methylphenyl)carbamoylpropyl)pyrrolidin-3-ylmethyl) benzamide.

$^1$H-NMR (CDCl$_3$,ppm) δ: 1.50–1.68(1 H,m), 1.80–2.11(3 H,m), 2.29(3 H,s), 2.33–2.79(9 H,m), 3.30–3.41(1 H,m), 3.48–3.58(1 H,m), 3.80(3 H,s), 4.39(2 H,s), 6.28(1 H,s), 7.05–7.11(2 H,m), 7.35–7.42(2 H,m), 7.75–7.84(1 H,br), 8.07(1 H,s), 8.74–8.81(1 H,br)

EXAMPLE 73

4-(3-tert-Butoxycarbonylaminomethylpyrrolidin-1-yl)-N-(3-chlorophenyl)butylamide (2.10 g) as starting compound was reacted and treated in the same manner as in Example 67 using 4-amino-5-chloro-2-methoxybenzoic acid (1.07 g) to give 4-amino-5-chloro-N-(1-(3-(3-chlorophenyl)carbamoylpropyl)pyrrolidin-3-ylmethyl)-2-methoxybenzamide.

$^1$H-NMR (CDCl$_3$,ppm) δ: 1.49–1.65(1 H,m), 1.80–2.11(3 H,m), 2.35–2.78(9 H,m), 3.25–3.35(1 H,m), 3.52–3.55(1 H,m), 3.87(3 H,s), 4.42(2 H,s), 6.28(1 H,s), 6.98–7.40(3 H,m), 7.66–7.70(1 H,m), 7.75–7.85(1 H,br), 8.04(1 H,s), 9.28–9.36(1 H,br)

EXAMPLE 74

4-Amino-N-(2-(3-tert-butoxycarbonylaminomethylpyrrolidin-1-yl)-ethyl)-5- chloro-2-methoxybenzamide (0.97 g) as starting compound was reacted and treated in the same manner as in Example 67 using 4-amino-5-chloro-2-methoxybenzoic acid (0.50 g) to give 4-amino-N-(1-(2-(4-amino-5-chloro-2-methoxybenzoylamino)ethyl)pyrrolidin-3-ylmethyl)-5-chloro-2-methoxybenzamide.

$^1$H-NMR (DMSO-d$_6$,ppm) δ: 1.38–1.55(1 H,m), 1.78–1.95(1 H,m), 3.82(6 H,s), 5.89(1 H,s), 5.90(1 H,s), 6.55(4 H,s), 7.66(1 H,s), 7.71(1 H,s), 7.90–8.01(1 H,br), 8.05–8.16(1 H,br)

EXAMPLE 75

4-Amino-N-(3-(3-tert-butoxycarbonylaminomethylpyrrolidin-1-yl)-propyl)-5-chloro-2-methoxybenzamide (1.70 g) as starting compound was reacted and treated in the same manner as in Example 67 using 4-amino-5-chloro-2-methoxybenzoic acid (0.76 g) to give 4-amino-N-(1-(3-(4-amino-5-chloro-2-methoxybenzoylamino)propyl)pyrrolidin-3-ylmethyl)-5-chloro-2-methoxybenzamide.

$^1$H-NMR (CDCl$_3$,ppm) δ: 1.65–2.20(3 H,m), 2.42–3.58 (12 H,m), 3.90(6 H,s), 4.39(4 H,s), 6.30(2 H,s), 7.80–7.98(2 H,br), 8.08(2 H,br)

EXAMPLE 76

4-Amino-N-(4-(3-tert-butoxycarbonylaminomethylpyrrolidin-1-yl)-butyl)-5-chloro-2-methoxybenzamide (1.35 g) as starting compound was reacted and treated in the same manner as in Example 67 using 4-amino-5-chloro-2-methoxybenzoic acid (0.60 g) to give 4-amino-N-(1-(4-(4-amino-5-chloro-2-methoxybenzoylamino)butyl)pyrrolidin-3-ylmethyl)-5-chloro-2-methoxybenzamide.

$^1$H-NMR (CDCl$_3$,ppm) δ: 1.50–1.70(4 H,m), 1.90–2.15(2 H,m), 2.43–2.81(7 H,m), 3.33–3.50(4 H,m), 3.85(3 H,s), 3.86(3 H,s), 4.38(4 H,s), 6.25(2 H,s), 6.26(2 H,s), 7.64–7.72(1 H,br), 7.83–7.91(1 H,br), 8.07(1 H,s), 8.08(1 H,s)

EXAMPLE 77

4-Amino-N-(4-((3R)-3-tert-butoxycarbonylaminomethylpyrrolidin-1-yl)butyl)-5-chloro-2-methoxybenzamide (2.28 g) was dissolved in 4N hydrochloric acid-dioxane solution (10 ml) and the mixture was stood at room temperature for 30 min. The reaction mixture was concentrated under reduced pressure. Dimethylformamide (30 ml) was added to the residue and the mixture was neutralized with triethylamine (2.23 ml). 4-Amino-5-chloro-2-methoxybenzoic acid (1.07 g) and 1-hydroxybenzotriazole (0.79 g) were added thereto, and the mixture was stirred at 0° C. for 15 min. Then, 1-ethyl-3-(3-dimethylaminopropyl)carbodiimide hydrochloride (1.12 g) was added, and the mixture was stirred at room temperature for 8 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.60 g of 4-amino-N-((3R)-1-(4-(4-amino-5-chloro-2-methoxybenzoyl-amino)butyl)pyrrolidin-3-ylmethyl)-5-chloro-2-methoxybenzamide.

$^1$H-NMR (CDCl$_3$+CD$_3$OD,ppm) δ: 1.45–1.70(5 H,m), 1.95–2.14(1 H,m), 2.21–2.84(11 H,m), 3.39(3 H,s), 3.41(3 H,s), 6.34(1 H,s), 6.36(1 H,s), 7.97(1 H,s), 7.98(1 H,s)

EXAMPLE 78

4-Amino-N-(5-((3R)-3-tert-butoxycarbonylaminomethylpyrrolidin-1-yl)pentyl)-5-chloro-2-methoxybenzamide (1.45 g) was dissolved in 4N hydrochloric acid-dioxane solution (10 ml) and the mixture was stood at room temperature for 30 min. The reaction mixture was concentrated under reduced pressure. Dimethylformamide (30 ml) was added to the residue and the mixture was neutralized with triethylamine (1.37 ml). 4-Amino-5-chloro-2-methoxybenzoic acid (0.66 g) and 1-hydroxybenzo-triazole (0.49 g) were added thereto, and the mixture was stirred at 0° C. for 15 min. Then, 1-ethyl-3-(3-dimethylaminopropyl)carbodiimide hydrochloride (0.69 g) was added, and the mixture was stirred at room temperature for 8 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.30 g of 4-amino-N-((3R)-1-(5-(4-amino-5-chloro-2-methoxybenzoylamino)pentyl)pyrrolidin-3-ylmethyl)-5-chloro-2-methoxybenzamide.

$^1$H-NMR (CDCl$_3$,ppm) δ: 1.33–1.90(7 H,m), 1.93–2.08(1 H,m), 2.33–2.76(7 H,m), 3.32–3.46(4 H,m), 3.87(3 H,s), 3.88(3 H,s), 4.36(2 H,s), 4.38(2 H,s), 6.28(2 H,s), 7.60–7.72(1 H,br), 7.82–7.88(1 H,br), 8.07(1 H,s), 8.10(1 H,s)

EXAMPLE 79

N-(3-(3-tert-Butoxycarbonylaminomethylpyrrolidin-1-yl)propyl)-4-pyridinecarboxamide (0.90 g) as starting compound was reacted and treated in the same manner as in Example 67 using 4-amino-5-chloro-2-methoxybenzoic acid (0.50 g) to give 4-amino-5-chloro-2-methoxy-N-(1-(3-(4-pyridinecarbonylamino)propyl)pyrrolidin-3-ylmethyl)benzamide.

$^1$H-NMR (CDCl$_3$,ppm) δ: 1.50–2.10(4 H,m), 2.35–2.90(7 H,m), 3.30–3.62(4 H,m), 3.90(3 H,s), 4.41(2 H,s), 6.30(1 H,s), 7.60–7.66(2 H,m), 7.71–7.83(1 H,br), 8.08(1 H,s), 8.68–8.78(3 H,m)

EXAMPLE 80

N-(3-(3-tert-Butoxycarbonylaminomethylpyrrolidin-1-yl)propyl)-6-chloro-4-methyl-3,4-dihydro-2H-1,4-benzoxazine-8-carboxamide (1.5 g) as starting compound was reacted and treated in the same manner as in Example 67 using 4-amino-5-chloro-2-methoxybenzoic acid (0.65 g) to give N-(3-(3-(4-amino-5-chloro-2-methoxybenzoylaminomethyl)-pyrrolidin-1-yl)propyl)-6-chloro-4-methyl-3,4-dihydro-2H-1,4-benzoxazine-8-carboxamide.

$^1$H-NMR (DMSO-D$_6$, ppm) δ: 1.60–1.68(1 H,m), 2.08–2.30(3 H,m), 2.39–2.58(7 H,m), 2.86(3 H,m), 3.24–3.46(6 H,m), 3.70(3 H,s), 4.27–4.33(2 H,m), 5.90(2 H,s), 6.41(1 H,s), 6.74(1 H,d,J=2.64 Hz), 6.85(1 H,d,J=2.64 Hz), 7.53(1 H,s), 8.10–8.19(2 H,br)

EXAMPLE 81

N-(4-(3-tert-Butoxycarbonylaminomethylpyrrolidin-1-yl)butyl)-6-chloro-4-methyl-3,4-dihydro-2H-1,4-benzoxazine-8-carboxamide (0.7 g) as starting compound was reacted and treated in the same manner as in Example 67 using 4-amino-5-chloro-2-methoxybenzoic acid (0.37 g) to give N-(4-(3-(4-amino-5-chloro-2- methoxybenzoylaminomethyl)-pyrrolidin-1-yl)butyl)-6-chloro-4-methyl-3,4-dihydro-2H-1,4-benzoxazine-8-carboxamide.

$^1$H-NMR (CDCl$_3$,ppm) δ: 1.50–1.75(5 H,m),1.98–2.13(1 H,m),2.31–2.92(7 H,m), 2.89(3 H,s),3.29–3.37(2 H,m), 3.35–3.52(4 H,m),3.88(3 H,s),4.28–4.43(4 H,m), 6.25(1 H,s),6.66(1 H,d,J=2.64 Hz),7.41(1 H,d,J=2.64 Hz), 7.73–7.80(1 H,br), 7.75–7.88(1 H,br),8.07(1 H,s)

EXAMPLE 82

N-(2-(3-tert-Butoxycarbonylaminomethylpyrrolidin-1-yl)ethyl)-1-methyl-1 H-indole-3-carboxamide (2.16 g) as starting compound was reacted and treated in the same manner as in Example 67 using 4-amino-5-chloro-2-methoxybenzoic acid (1.1 g) to give N-(2-(3-(4-amino-5-chloro-2-methoxybenzoylaminomethyl)pyrrolidin-1-yl) ethyl)-1-methyl-1 H-indole-3-carboxamide.

$^1$H-NMR (CDCl$_3$,ppm) δ: 1.57–1.78(1 H,m),2.02–2.18(1 H,m), 2.50–2.98(7 H,m), 3.39–3.73(4 H,m), 3.75(3 H,s), 3.81(3 H,s), 4.31(2 H,s), 6.11(1 H,s), 7.18–7.36(4 H,m), 7.66–7.75(1 H,br), 7.88–7.97(1 H,br), 7.99–8.10(1 H,m), 8.08(1 H,s)

EXAMPLE 83

N-(3-(3-tert-Butoxycarbonylaminomethylpyrrolidin-1-yl)propyl)-1-methyl-1 H-indole-3-carboxamide (0.44 g) as starting compound was reacted and treated in the same manner as in Example 67 using 4-amino-5-chloro-2-methoxybenzoic acid (0.26 g) to give N-(3-(3-(4-amino-5-chloro-2-methoxybenzoylaminomethyl)pyrrolidin-1-yl)propyl)-1-methyl-1H-indole-3-carboxamide.

$^1$H-NMR (CDCl$_3$,ppm) δ: 1.60–1.75(1 H,m), 1.91–2.18(3 H,m), 2.60–3.14(7H,m), 3.36–3.49(2 H,m), 3.53–3.80(2 H,m), 3.84(3 H,s), 3.86(3 H,s), 4.38(2 H,s), 6.24(1 H,s), 7.18–7.45(4 H,m), 7.70–7.88(2 H,m), 8.05(1 H,s), 8.08–8.14(1 H,m)

EXAMPLE 84

N-(4-(3-tert-Butoxycarbonylaminomethylpyrrolidin-1-yl)butyl)-1-methyl-1 H-indole-3-carboxamide (0.67 g) as starting compound was reacted and treated in the same manner as in Example 67 using 4-amino-5-chloro-2-methoxybenzoic acid (0.42 g) to give N-(4-(3-(4-amino-5-chloro-2-methoxybenzoylaminomethyl)pyrrolidin-1-yl) butyl)-1-methyl-1 H-indole-3-carboxamide.

$^1$H-NMR (CDCl$_3$,ppm) δ: 1.50–1.78(5 H,m),1.92–2.08(1 H,m),2.36–2.80(7 H,m), 3.35–3.60(4 H,m),3.80(3 H,s), 3.85(3 H,s),4.31(2 H,s),6.24(1 H,s), 7.20–7.37(4 H,m), 7.65(1 H,s),7.80–7.85(1 H,br),7.90–7.97(1 H,br),8.07(1 H,s)

EXAMPLE 85

N-(4-((3R)-3-tert-Butoxycarbonylaminomethylpyrrolidin-1-yl)-butyl)-1-methyl-1 H-indole-3-carboxamide (1.94 g) was dissolved in 4N hydrochloric acid-dioxane solution (40 ml) and the mixture was stood at room temperature for 60 min. The reaction mixture was concentrated under reduced pressure. Dimethylformamide (30 ml) was added to the residue and the mixture was neutralized with triethylamine (1.25 ml). 4-Amino-5-chloro-2-methoxybenzoic acid (0.91 g) and 1-hydroxybenzotriazole (0.67 g) were added thereto, and the mixture was stirred at 0° C. for 15 min. Then, 1-ethyl-3-(3-dimethylaminopropyl)carbodiimide hydrochloride (0.95 g) was added, and the mixture was stirred at room temperature for 8 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.75 g of N-(4-((3R)-3-(4-amino-5-chloro-2-methoxybenzoylaminomethyl)pyrrolidin-1-yl)butyl)-1-methyl-1 H-indole-3-carboxamide.

$^1$H-NMR(CDCl$_3$,ppm) δ: 1.50–1.78(5 H,m), 1.89–2.13(1 H,m), 2.40–2.81(7 H,m), 3.35–3.56(4 H,m), 3.80(3 H,s), 3.84(3 H,s), 4.35(2 H,s), 6.25(1 H,s), 6.33–6.45(1 H,br), 7.20–7.38(3 H,m), 7.65(1 H,s), 7.78–7.88(1 H,br), 7.96–8.00(1 H,m), 8.05(1 H,s)

EXAMPLE 86

N-(4-((3S)-3-tert-Butoxycarbonylaminomethylpyrrolidin-1-yl)-butyl)-1-methyl-1 H-indole-3-carboxamide (1.94 g) as starting compound was reacted and treated in the same manner as in Example 67 using 4-amino-5-chloro-2-methoxybenzoic acid (0.67 g) to give N-(4-((3S)-3-(4-amino-5-chloro-2-methoxybenzoylaminomethyl)pyrrolidin-1-yl)butyl)-1-methyl-1 H-indole-3-carboxamide.

$^1$H-NMR(CDCl$_3$,ppm) δ: 1.50–1.78(5 H,m), 1.89–2.13(1 H,m), 2.40–2.81(7 H,m), 3.35–3.56(4 H,m), 3.80(3 H,s), 3.84(3 H,s), 4.35(2 H,s), 6.25(1 H,s), 6.33–6.45(1 H,br), 7.20–7.38(3 H,m), 7.65(1 H,s), 7.78–7.88(1 H,br), 7.96–8.00(1 H,m), 8.05(1 H,s)

EXAMPLE 87

N-(5-(3-tert-Butoxycarbonylaminomethylpyrrolidin-1-yl)pentyl)-1-methyl-1 H-indole-3-carboxamide (0.89 g) as starting compound was reacted and treated in the same manner as in Example 67 using 4-amino-5-chloro-2-methoxybenzoic acid (0.42 g) to give N-(5-(3-(4-amino-5-chloro-2-methoxybenzoylaminomethyl)pyrrolidin-1-yl) pentyl)-1-methyl-1 H-indole-3-carboxamide.

$^1$H-NMR(CDCl$_3$+CD$_3$OD,ppm) δ: 1.20–1.78(7 H,m), 2.05–2.20(1 H,m), 2.58–3.53(11 H,m), 3.83(3 H,s), 3.90(3 H,s), 6.35(1 H,s), 7.20–7.41(3 H,m), 7.72(1 H,s), 7.95–8.08(2 H,m)

EXAMPLE 88

N-(5-((3R)-3-tert-Butoxycarbonylaminomethylpyrrolidin-1-yl)-pentyl)-1-methyl-1 H-indole-3-carboxamide (1.53 g) was dissolved in 4N hydrochloric acid-dioxane solution (10 ml) and the mixture was stood at room temperature for 30 min. The reaction mixture was concentrated under reduced pressure. Dimethylformamide (30 ml) was added to the residue and the mixture was neutralized with triethylamine (1.45 ml). 4-Amino-5-chloro-2-methoxybenzoic acid (0.70 g) and 1-hydroxybenzotriazole (0.51 g) were added thereto, and the mixture was stirred at 0° C. for 15 min. Then, 1-ethyl-3-(3-dimethylaminopropyl)carbodiimide hydrochloride (0.73 g) was added, and the mixture was stirred at room temperature for 8 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.89 g of N-(5-((3R)-3-(4-amino-5-chloro-2-methoxybenzoylaminomethyl)pyrrolidin-1-yl)pentyl)-1-methyl-1 H-indole-3-carboxamide.

$^1$H-NMR(CDCl$_3$,ppm) δ: 1.38–1.71(7 H,m), 1.95–2.10(1 H,m), 2.40–2.79(7 H,m), 3.37–3.53(4 H,m), 3.81(3 H,s), 3.87(3 H,s), 4.39(2 H,s), 5.98–6.10(1 H,br), 6.28(1 H,s), 7.18–7.36(3 H,m), 7.68(1 H,s), 7.80–7.88(1 H,br), 7.94–7.97(1 H,m), 8.07(1 H,s)

EXAMPLE 89

N-(5-((3S)-3-tert-Butoxycarbonylaminomethylpyrrolidin-1-yl)-pentyl)-1-methyl-1 H-indole-3-carboxamide (1.48 g) as starting compound was reacted and treated in the same manner as in Example 67 using 4-amino-5-chloro-2-methoxybenzoic acid (0.68 g) to give N-(5-((3S)-3-(4-amino-5-chloro-2-methoxybenzoylaminomethyl)pyrrolidin-1-yl)pentyl)-1-methyl-1 H-indole-3-carboxamide.

$^1$H-NMR(CDCl$_3$,ppm) δ: 1.38–1.71(7 H,m), 1.95–2.10(1 H,m), 2.40–2.79(7 H,m), 3.37–3.53(4 H,m), 3.81(3 H,s), 3.87(3 H,s), 4.39(2 H,s), 5.98–6.10(1 H,br), 6.28(1 H,s), 7.18–7.36(3 H,m), 7.68(1 H,s), 7.80–7.88(1 H,br), 7.94–7.97(1 H,m), 8.07(1 H,s)

EXAMPLE 90

N-(5-(4-tert-Butoxycarbonylaminomethylpiperidin-1-yl) pentyl)-1-methyl-1 H-indole-3-carboxamide (1.12 g) was dissolved in 4N hydrochloric acid-dioxane solution (30 ml) and the mixture was stood at room temperature for 1 hr. The reaction mixture was concentrated under reduced pressure. Dimethylformamide (30 ml) was added to the residue and the mixture was neutralized with triethylamine (0.68 ml). 4-Amino-5-chloro-2-methoxybenzoic acid (0.49 g) and 1-hydroxybenzotriazole (0.36 g) were added thereto, and the mixture was stirred at 0° C. for 20 min. Then, 1-ethyl-3-(3-dimethylaminopropyl)carbodiimide hydrochloride (0.52 g) was added, and the mixture was stirred at room temperature for 12 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.60 g of N-(5-($^4$-(4-amino-5-chloro-2-methoxybenzoylaminomethyl)piperidin-1-yl)pentyl)-l-methyl-1 H-indole-3-carboxamide.

$^1$H-NMR(CDCl$_3$,ppm) δ: 1.25–1.79(11 H,m), 1.85–2.04(2 H,m), 2.28–2.41(2 H,m), 2.89–3.03(2 H,m), 3.25–3.36(2 H,m), 3.42–3.55(2 H,m), 3.80(3 H,s), 3.87(3 H,s), 4.42(2 H,s), 5.97–6.15(1 H,br), 6.29(1 H,s), 7.20–7.38(3 H,m), 7.66(1 H,s), 7.65–7.82(1 H,br), 7.90–7.96(1 H,m), 8.10(1 H,s)

EXAMPLE 91

N-(6-((3R)-3-tert-Butoxycarbonylaminomethylpyrrolidin-1-yl)-hexyl)-1-methyl-1 H-indole-3-carboxamide (0.62 g) as starting compound was reacted and treated in the same manner as in Example 67 using 4-amino-5-chloro-2-methoxybenzoic acid (0.28 g) to give N-(6-((3R)-3-(4-amino-5-chloro-2-methoxybenzoylaminomethyl)pyrrolidin-1-yl)hexyl)-1-methyl-1 H-indole-3-carboxamide.

$^1$H-NMR(DMSO-d$_6$,ppm) δ:1.20–1.71(9 H,m), 1.80–1.94(1 H,m), 2.05–2.20(1 H,m), 2.49(6 H,s), 5.90–5.95(1 H,br), 6.48(1 H,s), 7.07–7.25(3 H,m), 7.42–7.52(1 H,m), 7.80–7.91(1 H,br), 8.08–8.18(1 H,m), 8.31(1 H,s)

EXAMPLE 92

N-(6-((3S)-3-tert-Butoxycarbonylaminomethylpyrrolidin-1-yl)-hexyl)-1-methyl-1 H-indole-3-carboxamide (1.00 g) as starting compound was reacted and treated in the same manner as in Example 67 using 4-amino-5-chloro-2-methoxybenzoic acid (0.50 g) to give N-(6-((3S)-3-(4-amino-5-chloro-2-methoxybenzoylaminomethyl)pyrrolidin-1-yl)hexyl)-1-methyl-1 H-indole-3-carboxamide.

$^1$H-NMR(DMSO-d$_6$,ppm) δ: 1.20–1.71(9 H,m), 1.80–1.94(1 H,m), 2.05–2.20(1 H,m), 2.49(6 H,s), 5.90–5.95(1 H,br), 6.48(1 H,s), 7.07–7.25(3 H,m), 7.42–7.52(1 H,m), 7.80–7.91(1 H,br), 8.08–8.18(1 H,m), 8.31(1 H,s)

EXAMPLE 93

N-(4-((3R)-3-tert-Butoxycarbonylaminomethylpyrrolidin-1-yl)-butyl)-1-methyl-1 H-indole-2-carboxamide (0.95 g) as starting compound was reacted and treated in the same manner as in Example 67 using 4-amino-5-chloro-2-methoxybenzoic acid (0.45 g) to give N-(4-((3R)-3-(4-amino-5-chloro-2-methoxybenzoylaminomethyl)pyrrolidin-1-yl)butyl)-1-methyl-1 H-indole-2-carboxamide.

$^1$H-NMR (CDCl$_3$,ppm) δ: 1.44–1.80(5 H,m), 1.89–2.08(1 H,m), 2.31–2.78(7 H,m), 3.31–3.52(4 H,m), 3.82(3 H,s), 4.05(3 H,s), 4.35(2 H,s), 6.23(1 H,s), 6.81(1 H,s), 7.05–7.38(4 H,m), 7.55–7.64(1 H,m), 7.72–7.83(1 H,br), 8.07(1 H,s)

EXAMPLE 94

N-(4-((3R)-3-tert-Butoxycarbonylaminomethylpyrrolidin-1-yl)-butyl)-1-isopropyl-1 H-indole-3-carboxamide (1.34 g) was dissolved in 4N hydrochloric acid-dioxane solution (30 ml) and the mixture was stood at room temperature for 60 min. The reaction mixture was concentrated under reduced pressure. Dimethylformamide (30 ml) was added to the residue and the mixture was neutralized with triethylamine (0.81 ml). 4-Amino-5-chloro-2-methoxybenzoic acid (0.59 g) and 1-hydroxybenzotriazole (0.44 g) were added thereto, and the mixture was stirred at 0C for 15 min. Then, 1-ethyl-3-(3-dimethylaminopropyl)carbodiimide hydrochloride (0.62 g) was added, and the mixture was stirred at room temperature for 8 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.62 g of N-(4-((3R)-3-(4-amino-5-chloro-2-methoxybenzoylaminomethyl)pyrrolidin-1-yl)butyl)-1-isopropyl-1 H-indole-3-carboxamide.

$^1$H-NMR (CDCl$_3$,ppm) δ: 1.53(6 H,d,J=6.6 Hz), 1.55–1.78(5 H,m), 1.88–2.05(1 H,m), 2.31–2.78(7 H,m), 3.33–3.55(4 H,m), 3.85(3 H,s), 4.36(2 H,s), 6.25(1 H,s), 6.25–6.35(1 H,br), 7.28–7.45(3 H,m), 7.75–7.85(2 H,m), 7.90–7.95(1 H,m), 8.07(1 H,s)

EXAMPLE 95

N-(4-((3R)-3-tert-Butoxycarbonylaminomethylpyrrolidin-1-yl)-butyl)-1-benzyl-1 H-indole-3-carboxamide (1.35 g) was dissolved in 4N hydrochloric acid-dioxane solution (30 ml) and the mixture was stood at room temperature for 60 min. The reaction mixture was concentrated under reduced pressure. Dimethylformamide (30 ml) was added to the residue and the mixture was neutralized with triethylamine (0.74 ml).

4-Amino-5-chloro-2-methoxybenzoic acid (0.54 g) and 1-hydroxybenzotriazole (0.40 g) were added thereto, and the mixture was stirred at 0° C. for 15 min. Then, 1-ethyl-3-(3-dimethylaminopropyl)carbodiimide hydrochloride (0.56 g) was added, and the mixture was stirred at room temperature for 8 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 1.03 g of N-(4-((3R)-3-(4-amino-5-chloro-2-methoxybenzoylaminomethyl)pyrrolidin-1-yl)butyl)-l-benzyl-1 H-indole-3-carboxamide.

$^1$H-NMR (CDCl$_3$,ppm) δ: 1.42–1.78(5 H,m), 1.85–2.03(1 H,m), 2.29–2.78(7 H,m), 3.35–3.64(4 H,m), 3.83(3 H,s), 4.31(2 H,s), 5.31(2 H,s), 6.22(1 H,s), 6.30–6.40(1 H,br), 7.08–7.35(6 H,m), 7.69(1 H,s), 7.75–7.84(1 H,br), 7.95–8.03(1 H,m), 8.07(1 H,s)

EXAMPLE 96

N-(4-(3-tert-Butoxycarbonylaminomethylpyrrolidin-1-yl)butyl)-N-methylbenzamide (0.57 g) as starting compound was reacted and treated in the same manner as in Example 67 using 4-amino-5-chloro-2-methoxybenzoic acid (0.30 g) to give 4-amino-N-(1-(4-(N-benzoyl-N-methylamino)butyl) pyrrolidin-3-ylmethyl)-5-chloro-2-methoxybenzamide.

$^1$H-NMR (CDCl$_3$,ppm) δ: 1.25–1.43(1 H,m), 1.45–1.79(4 H,m), 1.90–2.11(1 H,m), 2.22–3.12(10 H,m), 3.23–3.55(4 H,m), 3.86(3 H,s), 4.47(2 H,s), 6.30(1 H,s), 7.30–7.45(5 H,m), 7.75–7.89(1 H,br), 8.07(1 H,s)

EXAMPLE 97

N-(4-(3-tert-Butoxycarbonylaminomethylpyrrolidin-1-yl)butyl)- 1-methyl-1 H-indole-3-carboxamide (1.00 g) as starting compound was reacted and treated in the same manner as in Example 67 using 4-amino-5-chloro-2-cyclopropylmethyloxybenzoic acid (0.56 g) to give N-(4-(3-(4-amino-5-chloro-2-cyclopropylmethyloxybenzoylaminomethyl)-pyrrolidin-1-yl)butyl)-1-methyl-1 H-indole-3-carboxamide.

$^1$H-NMR (CDCl$_3$,ppm) δ: 0.45–0.53(2 H,m), 0.62–0.75(2 H,m), 1.20–1.35(1 H,m), 1.50–1.79(5 H,m), 1.98–2.13(1 H,m), 2.39–3.00(7 H,m), 3.38–3.55(4 H,m), 3.70–3.85(5 H,m), 4.35(2 H,s), 6.20(1 H,s), 6.35–6.45(1 H,br), 7.18–7.35(3 H,m), 7.71(1 H,s), 7.95–8.05(1 H,br), 8.09(1 H,s), 8.10–8.15(1 H,br)

EXAMPLE 98

N-(4-(4-tert-Butoxycarbonylaminomethylpiperidin-1-yl) butyl)-1-methyl-1 H-indole-3-carboxamide (1.40 g) was dissolved in 4N hydrochloric acid-dioxane solution (50 ml) and the mixture was stood at room temperature for 2.5 hr. The reaction mixture was concentrated under reduced pressure. Dimethylformamide (30 ml) was added to the residue and the mixture was neutralized with triethylamine (1.45 ml). 4-Amino-5-chloro-2-methoxybenzoic acid (0.64 g) and 1-hydroxybenzotriazole (0.49 g) were added thereto, and the mixture was stirred at 0° C. for 15 min. Then, 1-ethyl-3-(3-dimethylaminopropyl)carbodiimide hydrochloride (0.67 g) was added, and the mixture was stirred at room temperature for 16 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.63 g of N-(4-(4-(4-amino-5-chloro-2-methoxybenzoylaminomethyl)-piperidin-1-yl)butyl)-1-methyl-1 H-indole-3-carboxamide.

$^1$H-NMR (CDCl$_3$,ppm) δ: 1.20–1.38(3 H,m), 1.45–1.99(6 H,m), 2.30–2.43(2 H,m), 2.88–2.99(4 H,m), 3.25–3.33(2 H,m), 3.45–3.56(2 H,m), 3.81(3 H,s), 3.88(3 H,s), 4.35(2 H,s), 6.15–6.22(1 H,br), 6.27(1 H,s), 7.20–7.35(3 H,m), 7.63(1 H,s), 7.65–7.75(1 H,br), 7.88–7.95(1 H,m), 8.10(1 H,s)

EXAMPLE 99

N-(3-((3R)-3-tert-Butoxycarbonylaminomethylpyrrolidin-1-yl)-propyl)-3-phenylpropylamide (1.74 g) as starting compound was reacted and treated in the same manner as in Example 67 using 4-amino-5-chloro-2-methoxybenzoic acid (0.90 g) to give 4-amino-5-chloro-2-methoxy-N-((3R)-1-(3-(3-phenylpropionylamino)propyl)pyrrolidin-3-ylmethyl) benzamide.

$^1$H-NMR (CDCl$_3$,ppm) δ: 1.45–1.68(3 H,m), 1.90–2.04(1 H,m), 2.25–2.72(9 H,m), 2.88–2.99(2 H,m), 3.25–3.50(4 H,m), 3.88(3 H,s), 4.43(2 H,s), 6.30(1 H,s), 6.75–6.86(1 H,br), 7.14–7.33(5 H,m), 7.72–7.82(1 H,br), 8.09(1 H,s)

EXAMPLE 100

N-(2-((3R)-3-tert-Butoxycarbonylaminomethylpyrrolidin-1-yl)-ethyl)-4-phenylbutylamide (1.55 g) was dissolved in 4N hydrochloric acid-dioxane solution (10 ml) and the mixture was stood at room temperature for 30 min. The reaction mixture was concentrated under reduced pressure. Dimethylformamide (30 ml) was added to the residue and the mixture was neutralized with triethylamine (1.7 ml). 4-Amino-5-chloro-2-methoxybenzoic acid (0.80 g) and 1-hydroxybenzotriazole (0.59 g) were added thereto, and the mixture was stirred at 0° C. for 15 min. Then, 1-ethyl-3-(3-dimethylaminopropyl)-carbodiimide hydrochloride (0.84 g) was added thereto, and the mixture was stirred at room temperature for 8 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 1.02 g of 4-amino-5-chloro-2-methoxy-N-((3R)-1(2-(4-phenylbutyrylamino)ethyl)-pyrrolidin-3-ylmethyl) benzamide.

$^1$H-NMR (CDCl$_3$,ppm) δ: 1.40–1.60(1 H,m), 1.88–2.04(3 H,m), 2.12–2.23(2 H,m), 2.33–2.75(9 H,m), 3.25–3.55(4 H,m), 3.87(3 H,s), 4.47(2 H,s), 6.25–6.38(2 H,br), 7.10–7.32(5 H,m), 7.75–7.88(1 H,br), 8.08(1 H,s)

EXAMPLE 101

3-tert-Butoxycarbonylaminomethyl-1-(2-methylsulfonylaminoethyl)pyrrolidine (2 g) as starting compound was reacted and treated in the same manner as in Example 67 using 4-amino-5-chloro-2-methoxybenzoic acid (1.25 g) to give 4-amino-5-chloro-2-methoxy-N-(2-methylsulfonylaminoethyl)pyrrolidin-3-ylmethyl) benzamide.

$^1$H-NMR (CDCl$_3$,ppm) δ: 1.48–1.64(1 H,m), 1.93–2.08(1 H,m), 2.40–2.79(7 H,m), 2.95(3 H,s), 3.15–3.58(4 H,m), 3.92(3 H,s), 4.41(2 H,s), 5.18–5.34(1 H,br), 6.33(1 H,s), 7.79–8.88(1 H,br), 8.09(1 H,s)

EXAMPLE 102

3-tert-Butoxycarbonylaminomethyl-1-(3-(1,1,3-trioxo-2,3-dihydro-1,2-benzisothiazol-2-yl)propyl)pyrrolidine (0.28 g) as starting compound was reacted and treated in the same manner as in Example 67 using 4-amino-5-chloro-2-methoxybenzoic acid (0.13 g) to give 4-amino-5-chloro-2-methoxy-N-(1-(3-(1,1,3-trioxo-2,3-dihydro-1,2-benzisothiazol-2-yl)propyl)pyrrolidin-3-ylmethyl)benzamide.

$^1$H-NMR (CDCl$_3$,ppm) δ: 1.50–1.58(1 H,m),1.95–2.12(3 H,m),2.39–2.74(7 H,m), 3.30–3.47(2 H,m),3.81–3.95(2 H,m),3.90(3 H,s),4.36(1 H,s),6.29(1 H,s), 7.80–7.94(3 H,m),8.04–8.08(1 H,m),8.09(1 H,s)

EXAMPLE 103

3-tert-Butoxycarbonylaminomethyl-1-(3-(2,3-dihydro-2-oxobenzimidazol-1-yl)propyl)pyrrolidine (1.31 g) as starting compound was reacted and treated in the same manner as in Example 67 using 4-amino-5-chloro-2-methoxybenzoic acid (0.7 g) to give 4-amino-5-chloro-N-(1-(3-(2,3-dihydro-2-oxobenzimidazol-1-yl)propyl)pyrrolidin-3-ylmethyl)-2-methoxybenzamide.

$^1$H-NMR (CDCl$_3$,ppm) δ: 1.48–1.68(1 H,m),1.93–2.11(1 H,m), 2.40–2.80(7 H,m), 3.43(2 H,t,J=6.3 Hz), 3.85(3 H,s), 3.95(2 H,t,J=6.9 Hz), 4.40(2 H,s), 6.26(1 H,s), 6.98–7.22(4 H,m), 7.77–7.89(1 H,br), 8.07(1 H,s), 9.18–9.30(1 H,br)

EXAMPLE 104

4-Amino-5-chloro-2-methoxy-N-(piperidin-4-ylmethyl)benzamide hydrochloride (8.0 g) was dissolved in dimethylformamide (100 ml) and toluene (100 ml). Potassium carbonate (9.9 g) and 4-bromopropylphthalimide (6.4 g) were added, and the mixture was stirred at 70° C. for 5 hr. The reaction mixture was concentrated under reduced pressure and the residue was extracted with ethyl acetate. The extract was dried over magnesium sulfate and concentrated under reduced pressure. The obtained residue was purified by silica gel chromatography to give 4.0 g of 4-amino-5-chloro-N-(1-(3-(2,3-dihydro-1,3-dioxo-1 H-isoindol-2-yl)propyl)piperidin-4-ylmethyl)-2-methoxybenzamide.

$^1$H-NMR (CDCl$_3$,ppm) δ: 1.05–1.22(2 H,m), 1.41–1.70(3 H,m), 1.75–1.95(4 H,m), 2.33–2.45(2 H,m), 2.80–2.93(2 H,m), 3.18–3.25(2 H,m), 3.72–3.80(2 H,m), 3.88(3 H,s), 4.43(2 H,s), 6.30(1 H,s), 7.65–7.88(4 H,m), 8.08(1 H,s)

EXAMPLE 105

4-Amino-5-chloro-2-methoxy-N-(piperidin-4-ylmethyl)benzamide hydrochloride (15.0 g) was dissolved in dimethylformamide (100 ml) and toluene (150 ml). Potassium carbonate (18.6 g) and 4-bromobutylphthalimide (12.7 g) were added, and the mixture was stirred at 70 ° C. for 2 hr. The reaction mixture was concentrated under reduced pressure and the residue was extracted with ethyl acetate. The extract was dried over magnesium sulfate and concentrated under reduced pressure. The obtained residue was purified by silica gel chromatography to give 13.6 g of 4-amino-5-chloro-N-(1-(4-(2,3-dihydro-1,3-dioxo-1H-isoindol-2-yl)butyl)-piperidin-4-ylmethyl)-2-methoxybenzamide.

$^1$H-NMR(CDCl$_3$,ppm) δ: 1.20–1.39(2 H,m), 1.55–1.98(9 H,m), 2.28–2.41(2 H,m), 2.85–2.97(2 H,m), 3.25–3.37(2 H,m), 3.66–3.78(2 H,m), 3.89(3 H,s), 4.42(2 H,s), 6.29(1 H,s), 7.65–7.86(4 H,m), 8.09(1 H,s)

EXAMPLE 106

4-Amino-5-chloro-2-methoxy-N-(piperidin-4-ylmethyl)benzamide hydrochloride (23.0 g) was dissolved in dimethylformamide (250 ml). Potassium carbonate (28.5 g) and 5-bromopentylphthalimide (20.4 g) were added, and the mixture was stirred at 50° C. for 8 hr. The reaction mixture was concentrated under reduced pressure and the residue was extracted with ethyl acetate. The extract was dried over magnesium sulfate and concentrated under reduced pressure. The obtained residue was purified by silica gel chromatography to give 20.0 g of 4-amino-5-chloro-N-(1-(5-(2,3-dihydro-1,3-dioxo-1H-isoindol-2-yl)pentyl)piperidin-4-ylmethyl)-2-methoxybenzamide.

$^1$H-NMR (CDCl$_3$,ppm) δ: 1.20–1.98(11 H,m), 2.00–2.11(2 H,m), 2.30–2.40(2 H,m), 2.85–2.97(2 H,m), 3.25–3.37(2 H,m), 3.66–3.78(2 H,m), 3.89(3 H,s), 4.42(2 H,s), 6.29(1 H,s), 7.63–7.85(4 H,m), 8.09(1 H,s)

EXAMPLE 107

4-Amino-5-chloro-2-methoxy-N-(piperidin-4-ylmethyl)benzamide hydrochloride (8.5 g) was dissolved in dimethylformamide (100 ml). Potassium carbonate (10.5 g) and 6-bromohexylphthalimide (7.2 g) were added, and the mixture was stirred at 70° C. for 16 hr. The reaction mixture was concentrated under reduced pressure and the residue was extracted with ethyl acetate. The extract was dried over magnesium sulfate and concentrated under reduced pressure. The obtained residue was purified by silica gel chromatography to give 4.2 g of 4-amino-5-chloro-N-(1-(6-(2,3-dihydro-1,3-dioxo-1H-isoindol-2-yl)hexyl)-piperidin-4-ylmethyl)-2-methoxybenzamide.

$^1$H-NMR (CDCl$_3$,ppm) δ: 1.30–1.82(13 H,m), 1.95–2.08(2 H,m), 2.33–2.42(2 H,m), 2.95–3.05(2 H,m), 3.25–3.38(2 H,m), 3.64–3.75(2 H,m), 3.89(3 H,s), 4.48(2 H,s), 6.32(1 H,s), 7.68–7.82(4 H,m), 8.08(1 H,s)

EXAMPLE 108

4-Amino-N-(1-(3-aminopropyl)piperidin-4-ylmethyl)-5-chloro-2-methoxybenzamide (0.70 g) was dissolved in dimethylformamide (10 ml). Triethylamine (0.30 ml) was added, and a solution of benzoyl chloride (0.25 ml) in methylene chloride was dropwise added under ice-cooling. The mixture was stirred at room temperature. Insoluble matter was filtered off and the filtrate was concentrated under reduced pressure. The obtained residue was purified by silica gel chromatography to give 0.15 g of 4-amino-N-(1-(3-benzoylaminopropyl)piperidin-4-ylmethyl)-5-chloro-2-methoxybenzamide.

$^1$H-NMR (CDCl$_3$,ppm) δ: 1.25–1.50(2 H,m), 1.62–1.95(5 H,m), 2.05–2.21(2 H,m), 2.62–2.75(2 H,m), 3.10–3.20(2 H,m), 3.25–3.38(2 H,m), 3.48–3.63(2 H,m), 3.86(3 H,s), 4.43(2 H,s), 6.29(1 H,s), 7.33–7.50(3 H,m), 7.65–7.75(1 H,br), 7.76–7.90(2 H,m), 8.09(1 H,s), 8.20–8.35(1 H,br)

EXAMPLE 109

4-Amino-N-(1-(4-aminobutyl)piperidin-4-ylmethyl)-5-chloro-2-methoxybenzamide (1.00 g) was dissolved in a mixed solvent of dichloromethane (20 ml) and dimethylformamide (15 ml). Triethylamine (0.57 ml) was added, and a solution of benzenesulfonyl chloride (0.35 ml) in methylene chloride was dropwise added under ice-cooling. The mixture was stirred at room temperature. Insoluble matter was filtered off and the filtrate was concentrated under reduced pressure. The obtained residue was purified by silica gel chromatography to give 0.57 g of 4-amino-N-(1-(4-benzenesulfonylaminobutyl)piperidin-4-ylmethyl)-5-chloro-2-methoxybenzamide.

$^1$H-NMR (CDCl$_3$,ppm) δ: 1.45–1.83(9 H,m), 1.98–2.15(2 H,m), 2.31–2.47(2 H,m), 2.88–3.10(4 H,m), 3.30–3.42(2

H,m), 3.89(3 H,s), 4.40(2 H,s), 6.28(1 H,s), 7.40–7.59(3 H,m), 7.78–7.90(3 H,m), 8.10(1 H,s)

EXAMPLE 110

4-Amino-N-(1-(5-aminopentyl)piperidin-4-ylmethyl)-5-chloro-2-methoxybenzamide (0.53 g) was dissolved in dimethylformamide (20 ml). 1-Methylindazole-3-carboxylic acid (0.27 g) and 1-hydroxybenzotriazole (0.25 g) were added, and the mixture was stirred at 0° C. for 15 min. Then, 1-ethyl-3-(3-dimethylaminopropyl)carbodiimide (0.35 g) was added, and the mixture was stirred at room temperature for 16 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.20 g of N-(5-(4-(4-amino-5-chloro-2-methoxybenzoylaminomethyl)piperidin-1-yl)pentyl)-1-methyl-1 H-indazole-3-carboxamide.
m.p. 74°~77° C.

EXAMPLE 111

5-(4-tert-Butoxycarbonylaminomethylpiperidin-1-yl) pentylamine (1.42 g) was dissolved in methylene chloride (15 ml). Triethylamine (1.39 ml) was added, and a solution of 2-chlorobenzoyl chloride (0.84 ml) in methylene chloride was dropwise added under ice-cooling. The mixture was stirred at room temperature for 2 hr. The reaction mixture was concentrated under reduced pressure. This was dissolved in 4N hydrochloric acid-dioxane solution (10 ml) and the mixture was stood at room temperature for 30 min. The reaction mixture was concentrated under reduced pressure. Dimethylformamide (30 ml) was added to the residue and the mixture was neutralized with triethylamine (2.05 ml). 4-Amino-5-chloro-2-methoxybenzoic acid (0.99 g) and 1-hydroxybenzotriazole (0.73 g) were added, and the mixture was stirred at 0° C. for 15 min. Then, 1-ethyl-3-(3-dimethylaminopropyl)carbodiimide hydrochloride (1.04 g) was added, and the mixture was stirred at room temperature for 8 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.63 g of 4-amino-5-chloro-N-(1-(5-(2-chlorobenzoyl) aminopentyl)piperidin-4-ylmethyl)-2-methoxybenzamide.

$^1$H-NMR (CDCl$_3$,ppm) δ: 1.38–1.92(11 H,m), 2.15–2.38(2 H,m), 2.52–2.70(2 H,m), 3.15–3.39(4 H,m), 3.42–3.55(2 H,m), 3.90(3 H,s), 4.45(2 H,s), 6.31(1 H,s), 6.32–6.48(1 H,br), 7.25–7.42(4 H,m), 7.58–7.68(1 H,m), 7.72–7.83(1H,br), 8.07(1 H,s)

EXAMPLE 112

5-(4-tert-Butoxycarbonylaminomethylpiperidin-1-yl) pentylamine (1.39 g) was dissolved in methylene chloride (15 ml). Triethylamine (1.36 ml) was added, and a solution of 4-chlorobenzoyl chloride (0.83 ml) in methylene chloride was dropwise added under ice-cooling. The mixture was stirred at room temperature for 2 hr. The reaction mixture was concentrated under reduced pressure. This was dissolved in 4N hydrochloric acid-dioxane solution (10 ml) and the mixture was stood at room temperature for 30 min. The reaction mixture was concentrated under reduced pressure. Dimethylformamide (30 ml) was added to the residue and the mixture was neutralized with triethylamine (1.99 ml). 4-Amino-5-chloro-2-methoxybenzoic acid (0.96 g) and 1-hydroxybenzotriazole (0.71 g) were added, and the mixture was stirred at 0C for 15 min. Then, 1-ethyl-3-(3-dimethylaminopropyl)carbodiimide hydrochloride (1.00 g) was added, and the mixture was stirred at room temperature for 8 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.50 g of 4-amino-5-chloro-N-(1-(5-(4-chlorobenzoyl) aminopentyl)-piperidin-4-ylmethyl)-2-methoxybenzamide.
m.p. 196°~198° C.

EXAMPLE 113

5-(4-tert-Butoxycarbonylaminomethylpiperidin-1-yl) pentylamine (1.50 g) was dissolved in methylene chloride (15 ml). Triethylamine (1.47 ml) was added, and a solution of benzenesulfonyl chloride (0.90 ml) in methylene chloride was dropwise added under ice-cooling. The mixture was stirred at room temperature for 2 hr. The reaction mixture was concentrated under reduced pressure. This was dissolved in 4N hydrochloric acid-dioxane solution (10 ml) and the mixture was stood at room temperature for 30 min. The reaction mixture was concentrated under reduced pressure. Dimethylformamide (30 ml) was added to the residue and the mixture was neutralized with triethylamine (1.35 ml). 4-Amino-5-chloro-2-methoxybenzoic acid (0.65 g) and 1-hydroxybenzotriazole (0.48 g) were added, and the mixture was stirred at 0C for 15 min. Then, 1-ethyl-3-(3-dimethylaminopropyl)carbodiimide hydrochloride (0.68 g) was added, and the mixture was stirred at room temperature for 8 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.80 g of 4-amino-N-(1-(5-benzenesulfonylaminopentyl) piperidin-4-ylmethyl)-5-chloro-2-methoxybenzamide.

$^1$H-NMR (CDCl$_3$,ppm) δ: 1.20–1.81(11 H,m), 1.90–2.05(2 H,m), 2.28–2.40(2 H,m), 2.88–3.05(4 H,m), 3.28–3.40(2 H,m), 3.90(3 H,s), 4.41(2 H,s), 4.95–5.11(1 H,br), 6.30(1 H,s), 7.48–7.62(3 H,m), 7.71–7.79(1 H,br), 7.85–7.90(2 H,m), 8.09(1 H,s)

EXAMPLE 114

4-Amino-N-(1-(6-aminohexyl)piperidin-4-ylmethyl)-5-chloro-2-methoxybenzamide (1.00 g) was dissolved in dimethylformamide (30 ml). 1-Methylindole-3-carboxylic acid (0.48 g) and 1-hydroxybenzotriazole (0.37 g) were added and the mixture was stirred at 0° C. for 15 min. Then, 1-ethyl-3-(3-dimethylaminopropyl)carbodiimide (0.53 g) was added, and the mixture was stirred at room temperature for 19 hr. The reaction mixture was concentrated under reduced pressure. Aqueous potassium carbonate solution was added to the residue and the mixture was extracted with ethyl acetate. The extract was dried over magnesium sulfate and concentrated under reduced pressure. The obtained residue was purified by silica gel chromatography to give 0.25 g of N-(6-(4-(4-amino-5-chloro-2-methoxybenzoylaminomethyl)-piperidin-1-yl)hexyl)-1-methyl-1 H-indole-3-carboxamide.

$^1$H-NMR (CDCl$_3$,ppm) δ: 1.20–1.78(13 H,m), 1.85–2.04(2 H,m), 2.28–2.41(2 H,m), 2.87–3.01(2 H,m), 3.28–3.38(2 H,m), 3.42–3.58(2 H,m), 3.81(3 H,s), 3.88(3 H,s), 4.42(2 H,s), 5.92–6.05(1 H,br), 6.27(1 H,s), 7.20–7.40(3 H,m), 7.65(1 H,s), 7.65–7.82(1 H,br), 7.87–7.96(1 H,m), 8.10(1 H,s)

EXAMPLE 115

4-Amino-N-(1-(6-aminohexyl)piperidin-4-ylmethyl)-5-chloro-2-methoxybenzamide (1.00 g) was dissolved in dichloromethane (25 ml). Triethylamine (0.42 ml) was added, and a solution of benzoyl chloride (0.32 ml) in methylene chloride was dropwise added under ice-cooling. The mixture was stirred at room temperature for 14 hr, and insoluble matter was filtered off. The filtrate was concentrated under reduced pressure. The obtained residue was purified by silica gel chromatography to give 0.35 g of 4-amino-N-(1-(6-benzoylaminohexyl)-piperidin-4-ylmethyl)-5-chloro-2-methoxybenzamide.
m.p. 159°~162° C.

EXAMPLE 116

4-Amino-N-(1-(6-aminohexyl)piperidin-4-ylmethyl)-5-chloro-2-methoxybenzamide (1.00 g) was dissolved in dimethylformamide (15 ml). A solution of phenyl isocyanate (0.30 ml) in methylene chloride was dropwise added under ice-cooling. The mixture was stirred at room temperature for 12 hr. and the reaction mixture was concentrated under reduced pressure. The obtained residue was purified by silica gel chromatography to give 0.30 g of 4-amino-5-chloro-2-methoxy-N-(1-(6-phenylureido)hexyl)piperidin-4-ylmethyl)benzamide.
m.p. 163°~166°C.

EXAMPLE 117

Hydrazine monohydrate (11.3 ml) was added to a solution of 4-amino-5-chloro-N-(1-(5-(2,3-dihydro-1,3-dioxo-1H-isoindol-2-yl)pentyl)-piperidin-4-ylmethyl)-2-methoxybenzamide (60 g) in ethanol (0.6 L), and the mixture was refluxed under heating for 4 hr. The precipitated crystals were filtered off, and the solvent was evaporated under reduced pressure. The obtained residue was purified by silica gel column chromatography (chloroform:methanol=10:1) to give 37.0 g of 4-amino-N-(1-(5-aminopentyl)piperidin-4-ylmethyl) -5-chloro-2-methoxybenzamide.
m.p. 60°–63° C.

EXAMPLE 118

4-Amino-5-chloro-N-(1-(3-(2,3-dihydro-1,3-dioxo-1H-isoindol-2-yl)propyl)piperidin-4-ylmethyl)-2-methoxybenzamide (7.7 g) as starting compound and hydrazine monohydrate (0.76 ml) were reacted and treated in the same manner as in Example 117 to give 3.6 g of 4-amino-N-(1-(3-aminopropyl)piperidin-4-ylmethyl)-5-chloro-2-methoxybenzamide.

$^1$H-NMR (DMSO-d$_6$) δ: 0.96–1.83(9 H,m), 2.22–2.29(2 H,m), 2.51–2.58(2 H,m), 2.78–2.86(2 H,m), 3.15(2 H,t,J= 5.9 Hz), 3.31(2 H,br), 3.83(3 H,s), 5.91(2 H,s), 6.48(1 H,s), 7.66(1 H,s), 7.86–7.93(1 H,m)

EXAMPLE 119

4-Amino-5-chloro-N-(1-(4-(2,3-dihydro-1,3-dioxo-1H-isoindol-2-yl)butyl)piperidin-4-ylmethyl)-2-methoxybenzamide (9.3 g) as starting compound and hydrazine monohydrate (1.4 ml) were reacted and treated in the same manner as in Example 117 to give 6.9 g of 4-amino-N-(1-(4-aminobutyl)piperidin-4-ylmethyl)-5-chloro-2-methoxybenzamide. m.p. 104°–107° C.

EXAMPLE 120

4-Amino-5-chloro-N-(1-(6-(2,3-dihydro-1,3-dioxo-1H-isoindol-2-yl)hexyl)piperidin-4-ylmethyl)-2-methoxybenzamide (15.9 g) as starting compound and hydrazine monohydrate (2.2 ml) were reacted and treated in the same manner as in Example 117 to give 13.5 g of 4-amino-N-(1-(6-aminohexyl)piperidin-4-ylmethyl)-5-chloro-2-methoxybenzamide.

$^1$H-NMR (CDCl$_3$) δ: 1.21–1.98(17 H,m), 2.28–2.36(2 H,m), 2.68(2 H,t,J=6.6 Hz), 2.91–2.98(2 H,m), 3.32(2 H,t, J=6.6 Hz), 3.89(3 H,s), 4.38(2 H,s), 6.29(1 H,s), 7.71–7.78(1 H,m), 8.10(1 H,s)

EXAMPLE 121

Benzaldehyde (0.76 g) was added to a solution of 4-amino-N-(1-(5-aminopentyl)piperidin-4-ylmethyl)-5-chloro-2-methoxybenzamide (2.0 g) in ethanol (50 ml), and the mixture was stirred at refluxing temperature for 3 hr. Sodium borohydride (0.53 g) was added to the reaction mixture under ice-cooling, and the mixture was stirred overnight at room temperature. Water was added to the reaction mixture, and the mixture was extracted with chloroform. The organic layer was washed with saturated brine, dried and the solvent was evaporated under reduced pressure. The obtained residue was purified by silica gel column chromatography (chloroform:methanol:ammonia=50:5:1) to give 1.78 g of 4-amino-N-((1-(5-benzylaminopentyl)piperidin-4-yl)methyl)-5-chloro-2-methoxybenzamide.

$^1$H-NMR(CDCl$_3$,ppm) δ: 1.22–1.94(14 H,m), 2.26–2.33(2 H,m), 2.62(2 H,t,J=7.3 Hz), 2.88–2.96(2 H,m), 3.32(2 H,t,J=6.6 Hz), 3.78(2 H,s), 3.88(3 H,s), 4.44(2 H,s), 6.29(1 H,s), 7.20–7.37(5 H,m), 7.72–7.78(1 H,m), 8.10(1 H,s)

EXAMPLE 122

4-Amino-N-(1-(5-aminopentyl)piperidin-4-ylmethyl)-5-chloro-2-methoxybenzamide (2 g) as starting compound and 4-fluorobenzaldehyde (0.71 g) were reacted and treated in the same manner as in Example 121 to give 2.3 g of 4-amino-5-chloro-N-((1-(5-(4-fluorobenzylamino)pentyl)-piperidin-4-yl)methyl)-2-methoxybenzamide.
m.p. 66°–68° C.

EXAMPLE 123

4-Amino-N-(1-(5-aminopentyl)piperidin-4-ylmethyl)-5-chloro-2-methoxybenzamide (2 g) as starting compound and 4-methoxybenzaldehyde (0.78 g) were reacted and treated in the same manner as in Example 121 to give 2.15 g of 4-amino-5-chloro-2-methoxy-N-((1-(5-(4-methoxybenzylamino)pentyl)piperidin-4-yl)methyl) benzamide.

$^1$H-NMR(CDCl$_3$,ppm) δ: 1.25–1.76(12 H,m), 1.84–1.94(2 H,m), 2.25-2.32(2 H,m), 2.57–2.63(2 H,m), 2.88–2.94(2 H,m), 3.31(2 H,t,J=5.9 Hz), 3.70(2 H,s), 3.79(3 H,s), 3.87(3 H,s), 4.48(2 H,s), 6.28(1 H,s), 6.82–6.87(2 H,m), 7.20–7.24(2 H,m), 7.72–7.77(1 H,m), 8.09(1 H,s)

EXAMPLE 124

4-Amino-N-(1-(5-aminopentyl)piperidin-4-ylmethyl)-5-chloro-2-methoxybenzamide (2 g) as starting compound and 4-methylbenzaldehyde (0.69 g) were reacted and treated in the same manner as in Example 121 to give 2.5 g of 4-amino-5-chloro-2-methoxy-N-((1-(5-(4-methylbenzylamino)pentyl)piperidin-4-yl)methyl) benzamide.

¹H-NMR(CDCl₃,ppm) δ: 1.25–1.77(12 H,m), 1.91–2.00(2 H,m), 2.30–2.37(5 H,m), 2.58–2.65(2 H,m), 2.92–2.99(2 H,m), 3.31(2 H,t,J=6.6 Hz), 3.75(2 H,s), 3.88(3 H,s), 4.46(2 H,s), 6.30(1 H,s), 7.10–7.27(4 H,m), 7.72–7.79(1 H,m), 8.08(1 H,s)

EXAMPLE 125

4-Amino-N-(1-(5-aminopentyl)piperidin-4-ylmethyl)-5-chloro-2-methoxybenzamide (2 g) as starting compound and 4-nitrobenzaldehyde (0.87 g) were reacted and treated in the same manner as in Example 121 to give 2.3 g of 4-amino-5-chloro-2-methoxy-N-((1-(5-(4-nitrobenzylamino)pentyl) piperidin-4-yl)methyl)benzamide.

¹H-NMR(CDCl₃,ppm) δ: 1.26–1.79(11 H,m), 1.91–2.03(2 H,m), 2.23(1 H,br), 2.31–2.38(2 H,m), 2.58–2.65(2 H,m), 2.92–3.00(2 H,m), 3.32(2 H,t,J=6.6 Hz), 3.89(5 H,s), 4.49(2 H,s), 6.31(1 H,s), 7.48–7.53(2 H,m), 7.74–7.81(1 H,m), 8.06(1 H,s), 8.15–8.18(2 H,m)

EXAMPLE 126

4-Amino-N-(1-(5-aminopentyl)piperidin-4-ylmethyl)-5-chloro-2-methoxybenzamide (2 g) as starting compound and 2-thiophenecarboxaldehyde (0.64 g) were reacted and treated in the same manner as in Example 121 to give 2.5 g of 4-amino-5-chloro-2-methoxy-N-((1-(5-(2-thienylmethylamino)pentyl)piperidin-4-yl)methyl) benzamide.
m.p. 67–69° C.

EXAMPLE 127

4-Amino-N-(1-(5-aminopentyl)piperidin-4-ylmethyl)-5-chloro-2-methoxybenzamide (1 g) as starting compound and cyclohexanecarboxaldehyde (0.32 g) were reacted and treated in the same manner as in Example 121 to give 1.2 g of 4-amino-5-chloro-N-((1-(5-(cyclohexylmethylamino) pentyl)piperidin-4-yl)methyl)-2-methoxybenzamide.

¹H-NMR(CDCl₃,ppm) δ: 0.83–1.80(22 H,m), 1.88–2.00(2 H,m), 2.29–2.37(2 H,m), 2.48(2 H,d,J=6.6 Hz), 2.59–2.68(2 H,m), 2.69–2.99(3 H,m), 3.32(2 H,t,J=5.9 Hz), 3.90(3 H,s), 4.43(2 H,s), 6.31(1 H,s), 7.71–7.79(1 H,m), 8.09(1 H,s)

EXAMPLE 128

4-Amino-N-(1-(5-aminopentyl)piperidin-4-ylmethyl)-5-chloro-2-methoxybenzamide (3 g) as starting compound and 4-pyridinecarboxaldehyde (0.84 g) were reacted and treated in the same manner as in Example 121 to give 1.14 g of 4-amino-5-chloro-2-methoxy-N-((1-(5-(4-pyridylmethylamino)pentyl)piperidin-4-yl)methyl) benzamide.

¹H-NMR(CDCl₃,ppm) δ: 1.25–2.00(14 H,m), 2.25–2.34(2 H,m), 2.61(2 H,t,J=7.3 Hz), 2.87–2.95(2 H,m), 3.32(2 H,t,J=6.6 Hz), 3.80(2 H,s), 3.88(3 H,s), 4.44(2 H,s), 6.29(1 H,s), 7.24–7.28(2 H,m), 7.70–7.78(1 H,m), 8.10(1 H,s), 8.51–8.54(2 H,m)

EXAMPLE 129

4-Amino-N-(1-(5-aminopentyl)piperidin-4-ylmethyl)-5-chloro-2-methoxybenzamide (2.1 g) as starting compound and 1-naphthaldehyde (1.13 g) were reacted and treated in the same manner as in Example 121 to give 1.71 g of 4-amino-5-chloro-2-methoxy-N-((1-(5-(1-naphthylmethylamino)pentyl)piperidin-4-yl)methyl) benzamide.

¹H-NMR(CDCl₃,ppm) δ: 1.25–1.75(12 H,m), 1.84–1.94(2 H,m), 2.26–2.32(2 H,m), 2.74(2 H,t,J=6.6 Hz), 2.87–2.95(2 H,m), 3.31(2 H,t,J=6.6 Hz), 3.87(3 H,s),4.22(2 H,s), 4.41(2 H,s), 6.27(1 H,s), 7.38–7.55(4 H,m), 7.71–7.77(2 H,m), 7.81–7.87(1 H,m), 8.09–8.12(2 H,m)

EXAMPLE 130

4-Amino-N-(1-(5-aminopentyl)piperidin-4-ylmethyl)-5-chloro-2-methoxybenzamide (1.98 g) as starting compound and 2-naphthaldehyde (0.74 g) were reacted and treated in the same manner as in Example 121 to give 1.81 g of 4-amino-5-chloro-2-methoxy-N-((1-(5-(2-naphthylmethylamino)pentyl)piperidin-4-yl)methyl) benzamide.

¹H-NMR(CDCl₃,ppm) δ: 1.22–1.74(12 H,m), 1.83–1.94(2 H,m), 2.26–2.33(2 H,m), 2.66(2 H,t,J=7.3 Hz), 2.88–2.94(2 H,m), 3.31(2 H,t,J=6.6 Hz), 3.87(3 H,s),3.94(2 H,s), 4.40(2 H,s), 6.27(1 H,s), 7.39–7.49(3 H,m), 7.70–7.82(5 H,m), 8.10(1 H,s)

EXAMPLE 131

4-Amino-N-(1-(5-aminopentyl)piperidin-4-ylmethyl)-5-chloro-2-methoxybenzamide (1.5 g) as starting compound and 1-methyl-1 H-indol-3-carboxaldehyde (0.81 g) were reacted and treated in the same manner as in Example 121 to give 1.0 g of 4-amino-5-chloro-N-((1-(5-((1-methyl-1 H-indol-3-ylmethyl)amino)pentyl)piperidin-4-yl)methyl)-2-methoxybenzamide.

¹H-NMR(CDCl₃,ppm) δ: 1.18–2.16(14 H,m), 2.17–2.23(2 H,m), 2.48(2 H,t,J=7.3 Hz), 2.82–2.88(2 H,m), 3.31(2 H,t,J=6.6 Hz), 3.73(3 H,s), 3.77(2 H,s), 3.87(3 H,s), 4.37(2 H,s), 6.26(1 H,s), 6.95–7.28(4 H,m), 7.64–7.76(2 H,m), 8.10(1 H,s)

EXAMPLE 132

4-Amino-N-(1-(3-aminopropyl)piperidin-4-ylmethyl)-5-chloro-2-methoxybenzamide (2 g) as starting compound and 3,4-dichlorobenzaldehyde (0.99 g) were reacted and treated in the same manner as in Example 121 to give 2.7 g of 4-amino-5-chloro-N-((1-(3-(3,4-dichlorobenzylamino) propyl)piperidin-4-yl)methyl)-2-methoxybenzamide.

¹H-NMR (CDCl₃,ppm) δ: 1.24–1.35(2 H,m), 1.52–1.96(5 H,m), 2.21(1 H,br), 2.37(2 H,t,J=7.3 Hz), 2.63(2 H,t,J=6.6 Hz), 2.88–2.97(2 H,m), 3.31(2 H,t,J=5.9 Hz), 3.72(2 H,s), 3.88(3 H,s), 4.44(2 H,s), 6.29(1 H,s), 7.12–7.19(1 H,m), 7.35–7.46(2 H,m), 7.72–7.78(1 H,m), 8.09(1 H,s)

EXAMPLE 133

4-Amino-N-(1-(6-aminohexyl)piperidin-4-ylmethyl)-5-chloro-2-methoxybenzamide (2.0 g) as starting compound and 4-methylbenzaldehyde (0.66 g) were reacted and treated in the same manner as in Example 121 to give 1.07 g of 4-amino-5-chloro-2-methoxy-N-((1-(6-(4-methylbenzylamino)hexyl)piperidin-4-yl)methyl) benzamide.

¹H-NMR(CDCl₃,ppm) δ: 1.21–1.96(16 H,m), 2.26–2.34(5 H,m), 2.60(2 H,t,J=7.3 Hz), 2.88–2.97(2 H,m), 3.32(2 H,t,J=5.9 Hz), 3.73(2 H,s), 3.89(3 H,s), 4.40(2 H,s), 6.29(1 H,s), 7.09–7.22(4 H,m), 7.71–7.78(1 H,m), 8.10(1 H,s)

EXAMPLE 134

4-Amino-N-(1-(6-aminohexyl)piperidin-4-ylmethyl)-5-chloro-2-methoxybenzamide (1.5 g) as starting compound and 4-methoxylbenzaldehyde (0.56 g) were reacted and treated in the same manner as in Example 121 to give 1.13 g of 4-amino-5-chloro-N-((1-(6-(4-methoxybenzylamino)hexyl)piperidin-4-yl)methyl)-2-methoxybenzamide.

$^1$H-NMR(CDCl$_3$,ppm) δ: 1.21–2.00(16 H,m), 2.26–2.32(2 H,m), 2.60(2 H,t,J=7.3 Hz), 2.89–2.96(2 H,m), 3.32(2 H,t,J=5.9 Hz), 3.71(2 H,s), 3.79(3 H,s), 3.88(3 H,s), 4.44(2 H,s), 6.29(1 H,s), 6.83–6.88(2 H,m), 7.19–7.24(2 H,m), 7.73–7.78(1 H,m), 8.09(1 H,s)

EXAMPLE 135

4-Amino-N-(1-(6-aminohexyl)piperidin-4-ylmethyl)-5-chloro-2-methoxybenzamide (2.0 g) as starting compound and 3,4-dichlorobenzaldehyde (0.97 g) were reacted and treated in the same manner as in Example 121 to give 1.42 g of 4-amino-5-chloro-N-((1-(6-(3,4-dichlorobenzylamino)hexyl)piperidin-4-yl)methyl)-2-methoxybenzamide.

$^1$H-NMR(CDCl$_3$,ppm) δ: 1.23–1.77(14 H,m), 1.84–1.95(2 H,m), 2.26–2.32(2 H,m), 2.58(2 H,t,J=6.6 Hz), 2.88–2.96(2 H,m), 3.32(2 H,t,J=5.9 Hz), 3.73(2 H,s),3.89(3 H,s), 4.41(2 H,s), 6.29(1 H,s), 7.15(1 H,dd,J=2.0,7.9 Hz), 7.37(1 H,d,J=7.9 Hz), 7.43(1 H,d,J=2.0 Hz), 7.72–7.78(1 H,m), 8.10(1 H,s)

EXAMPLE 136

Acetaldehyde (0.32 ml) and sodium cyanoborohydride (0.36 g) were added to a solution of 4-amino-N-(1-(5-aminopentyl)piperidin-4-ylmethyl)-5-chloro-2-methoxybenzamide (1.0 g) in methanol (20 ml), and the mixture was stirred at room temperature for 1 hr. A 10% aqueous sodium hydroxide solution was added to the reaction mixture, and the mixture was extracted with chloroform. The organic layer was washed with saturated brine, dried and the solvent was evaporated under reduced pressure. The obtained residue was purified by silica gel column chromatography (chloroform:methanol=5:1) to give 0.55 g of 4-amino-5-chloro-N-((1-(5-diethylaminopentyl)piperidin-4-yl)methyl)-2-methoxybenzamide.

$^1$H-NMR(CDCl$_3$,ppm) δ: 1.08(6 H,t,J=7.3 Hz), 1.24–1.77 (11 H,m), 1.87–1.99(2 H,m), 2.28–2.37(2 H,m), 2.45–2.54(2 H,m), 2.61(4 H,q,J=7.3 Hz), 2.91–2.98(2 H,m), 3.32(2 H,t, J=6.0 Hz), 3.89(3 H,s), 4.53(2 H,s), 6.33(1 H,s), 7.72–7.80(1 H,m), 8.08(1 H,s)

EXAMPLE 137

4-Amino-N-(1-(5-aminopentyl)piperidin-4-ylmethyl)-5-chloro-2-methoxybenzamide (1.0 g) as starting compound, 37% formalin (0.45 ml) and sodium cyanoborohydride (0.34 g) were reacted and treated in the same manner as in Example 136 to give 0.48 g of 4-amino-5-chloro-N-((1-(5-dimethylaminopentyl)piperidin-4-yl)methyl)-2-methoxybenzamide.

$^1$H-NMR(CDCl$_3$,ppm) δ: 1.24–1.78(11 H,m), 1.83–1.97(2 H,m), 2.15–2.35(10 H,m), 2.88–2.97(2 H,m), 3.32(2 H,t,J=6.6 Hz), 3.89(3 H,s), 4.43(2 H,s), 6.29(1 H,s), 7.70–7.78(1 H,m), 8.10(1 H,s)

EXAMPLE 138

4-Amino-N-(1-(6-aminohexyl)piperidin-4-ylmethyl)-5-chloro-2-methoxybenzamide (1.0 g) as starting compound, acetaldehyde (0.31 ml) and sodium cyanoborohydride (0.38 g) were reacted and treated in the same manner as in Example 136 to give 0.35 g of 4-amino-5-chloro-N-((1-(6-diethylaminohexyl)piperidin-4-yl)methyl)-2-methoxybenzamide.

$^1$H-NMR(CDCl$_3$,ppm) (δ: 1.02(6 H,t,J=7.3 Hz), 1.24–1.96(15 H,m), 2.26–2.33(2 H,m), 2.37–2.44(2 H,m), 2.52(4 H,q,J=7.3 Hz), 2.89–2.96(2 H,m), 3.32(2 H,t,J=6.6 Hz), 3.90(3 H,s), 4.40(2 H,s), 6.30(1 H,s), 7.72–7.78(1 H,m), 8.10(1 H,s)

EXAMPLE 139

4-Amino-N-(1-(5-aminopentyl)piperidin-4-ylmethyl)-5-chloro-2-methoxybenzamide (2.0 g) as starting compound, cyclohexanone (0.73 ml) and sodium cyanoborohydride (0.86 g) were reacted and treated in the same manner as in Example 136 to give 1.42 g of 4-amino-5-chloro-N-((1-(5-(cyclohexylamino)pentyl)piperidin-4-yl)methyl)-2-methoxybenzamide.

$^1$H-NMR(CDCl$_3$,ppm) δ: 0.99–1.96(24 H,m), 2.27–2.45(3 H,m), 2.62(2 H,t,J=7.3 Hz), 2.88–2.97(2 H,m), 3.32(2 H,t,J=6.6 Hz), 3.90(3 H,s), 4.39(2 H,s), 6.29(1 H,s), 7.72–7.77(1 H,m), 8.10(1 H,s)

EXAMPLE 140

4-Amino-5-chloro-N-((1-(5-(4-chlorobenzylamino)pentyl)piperidin-4-yl)methyl)-2-methoxybenzamide (1.8 g) as starting compound, acetaldehyde (0.26 ml) and sodium cyanoborohydride (0.29 g) were reacted and treated in the same manner as in Example 136 to give 1.05 g of 4-amino-5-chloro-N-((1-(5-(N-(4-chlorobenzyl)-N-ethylamino)pentyl)-piperidin-4-yl)methyl)-2-methoxybenzamide.

$^1$H-NMR (CDCl$_3$,ppm) δ: 1.01(3 H,t,J=7.3 Hz), 1.20–1.76(11 H,m), 1.86–1.98 (2 H,m), 2.20–2.52(6 H,m), 2.88–2.97(2 H,m), 3.32(2 H,t,J=6.6 Hz), 3.49(2 H,s), 3.88(3 H,s), 4.50(2 H,s), 6.30(1 H,s), 7.25(4 H,s), 7.73–7.81(1 H,m), 8.08(1 H,s)

EXAMPLE 141

4-Amino-5-chloro-N-((1-(5-(4-fluorobenzylamino)pentyl)piperidin-4-yl)methyl)-2-methoxybenzamide (1.8 g) as starting compound, acetaldehyde (0.25 ml) and sodium cyanoborohydride (0.28 g) were reacted and treated in the same manner as in Example 136 to give 1.0 g of 4-amino-5-chloro-N-((1-(5-(N-ethyl-N-(4-fluorobenzyl)amino)pentyl)-piperidin-4-yl)methyl)-2-methoxybenzamide.

$^1$H-NMR (CDCl$_3$,ppm) δ: 1.01(3 H,t,J=7.3 Hz), 1.22–1.76(11 H,m), 1.84–1.97(2 H,m), 2.24–2.42(4 H,m), 2.47(2 H,q,J=7.3 Hz), 2.88–2.97(2 H,m), 3.32(2 H,t,J=5.9 Hz), 3.49(2 H,s), 3.89(3 H,s), 4.44(2 H,s), 6.29(1 H,s), 6.91–7.00(2 H,m), 7.24–7.30(2 H,m), 7.71–7.78(1 H,m), 8.10(1 H,s)

EXAMPLE 142

4-Amino-5-chloro-N-((1-(5-(3,4-dichlorobenzylamino)pentyl)-piperidin-4-yl)methyl)-2-methoxybenzamide (2.0 g) as starting compound, acetaldehyde (0.27 ml) and sodium cyanoborohydride (0.3 g) were reacted and treated in the same manner as in Example 136 to give 0.82 g of 4-amino-5-chloro-N-((1-(5-(N-(3,4-dichlorobenzyl)-N-ethylamino)pentyl)-piperidin-4-yl)methyl)-2-methoxybenzamide.

$^1$H-NMR (CDCl$_3$,ppm) δ: 1.01(3 H,t,J=7.3 Hz), 1.20–1.77(11 H,m), 1.82–1.95(2 H,m), 2.23–2.32(2 H,m), 2.35–2.42(2 H,m), 2.48(2 H,q,J=7.3 Hz), 2.86–2.96(2 H,m), 3.32(2 H,t,J=6.6 Hz), 3.47(2 H,s), 3.89(3 H,s), 4.39(2 H,s), 6.29(1 H,s), 7.15(1 H,dd,J=2.0,8.0 Hz), 7.35(1 H,d,J=8.0 Hz), 7.43(1 H,d,J=2.0 Hz), 7.70–7.78(1 H,m), 8.11(1 H,s)

EXAMPLE 143

4-Amino-5-chloro-2-methoxy-N-((1-(5-(4-methoxybenzylamino)pentyl)-piperidin-4-yl)methyl)benzamide (1.5 g) as starting compound, acetaldehyde (0.22 ml) and sodium cyanoborohydride (0.24 g) were reacted and treated in the same manner as in Example 136 to give 0.8 g of 4-amino-5-chloro-N-((1-(5-(N-ethyl-N-(4-methoxybenzyl)amino)pentyl)-piperidin-4-yl)methyl)-2-methoxybenzamide.

$^1$H-NMR (CDCl$_3$,ppm) δ: 1.02(3 H,t,J=7.3 Hz), 1.20–1.77(11 H,m), 1.87–1.98(2 H,m), 2.26–2.54(6 H,m), 2.89–2.97(2 H,m), 3.32(2 H,t,J=6.6 Hz), 3.50(2 H,s), 3.79(3 H,s), 3.89(3 H,s), 4.46(2 H,s), 6.30(1 H,s), 6.81–6.87(2 H,m), 7.20–7.24(2 H,m), 7.73–7.81(1 H,m), 8.09(1 H,s)

EXAMPLE 144

4-Amino-5-chloro-2-methoxy-N-((1-(5-(4-methylbenzylamino)pentyl)-piperidin-4-yl)methyl)benzamide (1.5 g) as starting compound, acetaldehyde (0.22 ml) and sodium cyanoborohydride (0.25 g) were reacted and treated in the same manner as in Example 136 to give 0.7 g of 4-amino-5-chloro-N-((1-(5-(N-ethyl-N-(4-methylbenzyl)amino)pentyl)piperidin-4-yl)-methyl)-2-methoxybenzamide.

$^1$H-NMR (CDCl$_3$,ppm) δ: 1.02(3 H,t,J=7.3 Hz), 1.20–1.76(11 H,m), 1.85–1.98(2 H,m), 2.25–2.53(6 H,m), 2.87–2.97(2 H,m), 3.32(2 H,t,J=6.6 Hz), 3.46(3 H,s), 3.51(2 H,s), 3.89(3 H,s), 4.44(2 H,s), 6.29(1 H,s), 7.07–7.23(4 H,m), 7.72–7.80(1 H,m), 8.09(1 H,s)

EXAMPLE 145

4-Amino-5-chloro-2-methoxy-N-((1-(5-(4-nitrobenzylamino)pentyl)-piperidin-4-yl)methyl)benzamide (1.5 g) as starting compound, acetaldehyde (0.21 ml) and sodium cyanoborohydride (0.24 g) were reacted and treated in the same manner as in Example 136 to give 0.6 g of 4-amino-5-chloro-N-((1-(5-(N-ethyl-N-(4-nitrobenzyl)amino)pentyl)-piperidin-4-yl)methyl)-2-methoxybenzamide.

$^1$H-NMR (CDCl$_3$,ppm) δ: 1.02(3 H,t,J=7.3 Hz), 1.21–1.78(11 H,m), 1.88–2.02(2 H,m), 2.27–2.54(6 H,m), 2.91–2.99(2 H,m), 3.32(2 H,t,J=5.9 Hz), 3.62(2 H,s), 3.90(3 H,s), 4.41(2 H,s), 6.30(1 H,s), 7.41–7.52(2 H,m), 7.70–7.88(1 H,m), 8.07–8.18(3 H,m)

EXAMPLE 146

4-Amino-5-chloro-2-methoxy-N-((1-(5-((2-thienylmethyl)amino)-pentyl)piperidin-4-yl)methyl)benzamide (1.5 g) as starting compound, acetaldehyde (0.23 ml) and sodium cyanoborohydride (0.25 g) were reacted and treated in the same manner as in Example 136 to give 0.96 g of 4-amino-5-chloro-N-((1-(5-(N-ethyl-N-(2-thienylmethyl)amino)pentyl)-piperidin-4-yl)methyl)-2-methoxybenzamide.

$^1$H-NMR (CDCl$_3$,ppm) δ: 1.05(3 H,t,J=7.3 Hz), 1.23–1.77(11 H,m), 1.88–2.00(2 H,m), 2.28–2.57(6 H,m), 2.91–2.99(2 H,m), 3.32(2 H,t,J=6.6 Hz), 3.80(2 H,s), 3.89(3 H,s), 4.46(2 H,s), 6.30(1 H,s), 6.86–6.96(2 H,m), 7.18–7.21(1 H,m), 7.72–7.80(1 H,m), 8.09(1 H,s)

EXAMPLE 147

4-Amino-5-chloro-N-((1-(5-(cyclohexylmmethylamino)pentyl)piperidin-4-yl)methyl)-2-methoxybenzamide (1.27 g) as starting compound, acetaldehyde (0.19 ml) and sodium cyanoborohydride (0.22 g) were reacted and treated in the same manner as in Example 136 to give 0.6 g of 4-amino-5-chloro-N-((1-(5-(N-ethyl-N-(cyclohexylmethyl)amino)pentyl)-piperidin-4-yl)methyl)-2-methoxybenzamide.

$^1$H-NMR (CDCl$_3$,ppm) δ: 0.75–0.94(2 H,m), 0.98(3 H,t, J=7.3 Hz), 1.09–2.00(22 H,m), 2.16(2 H,d,J=7.3 Hz), 2.28–2.41(4 H,m), 2.48(2 H,q,J=7.3 Hz), 2.91–3.00(2 H,m), 3.32(2 H,t,J=6.6 Hz), 3.90(3 H,s), 4.39(2 H,s), 6.30(1 H,s), 7.72–7.79(1 H,m), 8.10(1 H,s)

EXAMPLE 148

4-Amino-5-chloro-2-methoxy-N-((1-(5-((4-pyridylmethyl)amino)-pentyl)piperidin-4-yl)methyl)benzamide (0.8 g) as starting compound, acetaldehyde (0.12 ml) and sodium cyanoborohydride (0.14 g) were reacted and treated in the same manner as in Example 136 to give 0.35 g of 4-amino-5-chloro-N-((1-(5-(N-ethyl-N-(4-pyridylmethyl)amino)pentyl)-piperidin-4-yl)methyl)-2-methoxybenzamide.

$^1$H-NMR (CDCl$_3$,ppm) δ: 1.02(3 H,t,J=7.3 Hz), 1.21–1.80(11 H,m), 1.90–2.03(2 H,m), 2.29–2.54(6 H,m), 2.92–3.00(2 H,m), 3.29–3.36(2 H,m), 3.54(2 H,s), 3.90(3 H,s), 4.39(2 H,s), 6.29(1 H,s), 7.25–7.29(2 H,m), 7.70–7.80(1 H,m), 8.10(1 H,s), 8.49–8.52(2 H,m)

EXAMPLE 149

4-Amino-N-((1-(5-benzylaminopentyl)piperidin-4-yl)methyl)-5-chloro-2-methoxybenzamide (2.0 g) as starting compound, propionaldehyde (0.13 ml) and sodium cyanoborohydride (0.35 g) were reacted and treated in the same manner as in Example 136 to give 1.05 g of 4-amino-5-chloro-2-methoxy-N-((1-(5-(N-n-propyl-N-benzylamino)pentyl)piperidin-4-yl)methyl)-benzamide.

$^1$H-NMR (CDCl$_3$,ppm) δ: 0.85(3 H,t,J=7.3 Hz), 1.20–1.75(13 H,m), 1.85–1.96(2 H,m), 2.24–2.43(6 H,m), 2.88–2.96(2 H,m), 3.31(2 H,t,J=6.6 Hz), 3.53(2 H,s), 3.87(3 H,s), 4.51(2 H,s), 6.30(1 H,s), 7.16–7.35(5 H,m), 7.71–7.79(1 H,m), 8.09(1 H,s)

EXAMPLE 150

4-Amino-N-((1-(5-benzylaminopentyl)piperidin-4-yl)methyl)-5-chloro-2-methoxybenzamide (2.0 g) as starting compound, acetone (0.3 ml) and sodium cyanoborohydride (0.35 g) were reacted and treated in the same manner as in Example 136 to give 0.43 g of 4-amino-5-chloro-N-((1-(5-(N-isopropyl-N-benzylamino)pentyl)piperidin-4-yl)methyl)-2-methoxybenzamide.

$^1$H-NMR (CDCl$_3$,ppm) δ: 0.99(6 H,d,J=6.6 Hz), 1.19–1.75(11 H,m), 1.87–1.98(2 H,m), 2.24–2.32(2 H,m), 2.38(2 H,t,J=6.6 Hz), 2.83–2.98(3 H,m), 3.32(2 H,t,J=6.6 Hz), 3.52(2 H,s), 3.89(3 H,s), 4.41(2 H,s), 6.28(1 H,s), 7.16–7.35(5 H,m), 7.71–7.78(1 H,m), 8.10(1 H,s)

EXAMPLE 151

4-Amino-N-((1-(5-benzylaminopentyl)piperidin-4-yl)methyl)-5-chloro-2-methoxybenzamide (1.46 g) as starting compound, acetaldehyde (0.19 ml) and sodium cyanoborohydride (0.43 g) were reacted and treated in the same manner as in Example 136 to give 0.8 g of 4-amino-5-chloro-N-((1-(5-(N-ethyl-N-benzylamino)pentyl)piperidin-4-yl)methyl)-2-methoxybenzamide.

$^1$H-NMR (CDCl$_3$,ppm) δ: 1.02(3 H,t,J=7.3 Hz), 1.20–1.74(11 H,m), 1.84–1.93(2 H,m), 2.24–2.31(2 H,m), 2.37–2.44(2 H,m), 2.49(2 H,q,J=7.3 Hz), 2.87–2.94(2 H,m), 3.32(2 H,t,J=6.6 Hz), 3.54(2 H,s), 3.89(3 H,s), 4.38(2 H,s), 6.28(1 H,s), 7.17–7.33(5 H,m), 7.71–7.76(1 H,m), 8.11(1 H,s)

EXAMPLE 152

4-Amino-5-chloro-2-methoxy-N-((1-(5-(1-naphthylmethylamino)pentyl)-piperidin-4-yl)methyl) benzamide (1.43 g) as starting compound, acetaldehyde (0.16 ml) and sodium cyanoborohydride (0.38 g) were reacted and treated in the same manner as in Example 136 to give 0.75 g of 4-amino-5-chloro-N-((1-(5-(N-ethyl-N-(1-naphthylmethyl)amino)pentyl)-piperidin-4-yl)methyl)-2-methoxybenzamide.

$^1$H-NMR (CDCl$_3$,ppm) δ: 1.06(3 H,t,J=7.3 Hz), 1.16–1.73(11 H,m), 1.80–1.89(2 H,m), 2.18–2.24(2 H,m), 2.44–2.50(2 H,m), 2.56(2 H,q,J=7.3 Hz), 2.83–2.90(2 H,m), 3.31(2 H,t,J=6.6 Hz), 3.88(3 H,s), 3.96(2 H,s), 4.38(2 H,s), 6.27(1 H,s), 7.35–7.52(4 H,m), 7.71–7.76(2 H,m), 7.80–7.85(1 H,m), 8.11(1 H,s), 8.30–8.34(1 H,m)

EXAMPLE 153

4-Amino-5-chloro-2-methoxy-N-((1-(5-(2-naphthylmethylamino)pentyl)-piperidin-4-yl)methyl) benzamide (1.50 g) as starting compound, acetaldehyde (0.18 ml) and sodium cyanoborohydride (0.40 g) were reacted and treated in the same manner as in Example 136 to give 1.1 g of 4-amino-5-chloro-N-((1-(5-(N-ethyl-N-(2-naphthylmethyl)amino)pentyl)-piperidin-4-yl)methyl)-2-methoxybenzamide.

$^1$H-NMR (CDCl$_3$,ppm) δ: 1.05(3 H,t,J=7.3 Hz), 1.20–1.72(11 H,m), 1.81–1.90(2 H,m), 2.22–2.29(2 H,m), 2.42–2.49(2 H,m), 2.54(2 H,q,J=7.3 Hz), 2.85–2.91(2 H,m), 3.31(2 H,t,J=6.6 Hz), 3.69(2 H,s), 3.87(3 H,s), 4.40(2 H,s), 6.27(1 H,s), 7.38–7.52(3 H,m), 7.72–7.83(5 H,m), 8.10(1 H,s)

EXAMPLE 154

4-Amino-5-chloro-N-((1-(5-(cyclohexylmethylamino) pentyl)piperidin-4-yl)methyl)-2-methoxybenzamide (0.79 g) as starting compound, benzaldehyde (0.19 g) and sodium cyanoborohydride (0.23 g) were reacted and treated in the same manner as in Example 136 to give 0.49 g of 4-amino-N-((1-(5-(N-benzyl-N-(cyclohexylmethyl)amino)pentyl) piperidin-4-yl)methyl)-5-chloro-2-methoxybenzamide.

$^1$H-NMR (CDCl$_3$,ppm) δ: 0.72–0.84(2 H,m), 1.09–1.80 (20 H,m), 2.01–2.13(2 H,m), 2.16(2 H,d,J=7.3 Hz), 2.32(2 H,t,J=7.3 Hz), 2.36–2.44(2 H,m), 2.99–3.07(2 H,m), 3.32(2 H,t,J=5.9 Hz), 3.48(2 H,s), 3.90(3 H,s), 4.40(2 H,s), 6.30(1 H,s), 7.17–7.33(5 H,m), 7.73–7.80(1 H,m), 8.10(1 H,s)

EXAMPLE 155

4-Amino-N-((1-(5-benzylaminopentyl)piperidin-4-yl) methyl)-5-chloro-2-methoxybenzamide (1.11 g) as starting compound, benzaldehyde (0.28 g) and sodium cyanoborohydride (0.33 g) were reacted and treated in the same manner as in Example 136 to give 0.3 g of 4-amino-5-chloro-N-((1-(5-dibenzylaminopentyl)piperidin-4-yl) methyl)-2-methoxybenzamide.

$^1$H-NMR (CDCl$_3$,ppm) δ: 1.21–2.07(13 H,m), 2.31–2.43(4 H,m), 2.94–3.01(2 H,m), 3.32(2 H,t,J=5.9 Hz), 3.53(4 H,s), 3.90(3 H,s), 4.37(2 H,s), 6.29(1 H,s),7.18–7.38 (10 H,m), 7.72–7.78(1 H,m), 8.10(1 H,s)

EXAMPLE 156

4-Amino-5-chloro-N-((1-(5-cyclohexylaminopentyl) piperidin-4-yl)-methyl)-2-methoxybenzamide (1.1 g) as starting compound, acetaldehyde (0.15 ml) and sodium cyanoborohydride (0.33 g) were reacted and treated in the same manner as in Example 136 to give 1.0 g of 4-amino-5-chloro-N-((1-(5-(N-ethyl-N-cyclohexylamino)pentyl) piperidin-4-yl)methyl)-2-methoxybenzamide.

$^1$H-NMR (CDCl$_3$,ppm) δ: 1.01(3 H,t,J=7.3 Hz), 1.03–1.96(23 H,m), 2.26–2.33(2 H,m), 2.39–2.58(5 H,m), 2.89–2.96(2 H,m), 3.32(2 H,t,J=6.6 Hz), 3.89(3 H,s), 4.40(2 H,s), 6.29(1 H,s), 7.71–7.77(1 H,m), 8.10(1 H,s)

EXAMPLE 157

4-Amino-5-chloro-N-((1-(3-(3,4-dichlorobenzylamino) propyl)-piperidin-4-yl)methyl)-2-methoxybenzamide (2.0 g) as starting compound, acetaldehyde (0.27 ml) and sodium cyanoborohydride (0.3 g) were reacted and treated in the same manner as in Example 136 to give 0.7 g of 4-amino-5-chloro-N-((1-(3-(N-(3,4-dichlorobenzyl)-N-ethylamino) propyl)-piperidin-4-yl)methyl)-2-methoxybenzamide.

$^1$H-NMR (CDCl$_3$,ppm) δ: 1.01(3 H,t,J=7.3 Hz), 1.25–1.45(2 H,m), 1.59–1.78(5 H,m), 1.92–2.04(2 H,m), 2.32–2.54(6 H,m), 2.92–3.00(2 H,m), 3.32(2 H,t,J=6.7 Hz), 3.48(2 H,s), 3.89(3 H,s), 4.42(2 H,s), 6.30(1 H,s), 7.15(1 H,dd,J=2.0,7.9 Hz), 7.35(1 H,d,J=7.9 Hz), 7.42(1 H,d,J=2.0 Hz), 7.71–7.79(1 H,m), 8.09(1 H,s)

EXAMPLE 158

4-Amino-5-chloro-N-((1-(4-(3,4-dichlorobenzylamino) butyl)piperidin-4-yl)methyl)-2-methoxybenzamide (1.9 g) as starting compound, acetaldehyde (0.26 ml) and sodium cyanoborohydride (0.3 g) were reacted and treated in the same manner as in Example 136 to give 1.1 g of 4-amino-5-chloro-N-((1-(4-(N-(3,4-dichlorobenzyl)-N-ethylamino) butyl)-piperidin-4-yl)methyl)-2-methoxybenzamide.

$^1$H-NMR (CDCl$_3$,ppm) δ: 1.01(3 H,t,J=7.3 Hz), 1.24–1.77(9 H,m), 1.86– 1.98(2 H,m), 2.26–2.53(6 H,m), 2.88–2.96(2 H,m), 3.32(2 H,t,J=6.6 Hz), 3.47(2 H,s),3.89(3 H,s), 4.41(2 H,s), 6.30(1 H,s), 7.15(1 H,dd,J=2.0,7.9 Hz), 7.35(1 H,d,J=7.9 Hz), 7.44(1 H,d,J=2.0 Hz), 7.71–7.78(1 H,m), 8.10(1 H,s)

EXAMPLE 159

4-Amino-N-((1-(4-benzylaminobutyl)piperidin-4-yl) methyl)-5-chloro-2-methoxybenzamide (0.5 g) as starting compound, acetaldehyde (0.07 ml) and sodium cyanoborohydride (0.15 g) were reacted and treated in the same manner as in Example 136 to give 0.35 g of 4-amino-5-chloro-N-((1-(4-(N-ethyl-N-benzylamino)butyl)piperidin-4-yl)methyl)-2-methoxybenzamide.

$^1$H-NMR (CDCl$_3$,ppm) δ: 1.02(3 H,t,J=7.3 Hz), 1.19–1.95(11 H,m), 2.26–2.32(2 H,m), 2.39–2.54(4 H,m), 2.89–2.96(2 H,m), 3.32(2 H,t,J=6.6 Hz), 3.54(2 H,s), 3.89(3 H,s), 4.38(2 H,s), 6.29(1 H,s), 7.18–7.35(5 H,m), 7.71–7.78(1 H,m), 8.10(1 H,s)

EXAMPLE 160

4-Amino-N-((1-(6-benzylaminohexyl)piperidin-4-yl) methyl)-5-chloro-2-methoxybenzamide (1.3 g) as starting compound, acetaldehyde (0.16 ml) and sodium cyanoborohydride (0.37 g) were reacted and treated in the same manner as in Example 136 to give 0.25 g of 4-amino-5-chloro-N-((1-(6-(N-ethyl-N-benzylamino)hexyl)piperidin-4-yl)methyl)-2-methoxybenzamide.

$^1$H-NMR (CDCl$_3$,ppm) δ: 1.02(3 H,t,J=7.3 Hz), 1.23–1.76(13 H,m), 1.86–1.97(2 H,m), 2.25–2.33(2 H,m), 2.37–2.43(2 H,m), 2.49(2 H,q,J=7.3 Hz), 2.91–2.97(2 H,m), 3.32(2 H,t,J=5.9 Hz), 3.54(2 H,s), 3.90(3 H,s), 4.37(2 H,s), 6.29(1 H,s), 7.19–7.35(5 H,m), 7.70–7.77(1 H,m), 8.11(1 H,s)

EXAMPLE 161

4-Amino-5-chloro-2-methoxy-N-((1-(6-(4-methylbenzylamino)hexyl)-piperidin-4-yl)methyl) benzamide (0.77 g) as starting compound, acetaldehyde (0.1 ml) and sodium cyanoborohydride (0.23 g) were reacted and treated in the same manner as in Example 136 to give 0.42 g of 4-amino-5-chloro-N-((1-(6-(N-ethyl-N-(4-methylbenzyl)amino)hexyl)-piperidin-4-yl)methyl)-2-methoxybenzamide.

$^1$H-NMR (CDCl$_3$,ppm) δ: 1.01(3 H,t,J=7.3 Hz), 1.21–2.04(15 H,m), 2.24–2.31(2 H,m), 2.33(3 H,s), 2.36–2.42(2 H,m), 2.48(2 H,q,J=7.3 Hz), 2.89–2.96(2 H,m), 3.32(2 H,t,J=6.6 Hz), 3.51(2 H,s), 3.89(3 H,s), 4.38(2 H,s), 6.29(1 H,s), 7.10(2 H,d,J=7.9 Hz), 7.20(2 H,d,J=7.9 Hz), 7.71–7.77(1 H,m), 8.11(1 H,s)

EXAMPLE 162

4-Amino-5-chloro-2-methoxy-N-((1-(6-(4-methoxybenzylamino)hexyl)-piperidin-4-yl)methyl) benzamide (0.9 g) as starting compound, acetaldehyde (0.12 ml) and sodium cyanoborohydride (0.26 g) were reacted and treated in the same manner as in Example 136 to give 0.55 g of 4-amino-5-chloro-N-((1-(6-(N-ethyl-N-(4-methoxybenzyl)amino)hexyl)-piperidin-4-yl)methyl)-2-methoxybenzamide.

$^1$H-NMR (CDCl$_3$,ppm) δ: 1.01(3 H,t,J=7.3 Hz), 1.22–1.77(13 H,m), 1.86–1.97(2 H,m), 2.25–2.32(2 H,m), 2.38(2 H,t,J=7.3 Hz), 2.48(2 H,q,J=7.3 Hz), 2.90–2.97(2 H,m), 3.32(2 H,t,J=5.9 Hz), 3.49(2 H,s), 3.79(3 H,s), 3.89(3 H,s), 4.39(2 H,s), 6.29(1 H,s), 6.80–6.86(2 H,m), 7.19–7.24(2 H,m), 7.71–7.77(1 H,m), 8.10(1 H,s)

EXAMPLE 163

4-Amino-5-chloro-2-methoxy-N-((1-(6-(4-nitrobenzylamino)hexyl)-piperidin-4-yl)methyl)benzamide (0.89 g) as starting compound, acetaldehyde (0.11 ml) and sodium cyanoborohydride (0.25 g) were reacted and treated in the same manner as in Example 136 to give 0.4 g of 4-amino-5-chloro-N-((1-(6-(N-ethyl-N-(4-nitrobenzyl)amino)hexyl)-piperidin-4-yl)methyl)-2-methoxybenzamide.

$^1$H-NMR (CDCl$_3$,ppm) δ: 1.02(3 H,t,J=7.3 Hz), 1.22–1.94(15 H,m), 2.23–2.30(2 H,m), 2.41(2 H,t,J=6.6 Hz), 2.50(2 H,q,J=7.3 Hz), 2.88–2.95(2 H,m), 3.32(2 H,t, J=5.9 Hz), 3.62(2 H,s), 3.90(3 H,s), 4.40(2 H,s), 6.30(1 H,s), 7.49–7.53(2 H,m), 7.72–7.78(1 H,m), 8.10(1 H,s), 8.13–8.17(2 H,m)

EXAMPLE 164

4-Amino-5-chloro-N-((1-(6-(3,4-dichlorobenzylamino) hexyl)piperidin-4-yl)methyl)-2-methoxybenzamide (1.11 g) as starting compound, acetaldehyde (0.13 ml) and sodium cyanoborohydride (0.3 g) were reacted and treated in the same manner as in Example 136 to give 0.75 g of 4-amino-5-chloro-N-((1-(6-(N-(3,4-dichlorobenzyl)-N-ethylamino) hexyl)-piperidin-4-yl)methyl)-2-methoxybenzamide.

$^1$H-NMR (CDCl$_3$,ppm) δ: 1.00(3 H,t,J=7.3 Hz), 1.20–1.95(15 H,m), 2.24–2.31(2 H,m), 2.38(2 H,t,J=6.6 Hz), 2.47(2 H,q,J=7.3 Hz), 2.88–2.96(2 H,m), 3.32(2 H,t, J=6.6 Hz), 3.47(2 H,s), 3.89(3 H,s), 4.38(2 H,s), 6.29(1 H,s), 7.15(1 H,dd,J=2.0,7.9 Hz), 7.35(1 H,d,J=7.9 Hz), 7.43(1 H,d,J=2.0 Hz), 7.71–7.77(1 H,m), 8.10(1 H,s)

EXAMPLE 165

4-Amino-5-chloro-2-methoxy-N-((1-(6-(2-thienylmethylamino)hexyl)-piperidin-4-yl)methyl) benzamide (0.8 g) as starting compound, acetaldehyde (0.12 ml) and sodium cyanoborohydride (0.26 g) were reacted and treated in the same manner as in Example 136 to give 0.8 g of 4-amino-5-chloro-N-((1-(6-(N-ethyl-N-(2-thienylmethyl) amino)hexyl)-piperidin-4-yl)methyl)-2-methoxybenzamide.

$^1$H-NMR (CDCl$_3$,ppm)δ : 1.05(3 H,t,J=7.3 Hz), 1.21–1.96(15 H,m), 2.25–2.32(2 H,m), 2.40–2.46(2 H,m), 2.52(2 H,q,J=7.3 Hz), 2.89–2.96(2 H,m), 3.32(2 H,t,J=6.6 Hz), 3.80(2 H,s), 3.90(3 H,s), 4.38(2 H,s), 6.29(1 H,s), 6.87–6.95(2 H,m), 7.18–7.24(1 H,m), 7.71–7.77(1 H,m), 8.11(1 H,s)

EXAMPLE 166

(1) A solution (150 ml) of 5-(4-tert-butoxycarbonylaminomethylpiperidin-1-yl)pentylamine (5.0 g) and benzaldehyde (2.0 g) in ethanol was stirred at 70° C. for 3 hr. After cooling, sodium borohydride (1.40 g) was added, and the mixture was stirred at room temperature for 2 hr. Water was added to the reaction mixture, and the mixture was extracted with ethyl acetate. The organic layer was washed with brine, dried and the solvent was evaporated under reduced pressure. The obtained residue was purified by silica gel column chromatography to give 3.7 g of N-benzyl-5-(4-tert-butoxycarbonylaminomethylpiperidin-1-yl)pentylamine.

$^1$H-NMR (CDCl$_3$,ppm) δ: 1.23–1.88(11 H,m), 1.44(9 H,s), 2.63(2 H,t,J=6.8 Hz), 2.60–2.32(4 H,m), 3.78(2 H,s), 7.23–7.35(5 H,m)

(2) A solution of N-benzyl-5-(4-tert-butoxycarbonylaminomethylpiperidin-1-yl)pentylamine (3.7 g) in methyl formate (30 ml) was refluxed under heating for 12 hr. After cooling, methyl formate was evaporated, and tetrahydrofuran (40 ml) and 2M trifluoroborane-dimethyl sulfide solution (19 ml) were added to the residue, which was followed by refluxing under heating for 6 hr. The solvent was evaporated, and ethanol (40 ml) and hydrochloric acid (3 ml) were added to the reaction mixture, which was followed by refluxing under heating for 3 hr. After cooling, water was added to the reaction mixture, and the mixture was extracted with ethyl acetate. The organic layer was washed with brine, dried and the solvent was evaporated under reduced pressure to give 3.60 g of N-benzyl-N-methyl-5-(4-aminomethylpiperidin-1-yl)pentylamine.

$^1$H-NMR (CDCl$_3$,ppm) δ: 1.20–1.88(11 H,m), 2.20(3 H,s), 2.63(2 H,t,J=6.8 Hz), 2.60–2.32(4 H,m), 3.78(2 H,s), 7.25–7.36(5 H,m) (3) A suspension of N-benzyl-N-methyl-5-(4-aminomethylpiperidin-1-yl)-pentylamine (3.52 g), 4-amino-5-chloro-2-methoxybenzoic acid (2.34 g), dicyclohexylcarbodiimide (2.39 g), 1-hydroxybenzotriazole (1.57 g) and triethylamine (2.35 g) in N,N-dimethylformamide (40 ml) was stirred at room temperature for 12 hr. The solvent was evaporated, and water was added to the residue, which was followed by extraction with chloroform. The organic layer was washed with brine, dried and the solvent was evaporated under reduced pressure. The obtained residue was purified by silica gel column chromatography to give 0.86 g of 4-amino-5-chloro-2-methoxy-N-((1-(5-(N-benzyl-N-methylamino)pentyl)piperidin-4-yl)methyl)-benzamide.

$^1$H-NMR (CDCl$_3$,ppm) δ: 1.22–1.97(13 H,m), 2.17(3 H,s), 2.27–2.38(4 H,m), 2.91–2.96(2 H,m), 3.32(2 H,t,J=6.6 Hz), 3.48(2 H,s), 3.89(3 H,s), 4.38(2 H,s),6.29(1 H,s), 7.19–7.34(5 H,m), 7.71–7.77(1 H,m), 8.10(1 H,s)

EXAMPLE 167

(1) A solution of 4-(3-tert-butoxycarbonylaminomethylpyrrolidin-1-yl)-butylamine (2.0 g) and benzaldehyde (0.86 g) in ethanol (50 ml) was stirred at 70° C. for 3 hr. After cooling, sodium borohydride was added, and the mixture was stirred at room temperature for 2 hr. Water was added to the reaction mixture, and the mixture was extracted with ethyl acetate. The organic layer was washed with brine, dried and the solvent was evaporated under reduced pressure. The obtained residue was purified by silica gel column chromatography to give 1.74 g of N-benzyl-4-(3-tert-butoxycarbonylaminomethylpyrrolidin-1-yl)butylamine.

$^1$H-NMR (CDCl$_3$,ppm) δ: 1.23–1.55(7 H,m), 1.44(9 H,s), 1.85–3.68(8 H,m), 3.79(2 H,s), 7.20–7.42(5 H,m) (2) Methyl formate (10 ml) was added to N-benzyl-4-(3-tert-butoxy-carbonylaminomethylpyrrolidin-1-yl)butylamine (1.74 g), and the mixture was refluxed under heating for 12 hr. After cooling, methyl formate was evaporated, and tetrahydrofuran (25 ml) and 2M trifluoroborane-dimethyl sulfide solution (9.3 ml) were added, which was followed by refluxing under heating for 6 hr. The solvent was evaporated, and ethanol and hydrochloric acid were added, which was followed by refluxing under heating for 3 hr. After cooling, water was added to the reaction mixture, and the mixture was extracted with ethyl acetate. The organic layer was washed with brine, dried and the solvent was evaporated under reduced pressure to give 1.06 g of N-benzyl-N-methyl-4-(3-aminomethylpyrrolidin-1-yl)butylamine.

$^1$H-NMR (CDCl$_3$,ppm) δ: 1.23–1.56(7 H,m), 2.19(3 H,s), 1.85–3.70(8 H,m), 3.78(2 H,s), 7.20–7.40(5 H,m)

(3) A suspension of N-benzyl-N-methyl-4-(3-aminomethylpyrrolidin-1-yl)-butylamine (1.06 g), 4-amino-5-chloro-2-methoxybenzoic acid (0.78 g), dicyclohexylcarbodiimide (0.79 g), 2-hydroxybenzotriazole (0.52 g) and triethylamine (1.1 ml) in N,N-dimethylformamide (20 ml) was stirred at room temperature for 12 hr. The solvent was evaporated, and water was added to the residue, which was followed by extraction with chloroform. The organic layer was washed with brine, dried and the solvent was evaporated under reduced pressure. The obtained residue was purified by silica gel column chromatography to give 0.19 g of 4-amino-5-chloro-2-methoxy-N-((1-(4-(N-methyl-N-benzylamino)butyl)pyrrolidin-3-yl)methyl)-benzamide.

$^1$H-NMR (CDCl$_3$,ppm) δ: 1.40–1.65(5 H,m), 1.95–2.06(1 H,m), 2.16(3 H,s), 2.26–2.76(7 H,m), 3.38–3.49(4 H,m), 3.73(2 H,s), 3.86(3 H,s), 4.40(2 H,s), 6.28(1 H,s), 7.20–7.31(5 H,m), 7.77–7.84(1 H,m), 8.09(1 H,s)

EXAMPLE 168

Potassium carbonate (2.2 g) and 5-phenoxypentyl chloride (1.2 g) were added to a solution of 4-amino-5-chloro-2-methoxy-N-(piperidin-4-ylmethyl)benzamide dihydrochloride (1.5 g) in dimethylformamide (40 ml), an the mixture was stirred at 70°–80° C. for 7.5 hr. Water was added to the reaction mixture, and the mixture was extracted with chloroform. The organic layer was washed with saturated aqueous sodium chloride solution, dried and the solvent was evaporated under reduced pressure. The obtained residue was purified by silica gel column chromatography (chloroform:methanol=5:1) to give crystals. The obtained crystals were recrystallized from ethyl acetate to give 0.82 g of 4-amino-5-chloro-2-methoxy-N-((1-(5-phenoxypentyl) piperidin-4-yl)methyl)benzamide.
m.p. 129°–132° C.

EXAMPLE 169

4-Amino-5-chloro-2-methoxy-N-(piperidin-4-ylmethyl) benzamide dihydrochloride (1.5 g) as starting compound, potassium carbonate (2.8 g) and 5-benzyloxypentyl bromide (2.08 g) were reacted and treated in the same manner as in Example 168 to give 0.82 g of 4-amino-N-((1-(5-benzyloxypentyl)piperidin-4-yl)methyl)-5-chloro-2-methoxybenzamide.

$^1$H-NMR(CDCl$_3$,ppm) δ: 1.31–1.79(11 H,m), 1.99–2.11(2 H,m), 2.38–2.47(2 H,m), 2.99–3.07(2 H,m), 3.32(2 H,t,J=6.6 Hz), 3.46(2 H,t,J=6.6 Hz), 3.89(3 H,s), 4.46(2 H,s), 4.48(2 H,s), 6.31(1 H,s), 7.21–7.38(5 H,m), 7.72–7.80(1 H,m), 8.09(1 H,s)

EXAMPLE 170

4-Amino-5-chloro-2-methoxy-N-(piperidin-4-ylmethyl) benzamide dihydrochloride (1.5 g) as starting compound, potassium carbonate (2.2 g) and 5-benzylthiopentyl chloride (1.4 g) were reacted and treated in the same manner as in Example 168 to give 0.57 g of 4-amino-N-((1-(5-benzylthiopentyl)piperidin-4-yl)methyl)-5-chloro-2-methoxybenzamide.

$^1$H-NMR(CDCl$_3$,ppm) δ: 1.29–1.99(13 H,m), 2.27–2.34(2 H,m), 2.41(2 H,t,J=7.3 Hz), 2.89–2.98(2 H,m), 3.32(2 H,t,J=6.6 Hz), 3.69(2 H,s), 3.90(3 H,s), 4.37(2 H,s), 6.29(1 H,s), 7.20–7.35(5 H,m), 7.71–7.77(1 H,m), 8.11(1 H,s)

EXAMPLE 171

4-Amino-5-chloro-2-methoxy-N-(piperidin-4-ylmethyl) benzamide dihydrochloride (1.3 g) as starting compound, potassium carbonate (2.0 g) and 6-(N-methyl-N-phenylamino)hexyl chloride (0.8 g) were reacted and treated in the same manner as in Example 168 to give 1.2 g of 4-amino-5-chloro-2-methoxy-N-((1-(6-(N-methyl-N-phenylamino)hexyl)piperidin-4-yl)-methyl)benzamide.

$^1$H-NMR(CDCl$_3$,ppm) δ: 1.16(2 H,m), 1.27(4 H,m), 1.54(5 H,m), 1.59(2 H,m), 1.85(2 H,t,J=11.2 Hz), 2.25(2 H,t,J=7.2 Hz), 2.85(3 H,s), 3.14(2 H,t,J=6.4 Hz), 3.27(2 H,t,J=6.4 Hz), 3.82(3 H,s), 5.90(2 H,s), 6.48(1 H,s), 6.54(1 H,t,J=7.3 Hz), 6.65(2 H,d,J=8.0 Hz), 7.13(1 H,t,J=9.2 Hz), 7.67(1 H,s), 7.87(1 H,t,J=6.0 Hz)

EXAMPLE 172

Potassium carbonate (0.57 g) and 5-bromo-1-phenyl-1-pentanone (0.80 g) were added to a solution (45 ml) of 4-amino-5-chloro-2-methoxy-N-(piperidin-4-ylmethyl) benzamide dihydrochloride (1.5 g) in dimethylformamide, and the mixture was stirred at 70°–80° C. for 7.5 hr. Water was added to the reaction mixture, and the mixture was extracted with chloroform. The organic layer was washed with saturated aqueous sodium chloride solution, dried and the solvent was evaporated under reduced pressure. The obtained residue was purified by silica gel column chromatography to give crystals. The obtained crystals were recrystallized from ethyl acetate to give 0.80 g of 4-amino-5-chloro-2-methoxy-N-((1-(5-oxo-5-phenylpentyl)piperidin-4-yl)methyl)benzamide.
m.p. 100°–102° C.

EXAMPLE 173

4-Amino-5-chloro-2-methoxy-N-(piperidin-4-ylmethyl) benzamide dihydrochloride (2.0 g) as starting compound, potassium carbonate (1.9 g) and 6-bromo-1-phenyl-1-hexanone (1.7 g) were reacted and treated in the same manner as in Example 172 to give 0.56 g of 4-amino-5-chloro-2-methoxy-N-((1-(6-oxo-6-phenylhexyl)piperidin-4-yl)methyl)benzamide.

m.p. 138–141° C.

EXAMPLE 174

4-Amino-5-chloro-2-methoxy-N-(piperidin-4-ylmethyl) benzamide dihydrochloride (1.3 g) as starting compound, potassium carbonate (2.1 g) and 7-bromo-1-phenyl-1-heptanone (0.92 g) were reacted and treated in the same manner as in Example 172 to give 0.80 g of 4-amino-5-chloro-2-methoxy-N-((1-(7-oxo-7-phenylheptyl)piperidin-4-yl)methyl)benzamide.
m.p. 128°–130° C.

EXAMPLE 175

4-Amino-5-chloro-2-methoxy-N-(piperidin-4-ylmethyl) benzamide dihydrochloride (1.5 g) as starting compound, potassium carbonate (2.5 g) and 8-bromo-1-phenyl-1-octanone (1.3 g) were reacted and treated in the same manner as in Example 172 to give 0.70 g of 4-amino-5-chloro-2-methoxy-N-((1-(8-oxo-8-phenyloctyl)piperidin-4-yl)methyl)benzamide.
m.p. 138°–140° C.

EXAMPLE 176

4-Amino-5-chloro-2-methoxy-N-(piperidin-4-ylmethyl) benzamide dihydrochloride (1.5 g) as starting compound, potassium carbonate (2.5 g) and 6-bromo-1-(4-methylphenyl)-1-hexanone (1.3 g) were reacted and treated in the same manner as in Example 172 to give 0.87 g of 4-amino-5-chloro-2-methoxy-N-((1-(6-(4-methylphenyl)-6-oxohexyl)piperidin-4-yl)-methyl)benzamide.
m.p. 130°–131° C.

EXAMPLE 177

4-Amino-5-chloro-2-methoxy-N-(piperidin-4-ylmethyl) benzamide dihydrochloride (1.1 g) as starting compound, potassium carbonate (2.0 g) and 6-bromo-1-(2,4-dimethylphenyl)-1-hexanone (0.94 g) were reacted and treated in the same manner as in Example 172 to give 0.63 g of 4-amino-5-chloro-N-((1-(6-(2,4-dimethylphenyl)-6-oxohexyl)piperidin-4-yl)methyl)-2-methoxybenzamide.
m.p. 106°–110° C.

EXAMPLE 178

4-Amino-5-chloro-2-methoxy-N-(piperidin-4-ylmethyl) benzamide dihydrochloride (2.0 g) as starting compound, potassium carbonate (3.0 g) and 6-bromo-1-(3,4-dimethylphenyl)-1-hexanone (1.1 g) were reacted and treated in the same manner as in Example 172 to give 0.82 g of 4-amino-5-chloro-N-((1-(6-(3,4-dimethylphenyl)-6-oxohexyl)piperidin-4-yl)methyl)-2-methoxybenzamide.
m.p. 115°–117° C.

EXAMPLE 179

4-Amino-5-chloro-2-methoxy-N-(piperidin-4-ylmethyl) benzamide dihydrochloride (1.1 g) as starting compound, potassium carbonate (1.0 g) and 6-bromo-1-(4-ethylphenyl)-1-hexanone (0.94 g) were reacted and treated in the same manner as in Example 172 to give 0.34 g of 4-amino-5-chloro-N-((1-(6-(4-ethylphenyl)-6-oxohexyl)piperidin-4-yl) methyl)-2-methoxybenzamide.
m.p. 140°–145° C.

EXAMPLE 180

4-Amino-5-chloro-2-methoxy-N-(piperidin-4-ylmethyl) benzamide dihydrochloride (1.5 g) as starting compound, potassium carbonate (2.5 g) and 6-bromo-1-(4-methoxyphenyl)-1-hexanone (1.4 g) were reacted and treated in the same manner as in Example 172 to give 1.4 g of 4-amino-5-chloro-N-((1-(6-(4-methoxyphenyl)-6-oxohexyl)piperidin-4-yl)methyl)-2-methoxybenzamide.
m.p. 133°–135° C.

EXAMPLE 181

4-Amino-5-chloro-2-methoxy-N-(piperidin-4-ylmethyl) benzamide dihydrochloride (1.1 g) as starting compound, potassium carbonate (2.0 g) and 6-bromo-1-(3,4-dimethoxyphenyl)-1-hexanone (1.0 g) were reacted and treated in the same manner as in Example 172 to give 0.56 g of 4-amino-5-chloro-N-((1-(6-(3,4-dimethoxyphenyl)-6-oxohexyl)piperidin-4-yl)methyl)-2-methoxybenzamide.
m.p. 102°–105° C.

EXAMPLE 182

4-Amino-5-chloro-2-methoxy-N-(piperidin-4-ylmethyl) benzamide dihydrochloride (1.5 g) as starting compound, potassium carbonate (2.5 g) and 6-bromo-1-(4-chlorophenyl)-1-hexanone (1.3 g) were reacted and treated in the same manner as in Example 172 to give 1.0 g of 4-amino-5-chloro-N-((1-(6-(4-chlorophenyl)-6-oxohexyl) piperidin-4-yl)methyl)- 2-methoxybenzamide.
m.p. 156°–158° C.

EXAMPLE 183

4-Amino-5-chloro-2-methoxy-N-(piperidin-4-ylmethyl) benzamide dihydrochloride (1.6 g) as starting compound, potassium carbonate (2.3 g) and 7-bromo-1-(4-chlorophenyl)-1-heptanone (2.2 g) were reacted and treated in the same manner as in Example 172 to give 0.60 g of 4-amino-5-chloro-N-((1-(7-(4-chlorophenyl)-7-oxoheptyl) piperidin-4-yl)methyl)-2-methoxybenzamide.
m.p. 137°–138° C.

EXAMPLE 184

4-Amino-5-chloro-2-methoxy-N-(piperidin-4-ylmethyl) benzamide dihydrochloride (0.23 g) as starting compound, potassium carbonate (0.34 g) and 6-bromo-1-(2,4-dichlorophenyl)-1-hexanone (0.20 g) were reacted and treated in the same manner as in Example 172 to give 0.11 g of 4-amino-5-chloro-N-((1-(6-(2,4-dichlorophenyl)-6-oxohexyl)piperidin-4-yl)-methyl)-2-methoxybenzamide.
m.p. 150°–155° C.

EXAMPLE 185

4-Amino-5-chloro-2-methoxy-N-(piperidin-4-ylmethyl) benzamide dihydrochloride (0.51 g) as starting compound, potassium carbonate (0.77 g) and 6-bromo-1-(3,4-dichlorophenyl)-1-hexanone (0.45 g) were reacted and treated in the same manner as in Example 172 to give 50 mg of 4-amino-5-chloro-N-((1-(6-(3,4-dichlorophenyl)-6-oxohexyl)piperidin-4-yl)-methyl)-2-methoxybenzamide.
m. p. 203°–205° C.

EXAMPLE 186

4-Amino-5-chloro-2-methoxy-N-(piperidin-4-ylmethyl) benzamide dihydrochloride (1.5 g) as starting compound, potassium carbonate (2.5 g) and 6-bromo-1-(4-fluorophenyl)-1-hexanone (1.3 g) were reacted and treated in the same manner as in Example 172 to give 1.0 g of 4-amino-5-chloro-N-((1-(6-(4-fluorophenyl)-6-oxohexyl) piperidin-4-yl)methyl)-2-methoxybenzamide.

m.p. 137°–139° C.

EXAMPLE 187

4-Amino-5-chloro-2-methoxy-N-(piperidin-4-ylmethyl) benzamide dihydrochloride (1.0 g) as starting compound, potassium carbonate (1.5 g) and 6-bromo-1-(2,4-difluorophenyl)-1-hexanone (0.9 g) were reacted and treated in the same manner as in Example 172 to give 0.55 g of 4-amino-5-chloro-N-((1-(6-(2,4-difluorophenyl)-6-oxohexyl)piperidin-4-yl)-methyl)-2-methoxybenzamide.
m.p. 115°–117° C.

EXAMPLE 188

4-Amino-5-chloro-2-methoxy-N-(piperidin-4-ylmethyl) benzamide dihydrochloride (0.57 g) as starting compound, potassium carbonate (0.82 g), and 6-bromo-1-(3,4-difluorophenyl)-1-hexanone (0.42 g) obtained by subjecting 6-bromohexanoyl chloride and 1,2-difluorobenzene to Friedel-Crafts reaction were reacted and treated in the same manner as in Example 172 to give 0.21 g of 4-amino-5-chloro-N-((1-(6-(3,4-difluorophenyl)-6-oxohexyl)piperidin-4-yl)methyl)-2-methoxybenzamide.
m.p. 177°–179° C.

EXAMPLE 189

4-Amino-5-chloro-2-methoxy-N-(piperidin-4-ylmethyl) benzamide dihydrochloride (0.86 g) as starting compound, potassium carbonate (2.0 g) and 6-bromo-1-(3-chloro-4-methoxyphenyl)-1-hexanone (0.82 g) were reacted and treated in the same manner as in Example 172 to give 0.45 g of 4-amino-5-chloro-N-((1-(6-(3-chloro-4-methoxyphenyl)-6-oxohexyl)-piperidin-4-yl)methyl)-2-methoxybenzamide.
m.p. 104°–106° C.

EXAMPLE 190

4-Amino-5-chloro-2-methoxy-N-(piperidin-4-ylmethyl) benzamide dihydrochloride (1.0 g) as starting compound, potassium carbonate (1.5 g) and 6-bromo-1-(3-fluoro-4-methoxyphenyl)-1-hexanone (0.94 g) were reacted and treated in the same manner as in Example 172 to give 0.90 g of 4-amino-5-chloro-N-((1-(6-(3-fluoro-4-methoxyphenyl)-6-oxohexyl)-piperidin-4-yl)methyl)-2-methoxybenzamide.
m.p. 112°–113° C.

EXAMPLE 191

4-Amino-5-chloro-2-methoxy-N-(piperidin-4-ylmethyl) benzamide dihydrochloride (0.57 g) as starting compound, potassium carbonate (0.82 g) and 6-bromo-1-(4-hydroxyphenyl)-1-hexanone (0.42 g) were reacted and treated in the same manner as in Example 172 to give 0.21 g of 4-amino-5-chloro-N-((1-(6-(4-hydroxyphenyl)-6-oxohexyl)piperidin-4-yl)methyl)-2-methoxybenzamide.
m.p. 177°–179° C.

EXAMPLE 192

4-Amino-5-chloro-2-methoxy-N-(piperidin-4-ylmethyl) benzamide dihydrochloride (2.0 g) as starting compound, potassium carbonate (3.0 g) and 6-bromo-1-(2-thienyl)-1-hexanone (1.6 g) were reacted and treated in the same manner as in Example 172 to give 0.27 g of 4-amino-5-chloro-N-((1-(6-oxo-6-(2-thienyl)hexyl)piperidin-4-yl) methyl)-2-methoxybenzamide.

m.p. 115°–118° C.

EXAMPLE 193

4-Amino-5-chloro-2-methoxy-N-(piperidin-4-ylmethyl) benzamide dihydrochloride (1.2 g) as starting compound, potassium carbonate (1.8 g) and 6-bromo-1-(1-methyl-1 H-indol-3-yl)-1-hexanone (1.0 g) were reacted and treated in the same manner as in Example 172 to give 0.71 g of 4-amino-5-chloro-2-methoxy-N-((1-(6-(1-methyl-1 H-indol-3-yl)-6-oxohexyl)piperidin-4-yl)methyl) benzamide.
m.p. 125°–127° C.

EXAMPLE 194

4-Amino-5-chloro-2-methoxy-N-(piperidin-4-ylmethyl) benzamide dihydrochloride (0.54 g) as starting compound, potassium carbonate (0.8 g) and 6-bromo-1-(2-benzo[b] thienyl)-1-hexanone (0.45 g) were reacted and treated in the same manner as in Example 172 to give 0.38 g of 4-amino-5-chloro-N-((1-(6-(2-benzo[b]thienyl)-6-oxohexyl) piperidin-4-yl)-methyl)-2-methoxybenzamide.
m.p. 157°–159° C.

EXAMPLE 195

4-Amino-5-chloro-2-methoxy-N-(piperidin-4-ylmethyl) benzamide dihydrochloride (0.50 g) as starting compound, potassium carbonate (0.75 g) and 6-bromo-1-(3-benzo[b] thienyl)-1-hexanone (0.42 g) were reacted and treated in the same manner as in Example 172 to give 0.32 g of 4-amino-5-chloro-N-((1-(6-(3-benzo[b]thienyl)-6-oxohexyl) piperidin-4-yl)-methyl)-2-methoxybenzamide.
m.p. 130°–132° C.

EXAMPLE 196

4-Amino-5-chloro-2-methoxy-N-(piperidin-4-ylmethyl) benzamide dihydrochloride (0.88 g) as starting compound, potassium carbonate (2.0 g) and 6-bromo-1-(3,4-methylenedioxyphenyl)-1-hexanone (0.80 g) were reacted and treated in the same manner as in Example 172 to give 0.62 g of 4-amino-5-chloro-2-methoxy-N-((1-(6-(3,4-methylenedioxyphenyl)-6-oxohexyl)piperidin-4-yl)methyl) benzamide.
m.p. 163° C. (decomposition)

EXAMPLE 197

4-Amino-5-chloro-2-methoxy-N-(piperidin-4-ylmethyl) benzamide dihydrochloride as starting compound and 6-bromo-1-(1-naphthyl)-1-hexanone were reacted and treated in the same manner as in Example 172 to give 4-amino-5-chloro-2-methoxy-N-((1-(6-(1-naphthyl)-6-oxohexyl)-piperidin-4-yl)methyl)benzamide hydrochloride.
m.p. 144°–146° C.

EXAMPLE 198

4-Amino-5-chloro-2-methoxy-N-(piperidin-4-ylmethyl) benzamide dihydrochloride (0.75 g) as starting compound, potassium carbonate (2.0 g) and 6-bromo-1-(2-naphthyl)-1-hexanone (0.80 g) were reacted and treated in the same manner as in Example 172 to give 0.40 g of 4-amino-5-chloro-N-((1-(6-(2-naphthyl)-6-oxohexyl)piperidin-4-yl) methyl)-2-methoxybenzamide.
m.p. 113°–116° C.

EXAMPLE 199

Potassium carbonate (0.87 g) and 4-phenylsulfonylbutyl chloride (0.40 g) were added to a solution (15 ml) of 4-amino-5-chloro-2-methoxy-N-(piperidin-4-ylmethyl) benzamide dihydrochloride (0.52 g) in dimethylformamide, and the mixture was stirred at 70°–80° C. for 7.5 hr. Water was added to the reaction mixture, and the mixture was extracted with chloroform. The organic layer was washed with brine and dried. The solvent was evaporated under reduced pressure, and the obtained residue was purified by silica gel column chromatography. The obtained oil was treated with hydrochloric acid-ethanol and the obtained crystals were recrystallized from ethyl acetate to give 0.10 g of 4-amino-5-chloro-2-methoxy-N-((1-(4-phenylsulfonylbutyl)piperidin-4-yl)methyl)benzamide hydrochloride.
m.p. 201°–203° C.

EXAMPLE 200

4-Amino-5-chloro-2-methoxy-N-(piperidin-4-ylmethyl) benzamide dihydrochloride (0.48 g) as starting compound, potassium carbonate (0.80 g) and 5-phenylsulfonylpentyl chloride (0.40 g) were reacted and treated in the same manner as in Example 199 to give 0.17 g of 4-amino-5-chloro-2-methoxy-N-((1-(5-phenylsulfonylpentyl)piperidin-4-yl)methyl)-benzamide hydrochloride.
m.p. 90°–92° C.

EXAMPLE 201

30% Aqueous hydrogen peroxide solution (0.22 ml) was added to a solution (10 ml) of 4-amino-5-chloro-2-methoxy-N-((1-(6-phenylthiohexyl)piperidin-4-yl)methyl)benzamide (1.3 g) in formic acid, and the mixture was stirred at room temperature for 2 hr. Water was added to the reaction mixture, and the mixture was extracted with chloroform. The organic layer was washed with brine and dried. The solvent was evaporated under reduced pressure, and the obtained residue was purified by silica gel column chromatography. The obtained oil was treated with hydrochloric acid-ethanol and the obtained crystals were recrystallized from ethyl acetate to give 0.17 g of 4-amino-5-chloro-2-methoxy-N-((1-(6-phenylsulfonylhexyl)piperidin-4-yl) methyl)benzamide hydrochloride.
m.p. 90°–92° C.

EXAMPLE 202

4-Amino-5-chloro-2-methoxy-N-(piperidin-4-ylmethyl) benzamide dihydrochloride as starting compound and 5-phenylsulfinylpentyl chloride were reacted and treated in the same manner as in Example 199 to give 4-amino-5-chloro-2-methoxy-N-((1-(5-phenylsulfinylpentyl)piperidin-4-yl)methyl)benzamide.

$^1$H-NMR(COCl$_3$,ppm) δ: 1.23–1.97(1 H,m), 2.26–2.31(2 H,m), 2.78(2 H,t,J=9 Hz), 2.88–2.93(2 H,m), 3.32(2 H,t,J= 6.1 Hz), 3.90(3 H,s), 4.38(2 H,s), 6.29(1 H,s), 7.48–7.63(5 H,m), 7.69–7.80(1 H,m), 8.10(1 H,s)

EXAMPLE 203

30% Aqueous hydrogen peroxide solution (0.22 ml) was added to a solution of 4-amino-5-chloro-2-methoxy-N-((1-(6-(phenylthio)-hexyl)piperidin-4-yl)methyl)benzamide (0.48 g) in formic acid (10 ml) under ice-cooling, and the mixture was stirred at room temperature for 2 hr. Dimethyl sulfide was added to the reaction mixture, and aqueous sodium hydroxide solution was added to make same alkaline. The mixture was extracted with chloroform. The organic layer was washed with brine and dried. The solvent was evaporated under reduced pressure, and the obtained residue was purified by silica gel column chromatography (chloroform:methanol=10:1). The obtained oil was treated with hydrochloric acid-ethanol and the obtained crystals were recrystallized from ethanol-ethyl acetate to give 0.17 g of 4-amino-5-chloro-2-methoxy-N-((1-(6-phenylsulfonylhexyl)piperidin-4-yl)methyl)-benzamide hydrochloride.
m.p. 90°–92° C.

EXAMPLE 204

4-Amino-5-chloro-2-methoxy-N-(piperidin-4-ylmethyl) benzamide dihydrochloride as starting compound and 5-bromo-1-(1-methyl-1 H-indol-3-yl)-1-pentanone were reacted and treated in the same manner as in Example 172 to give 4-amino-5-chloro-2-methoxy-N-((1-(5-(1 -methyl-1 H-indol-3-yl)-5-oxopentyl)piperidin-4-yl)methyl) benzamide.
m.p. 87°–89° C.

EXAMPLE 205

4-Amino-5-chloro-2-methoxy-N-(piperidin-4-ylmethyl) benzamide dihydrochloride as starting compound and 6-bromo-1-(2-methyl-3-benzo[b]furyl)-1-hexanone were reacted and treated in the same manner as in Example 172 to give 4-amino-5-chloro-2-methoxy-N-((1-(6-(2-methyl-3-benzo[b]furyl)-6-oxohexyl)piperidin-4-yl)methyl) benzamide.
m.p. 133°–135° C.

EXAMPLE 206

4-Amino-5-chloro-2-methoxy-N-(piperidin-4-ylmethyl) benzamide dihydrochloride as starting compound and 6-bromo-1-(3-chlorophenyl)-1-hexanone were reacted and treated in the same manner as in Example 172 to give 4-amino-5-chloro-2-methoxy-N-((1-(6-(3-chlorophenyl)-6-oxohexyl)piperidin-4-yl)methyl)benzamide hydrochloride.
m.p. 128°–132° C.

EXAMPLE 207

4-Amino-5-chloro-2-methoxy-N-(piperidin-4-ylmethyl) benzamide dihydrochloride as starting compound and 7-bromo-1-(1-methyl-1 H-indol-3-yl)-1-heptanone were reacted and treated in the same manner as in Example 172 to give 4-amino-5-chloro-2-methoxy-N-((1-(7-(1-methyl-1 H-indol-3-yl)-7-oxoheptyl)piperidin-4-yl)methyl) benzamide hydrochloride.
m.p. 222°–224° C.

EXAMPLE 208

4-Amino-5-chloro-2-methoxy-N-(piperidin-4-ylmethyl) benzamide dihydrochloride as starting compound and 6-bromo-1-(1 H-indol-3-yl)-1-hexanone were reacted and treated in the same manner as in Example 199 to give 4-amino-5-chloro-2-methoxy-N-((1-(6-(1H-indol-3-yl)-6-oxohexyl)-piperidin-4-yl)methyl)benzamide hydrochloride.
m.p. 165°–168° C.

EXAMPLE 209

4-Amino-5-chloro-2-methoxy-N-(piperidin-4-ylmethyl) benzamide dihydrochloride (1.56 g) as starting compound and 6-bromo-1-(1-ethyl-1 H-indol-3-yl)-1-hexanone (1.50 g) were reacted and treated in the same manner as in Example 199 to give 0.41 g of 4-amino-5-chloro-2-methoxy-N-((1-(6-(1-ethyl-1 H-indol-3-yl)-6-oxohexyl) piperidin-4-yl)methyl)-benzamide hydrochloride.

m.p. 179°–181° C.

EXAMPLE 210

4-Amino-5-chloro-2-methoxy-N-(piperidin-4-ylmethyl) benzamide dihydrochloride (1.50 g) as starting compound and 6-bromo-1-(1-propyl-1 H-indol-3-yl)-1-hexanone were reacted and treated in the same manner as in Example 172 to give 0.83 g of 4-amino-5-chloro-2-methoxy-N-((1-(6-(1-propyl-1 H-indol-3-yl)-6-oxohexyl)piperidin-4-yl)methyl) benzamide.

$^1$H-NMR (CDCl$_3$,ppm) δ: 0.97(2 H,t,J=7.7 Hz), 1.34–1.97(15 H,m), 2.31–2.36(2 H,m), 2.86(2 H,t,J=7.7 Hz), 2.93–2.97(2 H,m), 3.32(2 H,t,J=6.1 Hz), 3.89(3 H,s), 4.13(2 H,t,J=7.0 Hz), 4.37(3 H,s), 6.29(1 H,s), 7.25–7.39(4 H,m), 7.71–7.73(1 H,m), 8.10(1 H,s), 8.35–8.42(1 H,m)

EXAMPLE 211

4-Amino-5-chloro-2-methoxy-N-(piperidin-4-ylmethyl) benzamide dihydrochloride (1.90 g) as starting compound and 6-bromo-1-(1-isopropyl-1 H-indol-3-yl)-1-hexanone (1.90 g) were reacted and treated in the same manner as in Example 199 to give 0.70 g of 4-amino-5-chloro-2-methoxy-N-((1-(6-(1-isopropyl-1H-indol-3-yl)-6-oxohexyl) -piperidin-4-yl)methyl)benzamide hydrochloride.
m.p. 104°–108° C.

EXAMPLE 212

4-Amino-5-chloro-2-methoxy-N-(piperidin-4-ylmethyl) benzamide dihydrochloride as starting compound and 6-bromo-1-(1-cyclohexylmethyl-1 H-indol-3-yl)-1-hexanone are reacted and treated in the same manner as in Example 199 to give 4-amino-5-chloro-2-methoxy-N-((1-(6-(1-cyclohexylmethyl-1 H-indol-3-yl)-6-oxohexyl) piperidin-4-yl)methyl)-benzamide.

EXAMPLE 213

4-Amino-5-chloro-2-methoxy-N-(piperidin-4-ylmethyl) benzamide dihydrochloride (1.50 g) as starting compound and 6-bromo-1-(1-benzyl-1 H-indol-3-yl)-1-hexanone were reacted and treated in the same manner as in Example 199 to give 0.43 g of 4-amino-5-chloro-2-methoxy-N-((1-(6-(1-benzyl-1 H-indol-3-yl)-6-oxohexyl)piperidin-4-yl)methyl) benzamide.
m.p. 145°–148° C.

EXAMPLE 214

4-Amino-5-chloro-2-methoxy-N-(piperidin-4-ylmethyl) benzamide dihydrochloride as starting compound and 6-bromo-1-(1,5-dimethyl-1 H-indol-3-yl)-1-hexanone are reacted and treated in the same manner as in Example 199 to give 4-amino-5-chloro-2-methoxy-N-((1-(6-(1,5-dimethyl-1H-indol-3-yl)-6-oxohexyl)piperidin-4-yl)methyl) benzamide.

EXAMPLE 215

4-Amino-5-chloro-2-methoxy-N-(piperidin-4-ylmethyl) benzamide dihydrochloride as starting compound and 6-bromo-1-(5-chloro-1-methyl-1 H-indol-3-yl)-1-hexanone are reacted and treated in the same manner as in Example 199 to give 4-amino-5-chloro-2-methoxy-N-((1-(6-(5-chloro-1-methyl-1 H-indol-3-yl)-6-oxohexyl)piperidin-4-yl)methyl)benzamide.

EXAMPLE 216

4-Amino-5-chloro-2-methoxy-N-(piperidin-4-ylmethyl) benzamide dihydrochloride as starting compound and 6-bromo-1-(5-methoxy-1-methyl-1 H-indol-3-yl)-1-hexanone are reacted and treated in the same manner as in Example 199 to give 4-amino-5-chloro-2-methoxy-N-((1-(6-(5-methoxy-1-methyl-1 H-indol-3-yl)-6-oxohexyl) piperidin-4-yl)methyl)benzamide.

EXAMPLE 217

4-Amino-5-chloro-2-methoxy-N-(piperidin-4-ylmethyl) benzamide dihydrochloride as starting compound and 6-bromo-1-(3-benzisothiazolyl)-1-hexanone are reacted and treated in the same manner as in Example 199 to give 4-amino-5-chloro-2-methoxy-N-((1-(6-(3-benzisothiazolyl) -6-oxohexyl)piperidin-4-yl)methyl)benzamide.

EXAMPLE 218

4-Amino-5-chloro-2-methoxy-N-(piperidin-4-ylmethyl) benzamide dihydrochloride as starting compound and 6-bromo-1-(3-benzisoxazolyl)-1-hexanone are reacted and treated in the same manner as in Example 199 to give 4-amino-5-chloro-2-methoxy-N-((1-(6-(3-benzisoxazolyl)-6-oxohexyl)-piperidin-4-yl)methyl)benzamide.

EXAMPLE 219

4-Amino-5-chloro-2-methoxy-N-(piperidin-4-ylmethyl) benzamide dihydrochloride as starting compound and 6-bromo-1-(4-amino-5-chloro-2-methoxyphenyl)-1-hexanone are reacted and treated in the same manner as in Example 199 to give 4-amino-5-chloro-2-methoxy-N-((1-(6-(4-amino-5-chloro-2-methoxyphenyl)-6-oxohexyl) piperidin-4-yl)methyl)benzamide.

EXAMPLE 220

4-Amino-5-chloro-2-methoxy-N-(piperidin-4-ylmethyl) benzamide dihydrochloride as starting compound and 6-bromo-1-(2-chlorophenyl)-1-hexanone are reacted and treated in the same manner as in Example 199 to give 4-amino-5-chloro-2-methoxy-N-((1-(6-(2-chlorophenyl)-6-oxohexyl)-piperidin-4-yl)methyl)benzamide.

EXAMPLE 221

4-Amino-5-chloro-2-methoxy-N-(piperidin-4-ylmethyl) benzamide dihydrochloride as starting compound and 6-bromo-1-(2-chloro-4-methylphenyl)-1-hexanone are reacted and treated in the same manner as in Example 199 to give 4-amino-5-chloro-2-methoxy-N-((1-(6-(2-chloro-4-methylphenyl)-6-oxohexyl)piperidin-4-yl)methyl) benzamide.

EXAMPLE 222

4-Amino-5-chloro-2-methoxy-N-(piperidin-4-ylmethyl) benzamide dihydrochloride as starting compound and 6-bromo-1-(3-chloro-4-methylphenyl)-1-hexanone are reacted and treated in the same manner as in Example 199 to give 4-amino-5-chloro-2-methoxy-N-((1-(6-(3-chloro-4-methylphenyl)-6-oxohexyl)piperidin-4-yl)methyl) benzamide.

EXAMPLE 223

4-Amino-5-chloro-2-methoxy-N-(piperidin-4-ylmethyl) benzamide dihydrochloride as starting compound and 6-bromo-1-(2,3-dichlorophenyl)-1-hexanone are reacted and treated in the same manner as in Example 199 to give 4-amino-5-chloro-2-methoxy-N-((1-(6-(2,3-dichlorophenyl)-6-oxohexyl)piperidine- 4-yl)methyl) benzamide.

EXAMPLE 224

4-Amino-5-chloro-2-methoxy-N-(piperidin-4-ylmethyl)benzamide dihydrochloride as starting compound and 6-bromo-1-(2-methoxyphenyl)-1-hexanone are reacted and treated in the same manner as in Example 199 to give 4-amino-5-chloro-2-methoxy-N-((1-(6-(2-methoxyphenyl)-6-oxohexyl)piperidin-4-yl)methyl)benzamide.

EXAMPLE 225

4-Amino-5-chloro-2-methoxy-N-(piperidin-4-ylmethyl)benzamide dihydrochloride as starting compound and 6-bromo-1-(3-methoxyphenyl)-1-hexanone are reacted and treated in the same manner as in Example 199 to give 4-amino-5-chloro-2-methoxy-N-((1-(6-(3-methoxyphenyl)-6-oxohexyl)piperidin-4-yl)methyl)benzamide.

EXAMPLE 226

4-Amino-5-chloro-2-methoxy-N-(piperidin-4-ylmethyl)benzamide dihydrochloride as starting compound and 6-bromo-1-(2-fluorophenyl)-1-hexanone are reacted and treated in the same manner as in Example 199 to give 4-amino-5-chloro-2-methoxy-N-((1-(6-(2-fluorophenyl)-6-oxohexyl)-piperidin-4-yl)methyl)benzamide.

EXAMPLE 227

4-Amino-5-chloro-2-methoxy-N-(piperidin-4-ylmethyl)benzamide dihydrochloride as starting compound and 6-bromo-1-(3-fluorophenyl)-1-hexanone are reacted and treated in the same manner as in Example 199 to give 4-amino-5-chloro-2-methoxy-N-((1-(6-(3-fluorophenyl)-6-oxohexyl)-piperidin-4-yl)methyl)benzamide.

EXAMPLE 228

4-Amino-5-chloro-2-methoxy-N-(piperidin-4-ylmethyl)benzamide dihydrochloride as starting compound and 6-bromo-1-(4-nitrophenyl)-1-hexanone are reacted and treated in the same manner as in Example 199 to give 4-amino-5-chloro-2-methoxy-N-((1-(6-(4-nitrophenyl)-6-oxohexyl)-piperidin-4-yl)methyl)benzamide.

EXAMPLE 229

4-Amino-5-chloro-2-methoxy-N-(piperidin-4-ylmethyl)benzamide dihydrochloride (1.50 g) as starting compound and 4-phenoxybutyl bromide (1.37 g) were reacted and treated in the same manner as in Example 168 to give 0.91 g of 4-amino-5-chloro-2-methoxy-N-((1-(4-phenoxybutyl)piperidin-4-yl)methyl)benzamide.
m.p. 71°–73° C.

EXAMPLE 230

4-Amino-5-chloro-2-methoxy-N-(piperidin-4-ylmethyl)benzamide dihydrochloride as starting compound and 6-phenoxyhexyl bromide (1.56 g) were reacted and treated in the same manner as in Example 168 to give 0.78 g of 4-amino-5-chloro-2-methoxy-N-((1-(6-phenoxyhexyl)piperidin-4-yl)methyl)benzamide.
m.p. 113°–115° C.

EXAMPLE 231

4-Amino-5-chloro-2-methoxy-N-(piperidin-4-ylmethyl)benzamide dihydrochloride (1.1 g) as starting compound, potassium carbonate (1.5 g) and 4-benzyloxybutyl bromide (1.0 g) were reacted and treated in the same manner as in Example 168 to give 0.32 g of 4-amino-5-chloro-2-methoxy-N-((1-(4-benzyloxybutyl)piperidin-4-yl)methyl)benzamide.

$^1$H-NMR (CDCl$_3$,ppm) δ: 1.40–1.81(9 H,m), 2.82(2 H,t), 2.98(2 H,t), 3.20(2 H,t), 3.44(4 H,m), 3.82(3 H,s), 4.45(3 H,s), 5.93(2 H,s), 6.48(1 H,s), 7.33–7.45(5 H,m), 7.66(1 H,s), 8.00(1 H,t)

EXAMPLE 232

4-Amino-5-chloro-2-methoxy-N-(piperidin-4-ylmethyl)benzamide dihydrochloride (1.00 g) as starting compound and 6-benzyloxyhexyl bromide (0.75 g) were reacted and treated in the same manner as in Example 168 to give 0.45 g of 4-amino-N-((1-(6-benzyloxyhexyl)piperidin-4-yl)methyl)-5-chloro-2-methoxybenzamide.
m.p. 91°–95° C.

EXAMPLE 233

4-Amino-5-chloro-2-methoxy-N-(piperidin-4-ylmethyl)benzamide dihydrochloride (1.0 g) as starting compound, potassium carbonate (1.5 g) and 5-(4-chlorobenzyloxy)pentyl chloride (1.5 g) were reacted and treated in the same manner as in Example 168 to give 1.3 g of 4-amino-5-chloro-N-((1-(5-(4-chlorobenzyloxy)pentyl)piperidin-4-yl)methyl)-2-methoxybenzamide.
m.p. 131°–132° C.

EXAMPLE 234

4-Amino-5-chloro-2-methoxy-N-(piperidin-4-ylmethyl)benzamide dihydrochloride (2.0 g) as starting compound and 5-(2-phenylethyloxy)-pentyl chloride were reacted and treated in the same manner as in Example 168 to give 0.69 g of 4-amino-5-chloro-2-methoxy-N-((1-(5-(2-phenylethyloxy)pentyl)piperidin-4-yl)methyl)benzamide.
m.p. 103°–104° C.

EXAMPLE 235

4-Amino-5-chloro-2-methoxy-N-(piperidin-4-ylmethyl)benzamide dihydrochloride (2.00 g) as starting compound and 5-(2-naphthylmethoxy)-pentyl chloride (1.88 g) were reacted and treated in the same manner as in Example 168 to give 1.45 g of 4-amino-5-chloro-2-methoxy-N-((1-(5-(2-naphthylmethoxy)pentyl)piperidin-4-yl)methyl)benzamide hydrochloride.
m.p. 161°–165° C.

EXAMPLE 236

4-Amino-5-chloro-2-methoxy-N-(piperidin-4-ylmethyl)benzamide dihydrochloride (1.50 g) as starting compound and 5-(cyclohexylmethoxy)pentyl bromide (1.30 g) were reacted and treated in the same manner as in Example 168 to give 0.51 g of 4-amino-5-chloro-2-methoxy-N-((1-(5-(cyclohexylmethoxy)pentyl)piperidin-4-yl)methyl)benzamide hydrochloride.
m.p. 103°–105° C.

EXAMPLE 237

4-Amino-5-chloro-2-methoxy-N-(piperidin-4-ylmethyl)benzamide dihydrochloride (2.5 g) as starting compound and 4-phenylthiobutyl bromide (2.48 g) were reacted and treated in the same manner as in Example 168 to give 0.84 g of 4-amino-5-chloro-2-methoxy-N-((1-(4-phenylthiobutyl)piperidin-4-yl)methyl)benzamide.
m.p. 102°–105° C.

EXAMPLE 238

4-Amino-5-chloro-2-methoxy-N-(piperidin-4-ylmethyl) benzamide dihydrochloride (2.00 g) as starting compound and 5-phenylthiopentyl bromide (1.54 g) were reacted and treated in the same manner as in Example 168 to give 0.70 g of 4-amino-5-chloro-2-methoxy-N-((1-(5-phenylthiopentyl)piperidin-4-yl)methyl)benzamide.
m.p. 143°–144° C.

EXAMPLE 239

4-Amino-5-chloro-2-methoxy-N-(piperidin-4-ylmethyl) benzamide dihydrochloride (2.5 g) as starting compound and 6-phenylthiohexyl chloride (2.76 g) were reacted and treated in the same manner as in Example 168 to give 1.40 g of 4-amino-5-chloro-2-methoxy-N-((1-(6-phenylthiohexyl)piperidin-4-yl)methyl)benzamide.
m.p. 68°–70° C.

EXAMPLE 240

4-Amino-5-chloro-2-methoxy-N-(piperidin-4-ylmethyl) benzamide dihydrochloride as starting compound and 4-(3-methoxyphenoxy)butyl bromide are reacted and treated in the same manner as in Example 168 to give 4-amino-5-chloro-2-methoxy-N-((1-(4-(3-methoxyphenoxy)butyl)-piperidin-4-yl)methyl)benzamide.

EXAMPLE 241

4-Amino-5-chloro-2-methoxy-N-(piperidin-4-ylmethyl) benzamide dihydrochloride as starting compound and 5-(3-methoxyphenoxy)pentyl chloride were reacted and treated in the same manner as in Example 168 to give 4-amino-5-chloro-2-methoxy-N-((1-(5-(3-methoxyphenoxy)pentyl)-piperidin-4-yl)methyl)benzamide.
m.p. 185°–187° C.

EXAMPLE 242

4-Amino-5-chloro-2-methoxy-N-(piperidin-4-ylmethyl) benzamide dihydrochloride as starting compound and 4-(3-methoxybenzyloxy)butyl bromide are reacted and treated in the same manner as in Example 168 to give 4-amino-5-chloro-2-methoxy-N-((1-(4-(3-methoxybenzyloxy)butyl)-piperidin-4-yl)methyl)benzamide.

EXAMPLE 243

4-Amino-5-chloro-2-methoxy-N-(piperidin-4-ylmethyl) benzamide dihydrochloride as starting compound and 5-(3-methoxybenzyloxy)pentyl bromide are reacted and treated in the same manner as in Example 168 to give 4-amino-5-chloro-2-methoxy-N-((1-(5-(3-methoxybenzyloxy)pentyl)-piperidin-4-yl)methyl)benzamide.

EXAMPLE 244

4-Amino-5-chloro-2-methoxy-N-(piperidin-4-ylmethyl) benzamide dihydrochloride as starting compound and 4-(3,4-dimethoxyphenoxy)butyl bromide are reacted and treated in the same manner as in Example 168 to give 4-amino-5-chloro-N-((1-(4-(3,4-dimethoxyphenoxy)-butyl)piperidin-4-yl)methyl)-2-methoxybenzamide.

EXAMPLE 245

4-Amino-5-chloro-2-methoxy-N-(piperidin-4-ylmethyl) benzamide dihydrochloride (1.5 g) as starting compound and 5-(3,4-dimethoxyphenoxy)pentyl chloride (1.3 g) were reacted and treated in the same manner as in Example 168 to give 1.46 g of 4-amino-5-chloro-N-((1-(5-(3,4-dimethoxyphenoxy)pentyl)piperidin-4-yl)methyl)-2-methoxybenzamide.
m.p. 85°–87° C.

EXAMPLE 246

4-Amino-5-chloro-2-methoxy-N-(piperidin-4-ylmethyl) benzamide dihydrochloride as starting compound and 4-(3,4-dimethoxybenzyloxy)butyl bromide are reacted and treated in the same manner as in Example 168 to give 4-amino-5-chloro-N-((1-(4-(3,4-dimethoxybenzyloxy)butyl)piperidin-4-yl)methyl)-2-methoxybenzamide.

EXAMPLE 247

4-Amino-5-chloro-2-methoxy-N-(piperidin-4-ylmethyl) benzamide dihydrochloride as starting compound and 5-(3,4-dimethoxybenzyloxy)-pentyl bromide are reacted and treated in the same manner as in Example 168 to give 4-amino-5-chloro-N-((1-(5-(3,4-dimethoxybenzyloxy)pentyl)-piperidin-4-yl)methyl)-2-methoxybenzamide.

EXAMPLE 248

4-Amino-5-chloro-2-methoxy-N-(piperidin-4-ylmethyl) benzamide dihydrochloride as starting compound and 4-(3,5-dimethoxyphenoxy)butyl bromide are reacted and treated in the same manner as in Example 168 to give 4-amino-5-chloro-N-((1-(4-(3,5-dimethoxyphenoxy)butyl)piperidin-4-yl)methyl)-2-methoxybenzamide.

EXAMPLE 249

4-Amino-5-chloro-2-methoxy-N-(piperidin-4-ylmethyl) benzamide dihydrochloride (2.0 g) as starting compound and 5-(3,5-dimethoxyphenoxy)pentyl chloride (1.4 g) were reacted and treated in the same manner as in Example 168 to give 4-amino-5-chloro-N-((1-(5-(3,5-dimethoxyphenoxy) pentyl)piperidin-4-yl)methyl)-2-methoxybenzamide.
m.p. 112°–113° C.

EXAMPLE 250

4-Amino-5-chloro-2-methoxy-N-(piperidin-4-ylmethyl) benzamide dihydrochloride as starting compound and 4-(3,5-dimethoxybenzyloxy)butyl bromide are reacted and treated in the same manner as in Example 168 to give 4-amino-5-chloro-N-((1-(4-(3,5-dimethoxybenzyloxy)-butyl)piperidin-4-yl)methyl)-2-methoxybenzamide.

EXAMPLE 251

4-Amino-5-chloro-2-methoxy-N-(piperidin-4-ylmethyl) benzamide dihydrochloride as starting compound and 5-(3,5-dimethoxybenzyloxy)pentyl bromide are reacted and treated in the same manner as in Example 168 to give 4-amino-5-chloro-N-((1-(5-(3,5-dimethoxybenzyloxy) pentyl)piperidin-4-yl)methyl)-2-methoxybenzamide.

EXAMPLE 252

4-Amino-5-chloro-2-methoxy-N-(piperidin-4-ylmethyl) benzamide dihydrochloride (1.3 g) as starting compound and 5-(4-chlorophenoxy)-pentyl bromide (1.0 g) were reacted and treated in the same manner as in Example 168 to give 4-amino-5-chloro-N-((1-(5-(4-chlorophenoxy) pentyl)-piperidin-4-yl)methyl)-2-methoxybenzamide.
m.p. 104°–105° C.

EXAMPLE 253

4-Amino-5-chloro-2-methoxy-N-(piperidin-4-ylmethyl) benzamide dihydrochloride (1.5 g) as starting compound and 5-(4-fluorophenoxy)-pentyl bromide (1.1 g) were reacted and treated in the same manner as in Example 168 to give 4-amino-5-chloro-N-((1-(5-(4-fluorophenoxy) pentyl)-piperidin-4-yl)methyl)-2-methoxybenzamide.
m.p. 105°–107° C.

EXAMPLE 254

4-Amino-5-chloro-2-methoxy-N-(piperidin-4-ylmethyl) benzamide dihydrochloride as starting compound and 4-(1-naphthyloxy)butyl bromide are reacted and treated in the same manner as in Example 168 to give 4-amino-5-chloro-N-((1-(4-(1-naphthyloxy)butyl)piperidin-4-yl)methyl)-2-methoxybenzamide.

EXAMPLE 255

4-Amino-5-chloro-2-methoxy-N-(piperidin-4-ylmethyl) benzamide dihydrochloride (1.5 g) as starting compound and 5-(1-naphthyloxy)-pentyl chloride (1.2 g) were reacted and treated in the same manner as in Example 168 to give 1.88 g of 4-amino-5-chloro-N-((1-(5-(1-naphthyloxy) pentyl)piperidin-4-yl)methyl)-2-methoxybenzamide.
m.p. 91°–93° C.

EXAMPLE 256

4-Amino-5-chloro-2-methoxy-N-(piperidin-4-ylmethyl) benzamide dihydrochloride as starting compound and 4-((3, 4-methylenedioxyphenyl)methoxy)butyl bromide are reacted and treated in the same manner as in Example 168 to give 4-amino-5-chloro-N-((1-(4-((3,4-methylenedioxyphenyl)methoxy)butyl)piperidin-4-yl) methyl)-2-methoxybenzamide.

EXAMPLE 257

4-Amino-5-chloro-2-methoxy-N-(piperidin-4-ylmethyl) benzamide dihydrochloride (0.72 g) as starting compound and 5-((3,4-methylenedioxyphenyl)methoxy)pentyl chloride (0.5 g) were reacted and treated in the same manner as in Example 168 to give 0.4 g of 4-amino-5-chloro-N-((1-(5-((3,4-methylenedioxyphenyl)methoxy)pentyl)piperidin-4-yl)methyl)-2-methoxybenzamide.

$^1$H-NMR (CDCl$_3$,ppm) δ: 1.25–1.42(4 H,m), 1.47–1.75(7 H,m), 1.90–1.98(2 H,m), 2.22–2.36(2 H,m), 2.93–2.98(2 H,m), 3.32(2 H,t,J=6.0 Hz), 3.43(2 H,t,J=6.6 Hz), 3.89(3 H,s), 4.38(4 H,s), 5.93(2 H,s), 6.28(1 H,s), 6.77(2 H,s), 6.83(1 H,s), 7.74(1 H,brs), 8.10(1 H,s)

EXAMPLE 258

4-Amino-5-chloro-2-methoxy-N-(piperidin-4-ylmethyl) benzamide dihydrochloride as starting compound and 4-((1, 4-benzodioxan-6-yl)-methoxy)butyl bromide are reacted and treated in the same manner as in Example 168 to give 4-amino-5-chloro-N-((1-(4-((1,4-benzodioxan-6-yl)-methoxy)butyl)piperidin-4-yl)methyl)-2-methoxybenzamide.

EXAMPLE 259

4-Amino-5-chloro-2-methoxy-N-(piperidin-4-ylmethyl) benzamide dihydrochloride as starting compound and 5-((1, 4-benzodioxan-6-yl)methoxy)pentyl chloride were reacted and treated in the same manner as in Example 168 to give 4-amino-5-chloro-N-((1-(5-((1,4-benzodioxan-6-yl) methoxy)pentyl)piperidin-4-yl)methyl)-2-methoxybenzamide.

$^1$H-NMR (CDCl$_3$,ppm) δ: 1.37–1.81(11 H,m), 2.04–2.18(2 H,m), 2.45–2.51(2 H,m), 3.06–3.17(2 H,m), 3.32(2 H,t,J=6.0 Hz), 3.43(2 H,t,J=6.6 Hz), 3.89(3 H,s), 4.24(4 H,s), 4.36(2 H,s), 4.45(2 H,s), 6.31(1 H,s), 6.79–6.88(3 H,m), 7.75–7.79(1 H,m), 8.08(1 H,s)

EXAMPLE 260

4-Amino-5-chloro-2-methoxy-N-(piperidin-4-ylmethyl) benzamide dihydrochloride as starting compound and 5-(1-naphthylthio)pentyl bromide are reacted and treated in the same manner as in Example 168 to give 4-amino-5-chloro-N-((1-(5-(1-naphthylthio)pentyl)piperidin-4-yl)-methyl)-2-methoxybenzamide.

EXAMPLE 261

To a solution of 4-amino-N-(1-(5-aminopentyl)piperidin-4-yl)-methyl)-5-chloro-2-methoxybenzamide (1.5 g) in dimethylformamide (30 ml) were added diisopropylethylamine (1.5 g) and 2-chloropyrimidine (0.89 g), and the mixture was stirred at 100° C. for 4 hr. The reaction mixture was added with water, and extracted with chloroform. The organic layer was washed with brine, dried and the solvent was evaporated under reduced pressure. The obtained residue was purified by silica gel column chromatography (chloroform:methanol=10:1). The obtained oily substance was treated with hydrochloric acid-ethanol, and the obtained crystals were recrystallized from ethanol to give 0.28 g of 4-amino-5-chloro-2-methoxy-N-((1-(5-(2-pyrimidinylamino)-pentyl)piperidin-4-yl)methyl) benzamide dihydrochloride.
m.p. 147°–149° C.

EXAMPLE 262

4-Amino-5-chloro-2-methoxy-N-(piperidin-4-ylmethyl) benzamide dihydrochloride (0.78 g) as starting compound and 6-bromo-1-(1,2-dimethyl-1 H-indol-3-yl)-1-hexanone (0.68 g) were reacted and treated in the same manner as in Example 172 to give 0.38 g of 4-amino-5-chloro-2-methoxy-N-((1-(6-(1,2-dimethyl-1 H-indol-3-yl)-6-oxohexyl)piperidin-4-yl)methyl)benzaminde.
m.p. 91°–92° C.

EXAMPLE 263

4-Amino-5-chloro-2-methoxy-N-(piperidin-4-ylmethyl) benzamide dihydrochloride (2.74 g) as starting compound and 6-bromo-1-(1-butyl-1 H-indol-3-yl)-1-hexanone (2.59 g) were reacted and treated in the same manner as in Example 199 to give 1.1 g of 4-amino-5-chloro-2-methoxy-N-((1-(6-(1-butyl-1 H-indol-3-yl)-6-oxohexyl)piperidin-4-yl)methyl)-benzaminde hydrochloride.
m.p. 146°–149° C.

EXAMPLE 264

4-Amino-5-chloro-2-methoxy-N-(piperidin-4-ylmethyl) benzamide dihydrochloride (0.58 g) as starting compound and 7-bromo-1-(3-chlorophenyl)-1-heptanone (0.45 g) were reacted and treated in the same manner as in Example 172 to give 0.11 g of 4-amino-5-chloro-2-methoxy-N-((1-(7-(3-chlorophenyl)-7-oxoheptyl)piperidin-4-yl)methyl) benzaminde.
m.p. 104°–105° C.

EXAMPLE 265

4-Amino-5-chloro-2-methoxy-N-(4-methoxypiperidin-4-ylmethyl)-benzamide dihydrochloride as starting compound and 1-(4-chlorobutylsulfonyl)naphthalene are reacted and treated in the same manner as in Example 172 to give 4-amino-5-chloro-2-methoxy-N-((4-methoxy-1-(4-(1-naphthylsulfonyl)butyl)piperidin-4-yl)methyl)-benzaminde.

EXAMPLE 266

4-Amino-5-chloro-2-methoxy-N-(4-methoxypiperidin-4-ylmethyl)-benzamide dihydrochloride as starting compound and 1-(5-chloropentylsulfonyl)naphthalene are reacted and treated in the same manner as in Example 172 to give 4-amino-5-chloro-2-methoxy-N-((4-methoxy-1-(5-(1-naphthylsulfonyl)pentyl)piperidin-4-yl)methyl) benzaminde.

EXAMPLE 267

4-Amino-5-chloro-2-methoxy-N-(4-methoxypiperidin-4-ylmethyl)-benzamide dihydrochloride as starting compound and 1-(4-chlorobutylsulfonyl)methylnaphthalene are reacted and treated in the same manner as in Example 172 to give 4-amino-5-chloro-2-methoxy-N-((4-methoxy-1-(4-((1-naphthyl)methylsulfonyl)butyl)piperidin-4-yl)methyl) benzaminde.

EXAMPLE 268

4-Amino-5-chloro-2-methoxy-N-(4-methoxypiperidin-4-ylmethyl)-benzamide dihydrochloride as starting compound and 1-(5-chloropentylsulfonyl)methylnaphthalene are reacted and treated in the same manner as in Example 172 to give 4-amino-5-chloro-2-methoxy-N-((4-methoxy-1-(5-((1-naphthyl)methylsulfonyl)pentyl)piperidin-4-yl)methyl) benzaminde.

EXAMPLE 269

4-Amino-5-chloro-2-methoxy-N-(piperidin-4-ylmethyl) benzamide dihydrochloride (0.98 g) as starting compound and 7-bromo-1-(1-methyl-1 H-indol-3-yl)-1-heptanone were reacted and treated in the same manner as in Example 172 to give 0.83 g of 4-amino-5-chloro-2-methoxy-N-((1-(7-(1-methyl-1 H-indol-3-yl)-7-oxoheptyl)piperidin-4-yl) methyl)-benzamide. This compound was treated with hydrochloric acid-ethanol to obtain its hydrochloride as crystals.
m.p. 222°–224° C.

EXAMPLE 270

To a solution of 4-aminomethyl-4-hydroxy-1-(6-oxo-6-phenylhexyl)-piperidine dihydrochloride (2.9 g) in dimethylformamide (50 ml) were added triethylamine (3.2 ml), 4-amino-5-chloro-2-methoxybenzoic acid (1.55 g) and 1-hydroxybenzotriazole (1.09 g), which was followed by the addition of 1-ethyl-3-(3-dimethylaminopropyl)carbodiimide (1.55 g) under ice cooling, and the mixture was stirred at room temperature for 6 hr. The reaction mixture was concentrated under reduced pressure, and the obtained residue was added with water and extracted with chloroform. The organic layer was washed successively with 10% aqueous solution of potassium carbonate and brine, and dried. The solvent was evaporated under reduced pressure, and the obtained residue was purified by a silica gel column chromatography (chloroform:methanol=10:1) to give 2.98 g of 4-amino-5-chloro-N-((4-hydroxy-1-(6-oxo-6-phenylhexyl)-piperidin-4-yl)methyl)-2-methoxybenzamide.
m.p. 102°–103° C.

EXAMPLE 271

4-Aminomethyl-4-methoxy-1-(6-oxo-6-phenylhexyl) piperidine dihydrochloride (2.25 g) as starting compound, triethylamine (2.4 ml), 4-amino-5-chloro-2-methoxybenzoic acid (1.16 g), 1-hydroxybenzotriazole (0.815 g) and 1-ethyl-3-(3-dimethylaminopropyl)carbodiimide (1.16 g) were reacted and treated in the same manner as in Example 270 to give 1.43 g of 4-amino-5-chloro-2-methoxy-N-((4-methoxy-1-(6-oxo-6-phenylhexyl)piperidin-4-yl)methyl) benzamide.
m.p. 91°–93° C.

EXAMPLE 272

4-Aminomethyl-4-methoxy-1-(4-phenylsulfonylbutyl) piperidine dihydrochloride (2.2 g) as starting compound, triethylamine (2.2 ml), 4-amino-5-chloro-2-methoxybenzoic acid (1.07 g), 1-hydroxybenzotriazole (0.75 g) and 1-ethyl-3-(3-dimethylaminopropyl)carbodiimide (1.07 g) were reacted and treated in the same manner as in Example 270 to give 1.44 g of 4-amino-5-chloro-2-methoxy-N-((4-methoxy-1-(4-phenylsulfonylbutyl)piperidin-4-yl)methyl) benzamide.
$^1$H-NMR (CDCl$_3$,ppm) 6:1.48–1.80(10 H,m), 2.26–2.34(4 H,m), 2.44–2.57(2 H,m), 3.09–3.15(2 H,m), 3.21(3 H,s), 3.48(2 H,d,J=5.3 Hz), 3.87(3 H,s), 4.46(2 H,s), 6.30(1 H,s), 7.53–7.70(3 H,m), 7.88–7.92(3 H,m), 8.08(1 H,s)

EXAMPLE 273

4-Amino-5-chloro-2-methoxy-N-(piperidin-4-ylmethyl) benzamide dihydrochloride (2 g) and 4-(benzylsulfonyl) butyl chloride (1.46 g) were reacted and treated in the same manner as in Example 199 to give 0.96 g of 4-amino-N-(( 1-(4-(benzylsulfonyl)butyl)piperidin-4-yl)-methyl)-5-chloro-2-methoxybenzamide hydrochloride.
m.p. 114°–116° C.

EXAMPLE 274

4-Amino-5-chloro-2-methoxy-N-(piperidin-4-ylmethyl) benzamide dihydrochloride and 5-bromo-1-(1-naphthyl)-1-pentanone were reacted and treated in the same manner as in Example 172 to give 4-amino-5-chloro-2-methoxy-N-((1-(4-(1-naphthoyl)butyl)piperidin-4-yl)methyl)-benzamide.
$^1$H-NMR (CDCl$_3$,ppm) δ: 1.35–1.88(9 H,m), 1.90–2.05(2 H,m), 2.38–2.43(2 H,m), 2.94–3.05(2 H,m), 3.07(2 H,t,J= 7.3 Hz), 3.32(2 H,t,J=6.0 Hz), 3.88(3 H,s), 4.41(2 H,brs), 6.29(1 H,s), 7.46–7.62(3 H,m), 7.74(1 H,br), 7.83–7.98(3 H,m), 8.10(1 H,s), 8.53(1 H,d,J=8.6 Hz)

EXAMPLE 275

4-Amino-5-chloro-2-methoxy-N-(piperidin-4-ylmethyl) benzamide dihydrochloride and 5-benzylsulfonylpentyl chloride were reacted and treated in the same manner as in Example 199 to give 4-amino-5-chloro-2-methoxy-N-((1-(5-benzylsulfonylpentyl)piperidin-4-yl)methyl)-benzamide.
$^1$H-NMR (CDCl$_3$,ppm) δ: 1.42–1.89(11 H,m), 2.26–2.35(2 H,m), 2.55–2.61(2 H,m), 2.86(2 H,d,J=7.9 Hz), 3.17–3.22(2 H,m), 3.34(2 H,t,J=5.9 Hz), 3.91(3 H,s), 4.24(2 H,s), 4.41(2 H,s), 6.31(1 H,s), 7.40(5 H,s), 7.77–7.82(1 H,m), 8.08(1 H,s)

EXAMPLE 276

4-Amino-5-chloro-2-methoxy-N-(piperidin-4-ylmethyl) benzamide dihydrochloride and 3-phenoxypropyl chloride were reacted and treated in the same manner as in Example 168 to give 4-amino-5-chloro-2-methoxy-N-((1-(3-(phenoxy)propyl)piperidin-4-yl)methyl)benzamide.

m.p. 132°–134° C.

EXAMPLE 277

4-Amino-5-chloro-2-methoxy-N-(piperidin-4-ylmethyl) benzamide dihydrochloride and 3-phenylthiopropyl chloride were reacted and treated in the same manner as in Example 168 to give 4-amino-5-chloro-2-methoxy-N-((1-(3-(phenylthio)propyl)piperidin-4-yl)methyl)-benzamide.
m.p. 146°–148° C.

EXAMPLE 278

4-Amino-5-chloro-2-methoxy-N-(piperidin-4-ylmethyl) benzamide dihydrochloride and 3-phenylsulfonylpropyl chloride were reacted and treated in the same manner as in Example 199 to give 4-amino-5-chloro-2-methoxy-N-((1-(3-(phenylsulfonyl)propyl)piperidin-4-yl)methyl)-benzamide.

$^1$H-NMR (CDCl$_3$,ppm) δ:1.14–1.24(2 H,m), 1.42–1.91(8 H,m), 2.27(2 H,t,J=7.0 Hz), 2.67–2.80(2 H,m), 3.04–3.14(2 H,m), 3.22(2 H,t,J=6.5 Hz), 3.81(3 H,s), 4.38(2 H,brs), 6.23(1 H,s), 7.45–7.88(5 H,m), 8.01(1 H,s)

EXAMPLE 279

4-Amino-5-chloro-2-methoxy-N-((1-(6-aminohexyl) piperidin-4-yl)-methyl)benzamide (2.0 g), 2-thiophenecarboxaldehyde (0.62 g), sodium borohydride (0.42 g) and ethanol (40 ml) were reacted and treated in the same manner as in Example 121 to give 1.0 g of 4-amino-5-chloro-2-methoxy-N-((1-(6-(2-thienylmethylamino) hexyl)piperidin-4-yl)-methyl)benzamide.

$^1$H-NMR (CDCl$_3$,ppm) δ: 1.20–1.95(16 H,m), 2.22–2.31(2 H,m), 2.38–2.49(2 H,m), 2.88–2.99(2 H,m), 3.34(2 H,t), 3.82(2 H,s), 3.91(3 H,s), 4.39(2 H,brs), 6.29(1 H,s), 6.88(1 H,d,J=2 Hz), 6.93(1 H,dd,J=3.3,5.5 Hz), 7.20(1 H,dd,J=1.3,5.2 Hz), 7.67–7.82(1 H,m), 8.11(1 H,s)

EXAMPLE 280

(1) 4-Amino-5-chloro-2-methoxy-N-(piperidin-4-ylmethyl)benzamide dihydrochloride (7.2 g) and 3,3-ethylenedioxy-3-phenylpropyl bromide (6.0 g) were reacted and treated in the same manner as in Example 172 to give 9.2 g of 4-amino-5-chloro-N-((1-(3,3-ethylenedioxy-3-phenylpropyl)piperidin-4-yl)methyl)-2-methoxybenzamide.

$^1$H-NMR (CDCl$_3$,ppm) δ: 1.24–1.38(2 H,m), 1.53–1.71(3 H,m), 1.88–1.96(2 H,m), 2.10–2.19(2 H,m), 2.40–2.46(2 H,m), 2.86–2.90(2 H,m), 3.29(2 H,t,J=5.9 Hz), 3.73–3.77(2 H,m), 3.86(3 H,s), 3.97–4.02(2 H,m), 4.47(2 H,s), 6.29(1 H,s), 7.28–7.45(5 H,m), 7.70–7.74(1 H,m), 8.07(1 H,s)

(2) Methanol (40 ml) and 1N hydrochloric acid (100 ml) were added to 4-amino-5-chloro-N-((1-(3,3-ethylenedioxy-3-phenylpropyl)piperidin-4-yl)methyl)-2-methoxybenzamide (8.8 g), and the mixture was stirred at refluxing temperature for 1.5 hr. The reaction mixture was further stirred under ice-cooling for 1 hr, and the precipitated crystals were collected by filtration to give 6.7 g of 4-amino-5-chloro-2-methoxy-N-((1-(3-oxo-3-phenylpropyl) piperidin-4-yl)methyl)benzamide hydrochloride.
m.p. 141°–143° C.

EXAMPLE 281

4-Amino-5-chloro-2-methoxy-N-(piperidin-4-ylmethyl) benzamide dihydrochloride (7 g) and 2-(phenylsulfonyl) ethyl bromide (5.6 g) were reacted and treated in the same manner as in Example 199 to give 2.74 g of 4-amino-5-chloro-2-methoxy-N-((1-(2-(phenylsulfonyl)ethyl)-piperidin-4-yl)methyl)benzamide hydrochloride.
m.p. 116°–117° C.

EXAMPLE 282

4-Amino-5-chloro-2-methoxy-N-(piperidin-4-ylmethyl) benzamide dihydrochloride (7 g) and 4-bromo-1-phenyl-1-butanone (4.93 g) were reacted and treated in the same manner as in Example 172 to give 3.1 g of 4-amino-5-chloro-2-methoxy-N-((1-(4-oxo-4-phenylbutyl)piperidin-4-yl)methyl)benzamide.
m.p. 148°–150° C.

EXAMPLE 283

Triethylamine (0.59 g) and 2-methylthio-2-imidazoline hydroiodide (1.4 g) were added to a solution of 4-amino-N-((1-(5-aminopentyl)-piperidin-4-yl)methyl)-5-chloro-2-methoxybenzamide (1.5 g) in methanol (20 ml), and the mixture was stirred at refluxing temperature for 4 hr. A 10% aqueous sodium hydroxide solution was added to the reaction mixture, and the mixture was extracted with chloroform. The extract was washed with brine and dried. The solvent was evaporated under reduced pressure, and the obtained residue was purified by silica gel column chromatography to give 0.84 g of 4-amino-5-chloro-N-((1-(5-(imidazolin-2-ylamino)pentyl)piperidin-4-yl)methyl)-2-methoxybenzamide.

$^1$H-NMR (DMSO-d$_6$,ppm) δ: 1.12–1.61(11 H,m), 1.75–1.82(2 H,m), 2.18–2.23(2 H,m), 2.79–2.83(2 H,m), 3.06–3.17(4 H,m), 3.52(4 H,s), 3.82(3 H,s), 5.92(2 H,s), 6.49(1 H,s), 7.66(1 H,s), 7.85–7.89(1 H,m)

EXAMPLE 284

4-Amino-5-chloro-2-methoxy-N-(piperidin-4-ylmethyl) benzamide dihydrochloride (1.50 g) as a starting compound, 2-benzylsulfonylethyl chloride (1.21 g) and potassium carbonate (1.54 g) were reacted and treated in the same manner as in Example 199 to give 1.72 g of 4-amino-5-chloro-2-methoxy-N-((1-(2-benzylsulfonylethyl)piperidin-4-yl) methyl)-benzamide,
m.p. 220°–223° C.

EXAMPLE 285

4-Amino-5-chloro-2-methoxy-N-(piperidin-4-ylmethyl) benzamide dihydrochloride (8.00 g) as a starting compound, 3-benzylsulfonylpropyl chloride (6.03 g) and potassium carbonate (13.4 g) were reacted and purified in the same manner as in Example 199 to give 4.40 g of 4-amino-5-chloro-2-methoxy-N-((1-(3-benzylsulfonylpropyl) piperidin-4-yl)methyl)-benzamide, m.p. 166°–168° C.

EXAMPLE 286

4-Amino-5-chloro-2-methoxy-N-(piperidin-4-ylmethyl) benzamide dihydrochloride (5.20 g) as a starting compound, 3-(4-fluorobenzyl)-sulfonylpropyl chloride (3.50 g) and potassium carbonate (8.70 g) were reacted and purified in the same manner as in Example 199 to give 2.90 g of 4-amino-5-chloro-2-methoxy-N-((1-(3-(4-fluorobenzyl) sulfonylpropyl)piperidin-4-yl)methyl)benzamide, m.p. 147°–148° C.

EXAMPLE 287

4-Amino-5-chloro-2-methoxy-N-(piperidin-4-ylmethyl) benzamide dihydrochloride (10.0 g) as a starting compound, 3-(4-chlorobenzyl)-sulfonylpropyl chloride (8.66 g) and potassium carbonate (16.8 g) were reacted and purified in the same manner as in Example 199 to give 7.60 g of 4-amino-5-chloro-2-methoxy-N-((1-(3-(4-chlorobenzyl) sulfonylpropyl)-piperidin-4-yl)methyl)benzamide, m.p. 175°–177° C.

EXAMPLE 288

4-Amino-5-chloro-2-methoxy-N-(piperidin-4-ylmethyl) benzamide dihydrochloride (10.0 g) as a starting compound, 3-(4-methoxybenzyl)-sulfonylpropyl chloride (8.50 g) and potassium carbonate (16.8 g) were reacted and purified in the same manner as in Example 199 to give 7.60 g of 4-amino-5-chloro-2-methoxy-N-((1-(3-(4-methoxybenzyl)-sulfonylpropyl)piperidin-4-yl)methyl)benzamide, m.p. 111°–112° C.

EXAMPLE 289

4-Amino-5-chloro-2-methoxy-N-(piperidin-4-ylmethyl) benzamide dihydrochloride (4.00 g) as a starting compound, 2-(2-phenylethyl)-sulfonylethyl chloride (3.25 g), potassium carbonate (3.30 g) and potassium iodide (1.97 g) were reacted and purified in the same manner as in Example 199 to give 3.71 g of 4-amino-5-chloro-2-methoxy-N-((1-(2-(2-phenylethyl)sulfonylethyl)piperidin-4-yl)methyl) benzamide, m.p. 161°–162° C.

EXAMPLE 290

4-Amino-5-chloro-2-methoxy-N-(piperidin-4-ylmethyl) benzamide dihydrochloride (5.20 g) as a starting compound, 5-bromo-1-(4-hydroxyphenyl)-1-pentanone (3.60 g) and potassium carbonate (8.7 g) were reacted and purified in the same manner as in Example 172 to give 3.71 g of 4-amino-5-chloro-2-methoxy-N-((1-(5-(4-hydroxyphenyl)-5-oxopentyl)-piperidin-4-yl)methyl)benzamide, m.p. 154°–156° C.

EXAMPLE 291

4-Aminomethyl-1-(3-(4-hydroxyphenyl)-3-oxopropyl) piperidine dihydrobromide (9.00 g) as a starting compound, 4-amino-5-chloro-2-methoxybenzoic acid (4.28 g), triethylamine (8.82 ml), 1-hydroxybenzotriazole (3.00 g) and 1-ethyl-3-(3-dimethylaminopropyl)-carbodiimide (4.27 g) were reacted and purified in the same manner as in Example 270 to give 3.40 g of 4-amino-5-chloro-2-methoxy-N-((1-(3-(4-hydroxyphenyl)-3-oxopropyl)piperidin-4-yl)methyl) benzamide, m.p. 191°–193° C.

EXAMPLE 292

4-Aminomethyl-1-(4-(4-hydroxyphenyl)-4-oxobutyl) piperidine dihydrobromide (3.67 g) as a starting compound, 4-amino-5-chloro-2-methoxybenzoic acid (1.69 g), triethylamine (4.65 ml), 1-hydroxybenzotriazole (1.20 g) and 1-ethyl-3-(3-dimethylaminopropyl)carbodiimide (1.69 g) were reacted and purified in the same manner as in Example 270 to give 3.03 g of 4-amino-5-chloro-2-methoxy-N-((1-(4-(4-hydroxyphenyl)-4-oxobutyl)piperidin-4-yl)methyl) benzamide, m.p. 199°–201° C.

EXAMPLE 293

4-Aminomethyl-1-(6-(2-hydroxyphenyl)-6-oxohexyl) piperidine dihydrochloride (1.54 g) as a starting compound, 4-amino-5-chloro-2-methoxybenzoic acid (0.82 g), triethylamine (1.7 ml), 1-hydroxybenzotriazole (0.58 g) and 1-ethyl-3-(3-dimethylaminopropyl)carbodiimide (0.82 g) were reacted and purified in the same manner as in Example 270 to give 1.15 g of 4-amino-5-chloro-2-methoxy-N-((1-(6-(2-hydroxyphenyl)-6-oxohexyl)piperidin-4-yl)methyl) benzamide hydrochloride, m.p. 143°–145° C.

EXAMPLE 294

4-Amino-5-chloro-2-methoxy-N-(piperidin-4-ylmethyl) benzamide dihydrochloride (0.96 g) as a starting compound, 6-bromo-1-(3-hydroxyphenyl)-1-hexanone (0.70 g) and potassium carbonate (1.60 g) were reacted and purified in the same manner as in Example 172 to give 0.17 g of 4-amino-5-chloro-2-methoxy-N-((1-(6-(3-hydroxyphenyl)-6-oxohexyl)-piperidin-4-yl)methyl)benzamide as a brown oil.

EXAMPLE 295

4-Amino-5-chloro-2-methoxy-N-(piperidin-4-ylmethyl) benzamide dihydrochloride (3.87 g) as a starting compound, 6-bromo-1-(2,4-dihydroxyphenyl)-1-hexanone (3.00 g) and triethylamine (6.5 ml) were reacted and purified in the same manner as in Example 172 to give 0.97 g of 4-amino-5-chloro-2-methoxy-N-((1-(6-(2,4-dihydroxyphenyl)-6-oxohexyl)piperidin- 4-yl)methyl)benzamide, m.p. 96°–99° C.

EXAMPLE 296 cis-4-Amino-5-chloro-2-methoxy-N-((3-methoxypiperidin-4-yl)methyl)-benzamide dihydrochloride (0.88 g) as a starting compound, 6-bromo-1-phenyl-1-hexanone (0.67 g) and potassium carbonate (1.37 g) were reacted and purified in the same manner as in Example 172 to give 0.67 g of cis-4-amino-5-chloro-2-methoxy-N-((3-methoxy-1-(6-oxo-6-phenylhexyl)-piperidin-4-yl)methyl) benzamide, m.p. 99°–101° C.

EXAMPLE 297

To a suspension of 4-amino-5-chloro-2-methoxy-N-((1-(6-(4-hydroxyphenyl)-6-oxohexyl)piperidin-4-yl)methyl) benzamide (10.0 g) in dichloromethane (60 ml) were added triethylamine (12.5 ml) and acetic anhydride (2.5 ml), and the resulting mixture was stirred at room temperature for 1 hr. The reaction mixture was concentrated under reduced pressure. Water was added to the residue and the mixture was extracted with chloroform. The organic layer was washed with brine and dried. The solvent was evaporated under reduced pressure and the obtained crystals were recrystallized from a mixed solvent of ethanolethyl acetate to give 8.50 g of 4-amino-5-chloro-2-methoxy-N-((1-(6-(4-acetoxyphenyl)-6-oxohexyl)piperidin-4-yl)methyl) benzamide acetate, m.p. 140°–141° C.

EXAMPLE 298

(1) To a solution of cis-4-amino-5-chloro-N-((3-hydroxy-1-tert-butoxycarbonyl)piperidin-4-ylmethyl)-2-methoxybenzamide (0.8 g) and potassium carbonate (1.43 g) in dimethylformamide (15 ml) was added 4,4-ethylenedioxy-4-phenylbutyl bromide (0.56 g), and the resulting mixture was stirred at 120° C. for 6 hr. Water was added to the reaction mixture and the mixture was extracted with chloroform. The organic layer was washed with brine and dried. The solvent was evaporated under reduced pressure and the residue was purified by silica gel column chromatography (chloroform:methanol=10:1) to give 0.8 g of cis-4-amino-5-chloro-N-((1-(4,4-ethylenedioxy-4- phenylbutyl)-3-hydroxy)-piperidin-4-ylmethyl)-2-methoxybenzamide.

$^1$H-NMR(CDCl$_3$, ppm) δ: 1.40–2.12(10 H,m), 2.26–2.37(2 H,m), 2.80–2.99(2 H,m), 3.26–3.57(2 H,m), 3.71–3.79(3 H,m), 3.87(3 H,s), 3.97–4.03(2 H,m), 4.42(2 H,br), 6.29(1 H,s), 7.25–7.47(5 H,m), 7.95–8.03(1 H,m), 8.08(1 H,s)

(2) To a solution of cis-$^4$-amino-5-chloro-N-((1-(4,4-ethylenedioxy-4-phenylbutyl)-3-hydroxy)piperidin-4-ylmethyl)-2-methoxybenzamide (0.74 g) in methanol (4 ml) was added 1N hydrochloric acid solution (10 ml), and the resulting mixture was stirred at refluxing temperature for 1.5 hr. The resulting crystals were collected by filtration to give 0.45 g of cis-4-amino-5-chloro-N-((3-hydroxy-1-(4-oxo-4-phenylbutyl))-piperidin-4-ylmethyl)-2-methoxybenzamide hydrochloride, m.p. 145°–148° C.

EXAMPLE 299

4-Amino-5-chloro-2-methoxy-N-(piperidin-4-ylmethyl)benzamide dihydrochloride (6 g) as a starting compound, potassium carbonate (10.1 g) and 3-benzyloxypropyl bromide (4.45 g) were reacted and treated in the same manner as in Example 199 to give 7.1 g of 4-amino-N-((1-(3-benzyloxypropyl)piperidin-4-yl)methyl)-5-chloro-2-methoxybenzamide, m.p. 82°–83° C.

EXAMPLE 300

4-Amino-5-chloro-2-methoxy-N-(piperidin-4-ylmethyl)benzamide dihydrochloride (6 g) as a starting compound, potassium carbonate (10.1 g) and 2-benzyloxyethyl chloride (3 g) were reacted and treated in the same manner as in Example 199 to give 6.36 g of 4-amino-N-((1-(2-benzyloxyethyl)piperidin-4-yl)methyl)-5-chloro-2-methoxybenzamide, m.p. 123°–125° C.

The formulation example of the compound of the present invention as a medicament is given in the following.

Formulation Example

| | |
|---|---|
| Compound of the invention | 10.0 (mg per tablet) |
| Lactose | 109.6 |
| Microcrystalline cellulose | 27.4 |
| Light anhydrous silicic acid | 1.5 |
| Magnesium stearate | 1.5 |

The compound of the present invention (30 g), lactose (328.8 g) and microcrystalline cellulose (82.8 g) are mixed. The mixture is compressed using a roller compactor to give flake-like compression product. Using a hammer mill, the flake-like compression product is pulverized. The pulverized product is passed through a 20-mesh sieve. Light anhydrous silicic acid (4.5 g) and magnesium stearate (4.5 g) are added and mixed. The mixture is punched with a 7.5 mm diameter pounder to give 3,000 tablets weighing 150 mg per tablet.

This application is based on application Nos. 60941/1994, 153686/1994, 7492/1995, 244040/1995, 77232/1996 and 68739/1997 filed in Japan, the contents of which are incorporated hereinto by reference.

What is claimed is:
1. A benzoic acid compound of the formula

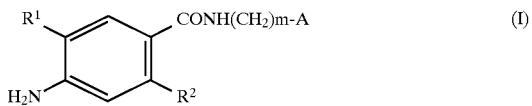
(I)

wherein
  $R^1$ is a halogen;
  $R^2$ is a lower alkoxy, a substituted lower alkoxy, a cycloalkyloxy or a cycloalkylalkoxy;
  m is 1 or 2; and
  A is

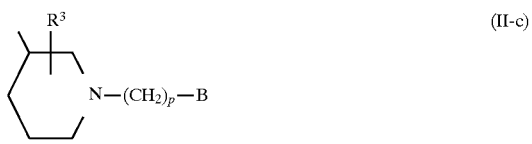
(II-c)

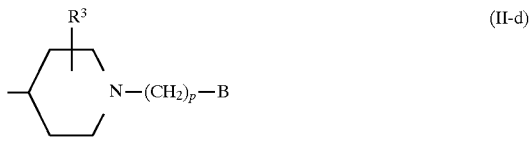
(II-d)

wherein
  $R^3$ is hydrogen, hydroxy, lower alkyl or lower alkoxy, p is an integer of 1–10, q is 2 or 3, and B is a group of the formula

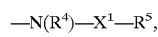—N(R$^4$)—X$^1$—R$^5$,

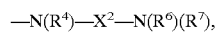—N(R$^4$)—X$^2$—N(R$^6$)(R$^7$),

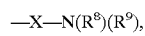—X—N(R$^8$)(R$^9$),

—Het,

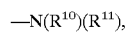—N(R$^{10}$)(R$^{11}$),

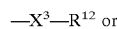—X$^3$—R$^{12}$ or

—X$^4$—R$^{13}$ wherein
  X$^1$ is CO, CS or SO$_2$, X$^2$ is CO or CS, R$^4$ is hydrogen, lower alkyl, phenyl, substituted phenyl, aralkyl or substituted aralkyl, R$^5$ is lower alkyl, cycloalkyl, crosslinked cycloalkyl, aryl, substituted aryl, aralkyl, substituted aralkyl, heteroaryl, substituted heteroaryl, heteroarylalkyl, substituted heteroarylalkyl or

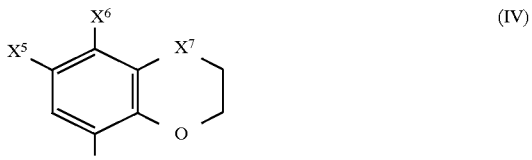
(IV)

wherein X$^5$ is halogen, X$^6$ is hydrogen or amino, and X$^7$ is a direct bond, methylene, oxygen atom, NH or N—CH$_3$,
  R$^6$ and R$^7$ are the same or different and each is hydrogen, lower alkyl, cycloalkyl, aryl, substituted aryl, aralkyl or substituted aralkyl, or R$^6$ and R$^7$ optionally form a ring together with the adjacent nitrogen atom, R$^8$ and R$^9$ are the same or different and each is hydrogen, lower alkyl, cycloalkyl, aryl, substituted aryl, aralkyl or substituted aralkyl or $R^8$ and $R^9$ optionally form a ring together with the adjacent nitrogen atom, Het is a 5- or 6-membered mono- or bicyclic heterocycle having amide or urea in the ring and having 1 to 5 hetero atom(s) selected from the group consisting of oxygen atom, sulfur atom and nitrogen atom, $R^{10}$ and $R^{11}$ are the same or different and each is hydrogen, lower alkyl, cycloalkyl, cycloalkylalkyl, aryl, substituted aryl, aralkyl, substituted aralkyl, heteroaryl, substituted heteroaryl, heteroarylalkyl or substituted heteroarylalkyl, $X^3$ is oxygen atom or sulfur atom, $R^{12}$ is lower alkyl, cycloalkyl, cycloalkylalkyl, aryl, substituted aryl, aralkyl, substituted aralkyl, heteroaryl, substituted heteroaryl, heteroarylalkyl or substituted heteroarylalkyl, $X^4$ is CO, CS, SO or $SO_2$, and $R^{13}$ is hydrogen, lower alkyl, cycloalkyl, cycloalkylalkyl, aryl, substituted aryl, aralkyl, substituted aralkyl, heteroaryl, substituted heteroaryl, heteroarylalkyl or substituted heteroarylalkyl, an optical isomer thereof or a pharmaceutically acceptable salt thereof.

2. A benzoic acid compound of the formula

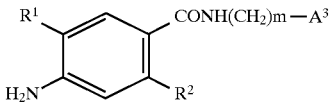
(I-1)

wherein $R^1$ is a halogen;

$R^2$ is a lower alkoxy, a substituted lower alkoxy, a cycloalkyloxy or a cycloalkylalkoxy;

m is 1 or 2; and $A^3$ is

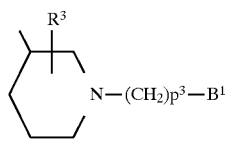
(II-1-c)

or

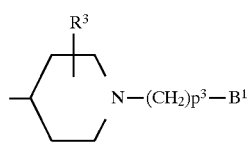
(II-1-d)

wherein $R^3$ is hydrogen, hydroxy, lower alkyl or lower alkoxy, $p^3$ is an integer of 1–6, q is 2 or 3, and $B^1$ is a group of the formula

—N($R^4$)—$X^1$—$R^5$,

—N($R^4$)—$X^2$—N($R^6$)($R^7$),

—$X^1$—N($R^8$)($R^9$) or

—Het wherein $X^1$ is CO, CS or $SO_2$, $X^2$ is CO or CS, $R^4$ is hydrogen, lower alkyl, phenyl, substituted phenyl, aralkyl or substituted aralkyl, $R^5$ is lower alkyl, cycloalkyl, crosslinked cycloalkyl, aryl, substituted aryl, aralkyl, substituted aralkyl, heteroaryl, substituted heteroaryl, heteroarylalkyl, substituted heteroarylalkyl or

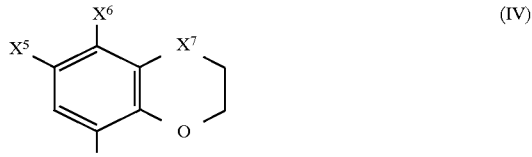
(IV)

wherein $X^5$ is halogen, $X^6$ is hydrogen or amino, and $X^7$ is a direct bond, methylene, oxygen atom, NH or N—$CH_3$, $R^6$ and $R^7$ are the same or different and each is hydrogen, lower alkyl, cycloalkyl, aryl, substituted aryl, aralkyl or substituted aralkyl, or $R^6$ and $R^7$ optionally form a ring together with the adjacent nitrogen atom, $R^8$ and $R^9$ are the same or different and each is hydrogen, lower alkyl, cycloalkyl, aryl, substituted aryl, aralkyl or substituted aralkyl or $R^8$ and $R^9$ optionally form a ring together with the adjacent nitrogen atom, and Het is a 5- or 6-membered mono- or bicyclic heterocycle having amide or urea in the ring and having 1 to 5 hetero atom(s) selected from the group consisting of oxygen atom, sulfur atom and nitrogen atom, an optical isomer thereof or a pharmaceutically acceptable salt thereof.

3. The benzoic acid compound of claim 2, which is expressed by the formula

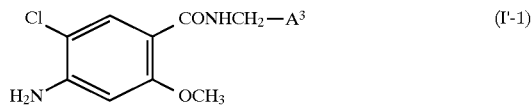
(I'-1)

wherein $A^3$ is as defined in claim 2, an optical isomer thereof or a pharmaceutically acceptable salt thereof.

4. The benzoic acid compound of claim 2, which is expressed by the formula

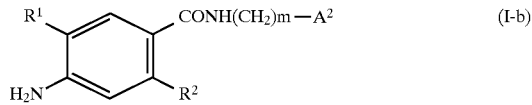
(I-b)

wherein $R^1$, $R^2$ and m are as defined in claim 2, and $A^2$ is

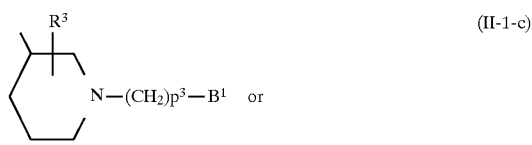
(II-1-c)

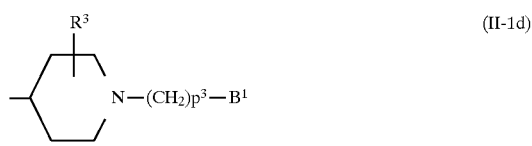
(II-1d)

wherein $R^3$, $p^3$ and $B^1$ are as defined in claim 2, an optical isomer thereof or a pharmaceutically acceptable salt thereof.

5. The benzoic acid compound of claim 4, which is expressed by the formula

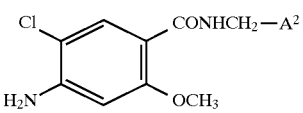

(I'-1-b)

wherein $A^2$ is as defined in claim 4,
an optical isomer thereof or a pharmaceutically acceptable salt thereof.

6. The benzoic acid compound of claim 2, wherein $B^1$ is a group of the formula

—N($R^4$)—CO—$R^5$,

—N($R^4$)—CO—N($R^6$)($R^7$),

—CO—N($R^8$)($R^9$) or

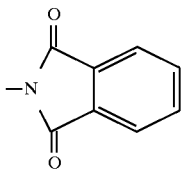

wherein $R^4$, $R^5$, $R^6$, $R^7$, $R^8$ and $R^9$ are as defined in claim 2, an optical isomer thereof or a pharmaceutically acceptable salt thereof.

7. The benzoic acid compound of claim 2, wherein $B^1$ is a group of the formula

—NHCOR$^5$ wherein $R^5$ is as defined in claim 2,
an optical isomer thereof or a pharmaceutically acceptable salt thereof.

8. The benzoic acid compound of claim 2, wherein $B^1$ is a group of the formula —NHCONHR$^{6\ a}$ wherein $R^{6\ a}$ is hydrogen, lower alkyl, cycloalkyl, aryl, substituted aryl, aralkyl or substituted aralkyl,
an optical isomer thereof or a pharmaceutically acceptable salt thereof.

9. The benzoic acid compound of claim 2, wherein $B^1$ is a group of the formula —CONHR$^{8\ a}$ wherein $R^{8\ a}$ is hydrogen, lower alkyl, cycloalkyl, aryl, substituted aryl, aralkyl or substituted aralkyl,
an optical isomer thereof or a pharmaceutically acceptable salt thereof.

10. The benzoic acid compound of claim 2, wherein $R^5$ is aryl, substituted aryl, aralkyl, heteroaryl or substituted heteroaryl,
an optical isomer thereof or a pharmaceutically acceptable salt thereof.

11. The benzoic acid compound of claim 2, wherein $R^6$ is lower alkyl, aryl or substituted aryl, and $R^7$ is hydrogen,
an optical isomer thereof or a pharmaceutically acceptable salt thereof.

12. The benzoic acid compound of claim 2, wherein $R^8$ is aryl or substituted aryl, and $R^9$ is hydrogen,
an optical isomer thereof or a pharmaceutically acceptable salt thereof.

13. The benzoic acid compound of claim 2, wherein $R^5$ is 1-methyl-3-indolyl, 1-isopropyl-3-indolyl, 1-benzyl-3-indolyl, 1-naphthyl, 2-naphthyl, phenyl, 2-chlorophenyl, 3-chlorophenyl, 4-chlorophenyl, 4-methylphenyl, 4-nitrophenyl, 4-amino-5-chloro-2-methoxyphenyl, 2-thienyl or 3-phenylpropyl,
an optical isomer thereof or a pharmaceutically acceptable salt thereof.

14. The benzoic acid compound of claim 2, wherein $R^6$ is ethyl, propyl, phenyl or 4-chlorophenyl,
an optical isomer thereof or a pharmaceutically acceptable salt thereof.

15. The benzoic acid compound of claim 2, wherein $R^8$ is phenyl,
an optical isomer thereof or a pharmaceutically acceptable salt thereof.

16. The benzoic acid compound of claim 2, wherein $p^3$ is an integer of 3 to 6,
an optical isomer thereof or a pharmaceutically acceptable salt thereof.

17. The benzoic acid compound of claim 2, wherein $p^3$ is an integer of 4 or 5,
an optical isomer thereof or a pharmaceutically acceptable salt thereof.

18. The benzoic acid compound of claim 2, wherein $R^3$ is hydrogen, $p^3$ is an integer of 2–5, and $B^1$ is a group of the formula —NHCOR$^{5\ a}$, —NHCONHR$^{6\ b}$, —CONHR$^{8\ b}$ or

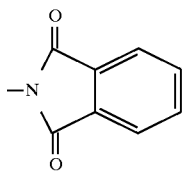

wherein $R^{5\ a}$ is aryl, substituted aryl, aralkyl, heteroaryl or substituted heteroaryl, $R^{6\ b}$ is lower alkyl, aryl or substituted aryl, and $R^{8\ b}$ is aryl or substituted aryl,
an optical isomer thereof or a pharmaceutically acceptable salt thereof.

19. The benzoic acid compound of claim 4, wherein $A^2$ is a group of the formula

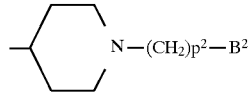

wherein $p^2$ is 4 or 5, and $B^2$ is a group of the formula

—NHCOR$^{5\ a}$ or

—NHCONHR$^{6\ b}$ wherein $R^{5\ a}$ is aryl, substituted aryl, heteroaryl or substituted heteroaryl, and $R^{6\ b}$ is lower alkyl, aryl or substituted aryl, or a pharmaceutically acceptable salt thereof.

20. The benzoic acid compound of claim 2, which is a member selected from the group consisting of:
N - ( 4 - ( 4 - ( 4 - a m i n o - 5 - c h l o r o - 2 - methoxybenzoylaminomethyl)piperidin-1-yl)butyl)-1-methyl-1 H-indole-3-carboxamide,
4 - a m i n o - 5 - c h l o r o - 2 - m e t h o x y - N - ( 1 - ( 4 - ( 1 - naphthoylamino)butyl)-piperidin-4-ylmethyl)benzamide, 4-amino-5-chloro-2-methoxy-N-(1-(4-(2-naphthoylamino)butyl)-piperidin-4-ylmethyl)benzamide, 4-amino-N-(1-(5-benzoylaminopentyl)piperidin-4-ylmethyl)-5-chloro-2-methoxybenzamide, 4-amino-5-chloro-N-(1-(5-(3-chlorobenzoylamino)pentyl)piperidin-4-ylmethyl)-2-methoxybenzamide, 4-amino-5-chloro-N-(1-(5-(4-methylbenzoylamino)pentyl)piperidin-4-ylmethyl)-2-methoxybenzamide and N-(5-(4-(4-amino-5-chloro-2-methoxybenzoylaminomethyl)piperidin-1-yl)pentyl)-1-methyl-1 H-indole-3-carboxamide, or a pharmaceutically acceptable salt thereof.

21. The benzoic acid compound of claim 2, which is a member selected from the group consisting of:

4-amino-5-chloro-2-methoxy-N-(1-(4-(3-n-propylureido)butyl)-piperidin-4-ylmethyl)benzamide, 4-amino-5-chloro-2-methoxy-N-(1-(5-(3-n-propylureido)pentyl)-piperidin-4-ylmethyl)benzamide, and 4-amino-5-chloro-N-(1-(5-(3-(4-chlorophenyl)ureido)pentyl)piperidin-4-ylmethyl)-2-methoxybenzamide, or a pharmaceutically acceptable salt thereof.

22. A benzoic acid compound of the formula

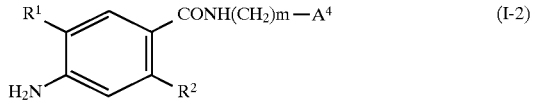

wherein $R^1$ is a halogen;

$R^2$ is a lower alkoxy, a substituted lower alkoxy, a cycloalkyloxy or a cycloalkylalkoxy;

m is 1 or 2; and $A^4$ is

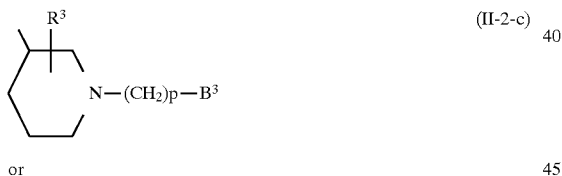

or wherein $R^3$ is hydrogen, hydroxy, lower alkyl or lower alkoxy, p is an integer of 1–10, q is 2 or 3, and $B^3$ is a group of the formula

wherein $R^{10}$ and $R^{11}$ are the same or different and each is hydrogen, lower alkyl, cycloalkyl, cycloalkylalkyl, aryl, substituted aryl, aralkyl, substituted aralkyl, heteroaryl, substituted heteroaryl, heteroarylalkyl or substituted heteroarylalkyl, $X^3$ is oxygen atom or sulfur atom, $R^{12}$ is lower alkyl, cycloalkyl, cycloalkylalkyl, aryl, substituted aryl, aralkyl, substituted aralkyl, heteroaryl, substituted heteroaryl, heteroarylalkyl or substituted heteroarylalkyl, $X^4$ is CO, CS, SO or $SO_2$, and $R^{13}$ is hydrogen, lower alkyl, cycloalkyl, cycloalkylalkyl, aryl, substituted aryl, aralkyl, substituted aralkyl, heteroaryl, substituted heteroaryl, heteroarylalkyl or substituted heteroarylalkyl, an optical isomer thereof or a pharmaceutically acceptable salt thereof.

23. A benzoic acid compound of the formula

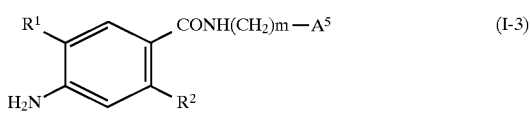

wherein $R^1$ is a halogen;

$R^2$ is a lower alkoxy, a substituted lower alkoxy, a cycloalkyloxy or a cycloalkylalkoxy;

m is 1 or 2; and $A^5$ is

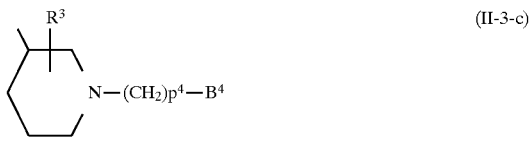

or

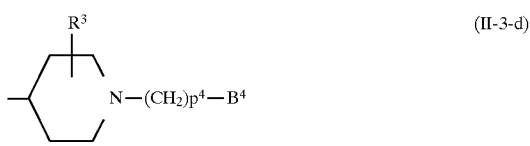

wherein $R^3$ is hydrogen, hydroxy, lower alkyl or lower alkoxy, $p^4$ is an integer of 1–8, q is 2 or 3, and $B^4$ is a group of the formula

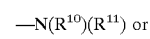

wherein $R^{10}$ and $R^{11}$ are the same or different and each is hydrogen, lower alkyl, cycloalkyl, cycloalkylalkyl, aryl, substituted aryl, aralkyl, substituted aralkyl, heteroaryl, substituted heteroaryl, heteroarylalkyl or substituted heteroarylalkyl, $X^3$ is oxygen atom or sulfur atom, and $R^{12}$ is lower alkyl, cycloalkyl, cycloalkylalkyl, aryl, substituted aryl, aralkyl, substituted aralkyl, heteroaryl, substituted heteroaryl, heteroarylalkyl or substituted heteroarylalkyl, an optical isomer thereof or a pharmaceutically acceptable salt thereof.

24. The benzoic acid compound of claim 23, which is expressed by the formula

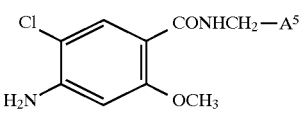 (I'-3)

wherein $A^5$ is as defined in claim 23,
an optical isomer thereof or a pharmaceutically acceptable salt thereof.

25. The benzoic acid compound of claim 23, which is expressed by the formula

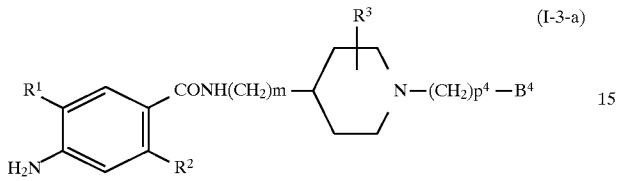 (I-3-a)

wherein $R^1$, $R^2$, $R^3$, m, $p^4$ and $B^4$ are as defined in claim 23, ps or a pharmaceutically acceptable salt thereof.

26. The benzoic acid compound of claim 23, which is expressed by the formula

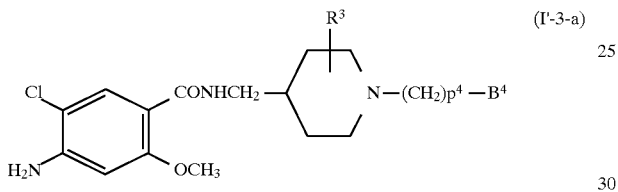 (I'-3-a)

wherein $R^3$, $p^4$ and $B^4$ are as defined in claim 23, or a pharmaceutically acceptable salt thereof.

27. The benzoic acid compound of claim 23, wherein $R^{10}$ and $R^{11}$ are the same or different and each is hydrogen, lower alkyl, cycloalkylalkyl, aralkyl, substituted aralkyl, heteroarylalkyl or substituted heteroarylalkyl,
an optical isomer thereof or a pharmaceutically acceptable salt thereof.

28. The benzoic acid compound of claim 23, wherein $R^{12}$ is aryl, substituted aryl, aralkyl or substituted aralkyl,
an optical isomer thereof or a pharmaceutically acceptable salt thereof.

29. The benzoic acid compound of claim 23, wherein $p^4$ is an integer of 3 to 8,
an optical isomer thereof or a pharmaceutically acceptable salt thereof.

30. The benzoic acid compound of claim 23, wherein $p^4$ is an integer of 4 to 6,
an optical isomer thereof or a pharmaceutically acceptable salt thereof.

31. The benzoic acid compound of claim 23, which is a member selected from the group consisting of:

4-amino-5-chloro-N-((1-(6-(N-ethyl-N-benzylamino) hexyl)piperidin-4-yl)methyl)-2-methoxybenzamide, 4-amino-5-chloro-N-((1-(5-(N-benzylamino)pentyl) piperidin-4-yl)-methyl)-2-methoxybenzamide, 4-amino-5-chloro-2-methoxy-N-((1-(5-(1-naphthylmethylamino)pentyl)-piperidin-4-yl)methyl) benzamide, 4-amino-5-chloro-N-((1-(5-(N-ethyl-N-(4-fluorobenzyl) amino)pentyl)-piperidin-4-yl)methyl)-2-methoxybenzamide, 4-amino-5-chloro-2-methoxy-N-((1-(5-(N-n-propyl-N-benzylamino)-pentyl)piperidin-4-yl)methyl) benzamide, 4-amino-5-chloro-N-((1-(5-(cyclohexylmethylamino) pentyl)piperidin-4-yl)methyl)-2-methoxybenzamide, 4-amino-5-chloro-N-((1-(4-(N-(3,4-dichlorobenzyl)-N-ethylamino)-butyl)piperidin-4-yl)methyl)-2-methoxybenzamide, 4-amino-5-chloro-N-((1-(6-(3,4-dichlorobenzylamino) hexyl)piperidin-4-yl)methyl)-2-methoxybenzamide, 4-amino-5-chloro-N-((1-(6-(N-ethyl-N-(4-methylbenzyl) amino)hexyl)-piperidin-4-yl)methyl)-2-methoxybenzamide, 4-amino-5-chloro-N-((1-(6-(N-ethyl-N-(4-nitrobenzyl) amino)hexyl)-piperidin-4-yl)methyl)-2-methoxybenzamide, 4-amino-5-chloro-2-methoxy-N-((1-(5-(4-methylbenzylamino)pentyl)-piperidin-4-yl)methyl) benzamide, 4-amino-5-chloro-N-((1-(6-(N-ethyl-N-(2-thienylmethyl) amino)hexyl)-piperidin-4-yl)methyl)-2-methoxybenzamide, 4-amino-5-chloro-2-methoxy-N-((1-(5-(2-naphthylmethylamino)pentyl)-piperidin-4-yl)methyl) benzamide, 4-amino-5-chloro-2-methoxy-N-((1-(6-(4-methoxybenzylamino)hexyl)-piperidin-4-yl)methyl) benzamide and 4-amino-5-chloro-2-methoxy-N-((1-(6-(2-thienylmethylamino)hexyl)-piperidin-4-yl)methyl) benzamide, or a pharmaceutically acceptable salt thereof.

32. The benzoic acid compound of claim 23, which is a member selected from the group consisting of:

4-amino-N-((1-(5-benzylthiopentyl)piperidin-4-yl) methyl)-5-chloro-2-methoxybenzamide, 4-amino-N-((1-(5-benzyloxypentyl)piperidin-4-yl) methyl)-5-chloro-2-methoxybenzamide, 4-amino-5-chloro-2-methoxy-N-((1-(5-phenoxypentyl) piperidin-4-yl)-methyl)benzamide, 4-amino-5-chloro-2-methoxy-N-((1-(5-phenylthiopentyl) piperidin-4-yl)-methyl)benzamide, 4-amino-5-chloro-N-((1-(5-(4-chlorobenzyloxy)pentyl) piperidin-4-yl)-methyl)-2-methoxybenzamide, 4-amino-5-chloro-2-methoxy-N-((1-(4-phenoxybutyl) piperidin-4-yl)-methyl)benzamide and 4-amino-N-((1-(6-benzyloxyhexyl)piperidin-4-yl) methyl)-5-chloro-2-methoxybenzamide, or a pharmaceutically acceptable salt thereof.

33. A benzoic acid compound of the formula

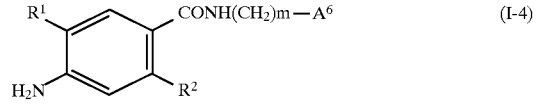 (I-4)

wherein $R^1$ is a halogen;

$R^2$ is a lower alkoxy, a substituted lower alkoxy, a cycloalkyloxy or a cycloalkylalkoxy;

m is 1 or 2; and $A^6$ is

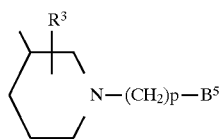

(II-4-c)

or

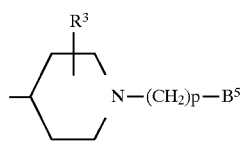

(II-4-d)

wherein
$R^3$ is hydrogen, hydroxy, lower alkyl or lower alkoxy, p is an integer of 1–10, q is 2 or 3, and $B^5$ is a group of the formula

wherein
$X^4$ is CO, CS, SO or $SO_2$, and $R^{13}$ is hydrogen, lower alkyl, cycloalkyl, cycloalkylalkyl, aryl, substituted aryl, aralkyl, substituted aralkyl, heteroaryl, substituted heteroaryl, heteroarylalkyl or substituted heteroarylalkyl,
an optical isomer thereof or a pharmaceutically acceptable salt thereof.

34. The benzoic acid compound of claim 33, which is expressed by the formula

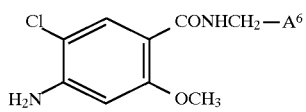

(I'-4)

wherein $A^6$ is as defined in claim 33,
an optical isomer thereof or a pharmaceutically acceptable salt thereof.

35. The benzoic acid compound of claim 33, which is expressed by the formula

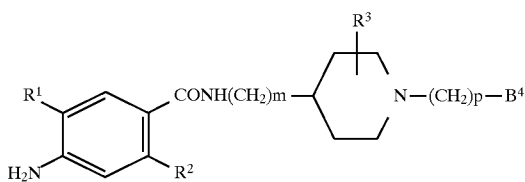

(I-4-a)

wherein $R^1$, $R^2$, $R^3$, m, p and $B^5$ are as defined in claim 33, or a pharmaceutically acceptable salt thereof.

36. The benzoic acid compound of claim 33, which is expressed by the formula

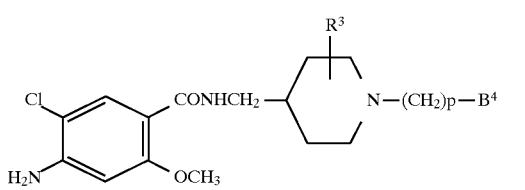

(I'-4-a)

wherein $R^3$, p and $B^5$ are as defined in claim 33, or a pharmaceutically acceptable salt thereof.

37. The benzoic acid compound of claim 33, wherein $X^4$ is CO and $R^{13}$ is aryl, substituted aryl, heteroaryl or substituted heteroaryl,
an optical isomer thereof or a pharmaceutically acceptable salt thereof.

38. The benzoic acid compound of claim 33, wherein $X^4$ is $SO_2$ and $R^{13}$ is aryl, substituted aryl, aralkyl or substituted aralkyl,
an optical isomer thereof or a pharmaceutically acceptable salt thereof.

39. The benzoic acid compound of claim 33, wherein p is an integer of 3 to 8,
an optical isomer thereof or a pharmaceutically acceptable salt thereof.

40. The benzoic acid compound of claim 33, wherein p is an integer of 4 to 6,
an optical isomer thereof or a pharmaceutically acceptable salt thereof.

41. The benzoic acid compound of claim 33, which is a member selected from the group consisting of:
  4-amino-5-chloro-2-methoxy-N-((1-(6-oxo-6-phenylhexyl)piperidin-4-yl)methyl)benzamide,
  4-amino-5-chloro-2-methoxy-N-((1-(7-oxo-7-phenylheptyl)piperidin-4-yl)methyl)benzamide,
  4-amino-5-chloro-2-methoxy-N-((1-(6-(1-isopropyl-1H-indol-3-yl)-6-oxohexyl)piperidin-4-yl)methyl)benzamide,
  4-amino-5-chloro-2-methoxy-N-((1-(6-(1-ethyl-1H-indol-3-yl)-6-oxohexyl)piperidin-4-yl)methyl)benzamide,
  4-amino-5-chloro-2-methoxy-N-((1-(6-(1-naphthyl)-6-oxohexyl)-piperidin-4-yl)methyl)benzamide,
  4-amino-5-chloro-N-((1-(6-(3-fluoro-4-methoxyphenyl)-6-oxohexyl)-piperidin-4-yl)methyl)-2-methoxybenzamide,
  4-amino-5-chloro-N-((1-(6-(3-chloro-4-methoxyphenyl)-6-oxohexyl)-piperidin-4-yl)methyl)-2-methoxybenzamide,
  4-amino-5-chloro-N-((1-(6-(3,4-dimethoxyphenyl)-6-oxohexyl)piperidin-4-yl)methyl)-2-methoxybenzamide,
  4-amino-5-chloro-N-((1-(6-(4-hydroxyphenyl)-6-oxohexyl)piperidin-4-yl)methyl)-2-methoxybenzamide,
  4-amino-5-chloro-2-methoxy-N-((1-(6-(1-methyl-1H-indol-3-yl)-6-oxohexyl)piperidin-4-yl)methyl)benzamide,
  4-amino-5-chloro-2-methoxy-N-((1-(5-(1-methyl-1H-indol-3-yl)-5-oxopentyl)piperidin-4-yl)methyl)benzamide,
  4-amino-5-chloro-2-methoxy-N-((1-(7-(1-methyl-1H-indol-3-yl)-7-oxoheptyl)piperidin-4-yl)methyl)benzamide,
  4-amino-5-chloro-2-methoxy-N-((1-(5-oxo-5-phenylpentyl)piperidin-4-yl)methyl)benzamide and
  4-amino-5-chloro-2-methoxy-N-((1-(6-(1H-indol-3-yl)-6-oxohexyl)-piperidin-4-yl)methyl)benzamide,
or a pharmaceutically acceptable salt thereof.

42. The benzoic acid compound of claim 33, which is a member selected from the group consisting of:
  4-amino-5-chloro-2-methoxy-N-((1-(4-phenylsulfonylbutyl)piperidin-4-yl)methyl)benzamide and
  4-amino-5-chloro-2-methoxy-N-((1-(5-phenylsulfonylpentyl)piperidin-4-yl)methyl)benzamide,
or a pharmaceutically acceptable salt thereof.

43. The benzoic acid compound of claim 33, which is 4-amino-5-chloro-2-methoxy-N-((1-(3-benzylsulfonylpropyl)piperidin-4-yl)methyl)-benzamide, or a pharmaceutically acceptable salt thereof.

44. A pharmaceutical composition comprising a benzoic acid compound of claim 1, 2, 22, 23 or 33 an optical isomer thereof or a pharmaceutically acceptable salt thereof, and a pharmaceutically acceptable additive.

45. A method for activation of serotonin 4 receptors comprising administering a benzoic acid compound of claim 1, 2, 22, 23 or 33 or an optical isomer thereof or a pharmaceutically acceptable salt thereof as an active ingredient to the patients in need of treatment.

46. A method for promotion of gastrointestinal motility comprising administering a benzoic acid compound of claim 1, 2, 22, 23 or 33 or an optical isomer thereof or a pharmaceutically acceptable salt thereof as an active ingredient to the patients in need of treatment.

47. A method of treatment for various gastrointestinal diseases selected from the group consisting of reflux esophagitis; gastroesophageal reflux; Barrett syndrome; intestinal pseudoileus; acute or chronic gastritis; gastric or duodenal ulcer; Crohn's disease; non-ulcer dyspepsia; ulcerative colitis; postgastrectomy syndrome; postoperative digestive function failure; delayed gastric emptying caused by gastric neurosis, gastroptosis or diabetes; gastrointestinal disorders; and irritable bowel syndrome, which comprises administering a benzoic acid compound of claim 1, 2, 22, 23, or 33 or an optical isomer thereof or a pharmaceutically acceptable salt thereof as an active ingredient to the patients in need of treatment.

48. A method of treatment for various gastrointestinal diseases selected from the group consisting of indigestion, meteorism, abdominal indefinite complaint, atonic constipation, chronic constipation and constipation caused by spinal cord injury or pelvic diaphragm failure, which comprises administering a benzoic acid compound of claim 1, 2, 22, 23 or 33 or an optical isomer thereof or a pharmaceutically acceptable salt thereof as an active ingredient to the patients in need of treatment.

* * * * *

UNITED STATES PATENT AND TRADEMARK OFFICE
CERTIFICATE OF CORRECTION

PATENT NO. : 5,864,039
DATED : January 26, 1999
INVENTOR(S) : Takeshi KAWAKITA et al.

It is certified that error appears in the above-identified patent and that said Letters Patent is hereby corrected as shown below:

On the title page, in the information under the heading "[63]", change "Pat. No. 5,802,887" to --abandoned--.

Column 187, claim 35, in Formula (I-4-a), change "$B^4$" to --$B^5$--.

Column 187, claim 36, in Formula (I'-4-a), change "$B^4$" to --$B^5$--.

Signed and Sealed this

Thirty-first Day of August, 1999

Q. TODD DICKINSON

Attest:

Attesting Officer

Acting Commissioner of Patents and Trademarks